US007550262B2

(12) United States Patent
Gelb et al.

(10) Patent No.: US 7,550,262 B2
(45) Date of Patent: Jun. 23, 2009

(54) PTPN11 (SHP-2) MUTATIONS AND CANCER

(75) Inventors: Bruce D. Gelb, Dobbs Ferry, NY (US); Marco Tartaglia, Rome (IT); Charlotte Niemeyer, Freiburg (DE)

(73) Assignee: Mount Sinai School of Medicine of New York University, New York, NY (US)

( * ) Notice: Subject to any disclaimer, the term of this patent is extended or adjusted under 35 U.S.C. 154(b) by 884 days.

(21) Appl. No.: 10/703,210

(22) Filed: Nov. 5, 2003

(65) Prior Publication Data

US 2004/0121384 A1 Jun. 24, 2004

Related U.S. Application Data

(60) Provisional application No. 60/424,170, filed on Nov. 5, 2002.

(51) Int. Cl.

| | |
|---|---|
| ***C12Q 1/68*** | (2006.01) |
| ***C12Q 1/44*** | (2006.01) |
| ***C12P 19/34*** | (2006.01) |
| ***C12M 1/34*** | (2006.01) |
| ***C07H 21/00*** | (2006.01) |
| *C12N 9/16* | (2006.01) |
| *C07H 21/04* | (2006.01) |

(52) U.S. Cl. .............................. 435/6; 435/7.1; 435/19; 435/91.2; 435/91.51; 435/196; 435/287.2; 536/23.2; 536/23.5; 536/25.32

(58) Field of Classification Search ....................... None
See application file for complete search history.

(56) References Cited

U.S. PATENT DOCUMENTS 6,156,551 A 12/2000 Neel et al.
6,200,807 B1 3/2001 Bennett et al.

FOREIGN PATENT DOCUMENTS

WO WO 99/46267 A1 9/1999

OTHER PUBLICATIONS

Loh, M.L. et al. Blood 103:2325-2331 (Mar. 2004; published online Nov. 26, 2003).*
Niihori, T. et al. Journal of Human Genetics 50:192-202 (Apr. 15, 2005).*
Arico M., et al., Blood 1997; 90:479-488.
Birnbaum RA, et al., Mol Cell 2000;5:189-95.
Bollag G, et al., Nat Genet 1996;12:144-8.
Bordin et al., Blood 2002;100:276-82.
Browett et al., Oncogene 1989;4:1029-1036.

(Continued)

*Primary Examiner*—Diana B Johannsen
(74) *Attorney, Agent, or Firm*—Darby & Darby, P.C.

(57) ABSTRACT

Diagnostic and therapeutic applications for certain types of cancer and precancerous conditions, including those deriving from hematologic cells, are described. Of particular interest are those cancers and precancerous conditions associated with increased signaling in the RAS-MAP kinase pathway. The diagnostic and therapeutic applications described herein are based on certain mutations in the protein tyrosine phosphatase gene PTPN11 and its expression product, PTPN11, promoting a gain-of-function in PTPN11 activity. Also described are nucleotide sequences, amino acid sequences, probes, and primers related to PTPN11 and PTPN11 variants, and cells expressing such variants.

2 Claims, 10 Drawing Sheets

OTHER PUBLICATIONS

Chan et al., Blood 2003;102: 2074-80.
Chang et al., Leukemia 2003;17:1263-1293.
Chauhan et al., J Biol Chem. 2000;275:27845-50.
Chen et al., Nat Genet. 2000;24:296-9.
Cunnick JM, et al., J. Biol. Chem. 2002;277:9498-9504.
de Groot et al., Cell Signal. 1998;10:619-628.
Drexler HG., Leukemia 1998;12:845-59.
Edmead et al., FEBS Lett 1999;459:27-32.
Emanuel PD, et al., Mol Med Today 1996; 2:468-475.
Emanuel PD, et al., Blood 1991;77:925-929.
Felix et al., J Clin Invest. 1992;89:640-647.
Feng, Exp Cell Res 1999;253:47-54.
Flotho C, et al., Leukemia 1999;13:32-7.
Fu et al., Biochem 2002;41:10700-10709.
Greaves M., Eur J Cancer. 1999;35:1941-1953.
Harrison CJ, Foroni L., Rev Clin Exp Hematol. 2002;6:91-113.
Hasle H, et al., Leukemia 1999;13:376-385.
Heo et al., Exp Mol Med 2002;34:211-223.
Iverson PO, et al., Blood 2002;99;4147-53.
Kalra et al., Blood 1994;84:3435-3439.
Kelly LM, Gilliland DG., Annu Rev Genomics Hum Genet. 2002;3:179-198.
Krajinovic et al., Blood 1999;93:1496-1501.
Kui, Cell Res 2000;10:279-288.
Lecoq-Lafon et al., Blood 1999;93:2578-85.
Lee et al., Leukemia 2002;16:486-507.
Lübbert et al., Blood 1990;75:1163-1169.
Luna-Fineman S, et al., Blood 1999;93:459-466.
Macaluso et al., J Cell Physiol 2002;192;125-130.
Maroun et al., Mol Cell Biol. 2000;20:8513-8525.
Miyajima et al., Int J Hematol. 1999;69:137-146.
Miyauchi J, et al., Blood 1994;83:2248-54.
Nakao et al., Leukemia 2000;14:312-315.
Neel, et al., Trends Biochem Sci. 2003;28:284-293.
Niemeyer CM, et al., Blood 1997; 89:3534-43.
O'Reilly et al., Mol Cell Biol 2000;20:299-311.
Ohtani et al., Immunity 2000;12:95-105.
Pathak et al., J Immunol 2001;167:3391-3397.
Pazdrak et al., J Exp Med 1997;186:561-8.
Qu et al., Blood 2001;97: 911-914.
Qu et al., Mol Cell Biol. 1998;18:6075-82.
Qu et al., Mol Cell Biol. 1997;17:5499-5507.
Reuter et al., Blood 2000;96:1655-1669.
Saxton et al., Nat Genet. 2000;24:420-423.
Saxton et al., EMBO J. 1997;16:2352-2364.
Shannon KM, et al., N Engl J Med 1994;330:597-601.
Shi et al., Mol Cell Biol. 2000;20:1526-1536.
Shi et al, J. Biol. Chem., 1998;273:4904-4908.
Shinohara et al., Urol Res 2002; 30:273-81.
Side Le, et al., Blood 1998;92:267-72.
Side L, et al., N Engl J Med 1997;336:1713-20.
Tamir et al., Curr Opin Immunol 2000;12:307-15.
Tang et al., Cell 1995;80:473-483.
Tartaglia et al., Am J Hum Genet 2002; 70:1555-63.
Tartaglia et al., Nat Genet. 2001;29: 465-468.
Tauchi et al., J Biol Chem 1995;270:5631-5.
Tauchi et al., J Biol Chem 1994;269:25206-25211.
Van Vactor et al., Curr Opin Genetics Development 1998;8:112-126.
Ward et al., Biochem Biophys Acta 1998;1448:70-6.
Welham et al., J Biol Chem 1994;269:23764-8.
Wiemels et al., Proc Natl Acad Sci USA. 2001;98:4004-4009.
Yokota et al., Int J Hematol. 1998;67:379-387.
You et al, J. Exp. Med., 2001;193:101-110.
You et al, Mol. Cell. Biol., 1999;19:2416-2424.
Yu et al., Oncogene 2003;22:5995-6004.
Zhang, Annu Rev Pharmocol Toxicol 2002;42:223-234.
Johan, MF et al, "Mutations in PTPN11 are uncommon in adult myelodysplastic syndromes and acute myeloid leukaemia." British Journal of Haematology, 124:843-844 (2004).
Mignon L. Loh et al. "Mutations in PTPN11 implicate the SHP-2 phosphatase in leukemogenesis." Blood. 103(6):2325-2331 (2004).
Marco Tartaglia et al. "Genetic evidence for lineage- and differentiation stage-related contribution of somatic PTPN11 mutations to leukemogenesis in childhood acute leukemia." Blood First Edition Paper, prepublished online Feb. 24, 2004; DOI 10.1182/blood-2003-11-3876.
Ahern, H., "Biochemical, Reagent Kits Offer Scientists Good Return in Investment," *The Scientist,* Jul. 24, 1995, vol. 9, No. 15, p. 20.
Tartaglia, et al. "PTPN11 and the Noonan Syndrome." from Inborn Errors of Development: The Mulecular Basis of Clinical Disorders of Morphogenesis, (Oxford Monographs on Medical Genetics, No. 49), 2004, pp. 895-903.
Tartaglia, et al. "Somatic Mutations in PTPN11 in Juvenile Myelomonocytic Leukemia, Myelodysplastic Syndromes and Acute Myeloid Leukemia." Nature Genetics, vol. 34, No. 2, Jun. 2003.

* cited by examiner

| | *PTPN11* | | | | | *NRAS* and *KRAS2* | | | | | |
|---|---|---|---|---|---|---|---|---|---|---|---|
| | Cases analyzed | | Cases with mutations | | | Cases analyzed | | Cases with mutations | | | |
| | | | | | | | | *NRAS* | | *KRAS2* | |
| | N | % | N | % | %[1] | N | % | N | % | N | % |
| **Immunophenotype** | | | | | | | | | | | |
| pro-B | 9 | 2.5 | | | | | | | | | |
| common | 183 | 51.8 | 20 | 87.0 | 10.9 | 150 | | 14 | 9.3[1] | 20 | 13.3[1] |
| pre-B | 112 | 31.7 | 3 | 13.0 | 2.7 | | | | | | |
| pre-B/B | 5 | 1.4 | | | | | | | | | |
| T-ALL | 44 | 12.5 | | | | | | | | | |
| not determined | 2 | | | | | | | | | | |
| Total | 355 | | 23 | | 7.4[2] | | | | | | |
| **Age (years)** | | | | | | | | | | | |
| 1-5 | 168 | 47.3 | 10 | 43.5 | | 74 | 49.3 | 8 | 57.1 | 9 | 45.0 |
| 5-10 | 118 | 33.2 | 7 | 30.4 | | 43 | 28.7 | 3 | 21.4 | 5 | 25.0 |
| > 10 | 69 | 19.4 | 6 | 26.1 | | 33 | 22.0 | 3 | 21.4 | 6 | 30.0 |
| median | 5.2 | | 5.7 | | | 5.0 | | 3.8 | | 6.5 | |
| range | 1.0-17.9 | | 1.7-17.9 | | | 1.0-17.9 | | 2.0-15.9 | | 1.5-15.9 | |
| **Sex** | | | | | | | | | | | |
| female | 145 | 40.8 | 9 | 39.1 | | 64 | 45.1 | 4 | 28.6 | 8 | 40.0 |
| male | 210 | 59.2 | 14 | 60.9 | | 86 | 60.6 | 10 | 71.4 | 12 | 60.0 |

FIGURE 6A

| | *PTPN11* | | | | | *NRAS* and *KRAS2* | | | | | |
|---|---|---|---|---|---|---|---|---|---|---|---|
| | Cases analyzed | | Cases with mutations | | | Cases analyzed | | Cases with mutations | | | |
| | | | | | | | | *NRAS* | | *KRAS2* | |
| | N | % | N | % | %[1] | N | % | N | % | N | % |
| **Gene rearrangements** | | | | | | | | | | | |
| *MLL-AF4* positive | 4 | *1.2* | | | | | | | | | |
| negative | 323 | *98.8* | 22 | *100* | | 141 | *100* | 14 | *100* | 19 | *100* |
| not tested | 28 | | 1 | | | 9 | | | | 1 | |
| *BCR-ABL* positive | 4 | *1.2* | | | | 1 | *0.7* | | | | |
| negative | 324 | *98.8* | 22 | *100* | | 140 | *99.3* | 14 | *100* | 19 | *100* |
| not tested | 27 | | 1 | | | 9 | | | | 1 | |
| *TEL-AML1* positive[3] | 65 | *23.0* | | | | 31 | *22.6* | | | 2 | *10.5* |
| negative | 217 | *77.0* | 20 | *100* | | 106 | *77.4* | 12 | *100* | 17 | *89.5* |
| not tested | 27 | | 3 | | | 13 | | 2 | | 1 | |
| *E2A-PBX1* positive | | | 0 | | | not tested | | | | | |
| negative | | | 17 | *100* | | | | | | | |
| not tested | | | 6 | | | | | | | | |
| ***PTPN11* mutations** | | | | | | | | | | | |
| positive | | | | | | | | | | 1 | *4.8* |
| negative | | | | | | | | | 23 | 22 | *95.2* |
| not tested | | | | | | | | | | | |
| **DNA index** | | | | | | not tested | | | | | |
| 1 | | | 8 | *38.1* | | | | | | | |
| > 1 | | | 13 | *61.9* | | | | | | | |
| not tested | | | 2 | | | | | | | | |

SEQUENCE LISTING

```
<160> NUMBER OF SEQ ID NOS: 39

<210> SEQ ID NO 1
<211> LENGTH: 1782
<212> TYPE: DNA
<213> ORGANISM: Homo sapiens
<220> FEATURE:
<221> NAME/KEY: CDS
<222> LOCATION: (1)..(1779)
```

```
<223> OTHER INFORMATION:

<400> SEQUENCE: 1

atg aca tcg cgg aga tgg ttt cac cca aat atc act ggt gtg gag gca        48
Met Thr Ser Arg Arg Trp Phe His Pro Asn Ile Thr Gly Val Glu Ala
1               5                   10                  15

gaa aac cta ctg ttg aca aga gga gtt gat ggc agt ttt ttg gca agg        96
Glu Asn Leu Leu Leu Thr Arg Gly Val Asp Gly Ser Phe Leu Ala Arg
            20                  25                  30

cct agt aaa agt aac cct gga gac ttc aca ctt tcc gtt aga aga aat       144
Pro Ser Lys Ser Asn Pro Gly Asp Phe Thr Leu Ser Val Arg Arg Asn
        35                  40                  45

gga gct gtc acc cac atc aag att cag aac act ggt gat tac tat gac       192
Gly Ala Val Thr His Ile Lys Ile Gln Asn Thr Gly Asp Tyr Tyr Asp
    50                  55                  60

ctg tat gga ggg gag aaa ttt gcc act ttg gct gag ttg gtc cag tat       240
Leu Tyr Gly Gly Glu Lys Phe Ala Thr Leu Ala Glu Leu Val Gln Tyr
65                  70                  75                  80

tac atg gaa cat cac ggg caa tta aaa gag aag aat gga gat gtc att       288
Tyr Met Glu His His Gly Gln Leu Lys Glu Lys Asn Gly Asp Val Ile
                85                  90                  95

gag ctt aaa tat cct ctg aac tgt gca gat cct acc tct gaa agg tgg       336
Glu Leu Lys Tyr Pro Leu Asn Cys Ala Asp Pro Thr Ser Glu Arg Trp
            100                 105                 110

ttt cat gga cat ctc tct ggg aaa gaa gca gag aaa tta tta act gaa       384
Phe His Gly His Leu Ser Gly Lys Glu Ala Glu Lys Leu Leu Thr Glu
        115                 120                 125

aaa gga aaa cat ggt agt ttt ctt gta cga gag agc cag agc cac cct       432
Lys Gly Lys His Gly Ser Phe Leu Val Arg Glu Ser Gln Ser His Pro
    130                 135                 140

gga gat ttt gtt ctt tct gtg cgc act ggt gat gac aaa ggg gag agc       480
Gly Asp Phe Val Leu Ser Val Arg Thr Gly Asp Asp Lys Gly Glu Ser
145                 150                 155                 160

aat gac ggc aag tct aaa gtg acc cat gtt atg att cgc tgt cag gaa       528
Asn Asp Gly Lys Ser Lys Val Thr His Val Met Ile Arg Cys Gln Glu
                165                 170                 175

ctg aaa tac gac gtt ggt gga gga gaa cgg ttt gat tct ttg aca gat       576
Leu Lys Tyr Asp Val Gly Gly Gly Glu Arg Phe Asp Ser Leu Thr Asp
            180                 185                 190

ctt gtg gaa cat tat aag aag aat cct atg gtg gaa aca ttg ggt aca       624
Leu Val Glu His Tyr Lys Lys Asn Pro Met Val Glu Thr Leu Gly Thr
        195                 200                 205

gta cta caa ctc aag cag ccc ctt aac acg act cgt ata aat gct gct       672
Val Leu Gln Leu Lys Gln Pro Leu Asn Thr Thr Arg Ile Asn Ala Ala
    210                 215                 220

gaa ata gaa agc aga gtt cga gaa cta agc aaa tta gct gag acc aca       720
Glu Ile Glu Ser Arg Val Arg Glu Leu Ser Lys Leu Ala Glu Thr Thr
225                 230                 235                 240

gat aaa gtc aaa caa ggc ttt tgg gaa gaa ttt gag aca cta caa caa       768
Asp Lys Val Lys Gln Gly Phe Trp Glu Glu Phe Glu Thr Leu Gln Gln
                245                 250                 255

cag gag tgc aaa ctt ctc tac agc cga aaa gag ggt caa agg caa gaa       816
Gln Glu Cys Lys Leu Leu Tyr Ser Arg Lys Glu Gly Gln Arg Gln Glu
            260                 265                 270

aac aaa aac aaa aat aga tat aaa aac atc ctg ccc ttt gat cat acc       864
Asn Lys Asn Lys Asn Arg Tyr Lys Asn Ile Leu Pro Phe Asp His Thr
        275                 280                 285

agg gtt gtc cta cac gat ggt gat ccc aat gag cct gtt tca gat tac       912
Arg Val Val Leu His Asp Gly Asp Pro Asn Glu Pro Val Ser Asp Tyr
    290                 295                 300
```

-continued

```
atc aat gca aat atc atc atg cct gaa ttt gaa acc aag tgc aac aat      960
Ile Asn Ala Asn Ile Ile Met Pro Glu Phe Glu Thr Lys Cys Asn Asn
305                 310                 315                 320

tca aag ccc aaa aag agt tac att gcc aca caa ggc tgc ctg caa aac     1008
Ser Lys Pro Lys Lys Ser Tyr Ile Ala Thr Gln Gly Cys Leu Gln Asn
                325                 330                 335

acg gtg aat gac ttt tgg cgg atg gtg ttc caa gaa aac tcc cga gtg     1056
Thr Val Asn Asp Phe Trp Arg Met Val Phe Gln Glu Asn Ser Arg Val
            340                 345                 350

att gtc atg aca acg aaa gaa gtg gag aga gga aag agt aaa tgt gtc     1104
Ile Val Met Thr Thr Lys Glu Val Glu Arg Gly Lys Ser Lys Cys Val
        355                 360                 365

aaa tac tgg cct gat gag tat gct cta aaa gaa tat ggc gtc atg cgt     1152
Lys Tyr Trp Pro Asp Glu Tyr Ala Leu Lys Glu Tyr Gly Val Met Arg
    370                 375                 380

gtt agg aac gtc aaa gaa agc gcc gct cat gac tat acg cta aga gaa     1200
Val Arg Asn Val Lys Glu Ser Ala Ala His Asp Tyr Thr Leu Arg Glu
385                 390                 395                 400

ctt aaa ctt tca aag gtt gga caa ggg aat acg gag aga acg gtc tgg     1248
Leu Lys Leu Ser Lys Val Gly Gln Gly Asn Thr Glu Arg Thr Val Trp
                405                 410                 415

caa tac cac ttt cgg acc tgg ccg gac cac ggc gtg ccc agc gac cct     1296
Gln Tyr His Phe Arg Thr Trp Pro Asp His Gly Val Pro Ser Asp Pro
            420                 425                 430

ggg ggc gtg ctg gac ttc ctg gag gag gtg cac cat aag cag gag agc     1344
Gly Gly Val Leu Asp Phe Leu Glu Glu Val His His Lys Gln Glu Ser
        435                 440                 445

atc atg gat gca ggg ccg gtc gtg gtg cac tgc agt gct gga att ggc     1392
Ile Met Asp Ala Gly Pro Val Val Val His Cys Ser Ala Gly Ile Gly
    450                 455                 460

cgg aca ggg acg ttc att gtg att gat att ctt att gac atc atc aga     1440
Arg Thr Gly Thr Phe Ile Val Ile Asp Ile Leu Ile Asp Ile Ile Arg
465                 470                 475                 480

gag aaa ggt gtt gac tgc gat att gac gtt ccc aaa acc atc cag atg     1488
Glu Lys Gly Val Asp Cys Asp Ile Asp Val Pro Lys Thr Ile Gln Met
                485                 490                 495

gtg cgg tct cag agg tca ggg atg gtc cag aca gaa gca cag tac cga     1536
Val Arg Ser Gln Arg Ser Gly Met Val Gln Thr Glu Ala Gln Tyr Arg
            500                 505                 510

ttt atc tat atg gcg gtc cag cat tat att gaa aca cta cag cgc agg     1584
Phe Ile Tyr Met Ala Val Gln His Tyr Ile Glu Thr Leu Gln Arg Arg
        515                 520                 525

att gaa gaa gag cag aaa agg aag agg aaa ggg cac gaa tat aca aat     1632
Ile Glu Glu Glu Gln Lys Arg Lys Arg Lys Gly His Glu Tyr Thr Asn
    530                 535                 540

att aag tat cct cta gcg gac cag acg agt gga gat cag agc cct ctc     1680
Ile Lys Tyr Pro Leu Ala Asp Gln Thr Ser Gly Asp Gln Ser Pro Leu
545                 550                 555                 560

ccg cct tgt act cca acg cca ccc tgt gca gaa atg aga gaa gac agt     1728
Pro Pro Cys Thr Pro Thr Pro Pro Cys Ala Glu Met Arg Glu Asp Ser
                565                 570                 575

gct aga gtc tat gaa aac gtg ggc ctg atg caa cag cag aaa agt ttc     1776
Ala Arg Val Tyr Glu Asn Val Gly Leu Met Gln Gln Gln Lys Ser Phe
            580                 585                 590

aga tga                                                             1782
Arg

<210> SEQ ID NO 2
<211> LENGTH: 593
```

-continued

```
<212> TYPE: PRT
<213> ORGANISM: Homo sapiens

<400> SEQUENCE: 2

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400
```

-continued

```
Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val Val His Cys Ser Ala Gly Ile Gly
    450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Glu Gln Lys Arg Lys Arg Lys Gly His Glu Tyr Thr Asn
    530                 535                 540

Ile Lys Tyr Pro Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Gln Lys Ser Phe
            580                 585                 590

Arg
```

<210> SEQ ID NO 3
<211> LENGTH: 22
<212> TYPE: DNA
<213> ORGANISM: Artificial Sequence
<220> FEATURE:
<223> OTHER INFORMATION: Exon 1 - forward PCR primer

<400> SEQUENCE: 3
gctgacggga agcaggaagt gg 22

<210> SEQ ID NO 4
<211> LENGTH: 20
<212> TYPE: DNA
<213> ORGANISM: Artificial Sequence
<220> FEATURE:
<223> OTHER INFORMATION: Exon 1 - reverse PCR primer

<400> SEQUENCE: 4
ctggcacccg tggttccctc 20

<210> SEQ ID NO 5
<211> LENGTH: 24
<212> TYPE: DNA
<213> ORGANISM: Artificial Sequence
<220> FEATURE:
<223> OTHER INFORMATION: Exon 2 - forward PCR primer

<400> SEQUENCE: 5
actgaatccc aggtctctac caag 24

<210> SEQ ID NO 6
<211> LENGTH: 22
<212> TYPE: DNA

```
<213> ORGANISM: Artificial Sequence
<220> FEATURE:
<223> OTHER INFORMATION: Exon 2 - reverse PCR primer

<400> SEQUENCE: 6

cagcaagcta tccaagcatg gt                                        22


<210> SEQ ID NO 7
<211> LENGTH: 22
<212> TYPE: DNA
<213> ORGANISM: Artificial Sequence
<220> FEATURE:
<223> OTHER INFORMATION: Exon 3 - forward PCR primer

<400> SEQUENCE: 7

cgacgtggaa gatgagatct ga                                        22


<210> SEQ ID NO 8
<211> LENGTH: 23
<212> TYPE: DNA
<213> ORGANISM: Artificial Sequence
<220> FEATURE:
<223> OTHER INFORMATION: Exon 3 - reverse PCR primer

<400> SEQUENCE: 8

cagtcacaag cctttggagt cag                                       23


<210> SEQ ID NO 9
<211> LENGTH: 25
<212> TYPE: DNA
<213> ORGANISM: Artificial Sequence
<220> FEATURE:
<223> OTHER INFORMATION: Exon 4 - forward PCR primer

<400> SEQUENCE: 9

gattgatcaa tcccttggag gaatg                                     25


<210> SEQ ID NO 10
<211> LENGTH: 21
<212> TYPE: DNA
<213> ORGANISM: Artificial Sequence
<220> FEATURE:
<223> OTHER INFORMATION: Exon 4 - reverse PCR primer

<400> SEQUENCE: 10

gtcaccagac ccaacgtggt g                                         21


<210> SEQ ID NO 11
<211> LENGTH: 24
<212> TYPE: DNA
<213> ORGANISM: Artificial Sequence
<220> FEATURE:
<223> OTHER INFORMATION: Exon 5 - forward PCR primer

<400> SEQUENCE: 11

ctgcagtgaa catgagagtg cttg                                      24


<210> SEQ ID NO 12
<211> LENGTH: 23
<212> TYPE: DNA
<213> ORGANISM: Artificial Sequence
<220> FEATURE:
<223> OTHER INFORMATION: Exon 5 - reverse PCR primer

<400> SEQUENCE: 12

gttgaagctg caatgggtac atg                                       23
```

<210> SEQ ID NO 13
<211> LENGTH: 21
<212> TYPE: DNA
<213> ORGANISM: Artificial Sequence
<220> FEATURE:
<223> OTHER INFORMATION: Exon 6 - forward PCR primer

<400> SEQUENCE: 13
tgcattaaca ccgttttctg t 21

<210> SEQ ID NO 14
<211> LENGTH: 23
<212> TYPE: DNA
<213> ORGANISM: Artificial Sequence
<220> FEATURE:
<223> OTHER INFORMATION: Exon 6 - reverse PCR primer

<400> SEQUENCE: 14
gtcagtttca agtctctcag gtc 23

<210> SEQ ID NO 15
<211> LENGTH: 23
<212> TYPE: DNA
<213> ORGANISM: Artificial Sequence
<220> FEATURE:
<223> OTHER INFORMATION: Exon 7 - forward PCR primer

<400> SEQUENCE: 15
gaacatttcc taggatgaat tcc 23

<210> SEQ ID NO 16
<211> LENGTH: 22
<212> TYPE: DNA
<213> ORGANISM: Artificial Sequence
<220> FEATURE:
<223> OTHER INFORMATION: Exon 7 - reverse PCR primer

<400> SEQUENCE: 16
ggtacagagg tgctaggaat ca 22

<210> SEQ ID NO 17
<211> LENGTH: 24
<212> TYPE: DNA
<213> ORGANISM: Artificial Sequence
<220> FEATURE:
<223> OTHER INFORMATION: Exon 8 - forward PCR primer

<400> SEQUENCE: 17
gacatcaggc agtgttcacg ttac 24

<210> SEQ ID NO 18
<211> LENGTH: 24
<212> TYPE: DNA
<213> ORGANISM: Artificial Sequence
<220> FEATURE:
<223> OTHER INFORMATION: Exon 8 - reverse PCR primer

<400> SEQUENCE: 18
ccttaaagtt actttcagga catg 24

<210> SEQ ID NO 19
<211> LENGTH: 22
<212> TYPE: DNA
<213> ORGANISM: Artificial Sequence
<220> FEATURE:

<223> OTHER INFORMATION: Exon 9 - foward PCR primer

<400> SEQUENCE: 19
gtaagctttg cttttcacag tg 22

<210> SEQ ID NO 20
<211> LENGTH: 25
<212> TYPE: DNA
<213> ORGANISM: Artificial Sequence
<220> FEATURE:
<223> OTHER INFORMATION: Exon 9 - reverse PCR primer

<400> SEQUENCE: 20
ctaaacatgg ccaatctgac atgtc 25

<210> SEQ ID NO 21
<211> LENGTH: 26
<212> TYPE: DNA
<213> ORGANISM: Artificial Sequence
<220> FEATURE:
<223> OTHER INFORMATION: Exon 10 - forward PCR primer

<400> SEQUENCE: 21
gcaagacttg aacatttgtt tgttgc 26

<210> SEQ ID NO 22
<211> LENGTH: 24
<212> TYPE: DNA
<213> ORGANISM: Artificial Sequence
<220> FEATURE:
<223> OTHER INFORMATION: Exon 10 - reverse PCR primer

<400> SEQUENCE: 22
gaccctgaat tcctacacac catc 24

<210> SEQ ID NO 23
<211> LENGTH: 24
<212> TYPE: DNA
<213> ORGANISM: Artificial Sequence
<220> FEATURE:
<223> OTHER INFORMATION: Exon 11 - forward PCR primer

<400> SEQUENCE: 23
caaaaggaga cgagttctgg gaac 24

<210> SEQ ID NO 24
<211> LENGTH: 24
<212> TYPE: DNA
<213> ORGANISM: Artificial Sequence
<220> FEATURE:
<223> OTHER INFORMATION: Exon 11 - reverse PCR primer

<400> SEQUENCE: 24
gcagttgctc tatgcctcaa acag 24

<210> SEQ ID NO 25
<211> LENGTH: 24
<212> TYPE: DNA
<213> ORGANISM: Artificial Sequence
<220> FEATURE:
<223> OTHER INFORMATION: Exon 12 - forward PCR primer

<400> SEQUENCE: 25
gctccaaaga gtagacattg tttc 24

<210> SEQ ID NO 26
<211> LENGTH: 22
<212> TYPE: DNA
<213> ORGANISM: Artificial Sequence
<220> FEATURE:
<223> OTHER INFORMATION: Exon 12 - reverse PCR primer

<400> SEQUENCE: 26
gactgttttc gtgagcactt tc 22

<210> SEQ ID NO 27
<211> LENGTH: 22
<212> TYPE: DNA
<213> ORGANISM: Artificial Sequence
<220> FEATURE:
<223> OTHER INFORMATION: Exon 13 - forward PCR primer

<400> SEQUENCE: 27
caacactgta gccattgcaa ca 22

<210> SEQ ID NO 28
<211> LENGTH: 22
<212> TYPE: DNA
<213> ORGANISM: Artificial Sequence
<220> FEATURE:
<223> OTHER INFORMATION: Exon 13 - reverse PCR primer

<400> SEQUENCE: 28
cgtatccaag aggcctagca ag 22

<210> SEQ ID NO 29
<211> LENGTH: 21
<212> TYPE: DNA
<213> ORGANISM: Artificial Sequence
<220> FEATURE:
<223> OTHER INFORMATION: Exon 14 - forward PCR primer

<400> SEQUENCE: 29
accattgtcc ctcacatgtg c 21

<210> SEQ ID NO 30
<211> LENGTH: 24
<212> TYPE: DNA
<213> ORGANISM: Artificial Sequence
<220> FEATURE:
<223> OTHER INFORMATION: Exon 14 - reverse PCR primer

<400> SEQUENCE: 30
cagtgaaagg catgtgctac aaac 24

<210> SEQ ID NO 31
<211> LENGTH: 22
<212> TYPE: DNA
<213> ORGANISM: Artificial Sequence
<220> FEATURE:
<223> OTHER INFORMATION: Exon 15 - forward PCR primer

<400> SEQUENCE: 31
caggtcctag gcacaggaac tg 22

<210> SEQ ID NO 32
<211> LENGTH: 21
<212> TYPE: DNA
<213> ORGANISM: Artificial Sequence
<220> FEATURE:
<223> OTHER INFORMATION: Exon 15 - reverse PCR primer

<400> SEQUENCE: 32
acattcccaa attgcttgcc t 21

<210> SEQ ID NO 33
<211> LENGTH: 300000
<212> TYPE: DNA
<213> ORGANISM: Homo sapiens
<220> FEATURE:
<221> NAME/KEY: misc_feature
<222> LOCATION: (1)..(300000)
<223> OTHER INFORMATION: where n may be a or g or c or t/u, unknown or other

<400> SEQUENCE: 33
gaattaaaga gagtccataa catatatgaa ataaaggccc cgggaacaga ctttggagac 60
atttttgggt tttaacagac atttcagtct tatattcata ttccaggcag atacacagtt 120
aagtagtttg agggccaaat tacaaagcat ggcactaatt tcatcagttt gagaatggat 180
aattgttttt gctccaaagg cccaaattca tctgaacaca ttaactcaat acttttacac 240
tgcaatggcc ttgtggttct agggtacttg tcaacaggga gtgtagagga gaactaagct 300
ggaagatcta gcaacccttt taatcaacaa ggaagaaaat gctgtgacaa cttctatgca 360
tggagtaact tgtgaaaggg agtgaacagg ggtctgatgt cctacaagtg aaaggagggt 420
cattctgaat agaaggagtg agctgacagg cctggtaagg tggctccacc tcaacaaaag 480
cccccagggc aaatgttttt ctgggattac agttagtact tggacctgtg aggactgcaa 540
gttcattttc ttttctagga agcgattatg actgaatacc ataccttcac caagtctttc 600
ggccaaccag ttcctaagac actacggctg ccatatccca gtgtgttgcc tccatattca 660
gcaaccttcc tactgtttgt gttaggcccc gcatatatca ccaacttcaa aacagaaaat 720
atactgttag actgtaaaag aaaaacaaaa acaacatcta caaataaaaa ggctgcaaaa 780
acatttgttt aaaatacaat tataaccagg cattggtgtc attatagtat aactaatatt 840
tcccgatttt tttaggtata actgatacta gtttggatgc aatcagtcat tggtatttac 900
agggaagcca cagagtaata acaattctta ataaaaagaa gtatactttt tatattacca 960
cactttaatt ggcttgggga cctcacatta aatagttata ctcagttatt gtacatcaat 1020
atttttgaaa tagctatttt aatgctaatt aataacaaat aactcattaa taacagtttg 1080
gccccttaag tcctccccaa aattaataaa gtgagcaaat acagatggaa atatggttat 1140
atctaacaca acaacaaaat aaaagcacca aaaaaaatca atgaataaat aagaattttt 1200
aaaaatgcaa caaattgaaa ataagccata tattcttagg atgttgctta atggtataaa 1260
aagaaaatga tacaaatttg ggccagaaag ggggctgctg cttcttgggt cagttttcat 1320
gtatcaatat ttctctaatt catttataac cagctggctg actttctaat cggcagaaga 1380
aacatttata gctcatttgg cattcaaaga cttccatagg aaaaataaag ctctggcttc 1440
tgtaaatacc aaaccctgtc ttctaatgtg cgctctgact gcttctcact gcatctaagt 1500
tcagatttag tagctctatc ttcagccctg aatgcttatt atttcgtgat ttcttaccct 1560
ttggggcctt ttgctgacac cagccaggga ccactggaaa agtaaatgta cttttatcca 1620
tgtagtaagc ctctttgtgc ttcaccattt aacactaatg tctactgcag gcataagtta 1680
gcgcatattg gaaatgcaaa atacagtttt taaaggagaa acaaaacgac accaactaaa 1740
atggcagcct ctcccatttc tatattaaaa gtcacttcac ctgaacctgg gaaatggggg 1800
tagccaatgc caggagctat gaattacggt ggactgatgc taggagagat atgtttctga 1860

-continued

```
aaggcctact aaagatcatc tcatatattt tcttgcttcc agctaaggtg agttttgaag   1920
acaaggcttt ggggacacct gggaatcttc actatcctaa aagataatgg ggaagaggat   1980
tctataactt gcccagaaat gtgtttcacc atctcatagt atatacagtt aagaagtcct   2040
ttatttttaa cctaaaaacc tccccggata gaattttttt aaaagtcagc ctcagaagtc   2100
agaatcccct gctaggattt aagcccattt gccctcacac agttcacagg ggagagagaa   2160
aacagatcac taagaagcta cataaaaata gtatgcacga agctattaga taatcctcca   2220
actgttcttt catatgttac atatttcatt agcctttccc cctaagacca catgacaggt   2280
tacaattcaa caattctaag tagaagaaaa tgcttcaacc cctaagatgc ttcctttcgt   2340
tcataactgt taagccacca ggttggaaac tactcttcct caaaaaaaga acaaatgttt   2400
aaataaatat aaaccagatc ctagcacctc tgaaaccctt ctaaaaagcc accttttccc   2460
aaaagataca tgagaagccc caagaattgg gcagtgagac ctttctagat gaatggacat   2520
cacacatctg ggtaacttc aagcacggag ggagggcagg gggtaagcag aatgaaaagg   2580
aacatttcct tcctctcata tatctaagca cctgaaagct tacaaagtac actttcaaca   2640
tatcattaaa acattgttct tagactgcag aggtggtgtt tctttaactc cctcaatcac   2700
taccccttcaa agataagaac tttatcttag gaaagttctc cttagagata tctgcagaca   2760
gaaatcagtc aagaatggtg accagcagca aagaaaaata agaagcatct aagaatcagc   2820
ttactcgagg tggaaccaat agtaacccag ttcttactta ctttgtcata gtcatattgc   2880
gaagagcatc tgctatcaaa tctaaggtac aggcagcgag ctcctgggat atggaccgtt   2940
tctttaaatt tatagttgtc tctgacgggg tggactgttt ccacagtctt tccagcagcc   3000
catggggcag gaatctttaa accagtgaga aatcctggct cttccttctc ttctaacatt   3060
ctaaacagaa aaagagaaag tgatttagct tagcagccaa ggaaaggaaa aacaatgtaa   3120
acattaaatt gctctttaat tttccacagc atgcagtatg ataacactga ggcttttaaa   3180
tgcttgatat cagtggcaat cagaaacatt ttaaaaattc ctacatttaa gggtttttc   3240
tttccttgtt gtcagatatt atacttgctt tttttttct tttttgcctt tttccaggac   3300
aagaagcaga gatatatttt catttttccc tcttttttc aagggcgaag cccagttgat   3360
atccaagaga agacctgatc aattctcatt taaaggtact cagaaaaaaa aaaaagatac   3420
tgtaaaggat ctttaagatt ggccactttg caaatcccac agggttagca tcctgtaaac   3480
atttcctttt gttgatatct acatgacaat tgttgaaaac tccaggagtc tacatagcta   3540
cttttcacca taatttttac taaagaaagg tgccttcaaa ggttctctta cctactgtaa   3600
ttgaactctc aaggacgaca tggagcctga ggttgtggaa tacaaactcc taagacttaa   3660
acttagttac catggaattc tcttattctt tcaactccga agcttgagct gcaaagcctt   3720
actgtccaat atggtagcta ctagtcacat gtggccattt caattaaatt gaatttaaat   3780
gaaataaaat ttaaaattca gctcctcagt cacattagct atattgcagg tgctaaataa   3840
ctacctgtgg ctatggaact agacagcaca gatagaagtt ttcatcactg cgaaaagctc   3900
aattccatag cctgctgctc tagagaaacc caggaaatct tttttaaaga cagctttaat   3960
gcaacataac tgacataata aattgcacat atttaaaaca tacaacttga taagtttgga   4020
catttgttat accattaagt ttccttcttc ctctttgtaa ccactccatt tctctgccag   4080
gtgatcactt atttgctgtc tgtcactaga gattagtttg cattttctag agttttatag   4140
tatgtggctt ctttcactca gggttaagta ttttgagatt atataaacat tgttgtatat   4200
aacaaaagtt cattcctttt tattgctgat tagagtccat tgtatgacta tatcacaatt   4260
```

```
tgcttatcca ttcacttact gatggacgtt tatgttgttt ccagttttgg gctcttctaa   4320
ccaaaactgt tacgaacctt aatgtcaaag ctttgtaaga acctatgctt tcttttcttg   4380
tgtgaatacc taaaagtgaa atagttgggt catacaatag gtgtatgttt aactttttaa   4440
gaaacagccg gcagggtgtg gtggctcacg cctgtaatcc cagcactttg ggaggctgag   4500
gtgggcggat catgaggtca ggagttcaaa accagcctgg ccaacacagt gagacctcgt   4560
ctctactaaa aaatacaaaa attagctggg tgtggtggcg tacgcctgta atcctagcta   4620
ctcatgaggc tgagacagga gaattgcttg aacccaggag gtggaggttg cagtgagctg   4680
agattgcgcc actgcactcc agcctgggtg acagaacaag gctccatctc agaaaaaaaa   4740
aaaaaagaaa cagccaaact gcctgccaaa gtcataaatat tttacatccc cactattagc   4800
atatgagaat ttcagatcaa ttttgaacta atctcttgat ccatggggaa atttatgcta   4860
accagttgct ataaatctac aaagcaatgc tacagttatc taaaatttc attctgaagt   4920
ctttttcttt tcacagctag ataatccttg ctaaaaatca ttttcataaa aggagtacta   4980
cgctttcacc caaagaaaac aagaaaaggg ttcctgcaag gaagcagcat tcattacctc   5040
tcatcaggga acagcctgca cttctggtct ggtgcaccac acggggaaca gcccacctca   5100
gcaaaaaccg gacactgggt tttaagcagc aacgccgtct gaaacacaaa accatcatta   5160
tgtcttccag ggctactgtc agttatctga atggtatgac agccaaactt agaggtctct   5220
cttaaatcat ctttttacaa tcctagtctg ctctccttca ttaagaaatg ctgtgctact   5280
tagaccactt aacattattt tacttaatgc tgtaatggaa tgcatcattt atattagcta   5340
ctattagctg gcaaggactc aggagacaaa ctataatggt aggtttttgg tagcattgta   5400
tattagcatt tttatagctg atcagccatg aacacttgct aaaaggttgc agttagtaat   5460
ttagtcaaac aaataaaatg ttttccctta ttatttattt ttatgacatg atatttttct   5520
tcattccatc attatttccc ttggtttctg aaaggcagga ttatgtttat tctgtcttca   5580
gtgaaagcaa acagccatcc tgtgaagcag gttggccaaa aagcagttca ctttggcaca   5640
ccaaggatca tacctggctg gtatagagta ccagctgcac tagctgaggc atcagggcat   5700
ccgccatgat cagagtctgt aaatttggat gcatcaagga ggtcagtaac actggaagaa   5760
ggtgaccaag catagtagcc ttagtaactt gttccaagcc ttttaaccta caaaaagttc   5820
aagaaaaaca cacagcctaa gcaatgccca aacatgtgaa gaagcactaa tgtcatcttt   5880
atctgacaat ttctcctaaa ctgcacctcc ttaaactact taagcacttt cagcgatagc   5940
aattcagtcc acaaatttc caccttctgc cactgaggga gaggggaaga acagaaataa   6000
agctattaat agatttcacc ttcagtctct gatttttgcc aaaaaattta taagctgcct   6060
ttttttttt tttttttt gacaggctct cactcttgtt acccaggctg gagtgcagtg   6120
gtacgatcac agctcactgc agccttgatc tcctgggtac aagtgatcct cccacctcgg   6180
tctcccaaat tgttgggatt acaggtatga actacttagg ttctaggttc taggttgcta   6240
catggtgcat ttcatagcac ctttgaagca ctttacaaat ggattctaaa atgccaatgg   6300
ctactacctg taaagttctc ttgcctctgg ggctgctggt cactatgcta cacagtgact   6360
ctaaacagga ggaagtgaat ggctacaaca ttgattcacc tgcccagagc tgtgacatcc   6420
attactggtc tagagaaact gaggcttgtc tggggcatgc agaagcaggc agatttcttc   6480
ccccaatttt tttttttatt atggtaaaat aaacatagca caaaatttac catcttaacc   6540
attttaagtg tacatttcag tgttattaaa taatgttgtg caaccatcac caccatccat   6600
```

-continued

```
ctccacaact ctttttgtgt tataaaaccc aaactctatg cgcattaaac aataactcct   6660
cattttcccc ttgcccccag cccccggcaa ccaccattct actttctgtc tctatgattt   6720
tgactcatct aagtaggcaa atttttaatt tatctttaaa atcacattct taatatccct   6780
gtcctctgct agaagagtta aggaatgtag aaagaaatgg attatgtaaa ttccttaagg   6840
ctacttagga tattggtagt ggaaccagaa acccaggctc tcccattaga cagaactacg   6900
tattactaag cctcaatgca atgcctatct gggttatact gttcccaatc ccaacctcct   6960
atctactctc tgggagtggg taagaaccaa gtccatagga acagacaggg ttacggaagc   7020
aaaaattaca ctgtaggatt cttttagatc tacagctcca acatgcaaat tgtcaaaaaa   7080
cacagtattc aatgcatctc taaaaacaaa ccagagcaga attttttttt ttttttgaga   7140
cagagtctcg ctctgtcacc caggctggag tgcagtggga tgatctcggc tcactgcaag   7200
ctccgcctcc caggttcagg ccattctcct gccttagcct cctgagtagc tgggactaca   7260
ggtgcctgcc accatgcctg gctaattttt tttttttttt ttgtattttt agtagagatg   7320
gggttacagc agaaatttta atgtgaaagg ctgagaaagg gctttattac tgtgaaagag   7380
aagtctgccc tctatatagg tcagccatgt atttggagaa gtaaaattac agtaaaatct   7440
tgaggtacca catcagtgtc atcctttgtg tagcagttgg taagtcactt cttcctccca   7500
aaagtcttta tcatgaggaa actaagtgtg catggtgctg accttgataa ttaaaggaaa   7560
ggccattttg ggagtgatgg cagtagaagt ctcaagtggc agagattagg ctgtgccctc   7620
cacaacctcg ctacccttag atcatggctg ttggcccaat ctcacctgaa agcacatgaa   7680
agagtgtgac tgcacttggc tttcaaacac ttgccctttt agcctattct cacaaaaatc   7740
tctctatata aaattgatcc ttctatattc taaaaagatt taatttcaat aaacaaactt   7800
ttcttcccac agggcagctg gtcacagccc acaatccatt cctcacctct gctcacggtc   7860
tgctatgtca ctatttatga gggcagttgt gacctgctgt agcatttcca acacttcatc   7920
acatccagtc aggatttggg tggcaagagc caaaatactg acttttagct cctaggcaga   7980
aaatatcatc atattatttt taagctttgt gatgaacata cgttcacaat gacaacatga   8040
aatgatgtat ttaatgatgt atttccaaat gaaataatga ggtggacaga ataagcccaa   8100
agcagtaaat tctgctagaa ataatgaggt ggccagaata agcccaaagc agtaaatggc   8160
aagtagcaat ttgggaggcc aaggtctgga gagctgacag aaatacgcag tatttcagag   8220
ggatcacact gagtccctag gagaaaaggc tcccatccca gccagcacaa gaaatatttc   8280
ccatcccatc cagcacaaga gagctcctgg tggccagccc agaaactgtc caggtggaag   8340
actgccttgg gtggtatgag gatagctaaa gagaaaaaca gaacagtaaa aggcgcatgt   8400
agaggcggtg aataaaatga gacaaaaaca caacattcta aaacagtaca agtgaccttt   8460
tactcaatgt cctaaacaaa tcacagttaa aaacaggcag ttaaaaaaat tcaattaaag   8520
tagcaagcag ttacaggcta ttaaacatta aaataactat tagagagttc gtgggagtac   8580
aaatactaaa taatgtgtta agaaagacta gctaacatca tagaaatgtt tagtttacaa   8640
ttattttcag ttaaaaaaat acaaactctt tgggggacat gtttccccag aaacctagac   8700
aactgagcct attcagcctt tcctaagagt ctttacattt ctatgtttaa ttaagaattt   8760
actaaggcta ggccgggcac ggtggctcat gcctgtaatc ccagcacttt gggaggccaa   8820
ggcaggtgga tcacttgagg tcaggagttc aagaccagtc tggacaacac ggtgaaaccc   8880
cgtctctact aaaatttcaa aaattagctg ggcattacag atgggcgcac atctgtaatc   8940
ccagctactc gggaggctga ggcaggagaa tcgtttgaac tcagaagatg gaggttgcag   9000
```

-continued

```
tgagccgaga ttgcaccacg gctctccagc ctgggcgaca aagagagact ccatctcaaa   9060
aaaaaaaaaa aaaaaaaaaa aaaagaatct actaaggcta aaatttagcc ttcaaataga   9120
aaaaactttc tcattgttgg aattttctgg ggtctttatt attattatat tttttgaaac   9180
acagtctcac tctgtcaccc aggctggagt gcagtggcat gatcagggct ccctgcaacc   9240
tccacctcct gggttcaagc aattctcacg cctcagcctc accagcagct ggaattacag   9300
gggagtgcca tcacgcccgg ctaatttttg tatttttcag tagagatggg gtttcaccat   9360
gttggccagg ctggtctcta actcttggcc tcaagtgatc cacctgcctc agcctcccaa   9420
agtgctggga ttacaggtgt cagccaccac acccagctgt ttttagtatt attgagattt   9480
tttttaatct ttaagagagt aggaactctg aactaatgat gagccaaatc atgttttaag   9540
tcacactaat gacattcatg atcatctact gactccatac cacatggcag caaagtgcca   9600
ggtatttaca gggcttgttg ttaatacagc aactttacaa agaagatgtt attgtccctt   9660
tttactgatg agaaaactaa ggcaagagaa gttaaataaa tattatcaac aacttaaatt   9720
aaaagtgcat gtatgtctgc ctatttaaaa atggattata caatgaggta aactcataag   9780
tacaaactat cagatgtatt atttaaatag tatatatgca taaaggagta agaaaggggc   9840
aaactgcatt ggcttttatc tttaactgtg gcttccttgg ttgatttttc agtgtgttta   9900
acattttaag aaagaataaa gttcttgtag atttctctga ttctcccaca aagatgaaat   9960
tctgaagaac aatgcaaaca acagccttga gcatctgtca aaattataac aaccatggct  10020
ataaaaaaat ctttggactg ctataaattg tcatgtggga acaagttagt gagtttacac  10080
agaagctaat ttaaaaataa tcacagaaaa tgaaattgac tataggttta gaaattagat  10140
tattccatac aaagattgaa aaaattatca ccttttaaaa gttattttaa tcaagagaat  10200
ataataaacc atctaaaatt ttgaaattat ttaatgctcc caagattttt atatatatat  10260
atatatacac acacacacac acacacacac acatacacat atatatgtct atgtagctat  10320
aactttcagg tacacatgag atcacttgta agtgccatat tttatagttc ttaaaagaag  10380
atggaagtaa acaaaggcac aaaaaggttg acaggagcac acggatgaca cattatgagt  10440
gtcacaagta ggtgactact gtgtaatgac ataaaaaatc tatggaatga gtggcctaat  10500
gttacctctc acaagaatat aagccacaag gtgaattctg acatcataaa acacagaaat  10560
ttagccaatt aagctgcttt tcacactggg tagaacgcat cgttaaaata aagcttggtg  10620
tttacctgta ccttcaatgt ctctccctgc aaggagctgt cactgtcatc attctcatca  10680
ggtttaatca aaatagtgtt actgagaagg tgattctgaa ctgccatcag atagcgcagg  10740
caggaggatg cagcctttaa tacaaataag ggcatttaaa tgatctaaat cctactgaaa  10800
gagcgatcat gtaatcctca tgtttttaaa agattttgac aaagaaaaca aaaagagaaa  10860
taaaaaaaac agaccaagtt agtttttcag gtgccttatt tccacatggc tttccataca  10920
tactttgaca cacttactat aactttctgc cttttggtac acaatcctca ctaattagaa  10980
tacttacttg aatttttgcc tcttaataat tattcttccc cctccctctc acacacatct  11040
ccattataga agaatactca aacccttaaa agaatctttt gattcctatt ggtctctata  11100
aaacactcat ggtttagaaa acaatgtaaa attaaaaatt aatagggaaa aaacactctc  11160
actagataaa acaaaaactc ccaaatctga tcaatttatt gcatcaagca atttaagcag  11220
ggggaatagt ctttggaaag tttttcaagt ggatttgtct agttctacat ttctagggta  11280
agtagtaatc cacggacttt cataaattat tattattatt atttgagacg gagtcttgct  11340
```

-continued

```
ctgtcaccca ggctggagtg cggtggcgcg atctcagctc actgcaaact ccacctcctg  11400
ggttcacgtg attctcctgc ctcagcctcc tgagtagctg ggattaccga tgtgtaccac  11460
cacaccctgc taatttttgt atttttaata gagacggggt ttcaccatgt tggtcagact  11520
ggtcttgaac tcctgacctc aggtgatcca cccaccttgg cctcccaaag tgctgggatt  11580
acaggcgtga gccactgcgc ccggcctttc ataaattatt gtaagtctgt atgtatacac  11640
acacctgtca atataataaa atgaaaacag ggatgcttga tataattttg ctttcattaa  11700
acacattttt acttacaggc acagttgaaa ggagcttttg aaaatcatct ttagagacag  11760
tttggcactt ggtgattaag atacaggatt ctcgtacaac aatcttcaga atgtagtgta  11820
aaagttcatc atttagtctt taaaatgcag gaaaaatgta acaataaaat attgatggtt  11880
tattcataaa aggataaatt ttatataatt agtataagat gacaaataaa agatacataa  11940
ttgattctta agcaaatcac cttagtaata atgctaacaa ctaggtatat tatttaaatc  12000
aaacttatag aaatcaaatg gcacccaact acaaagtcaa agtattttat aaataacata  12060
taaaaacaac accttcgtcc ccttcaccag ctctaacaca catactcagc ctttctcata  12120
aaccagcaat ttggatggta ctctgaacca agatctccta agtaagttcc atctgttatt  12180
tttgctaaag accctttccc caggcccaac ttactttact gataaaactg aaatgtgcaa  12240
ttatcagttc tgaggggaac tgtggaatct attatctttc aactggtcca tgctttaggt  12300
ttaacatgct aacgatcgta ttagttataa caggagacta aagttgatca aacacattta  12360
aatgtaaact aacgactgag aacacaaagg ctagaagtga ataatataac tggtgtcacc  12420
tgtaatgatc atcctcatca ctgccaaatc ggttgttttg gagctgttca gccaggttgg  12480
ttaggatcac atcccgtagc tgggagagtc cactgtttct ctctcctaac acagaagaaa  12540
gctccatcaa ctaccctggt aatgactcct agaatactga tgctattttt aaaaagtttt  12600
taaacaaata gattgtcggc aagctagggg caccagacat acggacttat acaaataaga  12660
gtggcaaaaa cgacatcaca acgaatccga ctttttaacc agcatcctga ttaaagtgta  12720
attaccctct tgatagatca tgaagtgtga ttttttattc cttaatgttg cttttaaatg  12780
ccaactgtct ttaacatagt accttttgtt gtgttgttta gtctaactta aaatgttagg  12840
ctctaatgtg tgaagataac tggcttagaa atcaccaata agtgattatt ttatttatta  12900
aacatctata gtcagataca ttatgctaag cagtggagac agaaagttta taaagcttgc  12960
agatatataa aacatggttt ttgctttcaa tctggttgaa gtgtaagcat atatgcagat  13020
acattctttc ttttttcttt gagacagggt ctcattctgt tgcccaggct agagtgcagt  13080
tgtgtcataa cagctcactg catcctcaac ctcttgggct gaagcaatcc tcctgcctca  13140
gactcctgag tagcttggat gacaaggcat gggccaccat gcccagctaa ttgtttttat  13200
tttttgtaga gtcagggtct tgctatgctg gccaggctgg tctcgagctc ctgggtcaag  13260
tcatcctcct gccttggcct accaaagtgc tgggattaca ggtgtgagcc accgtgcctg  13320
gcctgcagat acatttctta aatatgctga ctaacataca tgaagaagtg taaatattat  13380
ctgaatatgc agttgtttcc ttggggacaa aaaaaggacg gctgttcaaa gataattaaa  13440
ggataattct taccttctgt taagaccagt ttaagtaagt tattgatttc agtttcacct  13500
gggtacaaga tatttaaacc agagctgaaa tgacaaaaaa gtcaaaaaca tttaagcaaa  13560
tgttctagaa aatcaactct aaatatttaa attcatattt ttattaaaga tgtcaattgg  13620
atgtgagggc aatctggctg cgacatctgt caccccattg atcgctgggg ttgattcggc  13680
tgatctggct ggctaggcag gtgtgccctt cctccctcac cgctccatgt gcgtccctcc  13740
```

-continued

```
cgaagctgcg cgctcggtcg aagaggacga ccatccccga tagaggagga ccggtcttcg  13800
gtcaagggta tacgagtagc tgcgctcccc tgctagaacc tccaaacaag atgtcaattg  13860
attacataaa actgtgaaat aacttttatc actaaaaagg cattaaaaaa aaattgagac  13920
agggtctcaa tatgttgccc aggttagtct taaactcctg agctcaagcg attcacctgc  13980
cttggcctcc caaagtgctg ggattgcagg tgtgagctac tgcacctggc ctaaaaaggc  14040
atttgaacct aaattcactg tcacgatcca gtccaatcac ttccctgata agtggcatcc  14100
ctctcctcct cttcctgtga attacccaaa tgataagtac ttggggctag atgcagaact  14160
ggttagagag aattggtaag ctatgaaaag tcaatgtagt caagcctaca tataactatt  14220
gtgcctcccc aaaaaaacac ttgagaaagt aaatttctaa ttctcagctt ttccgaagag  14280
aagggaagaa caatattgca aatggcatca gaatcttttt tcttttcatt aatttatttg  14340
tgtgtgtgct tatatgtgtg catgtgtgtg ttttagacag gatctcactg tcacccaggc  14400
tggagtgcat ggagtgcagt ggtgtgatct cagctcattg cagccttgac ctcccaggct  14460
caagtgatcc tcccacctca gtctcccaaa tagctgggac tacaggttct tgccagggca  14520
tcgggctaat tttgttttta cttttttgt agagacaagg tcttactatg ttgcccagac  14580
tggtctcaaa cttggcctcg gcgatccacc tgccatggcc cctcaaagtg ctggggatta  14640
caggcatgag ctaacacact cagcctcttt tcttttttaa ttgaggttta acatttaatc  14700
aagtgcacat atttacagtg tacaatctga taagtctgac atatgtatac accaatgaaa  14760
ccatcaccac aatcaagata gtgaatatac ccatcccctc caaaagtttc ctcagagcat  14820
cagatttcaa tcattgcctt aatgctccac agaaagagat tcgaagcata atgtgctgtg  14880
gaaggaaaac aacttcctgt catctatgct caccccctgtc atacagatct ttcagaccaa  14940
ccattcagct ctctcttgga cactaaatta tacttaatca ctttaaggct gtattcctgt  15000
ataaaagttt gctgaggcca ggcgtggtgg ctcacacctg taatcccagt actttgggag  15060
gccaaggtgg gtggatcacc tgaggtcagg agttcgagac cagcctggcc aacgtggtga  15120
aaccccatct ctactaaaaa tacaaaaatt agccaggcat ggtggcacat gcctgtaatc  15180
ccatctactt gagaggctga ggcaggagaa tcacttgaag ccaggaggcg gagattgcgg  15240
tgagctgaga tcacaccact gcactcgagc ctgggcaaca agagtgaaac tccgtctcaa  15300
acaagcaaaa agaaaaaaag ttcactgaac taaaaaaaca aaccaaaaaa aaaaaagact  15360
tacaataaat agaaaatggc ctataaattc tgctctcttg tctgaaaagg tttttttttt  15420
tttttttttt ttttgaggcg gagtttcgct ctgtcgccca ggctggagtg cagtggcgcg  15480
atctcgactc actgcaagct ccgcctcccg ggttcacgcc attctcctgc ctcagcctcc  15540
cgtgtagctg ggactacagg agcgcgccac catgcccggc taatttttgt atttttagta  15600
gagacggggt ttcaccgtgt tagccaggat ggtctcgatc tcctgacctc gtgatccgcc  15660
cgtctcggcc tcccaaagtg ctgggattac aggcgtgagc caccgcgccc ggccctgaaa  15720
aggttttaaa caggttgata aaggcttgca ttgttgagca cttactttgc atcaggcctt  15780
accttaggaa aacctcacaa acccataaaa caggtgctat ttttatgccc atcttacagc  15840
taaggaaatg cgaaccttaa accaaggtca cactagtgag tggcaaagtc tagaacccag  15900
gtctgcctgt tgccaaagcc tgcttcttaa ccaccctgcc acactctgca aaatgagatc  15960
agcttgcaaa caatcaaaat atccacttaa agggttggtt ttgtttgttt gtttgtttgt  16020
tttagatcca aacagtgaga taaggaaatg caggtacaca gttggctttg gtcctctgaa  16080
```

-continued

```
ggtggggcca caaacccctc tccagtgaaa ttatccccaa tccatgaggt cccaattgtg  16140
ggatggggta agaggcattt atactaccag ctttcaggga agattacaat gccttgcaga  16200
agaatcattt tgcagagagc actacaaaaa tcattagctg tttacctgat ggcaaggcag  16260
acttccttct gaatttcagg gcaaatttga tcttttggag ccatcaacaa ctgccaaaga  16320
agcaatcccg accgtcgaat gatgtctcga ttcctttcag tttgtgggct gaagaaaaat  16380
ttaaatacca cctacagaaa cagaaggagt ctatctaaaa atgctaattc tactggggat  16440
aaaattatct ctacaaagaa agtacatggt agatatccta tgaacaaata accaggtgga  16500
ttttgtttaa ccacaatctc ttctactgtg taacggtata attatagtaa atattttgca  16560
tatattaatt gtaatacgct atgtatagca atactccatt aagcacagtg caatgaatat  16620
gataattcta actccaggat cagaaggtgg taagatgcag aacaggaaaa tcattaaatt  16680
tttcttctgg taaaaatgaa ctggctgaag ccaaggtttg cgtttccttt tctctatcat  16740
cttatttatt tcaaaacagt gtatttacct gaaagacaac gagaatgcag cgtataatac  16800
aggtatctcc attaaccatg gccttctcca taatgtcaca aatactgcta agatgatgtg  16860
cttcaattgg atgctgcttg cccaagacac ttgtgattgg aagattgggg ttggtggcaa  16920
gaagattgag ttggtgtatg cacatcgcac caacgtggtg caataattgg tttataacct  16980
cattcgtggt tatagcctct tctagaagat gaaaaggaaa ctgagtgagg aaagacatct  17040
ctatgggtgg tccccaaaga atagaccttt gacttacaaa aggtgtgtgc gcactagaaa  17100
aggatatttt ggctataatc tctttcactg ctgccagaga acgcttctcc ctgccacagg  17160
tgctggggtg aaaacacttg gggagttcat ttgtttggaa cataagtagc taccacttcc  17220
tgagcccttt ttatatgctg aagaatgggc tgaatgcttt acatggttct caacttagac  17280
tattttagcc ctgttttgta gagcaataaa ccaagagtca gagaagttaa ggtacttgcc  17340
ctaggtcaca cagctaagaa gtggtagaac tgggatttgg attcaggcca cctcattcca  17400
cagcccctac tggtaaccat tctagtaaaa cctctccata tcctatgtct gctccatatt  17460
agaactcctg tctataaata gctcctcatg ttttgacatg ttaagctgaa aatgcccgtt  17520
agataaccaa gtggaagtga atccacagtc tggagttcag gcaagaggct tggtagtcag  17580
taatataaag tggactttct tttctacttt ttgctttttc aaaaaaaaag ctttatcaag  17640
atataattta cattccataa aactcgccca ctctaaatgc acaactcacc aagttttagt  17700
aaatttacac aaataccaaa atcaagaatg aaagctgaga aaaaacactg accctacaga  17760
tactaattac tgtggtgatt aacatttgtc tacatgaact ggctttggtc ctctgaagga  17820
ccaagtctac aagttctctg atatgcttct tctaggaggt ggagcttaat tccccttccc  17880
ttcagtgtgg tcgagactaa cagagtgtgg aaagggagaa gtggaatctt aatagtggag  17940
aaatctggca gacatcattt aaacaaagtg atcagttttt aatatcacta gtaataagtc  18000
atgtcaatat catgtacctt ggaatagaag taatgtgaag ggataccctc ttctgtggta  18060
ttcttccccc aatccgtaac ttcagtctaa ccatgagaaa gcatcagatg aacccacagg  18120
gaaggaaatt ctattctgca aatgtgtgac cagtactccc caagtgtcct gttctgctct  18180
tcagacagaa caactctact aatctatggc ccaggtttgc tgctttcttc tcccagcagc  18240
tcagatctgc tgttgagcca ctctactgaa tttttctttt caaatctgga atttccattt  18300
tttttgttg ttgttgtttt gttttgtttt ttaaaataat ctctttactg aaattctcaa  18360
tttgcttaat catagtcatc atacttgcct ttaatttttt taaacttgga ttccttcagt  18420
tctttaaatg tatttataat ggctgcttta agtcttcatc tgactttaaa gtcatcagtc  18480
```

-continued

```
caacatctgc atttctcctg cattgcatgg ttactgattt ctctgctcag tttatttttt  18540
caaatacttg tttctttctt gcatttattt tttttaattt tatcttattt tattttttttg  18600
agacagagtt tcaaaaaagt taagttgttg cccaggctgg ggtgcaatgg catgatctca  18660
gctcactgca acctcagcct cccagttcaa gtgattctcc tgccctagcc tcccaagtag  18720
ctgagactac aggcgcctgc caccacaccc agctaacttt tttgtatttt tagtagagat  18780
ggggtttccc cgtgttggcc aggctggtct cgaactcctg acctcaggtg atctgcctgc  18840
ctcagcctcc caaagtgctg ggattacagg tgtgggccac agcgcctagc ctcatttatt  18900
tttaattatt cttgtttttc tttttcagcc tggcttccta gggttcaccc ctatctgtat  18960
tccttagtgg ttgtcaacca atgattgtgg tcaaacacct tgagccagta atactttcac  19020
cctggatgga tctgtgtatt tcgggagaag tgcagcaaag ttcacgcggt tttaaactct  19080
gctctggttt ttactttctg ttgggccctc tcacatcttt gcatgtgtat gcagactcat  19140
gtttagccag aattgtgtga gtagcttagg ctgtcttagg cctcttctgt gtagatgtgt  19200
ggtcccccac agctttctca ctatccagat ctcactagta aacttctagc tagtcagctg  19260
ggccactgct tgccctaact gggatcaaga tctaagacct gctgagccac tggtctctgt  19320
ttgtttgcca ccaagatgac tactgttact gacaatgcta ctggacatga ggtttttcca  19380
cgctctgctc cctatcaagt cagccccctc tggcagcaaa gctgctgctt ttcactatct  19440
tctccaccct gagagaaatt actgtgctga ccaagcttga ggtggtcagc atagtaattc  19500
tctcaatgca gactgaggtg gaggatagga gcagttctag ctaagaacac catggacttc  19560
cactgttctt acccaaagtt caaggttttt taaaatgaat aacaactctc aatttagtgt  19620
atgccttggc aatttccagg gcctggaaat ggttgttttt gataattgcc tgttttagtg  19680
ttgctttacg ggtaggggac ttgctgagtg attaattcct ccatattagc atagttgact  19740
ttaaagccaa aagattttaa tattaactta gtattaagaa tgttcatatt aatattgaaa  19800
aatacaaagg tccttcactg gtaattctat ctaagtttgt gtataattaa gtcattacca  19860
atgcaaaaca ttacaacagc aaataatccc atgccaaata caaataatca atttttgcaa  19920
caaagttcca acaatttcag gaaggacata acaattttcc tttaaaaaag tctatggacc  19980
acctcaaaag ctctatttat ttacatactt atttacttaa tcataactca tctttcatgg  20040
ttacagataa caaaggactt taggtttcaa aagttcaaag agggaaaact ggtgacacat  20100
tctggggttg ggctatgttt tcacctacta atgctgtggt attctctcat atttcagagg  20160
aaaatctttt cctgcaagac cctgagtgca cctcaccttt gggctcagtg ataatgtgac  20220
tgactccaag tctctggcag acataatgga aggcttgatt cccagggtta caccactgat  20280
cgatatagtc atttgagcat gtccatagca tgttgttcac tgtgtcataa cacgctcctg  20340
caaaaagagc atactgtatt cagtcaccat gccaccagct acctgtatac atatttctca  20400
caagcactgc tacaaagtgg aagggcaagg atgctctcta atgttgacaa cccacaaccc  20460
tagtcccaca gatttatttg gtaaggcact aggttgggac tcggcaaagg ccagcattta  20520
atttttaatt ttgcttaact cctgtgtgag gagtaaatct cacaaaatag atagctctta  20580
gtaactgatt tatctgtgac ctacttccaa agaggattta agtggcttac attaaaaaca  20640
caggtataat aggaccaatt aacattaatg caaaataaaa agccctaata actgagccca  20700
aaacttagaa ataagcttcc taccacccac ggcaaagaga aagtccagta tattacttaa  20760
tgttcatttt ctaacaataa caggtatacc aattcctcac aggaaataaa ctttttgtgg  20820
```

-continued

```
cataaacctg agaatttctt ataggcatca tcacacaacc taatcaatag tatcttcaat  20880
tgcagtttat tcagaggaat tttacatatg gcaatgtctt atactcattc ccaaaattaa  20940
aatttaatat aaaaaaattc tttctggctg gacacaatgg ctcatgcctg taatcccagc  21000
actttgggag gccaaggcag gaagattgct tgagcctagg agtttgagac cagcctgggt  21060
gacatagtga gaccttggct ctacaaaaaa taaacaaaat tagctgggca tggtggtgtg  21120
ctcctgtagt cccagttact caggaggctg agatgggagg actgcttgag cccaggaggt  21180
agaggctgca gtgagccaag atcgtaacac ttcactccag cctaggtgac agaagagacc  21240
ctgtctcaaa caaaacaaaa caaaacaaaa caaaaaacgt ctttcttttc aagaaaacta  21300
gaatgccaca gggaactggc aagacagttc aagagaaatt tgctaaaact tgaaattttc  21360
caaagatatg tgcaagttta tttcttaccc aatcctggta cgagagcacc acgccccagt  21420
gagcttccag cagcatctat gagatctgca cgacttgtaa actgaccatc cgaaatatta  21480
tacaccaagc tggaggctag gactttggaa acaaacatta agctgtttaa tgagcctgaa  21540
gattattttt aaagtttaaa ttttaggctt ttaacaagac ttttataaaa atcacaccct  21600
tttcttgttg ttgtgtattg gtggtaattg gtggtaaaga gatggagaat acatgcataa  21660
gaccacagaa agaaaactgt caccaccaga aattttccta aatttaatac cgaaccatag  21720
ttttcaaagt gtttttaaaa tggcaacttt tgcatgacgg ttctttccga tatacattat  21780
caaaagggta actgcaagag gggttatgat cactaatatc acaagatgca aatgtttaca  21840
agaaacactt ggcagttagt cagtgttcaa taaagcttgg tgtatactca aacacagctc  21900
agctgcaatc tttcctaata ctggctctac aacttggaca caccctggct ttttccctta  21960
acacaggata gtgcagtatt aaagagcatg gactttgggc ttcagagttt gaattccagc  22020
tctaaaactt ttgggtggcc ctgggaaagt cattgaacat ttcagtttcc tcatttctag  22080
agtggaaata ataaaagtcc taccttatat agttatttta aagaataaat gagttaaaat  22140
atgtcaagga tccacaccag catatatata tatatatatg tattaattgc tatcattgat  22200
tttattttct tccccatttt caaacaaaac tttagcactg tgtctcttga gttttcttct  22260
ttttcatatt ttaatcaccc tagtagccca gatccgcatc gtgcctaact taagttataa  22320
cataaatgat actctttttt ctattttcta ctgtttcatt aaacaaaatg ggacagtgga  22380
aaatagacct ccaaatctct tttttcatgg tacttaacca tacatatgct ttctccccac  22440
ttggccactt atatgaataa tatccgttct ttatggctta aactcaaaac ctcatgaagt  22500
ctctcctttc taccccactc cacaatgagc ctttctttct cagattgtgc agctcacaaa  22560
tctgctccac atggatcctt ccagcaggga tgcagcattg tctatcattt tctcattgtc  22620
tcacatatct acgtcatctc tcctaactag actaagagct gttaaaggca agcaccaatt  22680
cttccacttt ctgagcagcc cccacagtag ccgaagagga acaggacaca gaaggaattt  22740
aagcatttac tgatttgttg cactaaagca gaatcactgt gtaagctata tcctcatgaa  22800
agaatggtac catgaagacc cactttaatt aaatggggtc aatttcaact gagcaaaaaa  22860
gccatgccaa ggagactaaa cacaatttaa taagactaat ggtcataata tgtggtaata  22920
ggaggaaaaa agagggggaa aaaaagaaaa gactgatggt caataacata aaaacccaat  22980
ttttattttt gttttattta tttatttaga gacagaatct cgctctgtcg ccaggctgga  23040
gtgcagtggc gcgatctagg ctcactgcaa cctccagctc ccaggttcaa gcaattctcc  23100
tgcctcagcc tcctgtgtag ctgggactac aggcacgcgc caccacgccc agctaatttt  23160
tgtattttag tagagatggg gtttcaccac gttggccacg atggtctcga tctcttgacc  23220
```

-continued

```
tcatgatctg cccgccacag cctcccaagt gctgggatta caggcgtgag ccactgcgcc  23280
tggccaaaaa acccaatctt taaatggata aaagactttg gaggaataga tattcctcca  23340
aagaaggtat acaaatggcc aataagcaca tgaaaagatg ctaagcatca ttagtcatta  23400
aggaaatgca taaaatcaca atgaggtaca acttcatatc cacaaagatg gctataatca  23460
gaaaaatgga aaataacaaa tgttggtgag gatgtagaga aaatagaacc attatacttt  23520
ggagatgaga acgtaaaatg gtatggccac tttgggaaac agtttagcag tccctccaag  23580
ggtaaacata cagttaccat atgacccagc gattccactc ctacgtatgt gcccaagagt  23640
atgaaaaaca tccacacaaa acttacatac taatgttcat aacagcatta ttcaaaatag  23700
ccaaaaagta gaaacaactc aaatgtccat caacttatga atggataaac aaaatgggat  23760
attatccaca ctatgaaata taattcaacc ataaaaagta atgaagtact gattcatgct  23820
gtaatatgga tgaacctcga aaacattatg ttaagtttaa aaagcagtca cagactcact  23880
ccatcctgcc accctgtgaa gacgcctgct tctcctttgc cttccgccat gattgtaagt  23940
ttcctaaggc ctctccagca atgcgcaact gatggataaa acaacttgga accaataaaa  24000
aagagctggg tctggtgtca agagacttgg accacatcac ttcacctgtc tgagcctcag  24060
tgaccacgta gtgatcccat ggctaaagac tgagaaagat ctaggatcac tggtgtccaa  24120
taataaatgc acatttgcaa gcactaagga gaaaacctca ctccatgtac tttcttcctg  24180
gagaccaagc ccactacagc aaggagtatc ttcaagcgag ggtggaattg tgcatgaata  24240
gagaatactc tccatctctt ctcacatcac acagctctcc agttgataca atattcaact  24300
atatttacat cgagggaaaa atgattctat atttatatat aactctccat aatgtgtcaa  24360
gtgtcctcac actatcctat gtggtaggta taatcatctg cacatttttt ttaatgggaa  24420
agttgaggct ttgaatgatt aatttcccca agataatagt tactaaaaga aacaagattt  24480
ttacatgtct gtctgcatct acttttatag ctcctgattt tattcgtagc tcagccacca  24540
taatatgcac agaatgagac aaaataataa gtggtatttt gctactatcg agtaaaacca  24600
aaaattaaaa atcaagcaaa taaacaaaca aacgaaaaag cagtcataaa aggccatatg  24660
ttgtataatt ccatttacat gaaaagtaga gtataggtaa ctccacagag acagaaagta  24720
gattggtaga tgccaggggt cagggagtag gagagcaact gttgatgagt atgaggtttc  24780
tttttggggt gacggataga ttagtggtaa tgactgcaca actctgtgaa catattaaaa  24840
accactgaat tgtatatttt aaaggggtga aatttacggt gtgtgagtta tatttcaata  24900
aagccaccgc ccccagcctg aggaacattt aattctatac tttatcccat ttaactatgt  24960
gtgcactctg aagccaaaat tacactgctt tcattactac agtgtgcctc cttataataa  25020
tatatggata ttttaaaata ctaacacatt tttacacatt tgcttttcta tgtcttatgc  25080
ttagtatttt gtatatgtgt cctaaaatgg aggtgtttta catatgtatt ttaatagctt  25140
tgaaattcta ttggcagggc gtggtggctc atgcctgtaa tcccagcact ttgggaggcc  25200
aaggtgggtg gatcacctga ggccaggaat tccagaacag actggccaac atggcgaaac  25260
gccatctcta ctaaaaataa aaaaattagc cgggcatggt ggcatgtgcc tgtaatctca  25320
gctactaggg aggctgaggc aggagaatca cttcaacccg ggaggcagaa gttgcagtag  25380
gctgagatca tgccactgca ctccagcctg ggtgacagag caagactccg tctaaaaaaa  25440
aagaaattct atcatagtga gtagagctct tgctgtatca tcagtaaata atgtgacaaa  25500
atattatttt atttcctaaa actttgttga actgattatt tctattaatt ttataggaca  25560
```

-continued

```
atagttttca aaactatact aatatgccat ccacaaaaaa ttatattgtt aaatcttcct  25620
agcctatttg ataattggta ttttttgtta tcagagagct attgcaaaca actatttaac  25680
aaagtaagtt ttaaataatt aataggaaag ctttaaattt cagagtttga gataaatcga  25740
ggaaagtgcc acaagtaaaa ttcacttact ttttaaagat gacaaaccac ttgttccacc  25800
aaaaagagat cgggtggcag agctgcctga tccccctgga ggaggcacca gcatcaccaa  25860
gtaggtgcca caggtatata tgggtgtctt ccgcagcatt tttagaggca gcccacagct  25920
agtatttgct ggagaaagga atgaaaatgc taaatcaaaa tatttgacac aaaagttaat  25980
ttgattacca acacagatta ggatataatg agggagaccc aaactcaaac aaagatttgg  26040
aaaacagatt tccagattag gaaaacagaa taagaagtaa tagctaagga aaaaaataat  26100
tatcttctgg ctccacagcc tgaccctgag cctcctattt atatggtctg aacatttctt  26160
gacagtgctc ccaatcctca atatgccatc atgcctctac aaattattcc aaaaaaataa  26220
atcctcacat ggactaaatc tcaaaataag agaagaatcc tagtatttgt ttgtgtttcc  26280
cctagaaaac tgatataggt tgagtacatt tatctgaaat gcctgggacc agaagtgttt  26340
tggatttcag atttttttcag aatttgaaat atttggatta tacttaagag ttgagcattc  26400
ctaattgaaa aatccaaaat ccaaaatatt ccagtgaaca tttcctttgt tttcatttat  26460
ttttactcat tacatctgag attagtgaga acatttcctt tgagcatcat gtaggcactc  26520
aaaaagtttc agatttggga gcattttaga tttttagatt tgggatgaac aacctatatt  26580
ccaatcaaga tcttggtttt tttttcccat tttatataga acaaattctt gacaggcttg  26640
tgatattaaa ctcataataa acagctttca acatgaaatc ggccaaaatt tcaacctaat  26700
gaaagctttc acaatatcta tcacaaaaca attttatagc tgtgtaattt attataaccc  26760
cttatataca tttttctttt ttttaagggt caatgacata aactgtcatt aggaaaataa  26820
ttattgtttc taatcaagag gtgtaaaatg tactttaatc tcccttactg gcatatctag  26880
aaagtggagt gaatttacgg attttctata tacaagccta gcgaggattg attatgtcaa  26940
cagagaatca actggagtgc tttacttaga aagctgtcag gctataaaat ataacttatt  27000
atctatagcc tggatagatg aaaatcattt ttagatggtt tagattagaa gagtgagtaa  27060
agtgaaacct aatctatctg atatttgttt tgaatgcttg tgcttctaaa aagctttttt  27120
tttttaagc tgcaagcccc caccaagtat attcttcatt aaggacataa attcaagaag  27180
ataaatttcc actggtaaga aacctaaaga cagcaataat tggaaaatta gcaactttgt  27240
gagtatacca ttttcaccaa gatgttttca atagacatat gcttattaag atggcaatag  27300
gtattagttt ttaatggaat aaaaactttt tttttttttt ttttttgaga ctgagtctca  27360
ctgttgtctg cctgggctgc agtacaatgg agccatctcg gctcactgca acttccactt  27420
cctgtgttcc agcaattctc ctgcctcagc ccctcccgag tagctgagac tacaggagcc  27480
caccatcaca cccggctaat ttttgtattt tcagtagaga tggggtttca ccatgttggc  27540
caggctggtc ttgaactcct gacctcaggt gatccaccca cctcagcctc ccaaaatgct  27600
gggattatag gcataagcca ctgcccctgg ccaaaacctt acagacacct tgaatgttcg  27660
cttacttttg aaaagtttct tagtttataa ctggtgaatt tttaatttaa tgtagcaaca  27720
tcacgttaaa gaatccacat aaaagtacga tgattgctta agcccaggag tttgagacca  27780
gcctggacaa cataacaaga cctcatgttt tttttaaaaa aaaaaagtac aatgagacca  27840
catgtttaga atacagatac ccgtttctac caaattctag tatatgtgct gccaaagcgt  27900
gcacatttct accaaattct aaatatgtcc ttgccttctg aggtctttct ttgatattat  27960
```

-continued

```
acatatttc aacaagcatt cttttagtat ttccattgtt tagggtaaga tttcattttc 28020
tcccaaggga caaacccaga tcaggccttc agcttgtcat gaaaatgttt atttaggtaa 28080
caacaaaaac aaaaacaaaa aaaactgtcc tctagaaagt atcttctaca gttggaatta 28140
tccacttacc caaatcataa aaactattaa caattttgcc acttaccttt gatacaaaag 28200
aagcctgtga aaataaaata ctgtccttaa attctaatat ggactaataa gtatttaatt 28260
tggtagtctc ataataaatt aactataaat attttctctt cctagcattt ccaactataa 28320
aaataaagca taagattaca ctgaattcat taaatgcata ttaattcaga tgcagttttc 28380
tacatatggc atctttttct agctttatct tttactgcag ttcatagttt gctataaatc 28440
caaatatttg gtatgtaatc tgtaaactct atggaataat ggttcttaat gtttttgggg 28500
gtcatagatg actctgaaaa tctaatgaaa gttatgacag atacatataa aatgatatct 28560
aaaactttga gggagtatgt ttaataacat actcccttaa aggtgtatcc tggttaagaa 28620
ctcctacttt aaaagtgcag aacagccagg cgcggtggct cacgcctgta atcccagcac 28680
tttgggaggc caaggtgggc ggatcacgag gtcaggagat cgagaccatc ctggctaaca 28740
cggtgaaacc ccgtctctac taaaaataca aaaaattagc caggcgtggt agcgggcgcc 28800
tgtagtccca gctactcggg aggctgaggc aggagaatgg cgtgaacctg ggaggcggag 28860
cttgcagtga gctgagatcg cgccactgca ctccagcctg gaagacagag caagactcca 28920
tctcaaaaaa caaaaacaaa aacaaaaaac aacaacaacg aaaaaaaaag tgcagaacaa 28980
tgtatatagt atactacctt ctattaagaa aaggcagaaa ttatgaacat ataaatttat 29040
ctttaattat atttgcataa acaaacactg gaaggataaa tgaaaactaa taaatatagt 29100
tacctgtggt ggggtagggt ggggtcacaa tataaaattt accaacatgg taagaataag 29160
acttctctgc atataccttt ttacattgtt ttgactttca aattctgtac gtgtattatc 29220
tattttaaaa cattaaatta aaaaactaaa tgataaattc taaaaaacaa aatatctact 29280
gtagaaggct tttctgttat ttgcttggtc aagactgtat ttagggaaga tgatgctaag 29340
tatcaggttt tctcattcac aaagcatacg caaaatatga aatcaactaa tttatatgaa 29400
tggtgatgat gataaggtgt ttacagttta acatggggct attttgcatt cttacaggtt 29460
catatgaatt tgtgtccata gcctacaaca tgtattggct tggaataaaa agctggacaa 29520
tgactggaag accaaataaa gtcaactatg caaaggaaag ggctttgtac agcacggacg 29580
aagtgctcaa taagacgtag ctgaacagag ctatacaagg aaacagatct gggaagcaca 29640
gagtaacata cctgcttgat cctctttcag tgtgttggag atggtggaac cagtcagggc 29700
agcaagcgtt gctgacgggg aggctctata ccgagaaagt ctacttagaa gcatctcatt 29760
aatgcttttg gcagattcgc cctcttttct cattagaatt gtacgttcct gaagtgggtt 29820
ggctacaaat acaccatttt caacctaaca tagaaaaaaa ggaggtccta aaatgatatc 29880
tgtttccatt tagttagcaa atttctactg aggatattat tgtgagtaaa taaaaaatat 29940
ttcaaaaact gctcctgagt agatgtatac cttaaaactt aaatgtgcta tagaaactac 30000
tacaaacaaa agagactatg ctaagtttga gatctttcac ttttcataat agctataatg 30060
tttaataggt ctatgaaaag ttgttgatta aaattcctta cactggattc cacaggcagc 30120
gcttactaat tacatgcctc tgacaggttg aagtcaaatg agaggaaaac aaatcaatca 30180
gtctttgatt tactgttaag gacaactatg aggataatgt cttctcgaaa tatcttcagt 30240
ggctaaaatc caaactcttt attaacagca gttaacatta gcaccagctg ctcaggccct 30300
```

-continued

```
ggcagagcaa gcctggacaa agccagactt tgctaaaaat acacatcaac ttcaactgga  30360
tctttgctgg tgctttgcag ttctttcatt catcacttgg ttattcccca gaaaaatctt  30420
tggagtggtg actccaaaat tccttcacca attttgagct tgactttcag cagaccacct  30480
ggttttcttc tttcttcttt tttttttttt ttttcttttt ccacctggct ttctgtattg  30540
ctaaaaagat ccagaccact tactataagc ttctcctact cacgtctctt ccaacttaag  30600
aatcttggga cccagcctca tttactattt cctttgtctt aattcagagg aagaaggatt  30660
tcacctcata ttattgaaga tgaacccttc cacttctgcc tcaagtcctg tgctcccctc  30720
tgcctcttca tcattagtgt ctccctctct attgagttcc ttctctttgt tttcaaatat  30780
tcacaggtct taaacaaaac cttggtggcc cattaaaata tcaccccttt tgtcaaatct  30840
ctcatggccc ctttctagat ccaagaactg ggtccccacc agcaaagaca ggcaggactg  30900
gcctgcagct gtggggtgtg gagataagag ggaatgggag tgcaaagtgg caaatcttca  30960
gaagcaaagg gaaagcaaaa gaggagtcca cagggaaagg ttggtaacac agaaggggca  31020
agagaaagtg agtaaactca ggagcacagc caggaaagat tcccaaaggt gggtgtacgt  31080
agtgggggag tcttttatga catattcaca aatgataaag aaaaagattt gttacagagt  31140
ccaaaaatgc tgtttctatt tccccatccc ctgcttttta accctttgca gttggtagtc  31200
tctgaattca gcacactcta atgagtcggc aatctcaatg gtccaccagt gacctaaaac  31260
caaaaccact gaccttttcc ttgacttcct tgcaggtcgc gccatcactg ccatccttct  31320
tgggattctg attccttagt gttggtggca gaacacaagc ctggtttgtt tctttttgtt  31380
tctttttttt gagacagggt cttgctctgt cactcaggct acagtgtagt ggtgtgatca  31440
cagctcactg aaccctcaat ctccccaggc tcagatgatc ctcccacccc agcctctcga  31500
gtagctggga ccacaggaat gcgccaccac atctggctaa tttttgtatt aatatttttt  31560
gtagagacag ggttttgcca tgttgcccag gctggtcctg aactcctagg ctcaagcaat  31620
ctgcctgcct cagcctctca aagtgctgga attacaggcg tgagccacca tgcccagcct  31680
ggtttgtttc tttttaacat gaacacttac ctctgtgtaa agtgctcact gtgctggcga  31740
gtgaagccag cacagtccct gccctccttc ctgtctctct ctttgctggt caacatcttc  31800
atttgcttaa atgggacctt tcccaagatt agacctaccc ctggtgtcca agacctccac  31860
ctggaatgct ctatccctag accttccaga gactggctct ttcctatcat tcaggtctta  31920
gttaaacgtt acccactcaa agaggtctgc cctggttgcc aatctaaaaa agaatcctcc  31980
ccagcacccc aacccagagc acatcatgct gtttcattat ctacacagca cgtactactc  32040
tctgaaatta ttttactcat gaagtcattt attctttgcc cttctacctt aacacgtccc  32100
aatgaatgcc aactccctga gaacagggat ccacctgcct tgtttgccat aacatcccca  32160
gcacttagga ggcattcaat gaatactcga ttgcttgctg aataaacaga tcagggccct  32220
cccccaaatc caactccgct tctctatggc aactcccaca tttctattta cagacccatc  32280
cttgctacta cgatctagtt ccacttttct aactgcccct caccctcccc accgacattt  32340
ctacttgaac agcctcctgt cacctaaaat tcaacacatc cacctcttac ttcattgtct  32400
taccccaact ctcctactag attaactttt agcaagcata gctctattta cattgcacaa  32460
ttctaaatat actccttcaa aagcatccaa gataaaaatc aatcacttta agcttggcat  32520
tcaaaagcat tacccaatct ggccctatga gaaaatcaat agatacctta aaaacaaaca  32580
aaacactata ttattgtatt tgagtacttt gaaaatactg caaagaaaaa ctgataaaac  32640
acctgtgtga tacaagtagg gctgaagttt gctgcaaaat ggtaaatctg ctggaaatcc  32700
```

-continued

```
ctactttagc aaaggcgctc ttcagggtaa gaagctgctg atttaggaag acaggaagag  32760
ctgggaggag tgagaagcag cccaggcttc cttcctggca accactctgg tccaagtcca  32820
catcatctca agagagatta ttagaccagc ctcccaacct gtcttcccac ttccacaggc  32880
accccaatgg tttactctct gcatagccag tgatcattta aaaatgtaaa taaagccagg  32940
cacagtggtt cacacctgta atcccagcac tttgggaggc caagaaggga agatcacttg  33000
agcccaggag ttcgagacca gcctgggcaa catagtttga gaccaacctg tctcaaacac  33060
acacacacac atacacacac aaaattatcc aagggcagtg gcacacgcct gtagtccctg  33120
ctacaaggga gactgaggcg ggaggattga aagagcccag gaagggaagg ctgcagtgaa  33180
ccatgattgc accactgcac tccagcctgg gcaacagagg gagatcctgt cccaccccgc  33240
cccaccaaaa aaaaaggtaa aaccatgtct tccctcattt aaaaccctgc agtggttttc  33300
caacacactt atgataaaat ccaaattact gacagggcct cacaagggcc aatgtctgct  33360
gacctcctca gcatcatctg cctcaactca accctctctc actacatttt tagctacact  33420
cgccttctgt cacacctcca aaataccatg cttcctccta atgctgggcc ttggtacttg  33480
ctattccctc ttgtgctacc catccgttgc agtttgcctg gaactgcagg ttttagcacc  33540
gaaagttcca tgtcatgagc aatcaatccc tcagtctcaa gcaaactggg atagttggtc  33600
accctgtctg tcaggatgga tggcttctta tcattcaggt ctcagctcaa atgtctttcc  33660
ttagaaaggc cttatgtgcc ccgcaagcta aaggagctcc ccatctccac cccatgcact  33720
ccctctcaca ttatcctgtt taattttctc cccagcattt atcactagct gaaattattt  33780
tgttcttatt gtttgcttcc gtattgtccc acttcccata ctctaatata agctccacga  33840
aaacaaaagc ttatttactg ggctacccag atacggcaat atagtatagg ctctcaatta  33900
atacagaatg aaggaagggt agcttagtca tctggatcat aactggaagg aaacaacaaa  33960
cccttaggga gaagagggga agactcttag tgtgtccatt actacattga caatacccttt  34020
aggaagtaac ataaggagag aaaaatagca ataaaattgt cactaataaa attttaaaac  34080
tgcagtttat atagagcaca tgggggcaga agacctctca gaacaaaaca gaagtgagga  34140
tattttttca aaagaggctt gaaaaggtaa aaaagagtta taggctgggt gcagtggctc  34200
ccagctggat tacgcctgta atcccagtag gtagaggcag aggcaggaga acagcttgag  34260
cccaggagtt agagaccaca gtgagacccc actctctaaa aaaaagaaaa aaagagttat  34320
agaagattct caagcaggaa tgtgtccaga gtagaagtag ccaaatcagg cagaaagatt  34380
acatgcttca gctattttgt agtcttaaag accagaattg tgttctagag tttcagaagg  34440
cctgttgctc catgtgggta gactgtcaca ttggtggccc ctaatgaatg atgcatcctt  34500
gtattcatgc ccttgtatag tccccgtcca agtctggacc tggtcagatg actttttttt  34560
ttttttctac attagaaagc aagttgctgg ccaggcacgg tggctcatgc ctgtaatccc  34620
agcactttgg gaggctgaag caggtggatc acttgaggcc aggagttcga gaccagcctg  34680
gccaacgtgg ttaaacccca tctctactaa aaatacaaaa ttagctaggt gtggtggtat  34740
gcacctgtaa ttccagttac tgaggcagga gaaccgcttg aacccaggag gcagaggttg  34800
cagtgagcgg agatcacacc tctgcactcc agcctaggtg acagagcaag actctgtctc  34860
aaaaaaaaaa aaaaaaagat gcagcaaggg gcagtggctc atgcctgtaa tcccagcact  34920
ttgggaggtt gaggctagcg attgcttgag cctaagagtt caagatcagc ctgggcaaca  34980
tggcaaaact cagtctataa aaaaaatata aaaattagcc aggcatggtg gcatgagcct  35040
```

-continued

```
gtagtcccag ctactcagga ggctgaggtg ggaggaatgc ttgagcccag agtggggagt  35100
ttgcagtgag tgagcagaga tagtagcacc actacactcc agcctgggcc atagagcaac  35160
acaatgtctc aaaaaaagaa agcatgatgc aagcagagac ttgatatcca cttgtcctct  35220
tgaaaagctc cttcctgaaa accagcttcc atgatgtcga gcttcagcat acattactga  35280
ataatggatg ccaagtggag agaggcccta gaggatgaca ggccatcttc agtggcacag  35340
cccaagctaa gctcccagtt gaatgaagct gcagatgtga cttcagcttc accatgcaga  35400
gcagaagaac cacccagctg agccccatca acctatacat cattgttacc tgaagttact  35460
tagcttgggg attgttcact gagtaaaagt aaataactga aataccttaa aagtcagaga  35520
aattctatga tccaaatgtt agaggtcatt ttatattaat aatagtttgt tagttaagca  35580
ggataatctc gacattccat tttgttacat catattccta aatatatctc ttctcctctc  35640
ttctttttct tttctttttg agacagggtc ttggtgtatc acccaagctg gagtgcagtg  35700
gcacgatcat ggctcactgc agccttgacc ttcagggctc aagcgatcct cccacctcat  35760
gctacttact agctgagact acaggtgtga accaccacac ccagctaatt aaaaaaaatt  35820
tttttgtaga aatggggtct cactatgttg cccaggctgg cctaaatata tttctatagt  35880
ctgcctttta taacaactag ttatctaatt ccatgcttag ttaacaaggt atcattttga  35940
gaggtaagca tggctagtta gattctgctc tctgatctta gtcgtttcaa tccattagtt  36000
ttccctgagt cttaggtacc aagagatcta tttggtataa tcaagctgag ctgactgttt  36060
tatgaaaaat gacataatgg aggaatacag atggtgttcc aagaattttt ttaatgttta  36120
ggtttttttt tctaatgata aaactaatat atggttactc ttggaaatct ggggggaaga  36180
aagaaaacta taaataagaa aagctaccat tattctttgt ttgtttgttt gtttttttga  36240
gacagtctca ctctgtcagc caggctggag tgcagtggca tgatctcagc tcactgcaac  36300
ctctatctcc cgggctcaag caattctcct ccctcaacct cccgagtatc tgggattaca  36360
ggtgtgtacc accacgccca gctaattttt gtatttttag tagagacagg gtttcaccat  36420
gttggccagg ctggtctcca actcctgacc tcaggtaatc ctcccgcttc ggcctcccaa  36480
agtgctggga ttacaggcat gagccaccgc actcggccta ttctttcttt ttaaagggat  36540
aatcagttaa tgttttaagt tctagcattt aaagaagtca ggccaggcac agtggctcat  36600
gtctttaatc ccagcacttt gagaggccga ggctggtaga ttgcttgagc tcaggagttt  36660
gagaccaacc tgggcaacat ggtgaaaccc catctataca aaacatacca aaattagccc  36720
agcaaggtgg tgtgtgcctg tggtcccagc tacttgggag gctaggtgag aggatcactt  36780
gagcccggga ggttgaggct acagtaagcc gtgatcatac cactgcactc cagcctgagt  36840
gataaagtga gagctagtct caaaaaaaat aatcaatcaa tcaatcaatc ataggctcta  36900
gaaaataatt ttttaaatta gctgggcatg gtggcgggcg cctgtggtcc cagctgtgag  36960
ggaggcagac gtgagaagat cgcttgagcc tgcaaggttc taggctgcag tgaactgtga  37020
tcacaccatt ccactccagc gtgggcaaaa gagcaacacc ctgtctcaaa aaataataat  37080
aataaataaa atataatgaa gaaatcaggc cggatgtggt ggctcacgcc tgtaatcaca  37140
acactttggg aggccgagga aggcagatca cctgaggtcg gaagtttgag accagcctga  37200
ccaaaatgga gaaaccctgt ctctactaaa aatacaaaaa ttagctgggc atggtggtgt  37260
atgcctgtag tcccagctac tcgggaggct gaggcagggg aatcacttga acctgggagg  37320
aggaggttgc ggtgagctga gatcacacca ttgcactcca gcctgagcaa caagagcgaa  37380
actccgtctc aaaaaaaaac aaaacaaaaa aaaaaaacaa atcacagata gttttggatg  37440
```

```
ctgcatgata ccactgggat caataaaagg atttgtcacc aatttttaaa agaatatatc  37500
ccgattctgc tcactttttt accacctcca tcattacttc accctcagtc caacacatta  37560
attatctttc acctggtctg tggcaacaac ttcctactaa tcccattcct gccccccttct  37620
cacaaggtgc attcttttaa aaaatgtttc tttacaaaat ttttcttaat actaaaatat  37680
acacaaaaag aaacatgtaa aaaatgtttc tttacaaaat ttttcttaat actaaaatat  37740
acacaaaaag aactagtaat atccgcttac tatcactcta gatacaagtt atcaagattt  37800
tgacatattt gcttcatctc tcccagtcat tatgtcattt cacccccaca tatttcagtg  37860
tatatcacta taaaatatag atattcttta ataactacaa tgtaatcaca cttattatta  37920
gcaataattc ttgacatcat ctaatattga gtccataatt caatttcccc aattttctca  37980
aaaatacttt ttacaggcca ggtgcagtgg ctcaagtcta taatcctagc actttgggag  38040
gctgaggtgg gagggtcact tgagcccagg agttcaaggc caacctgggc aacatagtga  38100
gacccccccca tctttaaaaa aaaagaaaaa agagccaggc gcagtggctc acatttgtaa  38160
tcccagcact ttgggaggcc gaggcgggcg gatcatgagg tcaggagatt gagaccatcc  38220
tggctaacat ggtgaaaccc cgtctctact aaaaatacaa aaaatcagcc aggcgtggtg  38280
gtgggcccct ctagtcccag ctactcggga ggctgaggca ggagaatggc gtgaaccggg  38340
gaggcggagc ttgcagtgag ccaagattgc gccactgcac tccagcctgg gtgacagagt  38400
gagtctccat ctcagaaaaa gaaaaaaaat actttttaca gttggcaatt ggtttgtttg  38460
attcaggaac caaacaagat gcaacctaca cattatatac atttggtttg tctctttaag  38520
tctcttctgg ctttattctt taccccaaac ctacaatgaa cctttaaaac acgatcccat  38580
cactttcctg ctcaacaatt tccaggagtc tcccatctca cttagaataa aatcccaata  38640
ccttgcaagg ccctataaga tatggccctg gctacgtctc caacttcatc tcccattact  38700
cactctcatc actccacttg agacacacag acttcttgtt gttcttcctc aacaagccaa  38760
cctcatgcct atctcagggg catctgcata tgccatttcc tgtctgtaat gctcttctgc  38820
cagatcttta catgtctcat tcctttattt tattcaggtg tcaatgtaaa taccacctcc  38880
tcagagaggc tcccctgatc attacctaga atagtcccac accaaacaca cactaaatca  38940
tttctctatt gctttacttc atcttccttt ataatattta ccaatgcttg aaactgtgct  39000
tctgtctcct ccacaagaat gtaagctcca tgaggacaga gatctcactg tcttttctat  39060
actgtatcac cagctcctag gatactacct ggcatgtaga aggccctttg taatgtagga  39120
gatgaatgaa tatgtgaaga catagctatc taaacttgag gctactgcat gaagtgccca  39180
gcacttacat cagtaaggct ggatgagaag cttccatttg tatacagtgg attaggatca  39240
caagcatgcc acaaaataaa aataccggga aaaaaatctt tcggccaggt gcggtggctc  39300
atgcctgtaa tcccagcact ttgggagacc gaggtggaca gatcacaagg tcaggagttt  39360
gagaccatcc tgggcaacat agtgaaaccc cgtccctact aaaaatacaa aaatttagcc  39420
aggggtggtg gcgggcacct gtaatctcag ctactaggga ggctgaggca ggagaattgc  39480
ttgaacccag gaggcggagg ttgcagtgag ctgagatcac accattgcac tccagcctgg  39540
gcagcaatga gagactccat gtaaaaaata agtaaaaaaa tatttcatga gggatgttat  39600
tgaggggatt caaatatcga atgagggcca gatgcagtgg ctcacgccta taatctcagc  39660
agtttgggag gccgaggcgg gtggatcact tgaggtcagg agttcgagac cagcctgacc  39720
aacatggtga aaccccgtct ctactaaaaa tacaaaaatt agctgggtgt ggtggtggtg  39780
```

-continued

```
cctgtaatcc cagctactca ggaggctgag gcaggagaat cgcttgaaca tgggaggcgg  39840
aggttgcggt gagccgagat cgcaccattg cactccagcc tgggcaacag agcaagactc  39900
tgtctcaaaa aaaaaaaaaa aaaaaaaatt agctgggcat ggtggtggtg gcttgcgcct  39960
gtaatctcag ccactcggga ggctgaggca ggaggattta ttgaacctgg gagacagagg  40020
ttgcagtgag ccgagatcgt gccactgtac tccagcctgg gcgacagaaa aagattccat  40080
ctcaaaatca atcaatcaat caatcaatct tgctttaaag tagaatttta cttcaataat  40140
agagcaaggt acagaagaat gtgtataata aatcaccatt tgtgtacaaa acagaaaagg  40200
aaaaacaaca caaacacatg cacttgtttg tatgtgctcc gtccgtggaa ggatgtagaa  40260
gaaaatgcta acctcacttg cctctgagga gggaaactgg gctaggaagc agggtaggtg  40320
agagacttct gtaccttctg agttgtataa ctatgtgaat atcatgttaa aaatattttt  40380
aattaaaaca acatagctat tactaagctt gaagagaaag ttatcaatac ttagttttct  40440
ttcttttttt gtgggcgggg aggcaaggtc tcactctgtc acccaggctg gagtgcagtg  40500
gcacaatcat agctcactac agccttgacc ttctgggctc aagcaatccc cctgcctgag  40560
ccccctaagt agctgggact acagtcatgc accaccacac ctggctaatt ttttttttatt  40620
ttttggagag atgaggtctc actttattgc tcagactggt cttctttttt cttttcttac  40680
aggccatgct aatttttttct gtatcattcc aattttgatg tctgtgctgc tgaagtgagc  40740
acttatcaat actcctaagt attggagtga aatcataatt accagcaaat ctaattcctt  40800
ccagtaatta ttattggcca catctatgtg acaagtatct acattattta gaaagcaaga  40860
ttaatcataa ctcagtagag aatttcaggg ctagaactct atgaatcatt tcatctaaag  40920
cattatttca taaagttttt tgcctggttt ggcccagcaa atcataggag gtctatggct  40980
aagccctatc atttgtgaat ttagaaacag gtactttttta aaatctattc aataacttaa  41040
attttaaaaa atgaaattaa aatatttcca tgtccccaca gtccattcca tcatccccct  41100
ccgatttctc tcctgttttc acatcaaacc cctggagaga aagatctatt cttttccatc  41160
ttatcctccc taccttaccc tcaaccaact ccatctggct gccactccta ttattcctca  41220
aaacagctct tgttagcgct gcaacggcct ccatattata cattcaaaag gcctctttca  41280
gtctgacctt gacttctcca gcagaattca atgctattaa acaagttctc ctttttataa  41340
aaaaattcct tttttaaaag ttaattttttc taaaaagccc attgttaaac tttaaaaaca  41400
tatgaaaaga tcaatggtgg aaagtaagtc ttgccccaac cagttgcctt ccccggggaa  41460
accaatactt ccagtctctt gtgatgttta attaattaat taattcattc atttagcaaa  41520
tatttaataa gcttctactg tgtgccgggt actattctag caccggaggg cgcagtggct  41580
catatctaca accacagcac tttgggaaga caaggcaggc cggactactt gagtccagga  41640
gttcgaggct agccgaggca acatagcgaa atcccgtctg aaaaaaaaaa agagagagaa  41700
acaaaaatcc cttccctgct ggagctgaca ttctaagcag gggagacggt caataaataa  41760
gcaaataaat gagcagtaag aagaaaacta aagcagggca aagaggatag ggaggaacag  41820
gattttattt tatacaaaat atttcatata gaatggtctt ttgttttata taaaatattt  41880
catatagaaa agtctttctg gtaaggtgat tttttttttt tttaagagac agggtcttac  41940
tctgtcaccc aggctggaat gcagtggtgc aatcctagct cactacagcc ttggactcct  42000
ggactgaagt gatccttcta cctcagcaac tggctaatat taattttttt tttttttttt  42060
tagtagagac agggcctcac tttgttgccc aggctcatct tgaactcctg gcttcaagtg  42120
atcctcctgc ttcagcctcc caaagtgctg ggattacagg catgagccac tgtacctggc  42180
```

```
cctttttttc tttttttgag acagggtctg tctcactccg ctgcccaggc tgcagtgcag  42240
tggtgtgatt gtacttctct gcagccttaa actcctgggc tcaagcaatc ctcccacctt  42300
agccctccaa atagctggga ctacggacat gcaccattaa attaaaaaaa aaatatatat  42360
atatatacac acacacacac acacatagtg atgtggtctc actctgttgc ccaggctggt  42420
ctcaaatcct tggccttaag ctatcctccc accttggcct cccaaagtgc tgggattaca  42480
ggtgtgagcc actgtgcctg gcctgataag gtgatatttg agcagagaca tttaaaaagt  42540
gagagaagca gccatgtggt tatctacagt ccaatattcc agcacaaggg acagaggggg  42600
aacatacttg gtgtgtgtga gtaacatgga ggaagcatgg ctaagtggca tgaacaagaa  42660
ggtatggtag gtgcagaggg tgtaggtgca gcaggtggta ggtgcacagg gtgtaggtgc  42720
agtggatgta ggttcagtgg atgtaggtgc agacagtggt aggtgcagac agtggtaggt  42780
gcagagcgtg tagatgcagt ggatgtaggt acagagggtg taggtgcagt ggatgtaggt  42840
gcagtggatg tgggtgcaga gggtgtaggt gcagtggatg tgggtgcaga gggtataggc  42900
gcagcaagtg gtaagtacag aaggtgtagg tggagtggat gtgggtgcag aggatgtagg  42960
tgcagagggt gtaggtgcag tggatgtaga tgcagatggt gtaggtgcag aggatgtagg  43020
cacacaaggt gtaggtgcag tagatatagg tgcagagggt gtaggtgcag tggatgtagg  43080
tgcattggac gtaggtgcaa agggtgtaag tacagtggat gtaggtgcag atggtgtagg  43140
tgcagaggaa gtaggtgcat tggatgtagg tgcaaagggt gtgagtacag tggatgtagg  43200
tgcagagggt gtaggtgcag caagtggtaa ctacagaggg tgtaggtgca gtggatctag  43260
gtgcagatgg tgtaggtgca gagggtatag atgcagtgga tgtaggtgca gatggtgtag  43320
gtgcagatgg tgtaggtgca gagggtgtag gtgcagtgga tgtaggtgca gaaggtggag  43380
gtgcagtgga tgtaggtgca gatggtgtag gtgcagaagg tggaggtgca gtggatgtag  43440
gtgcagatgg tgtaggtgca gagggtgtag gtgcagtgga tctaggtgca gattgtgtag  43500
gtgcagaggg tataggtgca gtggatgtag gtgcagatgg tgtaggtgca gaggatgcag  43560
gtgcagaagg tgtaggtgca gtggatatag gtgcagatgg tgtaggtgta gatggtgtag  43620
gtgtatggat gtaggtgcag agggtgtagg tgctgtggat gtaggtgcag agggtgtagg  43680
tacagtggat gtagatgcag aaggtgtagg tgcagagggt gtaggtgcag tgaatgtagg  43740
tgcagagggt gtagatgcag tggatgtagg tgcagaggat gtaagtgcag caagtggtaa  43800
gtgcagaagg tgtaggtgca gtgaatgtag gtgcagaggg tgtaggtgca gtggatgtag  43860
gtgcagaggg tgtaaatgca gcaagtggta agtgcagaag gtgtaagttc agtggatgta  43920
ggtgcagaag gtataggtgc aacaggttgt aggtgcagtg gatggcagta cagagggtgt  43980
aggtgcagtg gggacccaat cattcagcac ctctatagaa gtaatgggat gggatacatt  44040
ttgaagatag agcagacagt atttgctgac tagatatgga atttggcagg ggtaggggga  44100
gaaggcagag tccagagtga caccaaaggt ctctggccag cactggaaag acacagatgc  44160
cattatctga aatggtaaag attttggaag gagcaaatct gagctaacct caggagttta  44220
gctgggggca tatttagctt gaggtgacca tcagatttcc aactggagaa gtctaatatt  44280
ctgtgcacat acaagcaaac agccacatca atatgcacct agagttttgg taacaggttt  44340
tggctgagaa gaaaatttga gcatcatcaa catatacagg tgtttgaggc cacaaaacaa  44400
gaggagatca actaagaagt taagacagtt gacagaagca gacacagcag agagaagagg  44460
tcctacagat aagactcagc aggaacaatc agcaagtaga agtatcatgg ggtgtccaca  44520
```

-continued

```
gccaaagtga tcaaccatgt caaataatag tggaccactg aattcagcaa tgtgggagcc  44580
actggtgaac ttcggaagaa ctgtttagtg gcatgatgag gatacatcaa gagcaatggg  44640
ttcaagagaa aatggaagga gaggaggcaa agacaatgaa aataaatgcc gtcaagagtt  44700
tcactataat agggagccaa aaaaatagag tgccttgagg tgggcacgaa tcaggagagt  44760
tggttttgtt ttttcaagat gggatatact ctaacgtatc tgtatgctgt ggtggacaat  44820
gaactgagag aggaaaagtt gttaacacag aagaaagaca attgcagaaa aattctgtcc  44880
cctagcccct tttattacac agcaggtagt gaatacacac agtgttctga gcttagcttt  44940
ctgtactaaa catggaaatt aatctacttc attctaggta gatctgcctc gtactttttt  45000
aatttttaaa aaattatatt aatttttttt tttttttttt ggtagagata gggtctcact  45060
atgttgcatg ttgcccaggc tggtctgaaa attccagact caagcgaacc tcctgcctca  45120
agcctcccaa agtgcttgga ttggccaggc atggtgggtt actcctgtaa tcccagcact  45180
ttgggaggtc aagcccggtg gatcacctga ggtcaggaga tcaagaccag cctggccaac  45240
acggtgaaac tctgtctcta ctaaaaatac aaaaattagc cagtgtggtg gcgggcgcct  45300
gtaatcccag ctactcagga ggctgaggcg ggagaatcac ttgaacctgg gaggtatagg  45360
ttgcagtcag ccgagatcac accactgcac tccagcctgg gtgacagagt gagactccat  45420
ctcaaaaaaa aaaaaaaaac acaaagtgct ggggttacag gcatgagcta ccatgcccag  45480
ctgccgtata tatttcacag tgttccattc tgtgaaagta ccataggcag taagccagat  45540
atctatgttt agcttcccaa gttagcgttt aaggaaagtt gctaaattag tggctgagtg  45600
acacttaaaa agtttttcaa tgatgaaaaa tttcaaacat atgcaaaaaa gagaatagta  45660
caatgagcct ccatgtaccc atgattcaga ttcaactatt gccacacctg tttaacctag  45720
cctcctattt tttctttttt gctcaactat tttaaggtga atcccagaca tcacgcaatt  45780
ccatttctga atattctgaa tacttcacta agcatcttta aaaatacgga cattttctta  45840
tgtatttcac caccatactt aaaaattaga ctgagttcag atgtggggac ctcacatctg  45900
taatcccaac actttgggag actgaggcag gaggatccaa tgagcccaga gttcaagacc  45960
agcctggaca acatggagaa acctcccacc cccgtctcta caaaagatac caaaattagc  46020
caggcatggt ggcacgtgcc tgtagtccca gctacttggg aggctgaggt gggaggttca  46080
cttgagccca ggagtctgag gctgcagtga gccgagatct agccactgca ctccaggctg  46140
ggtgacagac agactctgtc tcaaaaaaca aacaaacaaa caaacaaaca aacaaacaaa  46200
gtaaactaag actaagcccc ttggtttcat ctaatattcc taatactttc atattcaaat  46260
tatctccaaa aagatttttt taattggttt gttttattca gactctgaat attattcaga  46320
agttgttctt ttaatgtaga gcaggttcct tcctcctcaa ctttttattt catgccgcag  46380
gcagggactg ttttttaatt gttctatttc ctccaaggca ggtatcagct tttgattaca  46440
taactatacg tctaaatata tctttatgtt gtcttcacag ttgattgaca ctttggttga  46500
atatgtactt ctaggttgaa aaacaatttc tggcaggagg caggggacac tgaactatta  46560
aaaaggaaga cccaaggcca ggcacagtgg ctcacgccta caagtccagc actttgggag  46620
gccaaggggg tggatcactt gaggtcagga gtttgagacg aggctggcca acatggtgaa  46680
accccgtctc tgctaaaaat acaaaaatta gctgggcatg atggcctgta gtcccagcta  46740
ctagggaagc tgaagcagga gaatcgcttc agcctgggag gtggaggttg cagtgagcga  46800
gatcatgcca ctccactcca gcctgagtga cagaggaaga ttccatctca aaaaaaaaaa  46860
aaaaagaaag aaagaaaaag aaagaaacaa aaacaatttc cctcagaatt ctgaaagtac  46920
```

-continued

```
tgctccattt tcgcatccag gaatgctatt ggatagcctg gtgcttttcg aattgctcaa  46980
catttgtata ttattttttt acatttctgg aagctttaga atcctctttt atccttggta  47040
atctgaaatt tcatgatggt gtgggcattt tgcattaact atgtcagaca ccttttaatc  47100
cagataccaa cgtccttcag tctgaagtct ttcctgtatt gtttcttttt tctttccgag  47160
acaggttctc actctgtcac tcatgctgga atgcagtggt gcaatcacag ctcactgcag  47220
tcttgacctc cagggctcaa gcaatcctcc tgcctcagcc tcccgagtag ctaagactac  47280
aggagtgtgc catcatgcct gcataatcta aaaaaaattt ttgtagaggt ggcatcccac  47340
tatgttgctc aggctggtct tgaacttctt ggccctacta gcattatagg catgaactac  47400
tgcacccagc ctgtattact tctttttctt tttctttttt ttttgagatg gagcctcgct  47460
gtgtcgccca ggctagagtg cagtggcaca atctcggctc actgcaacct ccacctccca  47520
ggttcaagga attctcctgc ctcagcctcc cgagtagctg ggactacagg tgcctgccac  47580
catgcccggc taattttttt tttattttta gtagagacgg ggtttcacca tcttggccag  47640
gctggtctcg aactcctgac cttgtgatcc acccacctcg gcctcccaaa gtgctgggat  47700
tacaggcatg agccaccacg cccggtcgta cttttttttt ttgagatgga gtcttgccct  47760
gttgcccagg ctggagtgca atagcgcgat ctcagctccg ccttggtgga gcctaccagg  47820
ttcaaatgat tctcctgcct cagcctccct agtagctggg ctttacaggt gcccaccacc  47880
atgcccagct aatttttgta tttttagtag ggacaaggtt tcaccacgtt ggccaggctg  47940
gtctcgaact gctgacctca tgatctgccc acctcagcct cccaaagtgt tgggattaca  48000
ggtgtgagcc actgcaccca gacctccgcc tgtattattt cttgatcatg tcatcctctt  48060
tattttctgt tctcttttttg gaactcctat tagcaagatt ttagatggat ggctccacca  48120
catcttttat cttttctctc atatttactg ttctttatct acttgtcctt tctgaaatat  48180
ttcttaactc tttcgataat catagtttta attttctctt tccctgataa ttcctttttg  48240
aggcatcctg tcctgtttta taatatgaat gcaatatctt cacatatctc acagagcagt  48300
tggtgcttat gtgaagtttt actctatttc ttcagctagc tgtttttttt tttaaggaaa  48360
atttgtatta ttttcattat ttttatgtac agaaaactca acagtataca tttaacccag  48420
tttagtggca agttctttag cctttgcctt ttcgagcttg gcaatgcaag ccacagactt  48480
gggacccaag atattgcctc cccagtgaca gcagatctca tcgtatctgt cattgtcatt  48540
ggtcctgata ccttccacca gcttagccaa agcgcctttg tcttccaagt tcacctgtgt  48600
gaaggcgaca gtggtgcagg tcttcctgtg gactagacgg cccagtcttg ccttcccctt  48660
gataatgcag taagggactc ccattttaca acacagggca ggcaagaaga caaccagctc  48720
gatggaatcc acatcgtgtg caatcaccac cagctgagct ttcttgttct ccaccaaggt  48780
ggtgatggtg ttaactcctg ctcgaagggc aggtggtctc ttagtgggga cgccccccttt  48840
gccagcagct ttcttctcag cctgggccaa cagcctctgc ttcttctctt gctttgtctc  48900
tggtctgtat ttgtgggcca gcttaagcag ttgagtaact gtttggcagt tcagggcctg  48960
ggtgaactgg ttaatagcag gaggcacttt cagctgctta tagaggatgg ctctctgctg  49020
ctgcaacctg acatagcggg ccatttcaca aagtaggtga gttctctttt gggctggatg  49080
tcctgtccaa taccaaaatt cttacgcctt ttctcaaaca gggaattcac cactttcttg  49140
gcctcctgct tcttcacaac agcaggggcc ggggccacct tcttcccctt ggccttcttt  49200
cctttcagcg tcttgggcag tgggaggcca gttagctgtt ttttaacttt ttctcatttt  49260
```

-continued

```
taatcttcat attagaagct ttcctcactt ttctaatgat ccttggtagt ctgctctttt  49320
tgtttaattt taaaactttt tattagggaa aattttcaac acacacaaaa gaaaaaagaa  49380
tagaacaatg agcttcctat gtgctgaacc cctggcttca atcattagca ctattttttt  49440
aacccatttg cctcccctcc atacacatac ctctccaaag tttggaattt tgtttgtttg  49500
ggtttttatt ttgtctgctc tttttttttt tttttttttt taacagttca gcactaatca  49560
ggaattctgt ggacagggtt gagtcttgct tgctggaaga catcacttgt gggtgattca  49620
ccagggaggc aagtcttttt cctagatgac cccaacatca gtatgagagg tctttttttcc  49680
agggtcattc agtttcttca gaaaataact aagtcttggg cctggacagc cagcatctga  49740
atgcaaatgt gtgaacagga agggggcctg caggcccttta tgtaaactca cggtctacca  49800
ccttgtctca caatggctgt gtaccacatc tgatgtccca gttgctaaca tgctctaagg  49860
ctggtggggt gagtcatctc tcttcctctg ggtattcccc taaacgtata cttggctttc  49920
tccacacgga agtatgagaa aggatactac actctccatc ttatcttcta aaagtagggg  49980
gataagagat actgcctaga gttcataaag aagaaataaa ggtttaactg taaattacaa  50040
agataactaa aagaaaaact aaaacaaagg aaatcaatat gctaggcgga atcagaaaag  50100
aaagagggag gccaggtgtg gtggctcagg cctgttatcc tagcactttg ggaggctgag  50160
gcatgctgat cacttgagct caggagttcg aagccagccc aagcaacatg gtgaaaccct  50220
gtctctacaa aaaaacacaa aaattagctg ggtgtggtca tgcacgccta agtcccagct  50280
acttgggagg ctgaggtggg aggatcacct gagcccagga ggttgaggcc acaatgagcc  50340
atgactgtgc cactgcattc cagcctgggt aacagagcaa gaccctctct ttctctctca  50400
aaataaaaaa aaaaaagaaa aaaaaaagga aggaaaaaaa gaaaagaggg agaattgaga  50460
caaactctca tctatcacag caaaaaagaa agaaaaatca actttgttta tatctggcgt  50520
tcataaatca agaaatagca atataagcgt tttacttagg gatatgaagg tcaccaccag  50580
aagaatgtga ttgcctgagg agcatgctgg gattggagga gtggggcaag ggtctcctgt  50640
ttttcattat gagcctgtat ccaaaaagaa aaaagtgtgt ggattttttt gatacaattt  50700
tttcttttaa ttaaaaaaaa gcatatcaga gaatcaggga attcttcaat gttcccatta  50760
ttcttaggct aaagacctaa tttttttttt tttttttttt ttttgagaca gggtctgtct  50820
ctgtcactca ggctggagca cactggtaca atcagggctc actgtcaccc caatcaacct  50880
tctggtcgac cttccaggct gaagtgatcc tactgctcag cctccttagt tgctgggact  50940
acaggcacat gccacaacac ccagctaatt tttgtatttt tttgcagaga cggggtctcg  51000
ctatgttgcc caggctagtc tctgacagag caggagcacc gtcatctcag acaaacactg  51060
ccactttaag ttccagctcc ctttttaaaa ctcctgggct caagagatcc tcccatctca  51120
gccttccaag cactgggatt acaggcatga gccactgtgc tcagccaaga cctaaatgaa  51180
aattccttaa acagctggta agtctcttta aaaaccaatt aaaaaaaaaa aaaagctttt  51240
ctgacaatta tgaacacatg ttcaatctgt agcagaccaa ttcaaagatt cactctggca  51300
gggacatttt gtaagataat ggttagagga cactgtgaga ttcaatagaa aaataacctg  51360
cacagttaaa ggttacgaga ctcctgatgg atagtctgct gctgggttgg atgactggct  51420
tcccagaaca tgttttaatc ctgttaaaat ttattagaaa attgcttcgg tgtttttgtt  51480
tttgtttttt tacaggaatg ctaatttctt cccagaagga gactgtaaat tacctcatga  51540
aaaaaggttt tgtcacagac ctggcttggg gcaatttgtt cttttataag tctctacaaa  51600
tcctacctag accggctctg tccaatagaa cattcttcat gatggaaatg ttctatatct  51660
```

-continued

```
ttgctgttca acgaagaagc cactagccat atggctactg agcacttgaa ctgtggctaa  51720
tcaagctatg caactccagt tttaatttta ttaaatttca agtgaaattt aaatagcaac  51780
gtatggctag cagccactgt gcaagacggt gtggatctaa agcgccgtgg ctcccagctg  51840
cttcttgccc caagccctcc tcctctctct gcattccagc cactctggcc cactttttct  51900
ccctaaaaca tgctgcctcc tgccacagac actttgcacg tgtggtatcc tctttctgga  51960
atgttcttcc ctcacctact ccccagcctc ttcatctggt acatgactac ttttccttca  52020
ctaattacga ttatctcgtg cgcttatttg ctcacttgtt tatggttaat ctttatgcct  52080
ctccaccatc atcaacccac ccaactctgg agcctgaata cacatcacat ttgggcaaga  52140
accctgccca ccctgcccat ctctgtactc ccaccaccta gacagaacac acttggctct  52200
cagtgagcat ttggctaata tctaaaaggt aagtgacatg tcacaatgtt gttatctctc  52260
tcagagactc ccaatttcta tctgtagacc cattcttgct actgtaatgt tgccccacat  52320
ttccaacaga ctgtgagcat ttctacttaa atacccttct gtctacacat taaataatgt  52380
tatctccagt catcagatta acattcagaa agcttggctc tacttattgt catacaactc  52440
caaacaaaga aaccttcaaa gacatctaag agaaaaatca attttaagga aacactgaac  52500
acactataca cgctgcaagg ttcttaggcc ctttgcacac caatataaaa agaaagcaaa  52560
cagaaatgtt tctgcaaaga tacaagcgag aaagttcaaa cttaccacaa gttcaaaaat  52620
gtccatgaag acagaatgtc ccttcggtgt tttctcattc aggctggcag gagaccagat  52680
ccaatagaag taagtgccat ctgaagacag gtgcacagtg ctcatggtgc tgccaatggg  52740
gaggtgattg gctggcattg gcaccacctg gcacacctgg gcatgaaagg gaggaaatct  52800
ccattagagc cacatataaa ttctgattaa tcctatcagc tcatcattaa tgccattatg  52860
cccaagatga gaattcacta ggctttctgg tcaaaataaa atggatattt atctctaata  52920
ataacataca caaattacat ggcaaaaata taaaagttca tacaatgggc aatagaataa  52980
atatgaacag ccatgcaaca gatgaaaagg ttcttgggat caattcaaat tactttttaa  53040
taggaaaaag tatttactaa acactttgaa tctgttatgc atatgtgttg tatctaacac  53100
ttattaaaaa caaagtttta gagaagcaac actttctgaa atttctttag taaatgaatt  53160
tatgataatt ttatttaaag gacaagaact gtgtcttatt cacctctata tctccagtac  53220
ctaacggaaa gcctaactca aagttattta atgaatatga aaagaaggaa aaaagagaca  53280
gcaaaagaaa gccaagagga aaagctgaga agagggagaa ggagaaacaa agtaaaaaat  53340
ataaaggccc atgacagatc ctaacttagc atatgagggc ttactgaaat tcaccaagtc  53400
catcaggagg aaaagacaaa caccaattct gtatattaaa catgaaggca tgtgtttcta  53460
atactaaaca tccttctgtt tcagcataat gaataagctt tgcatcattt cacattaaat  53520
gtgtagctac atactaattt ttactgccaa agacaggcac ttaaaatgac tgaacattag  53580
aaccacaaaa acctgctggc taggtttaaa aaaaaaatcc agaaatagaa gagctgagaa  53640
actcaaaata aaaataatta gagaaagtca gatgccttca gagaacagtg agaacaatgt  53700
tcaatttccc attactttgg gagggggcac tagttttccc aaggcgatct ctgacccctc  53760
aattgatttc acatgaactt ttttccagac ctgttttgtc tagctcaaaa gtaaaaactc  53820
atttagttga tgtaaccata ctttgaacct acagtgccag gaagactaga aagttgacag  53880
ctactaattg gcctgtgcta tccccaaagt gctccattgc aatgcacata tctagtttgt  53940
gacctacagc cctgctttct tggacagtgt caaagtttct gcaacaacac tgaggaacct  54000
```

-continued

```
ggcactactt caaatgtaaa tcatgttttg agatttaaca tctgtttaac taccagtctt  54060
ataacttcta tttcaaatga gtatgagaca ttctcatctg tctgcacttg tgacaagaaa  54120
ttaggttaat tgggcatcta tttgttaatt tgttcatttt attcatccaa caattattga  54180
gcacctacta tgtgctctgg agatgacagt ggtgaacaag actcagtccc tgttctctag  54240
gacaggcagt tgagtgacaa acaagaagaa atgtaacatt acacttaatt tctagatgtg  54300
actactctta gagcactcac tccacagacg ccaactctaa tcatttaatc caactttgtt  54360
tgaaaggcag aaagttgcag tgtaaagagt tcaaagtact gggcagagaa ccaaaggttc  54420
aagttctggt gccgctacta ttggctgtat ggccttaggc aagttactta acctctctga  54480
gctgtattct tacactcaac aataaacact tgctgaatgc ttactaggtg cctagcctca  54540
gtttccttat ctgtaagata aacctacata gtaatgcctc acaggtagga agaggaagtg  54600
tatgttaatt gcctaggcca aggcctagca cataggagat gctgaggaat ggtagttacc  54660
atcattgtta ttattatcag tcaaatgtct ggcagtgtgt tatgttctaa ggatacacag  54720
atgagtagga cagggtccat acctaaaggt gtgcatggtc agtgaagtca gacagaaaag  54780
caggtaactg cagtataata cagcaagtgc catggcagag tgcttacgag agcactaaag  54840
ccaagctctc aatccctagc acacaatgat tttactctac actcatttca aagctccctt  54900
tcccacagag aggctgttta gaacaaattg aataaggaaa tgatgccttc ccaaaataga  54960
tctggttcaa aaaaagcaaa aaaaaaaaca aaaacaaaac aaaaaaaaaa aaccagctag  55020
tatttatacc atctttgact gtctagaatt ttttcttaat tataaaaaaa agtttgttgt  55080
aggctgcaga aacttagaga acacattcac tcagttcata tgggaaaagt ctaagacatt  55140
aaataaaaaa cagaatgccc aaactataac aattaaaagg atgccactct gggaggaaaa  55200
tatatcaact gtattattat tacttctgat gatataggaa ctttctttat tgcctctaaa  55260
atatgtttta aaaatgcctt ggttttctgt ttacctgaag ggtgttctgg tcaatgacct  55320
ggaaaaggga gtgaggttta ttatcgaaag agacaggccg gtggagaaga ctgccgctgc  55380
caaaagccac ccatcctggt tccaactcct cgttccggca gtacacaaaa cctctgtgga  55440
atgaaatgga gcacaggctg aatcacctgg ctatgtcaga aaccccacac aagctacaac  55500
agacacaaac aacattttcg acctaatttt aaaaaatgag taagtatgta aaacatctga  55560
aggaaagtga atgtattaca ttaacttcag gactgccaaa ctatagcaaa tattgacttt  55620
ccacaataac ttagagggga gaaaaatttg ggggaaaaga tctaaatgta tacaaggctt  55680
tcaaactgta gtttcttttg gcagcagttt atagatctta tatcccaact gaaaatcact  55740
tgctaatcca atgtcaaacc caagttcaaa gagacttaag tagaaaaatg tccacttatt  55800
aacatggaga agtcactgat attgttacaa aaatactgat catggaggac tttctggctg  55860
gaaacaatga tcttggggct accaaactct tctgggccaa aacaaggcta aaatgcatta  55920
acagaacaag atggggaaag gtggcaataa gagaagattg gaattatttg aattagttca  55980
gacttgttat ttagttacta gtctatgggg agctggaatc tacccacagt gtcttcttca  56040
gagatttatg taaggaggat aatgttctag cccaatcatt caggaagttc catgcaactg  56100
acctgagagt accatgtaat ccagatccca atttgcttac tcctcttcca actgagttag  56160
tagtatacag gtaaagacca tctgccgtga gacagcgtcc caagtcagca tctgaaatcg  56220
ttttttcaca ggtaaattat atatatgttt tttctattga aattataaac atgctttttc  56280
taatgaaaaa gccattagga ggttgagtga aagattactt ctcacttcta aaataagagc  56340
ttcaatgtga ctttcaggga agatggcttg agcccccaaa tcaaacatcc aaaatgcatg  56400
```

-continued

```
tggaccagag accaagatat ggtcagacag ttaccagcag gggaatgtgg tttagcccgc  56460
caaatgtttt tctttctttt tttttgaaaa gcttgtactt agtcaagtca ttcctaattc  56520
taatttgaaa tgactaatca taattctaat ttgaaatgac taagaataca gtacaacact  56580
tttattagta attgcatagt aagagaggca tgagctctta tgagctcagt aagtgaccct  56640
gaacctcttt gaacgtcagt ttcttcatct gtaagatgag gataataata tgtacctcaa  56700
gggttacagt gatggccaga tgagataata gaggtaaata catctatact gctctctgat  56760
gcaaagctag tattccataa atggcaaatg aaattgtgtt aatatactaa tgatatacat  56820
taaactaaaa tctgcctctg tagattttcc attcagagat cctaatttta gtctctggag  56880
ggacaaagca caaaagtttc atatcttttc tattttaaaa cagcaatatg tttcccctta  56940
gctctgtctt cctcaatcta aaacagtatc tctctatatg atggtaattg gtttagtaac  57000
tcaaattcca aagaatttgc cttaaaatag agcttatgga taaaactttc attgtttatt  57060
ttcataatca ttctgctcac tatgtttaag tggagtcttt ccacctgaag catgccatat  57120
tagctggagg aaatgcaatg tcacaccgtc aaattagtac taaaaatgct gttagcttaa  57180
aaattcagtc tactaatctg agacaactgg gacctgtacc tattggttcc tcaatgaaaa  57240
aatttgttaa agtgggtaac catttttaaa acattaattt cacaccttaa acattttaat  57300
ttaaaactta tagattacat ttattcatca atttttagat taaggcccaa ggccttctgg  57360
gtatggctct gtcgaggggc agaagtgaaa aggacaaaca aaacaagatt ggccaggaat  57420
ggatacttgt tgaagctgag tgatgagtac acagggctta ttatagtatt ctctcaacat  57480
cagtcaaatg tggaatgttt caatattaaa agttacactg tggccaggca cagtggctca  57540
tgcctgtaat cccaacactt tgggaggccg aggcgggcag atcacctgag gtcaggagtt  57600
caagaccagc ctggccaaca tggtgaaacc ccatctctac taaaaataca aaaattagcc  57660
gggcatggtg gtgggcactt gtaatcccag ctactaggga ggctgaggca ggagaattgc  57720
ttgaacctgg gaggcagagg ttgcagtgag ccaagatcgc gccactgcac tgtagcctag  57780
gcgacaagag cgaagctctg tctcaaaaaa aaaaaaagat tacataaatt agtctaaaaa  57840
ctatataaga aaaacaggcc aggcgccgtg gctcgcacct acaatcctgg cactttggga  57900
ggctgaggtg gtgggaggat ggcttgagct taggagttaa agaccagctt gggcaacaaa  57960
gcgagatccc cgtctctaca taaataaata aataaataaa taaataaata aagtaattat  58020
ccaggcatgt tagtgcatgc ctgtggtccc agctactcag gtggctacgg tggaaggact  58080
gcttgagcct gggaggtcga ggctgcagtt gtgattgcac cactgcactc caacttgggc  58140
aacagagcga gaccccatct caaaaaaaaa aaaaaaagaa aagaaaaaga aaaaagagag  58200
agagaaaaaa agaaaaccat ttctccctag atgcaaaacc aaaggttcag gaaaatgaaa  58260
gcaaacagat cagcttaatg ccatcctcct cagtgagaaa ctaccccaag ggagatacca  58320
aatggagttt tttaaaagga gagaatcaag aaagaagttt tagttctata ttaagaagta  58380
agttggagcc gataatgtct gagaacttct tgggtactgc aggcattctc cctctcctgt  58440
tgactctagt tgaattagtg aaggaaataa atcacattta aaagccttgc cgcttcttct  58500
ccacacactc tcatgcctgt ttagaagaaa tggtagacca tggaaaggta caagccctgg  58560
gctgagagat gcgagggggc ctgccgctta gattctcctc cgtgctggtg gggttgccca  58620
ggaaggctgc cccatggaaa gtgggaaatg aaagggaggg aggaacagac tctctgtccc  58680
acacctgatg aacaccagtt tcttagagac tcacttcgtg gagtttttct aaaacattca  58740
```

-continued

```
acttcttaat ggcaactatt tcctgggttt ttttaaaatt cctatttcat cagttatgta  58800
agatttaatg ataaaatcac aataataagt accagttaca attaacaaac tggtttggga  58860
gcaagcctac ctcttggcaa gcctgcaatt ccgctggtgg gagcagagct gaccagccct  58920
gtgggttcag tgggccacgg cagggcagca gcctagacat tttactgagt gaatggagag  58980
gtctatccca tctgccaagt cagttaagag agcttctgcc atttttgttg agataatgta  59040
agaaactgac atgtaatact gtaaagctct gtaaaaacat tttaacctag cttatttgtt  59100
taaagtagat gttaacaatt catgctccct tgaacctctt catttttgc ttttaggaca  59160
ggagggctca ttaacacaca cacaataaat tactaaagga aatattatca agcagtaaga  59220
cctgatattc tattagcaga caaaaaaatt caacttaagg ctatcatacc caaactcaaa  59280
tatccagcag ccaatttaag taattcatgg ctccttggca agagtgtatg gatgatatct  59340
tttccttgtg ataataaaac ctatccattt tcttacctca ccagtatcag cttttatacg  59400
tttactgata aagcagacaa tgaacatact gaatagaaat ctggagctct taattaaaag  59460
gaacatacag agttatagcc atatcatttg ctacagtgat ctaaaacctc tttatttaca  59520
tcttactatt aatcacagga caaaaacttt tacattacct ttattttcag aactggagcc  59580
agtgttgcta tccggcgcag gcaacatgtc ttcataaccc catgatacta tgtgtttgcc  59640
cccaagcaaa caggagggag atccaggccc cccttccaaa agcaacagcc tatatggggg  59700
agaaagaaaa tcacaaagac actgagacaa tccatttcag caagaagtat acctgctacc  59760
ccaaagagta gaaaccaaaa ttttaaaact aagatgtata atattttata caaatattat  59820
tcaaaaaaga catttatagt atttttattt tttatttatg tttctttttt ttttgagaca  59880
gagtctcgct ctgtcaccca ggctggagtg cagtggtgcg atctcagctg actgaaacct  59940
ccacctcctg ggttcaagcg attctcctgc ctcagcctcc agagtagatg ggaccacagt  60000
cacctgccac aatgcccggc taattttttt tttttttttt ttttttgag acagagtctc  60060
gctctgtcac tcaggctgga gtgcagtggc gtgatctcgg ttcactgcaa gctccacctc  60120
ccaggttcat gccattctcc tgcctcggcc tcccaaacag ctgggactac aggggctcac  60180
catcacgccc ggctaatttt ttggtatttt tagtagagat ggggttttgc catgttggca  60240
ggctggtttt gaactcctga cctcaagtga tcctcccgcc ttggcctccc aaagtgctgt  60300
gatcacacgc atgagccatc acgccctgct acaatatttt taaattaaaa aattacgaag  60360
ctatgtttat aaaaattata tctgtgtgta aaatatacta ttttatgtgt atttttgtgt  60420
gtgacagaga gacagagtgg gttatgaatt aggaagcata tgtaccaaaa tgttaggagt  60480
agttatcttt gggtaatgag attatgaatg attttcactt tcttcattat accttaatat  60540
attatcatct caaaatttgc atcagaattc attataagct attgcatctt tattttttga  60600
aacagagtct cgccctgtca cctaggctgg agtgcagtgg tgtgatctcg acttactgta  60660
acctctgctt cctagcctca agcaatcctc ctgcttcagc ctccctagta gctgggacca  60720
caggcacgca ccaccacact catgagttat tatgccccac cagctattgc atttttaaag  60780
acatagaact aaaaaataat gaaaaataac atgctctaaa aactttccaa aaaggaaaga  60840
taaaaaataa aattcttaag aaggtaaata tgagtctata cttattttaa aatgaatcac  60900
taattgataa gagtttagca atctacttaa taaaggaagc atttggcaca aatctgccta  60960
gtttggaagg agggtaagga tacaaagtga caacttacct atatagcaca tcagctacag  61020
gcagggaccc tagatccgtc tgtttctgta atagatggac tgtgtggacg aaagttttca  61080
atgatcccct aaaaataaaa ggaaggaaca gtaaatcatc aaaatttaaa atcaaataat  61140
```

```
ttaggtcatt aatgctaatt taattaacca catggaaaag ttccaaaatg tgtctctctg  61200
cttctgctgg tcagatgatg tgttgtaaaa aaaatacttg attattaact atcaccattg  61260
gctcatacac aaagatacaa tgaaaacaac accatgccaa ttatgaagaa gttctccttg  61320
catttggaaa agtaaacaat tttcccctgg cataaaagtt caaaacataa ggctcgagca  61380
caaagaactt gtggctatta tgcttggtta ctatatcacc aagtcaccct ctggaggatc  61440
ataaagtcta acagtatttc caggcttgat tttaaaatct ttgctaagtt cattcatttg  61500
gaaaaacagc taactaaact ccatcacatt aaatatgacc aaaaagaata tattcaaata  61560
aataatgctc tgtgctgaga gatgctcctt ctgtatccct ctgactgcac atagttgtaa  61620
tacttgcaac agggctcacc gctacctgaa ttccttgtgg tttccaagac tcaaggctct  61680
gggaagtctg tcatatggtc agcaagatct aaaagaaggt gcttttaaga tgcacaagac  61740
ttacctggcc gcatcccaag tacaaatcac cacaagaaca cttcctgaac taaatgatcg  61800
cctgtatctg acgggctgac ttcgacttgc tgccttagtc tcttagccaa ggctttaatt  61860
gctgggtatc atatgcctaa acgccaatag aaatggaata cctaacgcag aaccaagtag  61920
gcctagagtc ttcctgttaa ttgccccttt cactatctct agtttcagag aataaaaaca  61980
aaagaatagc attaatagaa ggcaaggagg cagcagatag agtataaaaa caagttggaa  62040
tcgggacaca tgggttctga aacctggctc tgccactcat cagctgcaca atctcagtcc  62100
tgtcacctaa ctcctatgga tttttgcttc ttcatctgcc caacagggac actttcctgg  62160
ggaacagtga ggtttaaaat aaagaagcaa aacctttaac atttagaaag tttagaacta  62220
ttaaccaact ctaaggaatt attacctgcc agattcaatc agatttgttt ttttaaaaga  62280
gacagggtct ggctgggtgc agtggctcac acctgtaatc ccagcacttt gggaggctga  62340
ggcaggagga ttgcttgaac acaggagttc aaggttgcag tgagctatga tcacaccact  62400
gcactccagc ctaggcaacg gaatgagacc atgtcttaaa aaaaaaaaaa aaaaaaaaaa  62460
gagagacagg gtctcattat gttgcctaga ctggtctcga actcctggcc tcaagagatg  62520
ctcctgcttt agcctcccaa agtgctgaaa ttatagatgt gagccaccat atccagcctt  62580
caatcagatt ttaagagtaa aatgtaaagt ccttccatgg ctcacaaacc cctatgtgat  62640
ctgggccctg ccaacttcat ctcctgcccc tctccttcta ctatcacgtt ccagaaaccc  62700
tgcccactgt gctgtcccct cagatacccc aagcacaaga ataatgtcag ttttgtcact  62760
cgccactcca tttacgtgga actctctgcc actggctgct tctcatcatc cagggcccag  62820
ttcaagtgtc atctcttcag taaggccttc cctggcatct ccagctaatg ctgctctcca  62880
cctccacagt cattctctat caaaatatct ctctgtcttt tcctatagtg aatattcctc  62940
tctacaatga tctgttacct atatttgttg ctcactgtct gcctccctca ctcctatgta  63000
agctctgcaa ttttaggcac ggtctacctg ctctccactg tatccctacc accaagagaa  63060
tgccttccgt gcagtaagtg agcaataagg ttttgcagaa tgacttaccc tgagtccatt  63120
caaccgtaag ctctgtgagg taagaaacct agaatcacta tatccctaag accgggcaag  63180
attcctgtac atcagaaatg ttcaataaat gttagttggt tgaatgaata atcttcataa  63240
taattttggg gaagggttac tttgtctttg agagcatcaa cccaaaaatt caataatatg  63300
ccactaataa ctttagtaag atgatctaac actgaaaagc acatgacttc tgaagtccag  63360
aacatgatat tggcaataaa atgtaggaac catgttaaaa aaaaaaaaac ccaagaagaa  63420
taaataaata aatacatcca tttcaacatt tctgctgaat gaaatttaga atgtccagca  63480
```

-continued

```
caggaagtaa gttcaataac tatttttggt ataggctgaa tttgggtaca caataaaaat  63540
gtgagtttta tgaaccaaca attaataact taaactgttt gaaactaaag agttgataat  63600
tattcctaac atcctaaatc tgtctaaaga tagtactgtc taaaagcaca ttttctcaaa  63660
tggaatttgc acagtgataa cagatcttgg acttgaaatt gtctctgcat atgcagaaaa  63720
taaatcaatc caatataaag cctttacaag gaaacttgtt tcagtaccac acaatgactc  63780
tagaattaag cacatgtcag gattcacaaa ccacagtttt aggggatcta aaactaggct  63840
atgacagctt gctcagagca aagaaactta caataaacac tggtgccatt ttgccttaaa  63900
aaaacccttg agattcaatc atttgaaggt caactttgaa actatacaga gaaaaacagg  63960
gcaagaagac ttataactaa gaacttcata attatccaag aagaattctc ccacagatgt  64020
ttggctaaaa gaaagaagat cccaaccaag gaaaaaattc tacggaagac agacagaata  64080
ctgacactaa tctgtcaggc tgtggtccta actgttctct aggcaattag tctactggaa  64140
aacaaaggta gtgaaacttc tttctcacaa acagatgcca gtgatcatac gggtcaatgg  64200
gtagaagaat gtataaaatt cctagaaaag caactccagg ccgggcaggg tggctcatgc  64260
ctgtaatccc agcactctgg gaggccaagg ccggcagatt gcttcagctc aggagtttga  64320
gaccagcctg ggcaacaagg ggaaaccccg tctctaccaa agatacaaaa aattagccag  64380
ccatggtggc aggtgcctgt agtcccagct actcgggagg ctgaggtggg aggatcacag  64440
tgagctgaga tcatgtcact gcacttcagc ctggtctttg agagcaagac cccatctcaa  64500
aaaaaaaaaa aaaaaaaaaa aaaaagagag gaataggcca ggcacagtgg ctcatgcctg  64560
tattccagta ctcttggagg ctgaggtggg cggatcactt gaggtcagga atttgagacc  64620
agtctggcca acatggtgaa accccatctc tactaaaaat acaaaaaaat tagttgggca  64680
cctgtaatcc cagctacttg ggaggctgag gcaggagaat cacttgaatc cgggaggtgg  64740
aagttgtggt gagccaagat catgccactg cactccagcc tgggtgacag agtgagactc  64800
tgtctcaaaa aaaagagaaa agaaaagaga aaagagagaa aagcaaaaag aaaagcaact  64860
ccaagcatat ttcctattga tagtgggttg atgacttgca catgaagaac agcatacaat  64920
tttttttttt tttaaagaca aagtcttggt ctgttgccca ggttagggtg cagtggcgcc  64980
aacttggctc actgcaacca ctgcttcctg ggtttaaatg attgtcctgc ctaagcctcc  65040
aggtagctgg gattacaggc acccaccaca acgcccggct aatttttgta tttttagtag  65100
agacagggtt tcaccatgtt ggccagggca gtctagaact cctgacctca agtgatctgc  65160
ccacctcagc ctcccaaagt gctaggatta caagcgtgag ccaccacgtc cagccatgtg  65220
tactactatt aaatctagat atatactgag aaatcttcca attaaattga tcaaaacaag  65280
tattaggtcc aaaaatataa tttgtgacca attttgtgac tgagtccagg tgaataatag  65340
cccactagct tgctgatgta cttcttatag acaggtatga aaaattaata gctctataaa  65400
gttttgacca tcctcctagg agaagtagac ataacatcct ctgctaacta cttgatgtaa  65460
aacactaacc atctaaggga caattagata tgtcaagggt tgattctcca ttttctgctg  65520
gttaagatgt tatcatggta taccagaaac agaaaacatg aactttggtt ccaactcagg  65580
cacctggtgc caagtttggt gaaagcatct catgcactgt caaggctgtg aaattcaata  65640
ctgaaagcaa agaaggactt ctgaatgtta agacttctat caaatatact tggcctcttc  65700
ttcattcacc caacccaggt ggcagtagtc acaaggtcac caaatgatac attcgatttt  65760
ccttacctgg cacaagccaa agccaccagg gcagcagcag cattttcttt ttgcttatgt  65820
gggatgtgtc ggcctgtgtc agaagtctcc tctagccaag agcacagcaa agtttcaatt  65880
```

-continued

```
ccattgagac agtcagcagg ctccttggtc aagctcaaag gctggcagtc acgaaggcag  65940
ttcaatagca cctcagcagt tatgttacag agagaggggt ctgttctact ctgggactga  66000
ataaggggga agaccagcag gagccccatc ctcgatgtga agggcgcttg ctcaggttgc  66060
tgcaacaagc cctggcgttt gagcagggcc aaagtttcct catcacctga actttccctt  66120
tcatgctgtt cttctaaggc cagctggcgc tgggcattcc acagtcctcg caaggcattc  66180
aggcggtatt ccagcagccg ggcataggca ttgctctgat tcccacaaac agagcgcaaa  66240
cgttctgcta attccgacgg gttcttggtc tcaaaggtta aaatctaagg aaaaagacga  66300
tggagaagtg ggtaaatatt actttcacca aagtcatcta aggaagaaaa tatgtttaat  66360
gatatcccaa aatagtcaac gccaaaaatt attttaatta caatcaaatg gaaaacgtat  66420
actgtaaagc cagctctttg ctgatggaat tgttcccctt ttggcttttc tgttaatgct  66480
tccatgaaaa ttgggattag acctaattga aagagcccaa atcataaaag aatatagtta  66540
agtgtgaaag tcagaaatta actccataat ttattttaga aaattgaagt ataaagccag  66600
gcgtggtggc tcacgcctgt aatcccaaca ctttgggagg ctgaggtggg tggatagctt  66660
gagcccagca gttggaaacc agcctgggca acatggtgaa accctctctc taccaaaaat  66720
acaaaaaata gccaggcttg gtggtgtgca cctgtcgttg cggctacttg ggagactgag  66780
gtgggaggat tgctaaagcc cgggaagtag aggctgcagt aagccatgat ggtgccctgc  66840
actacagcct gagtgacaga gcgagaccct gtctcaaaaa ataatactac aaaaaaaaag  66900
gaaaaaaatt gaagcataaa cctttagtaa atgatcttga gttataaatg ttgtttctag  66960
gacaggcgcg gtggctcacg cctgtaatcc cagcactttg gaaggcagag gcgggcagat  67020
catgaagtca ggagttcgag gccagcctgg ccaacatggt gaaacaccat ctctactaaa  67080
aatacaaaaa aaattagcca ggcgtggtgg cccacgcctg tagtcccagc tactcaggac  67140
cctgaggcag aagaattgct cgaacccggg aggtagaggt tgcagtgagc cgagatcgca  67200
ccactgaact ccagcctggg tgacagagtg agactctgtc ttaaaaaaaa aaagttaaag  67260
tttctaactc ctattaccag atagagtact agtaaaaatg gaaccaagtt ttatctctgt  67320
tcttcaaaac ctaatatata tatgtttaat aaatgatgga ttattcacgg ttctttggtt  67380
gtgaagcata ccccattctt tttttttgag atggagtctt gctctcttgc ccaggctgga  67440
gtgcaatggc cgatctcagc tcactgcaac ctccacctcc caggttcaag caattctgcc  67500
tcagcctccc taatagctgg gattacaagg gtgtgccacc atgcccggct aatttttgta  67560
tttttagtag agacgaggtt tcgccacatt ggccaggctg gtcttgaact cctgacctca  67620
ggtgatctgc ccacctcggc ctcccaaagt gctgggatta caggcctgag ccactatgcc  67680
tggcagcata ccccattctt aatagtgtta acccattatt ttaatttgtg acatggtaga  67740
gatttatcca attcatatta gattgttttc ttgccaaaac attcaattat caggaggcct  67800
ccattttcag cagctgggga taataaaacc attatatctt ctatcagcta agaaaggaac  67860
cagctctcaa gatcaaacta aatctcaaga atcaaactaa atttacaatg caaagagttt  67920
atgcacataa atttgactag atcaaaacca acagactact gtaatcaaca aaggagggca  67980
ctctaggagc aagcacactg aaacagatta tcagacaata gaggtgcctg gttcacagta  68040
gaccagaaag tcagggtggg aagaggcctg ggacaaaagt aaagaaaatt ctgccaggtc  68100
tttggcactg acattaagaa aggtcatagt gcagtttatt tcccttacaa actggaaaaa  68160
tactctttta tctcaaattt tgcctttaga aacttgttat taatatttta gcccaataaa  68220
```

-continued

```
ataacaagaa tttccaaaac aatgcaaacg ctgtaattgc cttgcttagc tacatatgca  68280
aatcactgaa ttgaactaaa aaaaaagttc acaatttaaa aacaacaaca caaaaccaaa  68340
acaaaagaag caagaagcta aagaaaaaca aagataagct gaattagaag ctactcaatt  68400
agcaaaggag aaagaactta taattagaca acaagtatta ctggcaaaga aagaaaaaga  68460
catccaaaaa aaaaaacatt acaaagaaat ggtaagctag gtgggtgaca tacgcctata  68520
cttccagctg cttgggaggc tgaggcagga ctgcttgaac ccaggagttc gaggctgtag  68580
tggctatgat cgtgcctgtg aatagccact gcactccagc ctaagcaaca tagtaagacc  68640
ttgtctgcta aaaaaaaaaa aaaagaagaa agaaaaagaa agaaaggcaa aaacttcgaa  68700
actcatctaa gatctggaat cacttttcca acaatgaggc agggtgggtt aaaatgatgg  68760
aagaaggcca ggtgtggtgg ctcatgcctg taatcctata actttgggag gccaaggtgg  68820
aaggactgcc tgaggccagg agttcaaggc tgcagtgagt tatgatggca ccagtgcact  68880
ccagcctggg tgacaggggg agaccctgtc tcaaaaaaga aaaaaaaaag aaatgatgca  68940
agtagaaaaa ctttgtaatc agcttgaact agaaagctta cagtagttga atgaaacaca  69000
tcatctacaa aagaagtagg aatggctgct ctggaaaaac agaagaaata aatgaacaaa  69060
ttacgaagga gaaacaggaa ggtggggctc gtatgtaata agcatctaag aatgcagaga  69120
aataaactgg cagaggtgga aatggcagca acaactggta agaagatgat ctgcagctac  69180
aagttaaagc tatgaatctc ttccctgctg gtatgaattc aagatgggaa gttggtaagt  69240
tattgctaat tacatcaaca tacattcttc tactgatgtc aagacaacca ccaaaggtgt  69300
tactggcaaa gcaaagagcc tccaaaaatt ggaccctcat caaaaagatg acaaacaaaa  69360
aaggcttttg ataaacttta aaaagaacat tgcctcaagc agacaatgaa acaccttcag  69420
aatgatttta cagtccatgc acccacttca ccccttggag aacgaacaga agctttttga  69480
acaagctttg aaaacacacc cagtcaacac acctgaaaga tgagagaaaa cagcacaaac  69540
tgccagtacc tggcaggaca aagaaaggct gcatgaaaag atgcaaggaa cttgccaaga  69600
tggtaaaagc aaagaaagct gctcaagagc aagtgttggc tgggcgcggt ggctcatgcc  69660
tgttatccca gcacttaggg aggaggaggt gggaggatca cttgaggcca ggagttcaag  69720
accagcctag tagtgagacc ttgtctctaa aaataaataa ataaaataaa ataaataaaa  69780
agagcaaggg tcgaatgcag atagagttaa gaaatgactt aatctttatt gggtgtgtac  69840
ttttataata aaactgaaaa tactgtgaaa acaaaacaac aaattccaat tcaaaaaatt  69900
aactataagt atctcagtta actaatatga aaaatattca tagttttaaa aaaattcagt  69960
gccagcttat cagatctgat gtaatatcag gatgccataa aatttcaacc cacaacttag  70020
caaagaaaga aactattgat aaacacaact actttaagga atctaatggc attttgttga  70080
gagaagccaa tttccaaggg ttatgttctg tatgatttca tttctgtgac attctgggaa  70140
aaaaaaaaaa ctatggtaat ggagaataga tcaatggtta ccggggttta ggggtaaggg  70200
gaggtagggt ctgactacac agggatagta tgagggagtt tttttggggg ggttgaagga  70260
attgttccca gttgtggtgg tggttacatg aattaataac atgttaaaat tcatagaact  70320
acacacctcc caaaaaaggc cagtttgact gtataacttt aaagattaaa taaaaggaaa  70380
aaaattccaa ccagactata gttgtattca actagatatc actgggtaaa gatatattga  70440
aaataatatc attaaaaata aaaattagag gtattttttta ctgaggtgct tctttctttc  70500
tttctttctt ccttccttcc ttccttcctt ccttccttcc ttccttcctt ccttccttcc  70560
ttccttcctt ccttccttcc ttccttcctt tctttctttc tttctttctt tctttctttc  70620
```

-continued

```
tttctttctt tctttctttc tttcctctct ctctttcttt cttttttta tttttttttt  70680
gacggggtct cactcaccca ggctggagta cagtggtgca atcttagctc actggagcct  70740
caagcttccc aggctcaggt ggtcaatcat cccacctcag cctcctgagt agctgggact  70800
agaggcatgt gccactatgc agctaatttt ttgtattttt tgtagagatg gggtctccc  70860
tacattgccc aggctagtct tgaactccag agctcaagcg atctgcttgc ctcagcctcc  70920
caaagtgcta agagtatagg catgatccac tgcgctcagc tacttactta gtttttaata  70980
caaccacatc aaacaaataa tgattgatta aatgtccttc accatcaagt aatataaaac  71040
tgtatttccc taccctttta tttagattca ccaaacacac attacctttt tatttttcag  71100
atggcagcag ataaaataac tcaagttcct taaaaaatga tcacatttca agggcaacca  71160
cctgccttga agctgttatc aaactcaaga aagtcatact gcctattttc atttgttttt  71220
tagtgctatt acccccaaaa atcagtaacc agcctccact attacaatca ataaagatta  71280
ctgaaatatt tttcaatgat atgaaaaact gcaaaatttt aactttgatc atcttcccag  71340
tcataaacat ctaaacaaat aataaagttt ttggcacttt aaaaaagctt ttcagtattg  71400
ttatttcttc cacccaaaac aactctttta tataaaatac ctacctatgt actcaacata  71460
catttttatt tatggtacac caatcatcta cttatgttat atgaagcaac tactaaaaaa  71520
attcaatata gtcttttatt gaactcaaat gatgaacaac tcagtaacat aaaacagggc  71580
tatttatttt tattattaaa catgagtact tctgaaatat gacatttcat ggtacataaa  71640
atgatgtgta tgacaaaatc tgttgctaac tccaaatatt aacttaatat agcttagaaa  71700
aatgacataa tatactctgc atttttctga ccattctatt tttacaagta ctccagttat  71760
atttagcatt caatttaaaa gacaagtgca ctgaaagaat ttgagttata atataattaa  71820
ccaaatatta tataacatac acacttaaat gactgttgtg tttattgatt tagcagtatc  71880
taaagcacac tatgctttca gaaatccatt aggctactca gcgttatcca tttcaggggc  71940
cccttatgaa aactcagaac tgtttgctat gccactgttt tttcagaatt ctaaagtttg  72000
aaggtcatgg cctaaaatca ttttataaaa agacatcata cctttgggtt tttgtaagtc  72060
agctatggca tatctattct ggtacttatg aatattaaat gatttgtctc agatcctcac  72120
ataaaaccac tgctcttgac caaaatgtca ttagaaatta atatttttct ctttaaaaaa  72180
gtggaaagct atttaaggaa aagggaatat ccctgtcatc cttaatcaga agtgttacta  72240
actgtacttt ggtgataatg ctaacgttac cctaattaag ggagtgactg ccaaagtaac  72300
tcacagcctt catgtatttt ttttaatcac acataacata tgtgttttgt tgccgttttt  72360
tttttttctt tttgagacag gttgactcca gcagccttgc tctgtcaccc aggctgctgg  72420
agtgcagtgg aacgatcatg gctcactgca gcctgagcct ctcaagtagc tggaaccaca  72480
ggcctgcacc accacactcg gctaattttt tgtatagaca gggtctcgct atgttgccca  72540
ggctagtctc aaattcctgg gctcaagcaa tcctcctgcc tcggcctccc aaagtgatgg  72600
gattgcaggc atgagccacc gcacctggcc aacataagtg tttttaaact aaggaaacag  72660
tcattctgga aagtctaatt gaatgtgggt aaaatattct ttgctggcca aatctggctt  72720
tgaacaagac tacaatatct gatagaagaa cagagtggtc aggccagctg tgatggctca  72780
cgcctgtaat cccaacactt tgggaggttc aggtgatctt gaggccagga gtttgagacc  72840
agcctgagca acatggcaag acagtctcta caaaataaaa aataattagc tgggtgtggt  72900
ggcatgcacc tatagtccca gctacctaaa aggctgaggc aggaggattg cttaagccca  72960
```

-continued

```
ggagttcaag gctgcagtga gctatgattg caccactgca ttccaacctg agtgacagag  73020
tgagaccctg tctcaaaaac aaaaacaaaa acaaaaaaaa cagatgatca atcagatcat  73080
tttagccaat ttactaattt atttccattt ttttctggga aaatactgga caacagatac  73140
cagccagcca tgatgtgaaa tgtgaaatgc caacctgcat ttcaagtaag tgtaggagtg  73200
aggataggca tatagacgct tttgaagttg tagagaatat tatatataca tataaggaca  73260
ttaactagac taatcattag cataaactac tataatcctg taaggataaa catcgatttc  73320
catctacttt gctgttcaga atagcagaga gataattatt gaaaagggtc aagtaagaag  73380
ctaaaatcat cttctctctt gtctatacaa atatatatac aaatatatat ttgagcatat  73440
ttctgaaaga aatagaaatt atatttctag gaatttgtcc taaagcaata ttctagaagt  73500
aagaaataca cagagatatt cattgcagta ttgtttatta tagtgggaaa ggtagaagca  73560
atctcaatgt ataaaaggga agtgttgggc caggcgcggt ggctcacgcc tgtaatccca  73620
gcactttggg aggccaaggt gggcagatca tgaggtcaag agttcgagac cagcctggtg  73680
aaaccccgtc tctactaaga atacaaaaat tagccgggtg tggtggcgca tgcctgtaat  73740
cccagctact cagaaggctg aggcaggaga actgcttgaa cccgggaggt ggaggttgca  73800
gtaagccaag atcgtgctac tgcattccag cctgggcgac agagcaaaac tccatctcgg  73860
ggaggagaaa aaaaggaagt gtttaattaa attataacat ctcaaaatga aatattaatg  73920
atttttattt tatattaaat aaaacattaa attaaattaa atcattaaat aaaaaattat  73980
taaaaccaca atagaaagca gtataaaaat tgcatatgcc ctctaattag gagtctgtaa  74040
aacacacttg ttcaattttg aaattagtgt ttgtgaaaat agaaacatgg atgttatttt  74100
ttctctgttt caaaaacaac agactaatga caagttacat tgttcataca gaagaaatgc  74160
ttagaacatc tgagtttcca aagacaaaaa aaagaaaagc agtcataact agcactgata  74220
atttttcaca cgcaaacgct atctttcaat aactggtagt caaacaaatg gtgacacaag  74280
taccacagga aatgctttcc ttacatcagt tcactagtcc catctgttgt actttggcag  74340
cagttaattt caaataatgt agagctgatt atgttcctgg ttaggacgga agacaggatg  74400
gtaaatggga aagaccctgc agatattggg aactatcaat gaacaataaa acctttcaat  74460
ttccaaaagg aaatgatgtt taaaactcag ggtcacttgg gctctaagca gatgaattat  74520
attactatac tccccggtat gggacattaa ccaattcaat tcattatatg aacctgtcag  74580
cataaaagga atttatactt ggattatttc aaaggagatc gactggctag acttgcaacc  74640
tcaatgtaaa actatttatt tatttattta tttatttatt tatttattta tttattttga  74700
gacagggtct tgccctgtca tccaggctgg agtgcagtgg tgcaatctca gcttactgca  74760
acctccacca cctgggctca agtgatcctc ccacctcagc ctcctgggta gctgggacta  74820
caggcattca ccactatgcc tagctaattt aaacattttt tagaggtggg gtttcaccat  74880
gttgtctagg ctgatctcaa actcctgggg ttcaagtgat cctcctgcct cagcctccca  74940
aagtgctggg attacaggca tgagccagta tgccctgcca atacaaaact tttaagtaaa  75000
ggcagaatac tgaaaccctc tcaaatgtta gaatagatgc ttaaaccttt ctacagattt  75060
tttttctacc atttttcaca taatgaagac agcaatcata gccaaattga attgcatgtt  75120
gcaatcaaca aagacttgaa aagctctcat gcgagccaag taagtacatc atgatgggag  75180
ggtggaattc tctcttacta aagcccaaat ccagggtgga tcacttatca attaaattag  75240
accctgaagc tgcacgacct tatccaactt ggaaatatgt gtttattcaa actcactttt  75300
caacatctct tatttgtaaa aagggtctta aacctaactg agaacgagga tattaaattt  75360
```

-continued

```
ccacacttta attcatgagt tttagcctct aactggatgc caaaactgga atggactctg  75420
acttcttgct agatttttta gttttggcta agccctgcaa aactttctcc agcatatggt  75480
gactttccca gatcttcata taactgctgg tgacagcagg attgtcagaa ttgtgaggac  75540
tccaatacat aagaaattac tgttcaaatt cttttaccat gaaagttcca tcttgttgtg  75600
gcccctgccc agttttcatc ttttgtgctg tccctttgac cagggttcta tttttccatc  75660
tccctgctct tgttgcctga atgcctaccc gactcagtgt aaatcctacc tttcaaaatt  75720
cagccctgct ccatcaagac ctactttgag aaactctgat ttcctctctt tctcttcccc  75780
tttccaaaac agtttctctg agttttcaca gtactgtata catacttctt atcagaaagt  75840
cagctacaaa ctataaggaa aagtgtttta gctgttttaa taagaatgta ttgatttgtt  75900
ttgggttttt tgtttttttt ttttttttta acagagtctc gctctgttgc ccaggctgga  75960
gtgcagtggt gcaatctcag cttattgcaa cctccgtctc ctgggttcaa atgattctcg  76020
tgcctcagcc tcccgagtag ctgggattac agatgtccac cacaacattg ggttaatttc  76080
tgtatttttg gtagagacag ggtttcgcca tgatggccag gctggtctcg aattcctggc  76140
ctgaagagat ccgcccacct cggcgtccca aagtgctgga attacaggca tgagccacca  76200
cacttggcct attgatttgt ttttaataaa tggtatctca gaggcatcaa atccatatct  76260
aaaattttct ccatgttaca aaatcatttt ttcatcaaca tcaaatcttg acaaaataaa  76320
tacagatcat atacctatgc ttagtaatta acagaataga atttggaggt tgggtacagt  76380
ggctcacgtc tgtaatctca atacttggga aggcctaaga ggtaggatcg attgcttgag  76440
cccaggagtt tgagacaaat ctgggcaaca tagtgagacc ccatctctac ttttttttaat  76500
aaaaatattt tttaaaaatc aaaaatttgg aggactagcc gggcgcagtg gctcacgcct  76560
ataataccag cactttggga ggccaaggtg ggcagatcac ctgaggtcag gagatcgaga  76620
ccagcctgac aaacacagtg aaaccccatc tctattaaaa atacaaaaat tagccgggcg  76680
tggtgatggg cgcctgtaat cccagctact tgggacgctg aggcaggaga atcccttgaa  76740
cctgggaggc ggaggttgca gtgagctgag atcgcaccac tgcactccag cctgggcaac  76800
agagtgatac tttgtctcaa aaaaaaaaaa aaaggaagac ataggactaa actcttcaaa  76860
atggtttgaa tactattgta cattttatta ttaggagtat ttagagaaag aagatatttc  76920
cacaaaattt ctgcagacta actttatctg ttgcttgaat tacatactta aagactaata  76980
tagtgcaaca tattcaccaa atgcttggca taaatatatt atggtaagaa aatcactatt  77040
gacaattttt aatacaaaac tataacaaat ttaaaaagga aactgaacag ctctgatacg  77100
tgtaacagtt accacactcc actatgatgt tatttattta cagtttgtct tccctttcaa  77160
ctgtgagccc caaaaggggg agaccatgtc atactcatgt ttgtgtcccc agagctgagc  77220
acagtgtctg gcacataaat gtttgataaa ttaatgaatg agaagataaa taaattccaa  77280
gaataatcct cttagggctt acacctggtt tccactgtac atctgagtaa tcctctccca  77340
cttggactaa ttttactttt gccttctgga atgatggaaa ataatcctct ctcttccaca  77400
taagaacctt ttaattagat gaagaaaata catgtggtga gggggagggg acatcagaat  77460
atgatttagg gcagctgttc tcaatcctga atattagaat tgttttgaca gcttttaaac  77520
aagagtagtg agttggtccc gccccggtct ggttacctca gaatatgtga ggatggggcc  77580
taggcatcgg ttttttttgtt ctggtgtgtt ttggtttgtt ttgttttttt tgagatggag  77640
tctcgctgta tcacccaggc tggagtgcac tggcatgatc tcgactcatg caactgccgc  77700
```

-continued

```
ctcccggatt caagtgattc tcatgcctca atctccctag tagctgggac tacaggcacg  77760
tgccaccacg cccagctatt ttttgcattt ttagtaaaga cagggtttca ccatgttggc  77820
caggatggtc ttgaactcct gacctcaggt gatcctcctg cctcggcctc ccaaagtgct  77880
gggattacag gcatgagcca ccacaccttg tccagcatca gtttttaaag cccacaggtg  77940
aatccaatgt gcagccaaga tttcaaacca ctgagttggg ggaactaggt tctatgccag  78000
cctctgcaaa taactctccc tcccccttagg cattttactt caggtctctc agtctgtatt  78060
tccgcatcta taaaacgagg gtagcacctc ccttcatttt acacagttgt taaaatctaa  78120
ggagatcatg tacagtcaat gctctgaaaa agttgaaatt gctaaataat tgttatgaca  78180
ttaaagatac tctttccatg tatagaccag atcaccaaca agaaagggaa tttttcctga  78240
tggtcataca acaaagacct gactagataa aagctgggag agtcaggggt ggcataagcg  78300
aggtttgagt taaacacaag cttcacttga gccaacactg ttttcaaaag ctaatgcaat  78360
cttagaatgc atcagtagaa ttccagtgtc agggacaagg gaggtaataa tcccatttat  78420
attctgcaat ggtcaaacta taactggaat atcctgttca gttccaagta cctcatttta  78480
agaagccatt aagagactag agtgtgtcca gaagaagatg atttgactaa tctggaaatc  78540
atgtcacatg aaaaatggtt aaggaactgg ggatgcgtgg cctacagaag agacgggtgg  78600
gaagggggag ctgtcttcct aagactgaag ggctgtcatg tggaagagga agacctattc  78660
tctattatac cacaagcaga aataggaagt tactggtatg cacaaagcat aataaagaac  78720
tttgataata tgtcactcaa acagtgtgca tcaaaatccc tggatgtgct cactttatat  78780
aaagattcct ggggcagggc gcggtggctc acacctataa tcccagcact ttcaggggct  78840
gaggcaggtg gatcacctaa ggtcgggagt ttgagaccag cctggccaac caacatggtg  78900
aaaccccatc tctactaaaa atacaaaaat tagccggtcc tggtggtatg agcctgtaat  78960
cccagctact ggggagggtg aggcaggata attgatcgct tgaacccagg aggtggaggt  79020
tgcagtgagc caagattgtg ccactgcact ccagcctggg tgacagatta agactctgtc  79080
tcaaaaaaaa aaaaaaaaaa aaagattcct ggaatccatt tctaaagatt tttccagagg  79140
tctaggatat tgccctggaa tctgcattta agcaagctcc ttgggtgact ttacggactc  79200
cttttataaa aaataatata atctttatta aagatttgtt gtaacataat tcacgtacca  79260
taaaattcat ccacctaaaa tataattcaa tggcctttag tataatacat tcacatttca  79320
gaacattttc atcacacacc cccaccctac tgcaaaaaaa aaaaacaaaa atcctgaacc  79380
cattagcagt cactctccat tttccccaaa tctcccagcc cttggcaacc actattctat  79440
tttctatatt tatagatttg cctattcttt acatttcata taaatggaat catattatgt  79500
gaggtctttt gtaattggtc tctttctctc agtatactgt tttcaagggt catccatatt  79560
ttaacatgtg tcaatatttc attcctttta ttgctgaata aaattccttt gtatagctag  79620
accacatttt atttatctat tcatcagttg atggacattt taattgtttt cattttcggc  79680
tattacgaat aatgctgcta tgaacattca tgcacaggtt atacagacat gtttccatcc  79740
cccttgtgta aatatctaaa aatggaacag ccgagtcaca tgttaactct atgtttacca  79800
tctagaggaa atgctagact gttttcctag atggctgcac cattttacat tcccactagc  79860
aacacatgag gattttaatt tctccacatc tttggtgcca cttgttatta tgtatttctg  79920
attatagtca tcctagtggg tgtgaagtgg tatgttcatg tagttttaac ttgcatttct  79980
ctaatgggta atgacgttga gcatcacatc ttttaatggg cttattggcc atttgtatat  80040
cttctttaga aaaaaaatta tccattttga gaaacaatga tattgccaga ttagtatgga  80100
```

-continued

```
caatagaggc cagacatggt ggctcatgcc tgtaattcca gcactttggg aggccaagga  80160
gggaggactg cttgagccca cgagttcaag accggggcaa cagagcaaaa tccctgtatc  80220
tattaaacaa acaaacaaaa aaagcacaat aatgcaaggg atagaaaaac atcaaatgtt  80280
taagtccaca agttcatact cttacaaaaa ggaaaattat cactagagga tgttggcaaa  80340
ccaattcatt attttgaaaa ttgcttaata taaggagaaa tgcaaacatt tatcctgatt  80400
tctcatatgt attctacacc taggtaagca aatggctgat gagagaaaac ttcactttaa  80460
gtaagtgggg ccaggtgcgg tggctcatgt ctgtaatccc agcagtttgg gaccccaagg  80520
tgggtggatc acctgaggtc aagagttcaa taccagcctg gccaatatgg tgaaacccca  80580
tctctactaa aaaacacaaa aattagctgg gtgtggtggt gcgtgctgta gtcccagcca  80640
cttgggaggc tgaggcagga gaatcgcttg aatcctggag gtggaggttg cagtgggccg  80700
agatcatgcc actgcactcc agcctgggcg acagagccag actccctctt aaataaataa  80760
ataaataaat aaataaataa ataaataaat aaagtgggag aaaatcttca caatctatac  80820
atctgacaaa ggactaatat ccataatcta cagtgaactc aaacaaatta gcaagaaaaa  80880
aaaaacaatc ccatcaaaaa gtggcctaag gacatgaata gacaattctc aaaagaagat  80940
atacaaatgg ccaacaaaca tatgaaaaaa tgctcaacat cactaatgat cagggaaatg  81000
caaatcaaaa ccacaatgtc ataccacctt actcctgcaa gaatggccat aatcggccag  81060
gcacggtggc tcacgcctgt aatcccagca ctttgggagg ccgaggcggg cagatcacga  81120
ggtcaggagt tcgagaccag cctggtcaac acagtaaccc ctgtctctac taaaaataca  81180
aaaaaaaaaa aaaaaaaaaa aatagccggc atggtgtggt gagtgcctgt aattccagct  81240
actcgagagg ctgaggcagg agaattgctt gaacctggga gggagaggtt gcagtgagga  81300
gagatcctgc cattgcagtc cagcctgggt gacaagagtg aaactctatc tcaaaaaaaa  81360
aaaaaaaagc cataatcaaa aaaattaaaa aataatacac gttggcatgg atgtggtgaa  81420
caaggaacac ttctgcattg ctggtgggaa tgtaaactag tacaaccact atggaaaaca  81480
gtgtggagat tccttaaaga actaaaagta gaattaccat ttgatccacc aatcccacta  81540
ctgcatatct acccagaaga aaagaagtca ttatacaaaa aagatacttg cacatgcatg  81600
tttacagcag cacaatttgc aattgcaaaa atgtgccacc cacccaaatg cccatcaacc  81660
aacaagtgga taaagaaact gtgatacaca cacacacaca cacacacaga cacacacaca  81720
caatggaata ctactcagcc ataaaaagga atgaattaat ggcatttgca gcaacctgga  81780
tgggactgga gactattact ctaagtgaag taactcagga atggaaaacc aaacatcgta  81840
tgttctcact tgtaagtggg agctaagtta tgaggatgca aaggcctaag aatgacacaa  81900
tggggtttgg ggactcaggg ggaaaagggt gggaagtggg tgaaggataa aagactataa  81960
attgcggctc atgcctgtaa tcccagcact ttgggaggcc gaggtgggca gatcacgagg  82020
tcaggagttc gagaccagcc tggccaacat ggtgaaaccc tgtctctaaa aatataaaaa  82080
ttagctgggc acagtggtgc gcgcctgtag tcccagctac tcgagaggct gaggcaggag  82140
aatcgcttga acccaggaag cggaggttgc agtgagccaa gatcacaccg ctgctctcca  82200
gtctgggtga cagagtgaga ctctgtctca aaaacaaaag actataaatt gggtgcagcg  82260
tatactgctc agatgatggg tgcaccaaaa cctcacaaat caccactaat gaacttactc  82320
atggaaccaa gcacaacctg ttccccaata acctatggaa ataaaaaata aaaataaata  82380
aataagtgtt ctagttaata agtgaaagac aaacaatcat tgttttgcaa tctctaccga  82440
```

-continued

```
tttaatagat ttaggcagtg agctttagca gctgcaaaca tcacaaaaag agacaagcag  82500
acattatgtg tgcactgatg aagttatata ccatcaccca tgaagaagtc ttgggaaaaa  82560
aaaaaatcaa acctgagtgg taccaaatca cggtctagag atccaaatat gaatttacag  82620
aaaatagtga acaaagaaaa aatatattaa actatatcat gaggatgaaa taagcaaaat  82680
ctagactgca gaaaacaaga caaataacca attttcttcg acaaataaac tgcaaggcag  82740
aaagtttgtg tgtggcggga aagaattata gtttaaaaaa catggccggg cgcggtggct  82800
catgcctgta atctcagcac tttgggaggc cgaggcaggt ggatcatgag gtcgggagat  82860
caagaccatt ctggctaaca cggtgaaacc ctgtctctac taaaaataca aaaaattagc  82920
tgggcatggt ggcaggcacc tgtagtccca gctactcagg aggctgaggc aggagaatgg  82980
cgtgaacctg ggaggcggag cttgcagtga gccgagatcg ctccactgca ctccaacctg  83040
ggcaacagag caagactccg tctcaaaaaa aaaaaaattc gcacaattat aaaaattgga  83100
aatttgaata ctgccaatat atttaattat attaaataat tattgttaat tttaaaagat  83160
atgattgatt gtggttatgt tttaaaagga gtactcatct tttgatatat acttaaatat  83220
ttatagataa gataacatgt aatggattta cttcaaagta atatgggaat aacatgggaa  83280
agagaaaaga aggtagaagt acaaatgaaa taagattagc cacgagctga taattgtcga  83340
acttgctgat gggtacataa gggtttatta tgtgattcac ctactcttac gtatttttac  83400
aattttccaa atttgttata ataagttttt taacaaaagc ttgtcaaaaa tgaaataggg  83460
tatattgaat gattatgatc actggctgtg atcaagaaga aactgatagc ctttcatgat  83520
agttcttgta atgtaaatga cacacaagaa tttttcttc caatgctagg aagctattaa  83580
aatcagcagc gttttaaaac aggcctagct aaatcacctc aattcaccac ttagttttgc  83640
agatagaaac tttgagactc aaaactgttt ataaacaact aatattaatt cagtttcctc  83700
agaagtaaat atatttgttt aaaagactta cctctaaggc acacaaatta atcaaatgag  83760
aaaatgcatt taaaactttt aagtgtcaaa tgcaattcac ctctaaggtc cacttactgt  83820
tagtatgagc aatattttta tcatcaaatg atatacttga tgagacaagg gggtaataca  83880
ttttctggga ttaacaacta atatctgttc cctcaaaata tatgcacaaa tatactatct  83940
aattgagcag aaaggttagc gttatcagaa agagagaaac agaaaaaaac tcttaccaat  84000
ctatgtttag ccaaaaaaga ttttgtatga tggcatagag taaaactaca agtaaacaaa  84060
acagaaacaa aagagtatga caattcacgt aatgagtacc aacaaatcac tggattattt  84120
tctagagaga agaaagaata tgtgcagaaa atattaactg gttgatggat gaggcaagtg  84180
aaataatagt tataatgcat tatctacaac acatgcataa acttaaccaa atccctcaac  84240
ttcattacta tagtattcaa cactacagta ttaacggttt tactttctta ttaatgtact  84300
ccattatttc ttgtttttgc attccaaact aaatttttta aaatttgcac tagttttaca  84360
gaattgctta gtaaaaatct cctgctggaa aaatgttgaa agaatgtgga gcaattcttt  84420
gacactcctg gtagaaatag aaattggttc aaaaaccttg gaaatcaatg tggcattatc  84480
cgattatgct gaaaatgcat tatattagtt tcctgtgcct actgtaacaa atcaccagga  84540
attttgtggc ttaaaacaac agatatttac tctctcacag ttctggaggc tagaagtctg  84600
aaatcggtat cactgggctg aaatcgaagt gtcggcaggg ctgcactccc tccaggggct  84660
ctagtaaaga atcggtttct tgcttcttcc agcttctgtt ggccaacagc attccctggc  84720
ttgtggccac ataactttaa tctcttcttt gtgtaatctc tctctgcctc tgtcttatgt  84780
agacacttat gattccattt aaatactgat gattccacat ctacaaagac cctttctcca  84840
```

-continued

```
tatgtgttag gccattcttg cattggtata aagaaatacc tgaggccggg cacagtggct  84900
cacgcctgta gttctacttt gcgaggctca agtgggcaga tcactggagg ccaggaattt  84960
gagaccagcc tggccaacat ggtgaaaccc catctctact aaaaatacaa aaattagcta  85020
gacatggtgg tgcgtgcctg tagtcacagt tactcaggag gctgaggcag agaatcgctt  85080
gaacccagga ggcgcaggtt ggagtgagcc aagatcacac cactacactc cagcctgggt  85140
gacagagtga gactctatct caaaaaaaga aagaaagaaa gaaagaaaaa agacatacct  85200
gagactcggt aatttataca gaaaagaagt ttaactggct cacagttctg caggctgtac  85260
agaaagcatg gtgccagcat ctgcttggct tctggggagg ccttacggag cttttacttg  85320
tggaggaagg tgaagcagga gcaggcatct ctcacatggc agagtgggag caagagagag  85380
ttaggaggag gtgccacata cttttaaaga aacagatctt ctgagaactc actcaccagt  85440
gaggacagca ccaagaatac gcccctatga cccaaacacc tcccatcagg cccaaccccc  85500
aacactgggg attataattc aacgtgagat ttggtaggga catatattca aactacatca  85560
ccatatagga taacatttac aggttgcagg gactagccta caatccatca atccactcct  85620
aggtaattcc ctatagaaat tcttgcacat gaacaccaca tgacacgaac aagaatattc  85680
gtagcaacac tgtttataat atcaaaaagt ggaaacaacc caaatatcca ccaacaggag  85740
aatgggtaca ctgtgtcata gttatataat ccaaaattat gcagcagtga aaataaatga  85800
agtatagtga cacatatcaa cacacaagaa tcatgtaaca catgcagggt ccaagaaaat  85860
gcaagtcaca aaaaaataca catgacatac tacatttata taataaagtc ttaaaacaca  85920
caaaactaaa ataagcccta tattgtttag ggctatatgc ataatatgat aaaataataa  85980
aagcaaaaga aaaacaaaat tcagaagggc agtttcctat gtggaagaga gggagtgttg  86040
gtcttgtaca gctgaccagg agctttaaag gtactagtaa gggtctatat cttaactgga  86100
tggtaggatc acaggaaaat aaggggtgtg tgtgtgtgtg tatgtttgtg tgtgtattta  86160
aaatggctac tcaaaagata gagatacaca aacatgcaca tacacatcca ctcagacctt  86220
ttaaatacag acagtccctg acttacgatg tgcttacatc tagataaacc taccataagt  86280
ggaaaatgta aactgaaaac acactttcag ccaggcacag tggctcatgc ctgtaatccc  86340
agcactctgg gaggctgagg caggtggatt acctaaggtc aggagttcga gaccagcctg  86400
gccaacatgg tgaaaccccg cctctacaaa atatacaaaa attagccagt catggtggta  86460
cacacctgta atcccagcta cttgggaagc tgaggcagga gaatcgtttg aacccgggag  86520
gcaatggttg cagtgagcca agattgcacc actgcactcc agcctgggtg acagagtgag  86580
actcaaaaaa aaaaaaagaa aagaaaactc actttcaact tacagtattt tcaatttatg  86640
atgggttttt caggatgtaa ttcatcataa gtcaaagaac atctgtatat gatataatta  86700
ataataaaaa attgtaattc ctattggttg ttattccagt actggaaagc agactaagat  86760
caccatcccc actgctgata agcacgaaat ggtttctcta gagatgtggc tctatcactg  86820
tataatgaaa gtattcccaa tgcaaggtgt gatgagccca agtgcttcac atttttagaa  86880
acagtgtgag ctgatgcaca agctacactt gggatgatgc tgcaatcagc tctgcctctg  86940
gaaggagcta ttgcttgtct gggagactaa agcctagacc aggagctctc ccattgaggt  87000
aggagggaga aactgtcttc caggtggcat ctggcaaggt ctagagatat ttttggttgt  87060
cgcaagtata gacgagctac tggcatctag tgggtagaga ccagggatgc tgcttacatc  87120
ctacaatgca caggacagcc ccacagcaaa gaatgatctg gctcaaaatg tcaatagtac  87180
```

-continued

```
tgaggatgag aacgcctggt ctatagtgac cccttgatag agtgtgtgca gtaaggctaa  87240
ctattgccat atgacattaa gtacaacaat accatctctc ataaaagata tagaaagccc  87300
ctgtttgcaa aatttatcaa tcctcagaat tgtgcatagg aacgattcta ttcatgtgcc  87360
gaatttgaca aattttatat ataattatta ggtaccagaa ggatgctgat agactgcatg  87420
ctcaagggtg ggatttaca ttaattcatc tttatacctt ctgcattcaa acctcaatgt  87480
gtcttgaata gtttctcctg aaatgaggca caaaacacaa tacctggcac aaggtaagca  87540
ctcaataaca tttactaata ttatttttaa aaatcttttt cgaattaact ctaaactctt  87600
gtcagtatag cttatagctt tgtctgtttt gctcaccaat gtatcacaag tgccagagaa  87660
cttggcacat aatagatgct agacaaatat ttactgaatg agcagcagat taaaaatgct  87720
acctgtcagt gcacatacat taaaaatgcc acctgctagg gaacatacat gctcccccaa  87780
acaagacaaa caagctacag aaggagcaac agacacaata aggcaccact tccaaatgca  87840
ctcccaggtc agcacttctg tttgagactt ctgacccttc acctttttta agatcagagg  87900
cattaacctg tgcctctaaa cctgtggttt gtaactgttt ggctgaatgt gaatatgcac  87960
ccagtgacta ctcaataaaa attcccaata actatggctg accactaagt ccctctaaga  88020
aacataagaa aggttaccta ttttatgcca ctgaatcttg cccttcctgt caattcctgc  88080
tcacagctgt gcctgactaa ttaaaactcc ctggaaacct cgtctatcgc tttacgggtt  88140
atttcttctg ctacatcaaa agactccact ttagaattca aatccatctg tctccctcag  88200
tctgcaaaga acaaatgttc agaaaaacta accgactagc taaaattaaa tgtacctttc  88260
ccagctaaga cttaatatgt gttgggggca gggagcaagc aatctaagga taaaccacta  88320
aaaagaagat aaaacaaagc ttaaccatat gagatagtac ttagatagtc attcaactcc  88380
catcttagca gaccagggac aaatccagaa attcttggtt gaaatggatt tatatccaaa  88440
ggcaaaattt tctggtgaag ctaatatatg acaaacattg ctcacccaaa ataatatgac  88500
tctagacccc aaaggtttgc tcatccattt tcctctcatt tggacctcag agagcctaaa  88560
ttggctcata acctatagct tcactttttg atatatgaaa tgatttattg ttgaaggcta  88620
actattgcca tctgacatta agtacaataa aatctctcac aaaaggattt attgttgaac  88680
tattggtcct atcccatgat cagaaaaaca ctaaaggccg ggcatggtgg ctcacacctg  88740
taatcctaac accttgggag gccaaggcaa gaggattgct tgagcctggg agttcaaaac  88800
cagcccgatc aacacaggaa gaccctgttt tcaacaaaaa aattaaaaat tagccagttg  88860
tgatagtgca tgcctgtagt cctacaggct caggaggctg aggtgggagg atcgcttgag  88920
cctaagagtt tgaggctgca gtgagcaatg accgtaccac tgcactccag cctgggtgac  88980
agagtaagac cctgtctatt taaaaacaaa caaacaaaca aaaaacaata agaaatgtaa  89040
tctagttttt atgacctttc tttggaacct ataacttcaa acttctaaga attgtttcaa  89100
ttattgaagt aaaatatata aaattgcctg atcttaatgc tgcttttact atcgcatctg  89160
agttacagtt ttgcctagaa gtaattacag gatgaataca cgaaaatatt ctagaacact  89220
gaaaaaaact ctagtgcaaa atggatttta agcaagaagt tgcctctgtg agatctgatt  89280
aaatttttgc tgccaaaacc acgtatgcca aattatgcca tgtcatacct atcttctgtg  89340
atgtcacaag acatctaaag ttcaacttct ctttccaata tgctttttca ccaaagaaat  89400
cctttcccta gtaagcaatg taacagttaa aatgaagcat aaatcacaac caaaaaattt  89460
tacttcttag aaagttcctt caaaaacact gtaatttatt acactgatgc acatgtaatt  89520
tacaacactc tgtaacactc agaggttact agtaaaatga aacaagtttc cttcttttat  89580
```

-continued

```
gttcaaaatc atataactgt acaattttag aatttcacaa aaactcctaa agctacagca  89640
aaatcacctc caaagacatg tcaaatcttt ttttattaca ctggaaatct gctgtaccaa  89700
atataacaga aaataaatgt acaaccactt aggcttaaac atatttttgt tacataaata  89760
tgttgtaaaa ggtttaacct gcatccttga tgtcccacag cacataggta gcattctttc  89820
aaaactatcc ttcaaattat ttgacattct atttctttga acactatttc taaataaatt  89880
aattaaacag caggttccaa atgcaattca acaagcttta tgtatgacat ggcttctgat  89940
gtacaaagca gtaatatgca ctgcaaggat taaaaaacat ttgaaggtac aaaaatattg  90000
aacactgttt gtattagaga aaaaactgag gctgtgcatg gtggctcagg tctgtaatcc  90060
cagcacttgg ggagaccagg gagggaggat cacttgaggt gaggaatttg agactagcct  90120
gggcaacacg gcaagacctc acctctacaa aaaaaaatta aaattagctg ggcatgatgg  90180
tacaagcctg tagtcttagc tacatgaaag gctgaagtgg gaggatttct tgaggccagg  90240
agttcaaggc tccagtgagc tatgatcacg ccactatact gcagcctggg caacagacag  90300
agagacccca tctcttggga aaaaaaaaag tgaaatcaac ctaaaatatt taccaacagg  90360
agaagggcta aatcacctgt gaggaagtta aaaaataaag aggctgagtg atatacatgt  90420
gaataaagct gaggccagat attgagtgaa aaaaacaagt tgcaaaaata tgcatataac  90480
aacattgatg tttttaaaaa gacaatactg tatgaatagc tccgatgggt agcatcttca  90540
ggttttgtga ctgaacaagc taagagttga gatgaacttg cctggaggac gccaactatg  90600
gcagggagga aaatggaatg ggttttgaat agggcttaat gtgaatccta aatctctctc  90660
cacaaggctt cctaaggcaa gtctgtagat catttaacaa cttttagtaa taaattttga  90720
tttccactca tttaaaactg taagggacaa cttttagaat tttaactcca agtatttcca  90780
acccttaatg gctttaagga gaaaaatcaa caacaactac agaaatatcc tagaatgtcc  90840
tgttttagca aaacactaaa actgaaaacc aaaaactgca ggggggttat aactggtcct  90900
ctggtttctg taacaattca gatgagtgtt atgcataaag aacatgacct ggtaaaccgc  90960
cacactataa gaaactaaac aagccatcca acacttctgt tcaaaataca aactccaaaa  91020
ctagcttaac tcagagctca caaaaaggtc aacagggcag aggcacataa gtatgaatac  91080
agaagaggat agactggggg gaagatggca gtaggtctct ggactgtctt gagtttttcc  91140
tatcacatat aaaatgtttg gattaagaaa aaaatcaggg ccagatgtgg tagctcacac  91200
ctgtaatccc agcactttgg gagcctgagg caggtggatc acatgaggtc aggagttcaa  91260
gaccagcctg accaacatgg tgaaaccccg tctctattaa aaatataaaa taagccaggc  91320
gtggtggcgc atgcctgtaa tcccagctat ttgggaggct gaggcaggag gactgcttga  91380
acctgggaga tacaggttgc agtgagctga gatcacgcca ttgcactcca gcctgggcaa  91440
tgagaatgaa actccgtctc aaaaaaagaa aagagaagag aagagaagag agaagagaag  91500
ataaaagata agatcaggct gggtacagag gtgcatgcct gtcccagcac tttgggaggc  91560
caaggcaaga ggatcacatg agcccaggag ttcaagacca gcctgactag tatagtaaga  91620
ctccatcttt taaaaattgc caaaaatagt agggtgtgat ggcatgtacc tgtggtccca  91680
gctactcagg aggctgaggc aagaggatta cttgagccta ggaggttgag gctgcagtaa  91740
gccatgatgg ccctgctgca cactccaacc tgggtgacag agcaagaccc tatcccctac  91800
caaaaaaaga aaaaaaaaaa gtgtgatgga agaacaaggt cagaagaaga aaaaagaaga  91860
aaaaaaccag gacaatgaaa cgatatgaaa acaataaaca agactctaac tcctgtctac  91920
```

-continued

```
aaaaacaaac aaaaccaacc aaccaaacaa gcaaacctta atagtataag aaacacaaaa  91980
gtaaatacca gaataagcaa ttagaggaaa attagtttac aagagaaaat taactatata  92040
ttaattatat tatggcattt gttacagagc ctggaagtaa attcatgaaa taatgaggtt  92100
cgagtaattt atcttttctt ccttttgctt tttcaaattt tgtcaggtga gtatgtatgg  92160
cttttgtaag atgctatttt agaaagaaca ggaagtagct ggccaggccg gtggctcacg  92220
aggtcaggag atcaagacca tcctggctaa cacagtgaaa ccccgtctct actaaaaata  92280
caaaaaatta gccgggcatg gtggcgggca cctgtagtcc cagctactcg ggaggctgag  92340
gcaggagaat ggcgtgaacc cgggaggcag agcttgcagt gagcagagat cgtgccactg  92400
cactccagcc tgggcgatag agcgagactc cgtctcaaaa acaaaataaa gaaagaaaga  92460
agagaaagca aacatggatc tttcctgaat gttctggagc tatggctcaa gaactcacag  92520
gaagtctggt agttaggaga aacatttacc aaatgtttat gatgtgctgg aataagaagc  92580
ttccattcgc tatagtcctt aacctggaaa accacagcat gaggtagcta aggagtgcga  92640
ctgccccatt tcacaggtga gaaaactgcg ggtttagaag gttaacccat tggccaaggt  92700
tacctcactt gtaattggtg tactagaatt aaaaggcagt ctctaaactc agagcccact  92760
ttgtgaacca cattacctgt gtttctcaca cacacctgat aagaatcacc ttgagcactg  92820
gtgaaaaaat catattcccc ctatgccttc tgccagagat cctgggaatc tgcatgttta  92880
acaggcatcc cagaaattct tttctctctc tccttttgtt tccttttctt tccctcccct  92940
cagatcactt tggtacatac cagcaattct taccaggtgc agcttgagaa actctgccca  93000
ccctcgactg ccactcaaac tttttattta ggatgaagcc tattactaca tataaactgg  93060
ctctcattgc aagatgagct atttaaatgc cagatactgc actccaagac aagcacaaac  93120
aaaacctaga ccatctatag ttgaagctac tcttggcttt ccagagagag agagaaattg  93180
tcactttata acataaatca ggaaagattt ttgtgttgag gctgccatag ttcttgaatt  93240
tctccagccc cgacagttgc tctgagagtc atattttccc cagccagaac tcagtggtgg  93300
ggaaaggagc agggcaatat gttgagtgac cactctattt gattgctctc ctttttttaaa  93360
atacgagaaa aggagacaga atttcacatt cctaaatcag agctttccta gctcttaatt  93420
atcaattatt atcaattatt tggattagta tttcatatat ccatatatac tggaaatgtt  93480
ggtgcccaag gcaaattgga gaattcatgt ccctcctaaa ggtattcaaa gtatttttga  93540
aaacctctgc acatcaaaca aaatctgtgg gttgaatctg gccttctaac tacagtttgc  93600
aattcctctg gcctcgactt ttcatgtttc tttttcata aatatataca tttatcatat  93660
aaaatatata tttatatatt tcaggaagga ggagcaaatg ttgaataaaa aatatctgat  93720
gataaatgag ttggtgtctg tcaagcaggc tctttgaaaa aggagactca gccaggcatg  93780
gtggctcatg tctgtaatcc caggactttc ggaggccgag gtgggtggat cacttgaggc  93840
cgggagttca agaccagcct ggccaacacg gcaaaaaccc atctctacaa aaatacaaaa  93900
attagccggg tgtgatggag cacgcttgta atcccagcta cttgggaagc tgaggcataa  93960
gaatcgcttg caacccggga ggcagtggtt gcagtgagcc aagattgcac cactgcactc  94020
cagcctggga gtcagagaga gaccctgtct caaaaacaca aaaaagaaag aaaagaaaac  94080
agagactccc ggattgggaa gaacctagca attgaaatac aaagccaggg aaacttaagg  94140
aatttacttg cacttcagtt acctaatatt aaccatcaat atgcaaatat catacgtcag  94200
aaccctagtg gagctatgat tcacaacctt tcttctattc caacatagct gagaaagaca  94260
tcacactctg tggtttccta aagccaagat gctcagggca gaaggagatg gggccccat  94320
```

-continued

```
ggcaggtggt aagaactgct gatttagaac ataaggacag tatgttagcc caagctgtgt  94380
ttgctctcat gccaattgct tgccagatga actgtacaca cattccattt atatggatga  94440
cgtgtaacag gacaatatac agaattccat gcttgagctt tttcaggctg tcacctcatg  94500
ggctctgcct ctatctttgc cccagtcttg agcagaaata gttcgcttct gagtctggat  94560
aggccataga gatctaccat aaaatagcag aacaccatga acttttataa tctgaacatt  94620
ttaaagacca agcattctaa ttgcaggtgg aaaaacttaa aaaattttta aatttaatca  94680
aatcgctgca gcacagagaa aagttatggt tgatattaag aaataaacta gattaacaca  94740
agagtagttc tacaagggaa tgcattagga ggagcatata ctttatctgg gtaaccctag  94800
catctttcta tttttataag cgacctctaa agcaagaggt gagaaaccta tcaattttat  94860
agttgagaga aataagcctc accaaacaga ctctactatg cccttgaaat aggttttaga  94920
atgctcctga atgttgtatc aaacagaact atagatggaa aacttaaaac ttatattcac  94980
taaaatatta tgtggagcat aatcctattt ttataaaaaa tgtgggccgg gagatcatgc  95040
ctgtaatccc agcactttag aggtcgaggc agatgaatcg cttgaggcca agaatttgag  95100
accagcctag caacatagct agaccctgtc tctataaaaa aaaattaaaa gatgagctgg  95160
acacagtggt gtgtgcgtat agtcccacct ccttgggatt gcttgagcac aggtattcga  95220
agttgcagtg agctatgatc acaccaccgc agtctagcta gcttgagcaa caaagtgaaa  95280
ccccctatct tttggggaaa aaaaagtgta tattagcaag aaatgaaaaa atatataaat  95340
aaataaaagt gcatgcatag gttttatata taaacctatg tatgtatata tactaagcat  95400
ttatatatct agagagagga agaggaggag caggttcaaa atcttaacag aggaattatg  95460
gttgattttc atcttctttt tttgttatct ttattttcca agttgtttac aataaacaca  95520
aattgccttt gaatgaggag gagggatatg atatcctggt aaaatactta aaatataaca  95580
ttaggtgaat aaacaggcta caaaacaaaa ataaaatatt tttactactt ttagaaatat  95640
tatgcataaa gaggccaggt gcggtggctc acgcctgtaa tcccagtttg ggaggccaag  95700
gcgggtggat catgaggtca ggagttcgag accagcctag ccaatatggt gaaaccccat  95760
ctgtactaaa aatacaaaaa cttagccggg tgtggtaaca catgcctata gtcccagcta  95820
ctggggaggc tgaggcagaa gaatcgcttg aacccaggag gcagaggttg agtgagccga  95880
gatcgcacca ctgcactcca gcctgggcga cagagcaaga ctcttgctcc aaaaaaaaaa  95940
aaaaaaaaaa aaagaaagaa aaagaaaaga aacattatgc ataaagaaac ctagaagaaa  96000
atacggccaa atcaacattt aaaaattttg ttgcatgtta tttccttatc aagttacttt  96060
ccagtgaaga gtctaattgg caaagataag gcatgctcct ggggaagaag tcagatgaaa  96120
acatctagtt ttgcttccct cttgttatat gaatctcaat ctcatgctga gaacagatgg  96180
caaaaaaaaa aattggcaca gaatgcaact acggcagtac aaatatggtg gtcagcagga  96240
aatacattat tcttaatttc aaccttttcc tggaaacagt gcctggagtg ttatggagta  96300
aaaatgggtg aacaggtgta ggaggatttt atttttggca agggctgaaa gcaaaggaga  96360
aaaattagtt tgatttaagg agcctactta attctagaaa agaaataaaa cagactggga  96420
acacattgaa taattttata tttctgtaaa tgttcatatt ttttggaaag gctatcaata  96480
atatgatatt tttctttttc tttttctttt ttttgagaca gggcctcatt ctgttgccca  96540
ggttggagtg cagtggcaca aacacagctc actgcagccc caaactcctg gactcaagtg  96600
attttcctgc ctcagcctcc catgtagctg gtcccacagg cgcgcaccac catgcctggc  96660
```

-continued

```
taattaattt attttattgt tgagacaggt tcttgccatg ttgcctaggc tgaactcctg  96720
ggctcaagtc atctcgtgcc ttggcctccc aaagtgctgg aattacaggc atgagccacc  96780
acacccagcc atacgatact ttttatttgg ataccaaatg tcttcttaga actctaaact  96840
caaaataaac gtgccattct catgatatgc taaaaggagg taataatcat ttctggggaa  96900
acagtatgtg ttatcagaaa taatattatt ttgtataact tctcttgctt tggcttcatt  96960
gattttagag cagcatcgtc atgttctcat aagcttttaa gtattctacc caagaatctg  97020
cttctgagag gtttaaagta cccatgttgt ttttctttat taaggatatg tactaacgct  97080
acacatgaag ccaatgaagt caaacaggcc ctccccaatc tgtcagtata tttttatcta  97140
acaagtttta gtgttcttgg atgaattcat ttttctaatc ttcaaagaat caaatatctt  97200
tatagtgtcc ctcaagtgag taagacttta tttcatcata agaaaaaata atacaatttt  97260
aaaagcttaa ggttgccagc aagacacacc ctcaatgttc attctccaca tacagcttgc  97320
tctgatttat ggtgccagta cttttggcca cacaattcac tacactttgt tctcctggtt  97380
actggtgtca gtgacagggc taggtcaact ctttggctaa tgtggctagc tcagtagatt  97440
agaaccaaat gcaagtatgg ctcaatttaa attaagggcc cattagtctc cctaaaaaag  97500
agcttaattc catgtcagaa atctactgga gtgtgaatgg cagcatacat catcactttc  97560
attcaaaatg tgtggtcagc ttggtcactg gccacctcgt ttcatattct acagaggaag  97620
acatgtttgg tttgggtaag ggtttatttc ccatgtcttg cagatctgaa gatctgtacc  97680
tagctttctg tgtaggtata tcaaatagcc agtccctgca ctcccctcct gacttgcttt  97740
atcaatgttt tcaaagaatt caaatctctt gcttccaaat agaagcttac tgtaagatga  97800
gcagtccctg tgcacaaagg agacaaggag accagcctca tgatcgcgtc agaagtggtg  97860
gtttggcact atcatctcta accaaatgtg cagggcaggg caggtttgca tctgccagga  97920
cacagataag ggagtatggc tgggcttcct tctcctatct caaaatatgg ctcataacag  97980
catggagatc ttctctaggt aaccaattta aataatcttt taatagtaga aaaccaggcc  98040
agtggtttag gaaacaagtc tgtttaagca agtattccaa caaagacaaa tctataaatt  98100
tccaggtctg tctataaact attcatagtg gctaaataaa tatcatgctt taataaatac  98160
aaatttctag gcaaggggta aaagtgaaag gtgttaattt agtgtgttta gttgtcttct  98220
tgcattaaag ctacagataa atcatggaag atcataaatg actattttta cttttttat  98280
gctacactga ctgacataaa gattttacta ccaaggatgg cataagtacc tacgtagtaa  98340
catagcctaa tagataaaat tactgtcggc atgtttaaaa ggcaaaaatt ctaacccaaa  98400
gtatctcagt catctcagtc actaatcttt ctgttattca gtttcttaat ctttaaaaca  98460
aagacagaat gaatatggcc taccatttcc cttcactttc ctattttggt gttttcattc  98520
aatttaacag atattcagca aaactaccac actatgggta gtgagaaggc tgaggagctc  98580
tcatataaat gcatatgcag ttatagggaa actaataact tttcctatta agaagctttt  98640
gctttttaat tttttaaatt tttttgagac agggtatgct cttgcacata agaacgtttc  98700
aattagatga agaaaatacc tatggtggcg aggaggggac atcagaagaa tatgagttag  98760
ggtagctgtt ctcaaccctg gctgaatatt agaattgctt tgagagcttt taaacgagac  98820
taatgagttg gtctcatccc agtctggtta ccttagaata tctgtggatg gagcatcttt  98880
ttttttttt ttttgagaca gagtcttgct cttgttgccc aggctggagt gctgcagcac  98940
aatctcggct cattgcaacc tccgcctcct gggctcaagc gattctcctg cctcagcctc  98999
ccgggtagct gggattacag gtgcctgcca ctacgcccag ctaattttta tatttttagt  99060
```

-continued

```
agagacaggg ttttaccatg ttggccaggc tggtctcgaa ctcctgacct caggtgatct  99120
gcccacctca gcctcccaaa gacatcattt ttttcccttc ttttttgaga caaggtcttg  99180
ctgtgttgcc caggctgaag tacggtggtg ccatcacagc tcactgcagc ctcaacctcc  99240
tgggctcaag caatcctccc acctcagcct cccaagtagc taagaccaca tgtatatgcc  99300
aaaatgccca gctagttttt tgattttttg tagagacaga gtctcgctat gttgccaggg  99360
ctggtctcga actccagggc tcaagttatg ctcttgcctc agcctcccaa agtgctgggg  99420
ttgcaggcat gagacaccac aaccagccca acataagtgt tttaaaataa gacaaccatc  99480
attctggctt gtgatgagac cttgtctgta atgaagaaaa cttcagaatt cctataagtc  99540
agttgccaaa aggctagaag catcattgat ttcctgttag caaacatcca taacaaagac  99600
taagtccttg ctttacccca gaccaaaaca gaacatcaac tctatggaaa ccagcagaag  99660
aatttcataa gaaccaagga gctgactgac agccacctga ctggcagcca ccattaccag  99720
gttaaaacta tgtctgatga tgtttcttga cagctctgcg ttccaagaat gagcacatgg  99780
cttcattaca atcaaggggc aacttaaaga acaggtgagg gattctttct aagtatcttt  99840
ctaggctaat ggatatttta tcaaacctgt cttatttccc taaattctaa acatgctact  99900
gagagaaaag gctctaaaat tattaaccca tgtacagact attttgtttt tgtcatttct  99960
cttatagaag aacatatatt actaaaaaaa gtcagcttcg tattgtcttt tatattttgt 100020
aaaatgtggc tctttcctga gtttcaacaa tgactggttg aatagagatg agtcatttta 100080
agaaactaca ggcggggtgt ggtggctcat gcctgtaatc ccagactttg ggagaacaag 100140
gagggtggat cacaaggtca ggagttcgat accagtctgg ccaatatggt aaaaccccat 100200
ctctactaaa aatacaaaat tagctgggtg tggtgggaaa ctacaaccag atcctttcat 100260
gcatcaaaga aaaacccaaa ataagttcta aacttcagct ttaaaaagtt aggctagaag 100320
aatcatttcc tgtcctcata gaatccactt gcttgctgaa aatattatag aaatagaact 100380
ttattaatgt gaagggtaat tttaatctca tcagttaaca tttgccaaaa tggaatatgt 100440
gctcgacagg attaataata gtggttttta gccagcacag tggtgcatgc ctgttgccca 100500
gctactcagg aggcagatgt aggacagtca cttgagccca ggagttcaaa gccagtctgg 100560
gtaacacagc aagaacctac ctctaagaat aataataata atagattttt attttttatt 100620
ttgatttttt ttgagatagg gtctcgctct gttgtctagg ctggagtgca gtggcgtgaa 100680
cacagctcac cgcagccacg acctaccagg ctcaagcaat cctcccacct cagcctcttg 100740
agtaggcacg tactaccgtg accagctaat tttttaattt tttgtaaaag caggatctcg 100800
ccatgttgcc aagactggtc ttgacctcct aggctcaagc atcctcctgc ctagggctcc 100860
caaagtgctg ggattacagg tgtgacctat cacccaatag tgtctttttt taatccattg 100920
gtttgaaatt cttcaccctg cctcctaaaa gagacagaaa gagggaaaaa cctgggtatg 100980
ttattcataa tgcttctatt aaaaccaagg agcagccagt agtttgagac tagtctgagc 101040
aaacatggtg aaacctcgtc tctacagaag atataaaatt agctgggtgt ggttgtacac 101100
acctgtagtc ccagctgctt gagaggctga gggaggagga ttgcatgagc ccaggaggca 101160
gacattgcag tgggccaaga ttgcgccatt gcacaccagc ttgggcaaca gagcagactg 101220
tctcaacaaa acaaaacaac aacacacaca cacacacgca cgcacaaaca cacatacaca 101280
cagcaacact tcaaatctca aattattttg ggtcaccacc aaaaaattat attctcaacc 101340
atggtctatg ctggttattc caatcctagt tcaatttcaa atcatcataa atattaagaa 101400
```

-continued

```
tttgagcctt tgtacaaata aaaactagac tcaaaacaaa gatgagcgct gccctacagg 101460
tcaaatattt attctatgct atatttaaat aagcataagg ttaagggttt gccaaatggg 101520
attttaattt tttttttttt gagatggagt cttgctgggt cacccaggct ggagtgcagt 101580
ggcgctatct cggctcactg caacctccgc ctcccgggtt caagccattc tcctgcctca 101640
gcctccagag tagctggaat tcaggtgcgt gccaccaggc ccagctaatt tttgtgtttt 101700
ttagtagaga cagggtttcg ccatgttggc caggctggtc tcagaactcc tgacttcagg 101760
cccgccttgg cctctcagag tgctgggata acaggtgtga gccaccgcgc cgggcgccaa 101820
atgggattca aaaaaaaaaa aaaaaaaaaa ttgtgggcca ggcacggtgg ccgacacctg 101880
taatcccagc tactcgggag gctgaggcag gagaatggct tgaacccgga aggcggaggt 101940
tgcagtaggc tgataccgcg ccactgcact ccagcctggg cgaccgagca agagactccg 102000
tctcaaaaat aaaaataaag gccaggcacg gtggctcaca ccagtaatcc cagcactttg 102060
ggaggccgaa gtggacagat cacctgaggt cgggagttcg agaccagcct gaccaacatg 102120
gagaaacccc atgtctacta aaaatacaaa aattagctgg gcgtggtggc acatgcatgc 102180
ctgtgatccc agctgcttgg gaggctgagg caggagaatc gcttgagccc gggaggcgga 102240
ggttgcagtg agcggaggtc gcaccactgc actccagcct gggagacagc gagactctgt 102300
ctcaaaaaaa caataaaaat aaaaataaaa ataaaataaa atgtgccatt ctatttcatt 102360
atataaagat ttattcaatc acattgtgtg gatgatatca cagatgcgaa cagtattagg 102420
aagcaaaaag caatcccttc acctttctta atactcaaat aatttttttt taatttgcca 102480
aaatgaaatc tagtaagtca aagggatctt atttctaagg actcttggat tataaacaga 102540
atttctagcg gggtgataac tggggagagt cacttggctc agtcactgac cttcctttat 102600
ccttaaattg agagtggcaa tttcatgacc ctgaatagta taaaaaatat gtccctcaaa 102660
cgtataagca ccatatgaag ctaatagcct ttgaaggtct atatttactg tgtcatagat 102720
aagctcaact acaattcgat ttgattaaaa aatcagtaca gtgatactct aatccaaaaa 102780
atatcaaatg attgctaaaa ataaagggga tattgtaaat ggcataaatt gcatcaaaat 102840
gggaatgaac actaaataat tacagctata tatgttctaa aaactaatga caaaagaaag 102900
ctgaaaaatc cccagtaact tctcattaga tcttttccgt ctcactctct ttctggtgtg 102960
tgttttttgt ttgtttgttt ttttgttttt tgtttttaga aagacagggt tgggctgtca 103020
cccagggtgg agtgcagtgg catgatcttg gctcactgca acctccattt cccaggctca 103080
aaccatccat ccacctcagc ctcccaagta gctgggacta caggcgtgca ccaccatgcc 103140
cagctaattt ttgtattttg gtagagacag ggttttgcca tgttgcctag gctggtctca 103200
aactcctggg ctcaagtgat ccnnnnnnnn nnnnnnnnnn nnnnnnnnnn nnnnnnnnnn 103260
nnnnnnnnnn nnnnnnnnnn nnnnnnnnnn nnnnnnnnnn nnnnnnnnnn nnnnnnnnnn 103320
nncaagtagt tcatcgatct tctttttttt tttcatttga gatggagttt tgccttgtca 103380
tctagatggg agtgcagtgg cccaatctca cctcactgca acctccgcct tccgggttca 103440
agcgattctc ctgcctctgc ctcctgagta gctgggatta caggcacccg ccaccatgcc 103500
tggctaattg tttgtatgtt tttagcagag acagggtttc accatgttgg ccaggctggt 103560
ctcaaactcc tgacctcagg caatccaccc acctcggcct cccaaagtgc tgggattgca 103620
ggtgagagcc actgcaccca gcccattata ttcttatggg accaccatta tgtatgccgt 103680
ccatcatcaa ctgaaccatc attatgtggc aaatgactat atataatatt ttttattttg 103740
acaaatattg tcaaaccacc ctcaaaataa ggtactggtt tggacgggca tagagtgtga 103800
```

-continued aatcccctgt tttccctcac ttgtgccaat actacataca ttaccaaact ctttcatctt 103860
tgtctatctg attaatggaa aatggtacca tgttagtttg catttctttg tgagactgag 103920
cactttttca tgttttcaga ccacttgtgt ttccttttct atgagttgtc agtttgtcgt 103980
tgctcatttc ctattagatt ttttttctta ctgatttgta ggagctcttg atataaccag 104040
aaaattaccc tttactgtat gtgttgcaaa tatttgtctc tggttttttt ccccccttttt 104100 tagtctgtgg tatttttttt cctacagagg ttcatgttgg cattgttaaa tttatcagat 104160
ttttccatta tgatttctgg gtttcttgcc atgcttagaa actgtcttaa ttcacagcaa 104220
tgttgtgtgg tggaaattaa ttaatacatg caaaatgttt agcacagaac gcccttggag 104280
tttcacattt ggaactagaa atttagatgt tatccagaag aaaacgttta gaaaaaagtc 104340
acagatctta acaggaccct gtacggcatg gcccctggtt gactctggtt ctctgatcac 104400
gtctccgatt tcctccagtt ggtacacgca gcttttacat gtgcttttcc ctctggtggt 104460
cccacagtca gatcccccat cctaccttct caaaaaaaac cctgcttctc aggggtgaca 104520
ctcaacatgg caatatagca tctaatcaca catttctaca gtcaccaggt tgaaggctag 104580
actggcagtt ccatgagggt gaaggacaca tctatttctt ttattgtttt ttagagatag 104640
ggtctcgctc tgtcccccag gctggagtgc agtggtgtga tcatggctca ctgcagctcc 104700
aactcctggg ctcaagcaat cctcccacct cagcatcccg agtaggaaca tgtctatttc 104760
ttcaccaccg tatctgcagc ccctagcaaa tggttaatac agagcagttc cttactaaac 104820
atttgtggcc agagggaagg aagagcaacc ttggggtaag ccccatcact gctctctcct 104880
acatccacac agtttcacat ctgtgacccg ggtggtgtca acaggaggct gtcaaggatg 104940
actccaactc cacgtactca agaggaagag gcagaaggca gctgacaaag ccctcttcaa 105000
actggcccca ccagcaattt atgtggcaaa aagatggtca ttgtttttaa tatacagtct 105060
cttctcaccc aatcggtggt actgacaagg atatttttcc ctatctgtat gctactgtag 105120
tcattttaat aagaatttgc aaagtgaatg tctaggacac ctatgcatat gagccaaaaa 105180
cttgctccaa agcctccccg tgcatttgga aacaccaaat gttgatatct gaaactaact 105240
tgcagtctgg gtaacaaagt aagaccgcat ctccaccaaa aaaaaaaaga aaaaaaattt 105300
taattagctg ggtgatggca catgcctata gtcatagcta ctctaaaggc tgaagcgagg 105360
tcaaaggttt gagaccagcc tgggcaacat agtgagacct catctctaga aaaaaaaaaa 105420
aaagttttgt aattacccag gcatggtggc ccacacctgt ggtcccatct actctagagg 105480
ctgagacggg aggattgctt gaacccaggc atctgaggct gcagtgagcc atggttgtgc 105540
cattacactc cagcctgggt gacagaccaa gactctgtct caagataaaa acaaaacaac 105600
aacaacaaca acaaacctat atgaatcaca aaattaaaaa gatgatttat ccatacttac 105660
attgttacaa acactatttt tccacaatta tgaactggct ctgataataa gaaaaaagca 105720
atatatggcc aggcgctgtg gctcacacct gtaatctcag cactttggga ggctgaggca 105780
ggcggatcac ctgaggctgg gagttcaaga ccagccccat ctctactaaa aatgcaaaaa 105840
atagccgagt gtggtggcac acacctgtaa tcccagctac ttgagaggct gaggcacaag 105900
aatcacttga actcaggagg cagaggttgc agtgagccga gatggtgcca ctgcactcca 105960
gcctgggcaa cagagcaaga ctctgtctca aaaaagaaaa aagaaaaatg tgatatgttg 106020
gctattatac attacagctg gttaaaatta cagcatgaag aactacannn nnnnnnnnnn 106080
nnnnnnnnnn nnnnnnnnnn nnnnnnnnnn nnnnnnnnnn nnnnnnnnnn nnnnnnnnnn 106140

-continued

```
nnnnnnnnnn nnnnnnnnnn nnnnnnngca agtagttcat catcaaataa tattagctaa 106200
tactgactgg gtgcagtggc ttacgcctgt aatcccagac ctttgggagg ccaagatggg 106260
aagatcactt gaacccagga gttcaagacc agcccaggca acatgatgag atcctgtcta 106320
tacaaaaaaa aaaaaaaaaa aaagaaagaa attagctggg cgcctgtggt cccagctact 106380
cgggaggctg aggttggaga atcgcttgag cccaggaggc agagtttgca gtgagccatg 106440
atcatgccac tgcactccag cctgggcaac agagcaagac cctgtctcaa aaaaaaaaaa 106500
aagatgaaga gtagtagcaa ctatgagttt cagcctgtta aactcaagac gtgccagaaa 106560
taatgaattt ttcagttttt atttattttt tattttggga caggatgtca ctctgtcacc 106620
caggctggag tgcagtggca tcatcaccac tgctcactgc atcctggact gccctggctc 106680
aagtgatcct tcagctttag cctcctgagt agctgggact acaggtgctt gccaccatgc 106740
ccagctcgtt tttgttgttg ctgtttgttt gtctttctgg gtttttattt gtttttgcag 106800
agacagggtc tcaccatgtt acccaggctg gtcttgaact cctgggctca agcaatcctc 106860
ccatgtcggc ttcccaaagt gctggaatta taggcatgaa ccactgtgcc tgccccagtt 106920
tttagaagtc gacttgcttc tgacttttaa aaccctgtag attaaacttt aggtattctt 106980
aatttttttt tgtcttttgg agacagtctc actctgttac ccaggctgga gtgtagtggc 107040
accatctcag ctcacagcaa cctcccctt ccgggttcaa atgattcttg tgccttagcc 107100
tcccgagtag ctgggatcac aggcaccagc caccaagcct ggctaatttt tttttttttt 107160
tttttgagac agagtctcgc tctgttaccc aggctggagt gcagtggtgc aatctcagct 107220
caccacaacc tctgcctcct gggttcaagc aattctcctg cctcagcctc ccaagtagct 107280
gggactacag gcatgcacca ccatgcctgg ctaatttttg tatttttagt agagacaggg 107340
ttttactatg ttggccaggc tggtcttgaa ctcctgacct cgtgataagc ctggctaatt 107400
tttgtatttt tagtagagat ggggtttctc catgttggcc aggctggtct cgaactcttg 107460
gcctcaagtg acctgcctgc cttggccttc ccaagtactg ggattacagg cgtgcgccac 107520
cgcacccggc ctacattcgg tattcttagg gcttgaggta gatcatatta ttcaaaagat 107580
ggcaacaata tctcccaccc aatttggtat tcttttttta tttttatttt ttatatattt 107640
ttattattat tattactatt attattatta ttataatcac ttcggctgcg gagtctcgct 107700
ctgtcgccca ggctggagtg cagtggtggg atctcggctc actgcaagct ccgcctcccg 107760
ggttcacgcc attctcctgc ctcagcctcc caagtagctg ggactacagg cgcccgccac 107820
tacgcccggc taattttttg tatctttagt agagacgggg tttcaccgtt ttagccggga 107880
tggtctcgat ctcctgacct cgtgatccgc ccgcctcgtc ctcccaaagt gctgggatta 107940
caggcgtgag caccgcgccc ggccggatct agggatcttt agatgttcct gagatcctta 108000
aaaagggacc tgtgaagtta aaacaatttg tcatactact gttaagacat tgtcctttta 108060
actcgagtgt agaatggagt tctcctgagg tgtaatacat aatgtgatac tgcaatagat 108120
tgaataaagc agatataaga atctgtctcc tacgaagcca gacatgaaat acatttgcag 108180
aaatgtaaaa ccattgtcct cataattttt tgttttggaa aaattatttt tttagagaca 108240
gggtcttgct ctgttgccca ggctggagtg cagtggtgca atcacagctc actgaagact 108300
cgaactccca ggctcaagcc atcctcccat ctcagcctct caagtagctg gaaccacagg 108360
tacacgcagg ctgggcttat ttatttttttg agacagagtt ttgctcttgt tgcccaggct 108420
ggagtgcaca cattacaggt gtgagccact gtgcctggct caagtttttt tttttaataa 108480
aaatgttact tatataaaca tgacatgtca ttttaaaata ttctagcaac tttttttttt 108540
```

```
tgagacagtc ttgctctgtc gcccaggctg gagtgcagtg gtgtgatgtc acttactgca 108600
acctctgcct cccgtccaaa ttctcctgcc tcagcctccc gagtagctgg gattatagat 108660
acctgccacc atgtccagct aatttttttt tgtattttta gtggagatgg ggtttcacca 108720
tgttcgccag gctggtttca aaatcctgac ctcagctgat cagcccactt cggcctccca 108780
aagggctggg attacaggtt gagccatggc acccagcctt ttttcacctt ttttggacac 108840
agggtctgtc atccaggatg gtgtgcagtg gtgaaatcac aggtcaccac agcctggacc 108900
tcctaggctc aagtgagcct cctggcccca cctcccaaaa tgtgggggtt tcaggtggaa 108960
gccagcacac acagcccatt tttcattttc cattggcaaa aatccaagtt tgataaccta 109020
cctataagaa gatgggtact ctgtacattt ccagaacaaa taaagtggtc taacacttgg 109080
gagtgtttgg aagaatctgc caaaattaaa atgcacaaat ctggcagggt gtggtggctt 109140
atgcctataa tcccaatacc ttgaggtcta ggcaggagga tagctagagc ccaggagttg 109200
aaccagccca ggcaatagga actggggcca tatgtgataa acgtgcccat gaacagccac 109260
tgcactggcc tgggaaacaa gagcacggcc tcataattat tggggaggag ttgagaattg 109320
agcacagcgg ggagaaatgg gagtttgttg tctgagtagt cagcagttat tctcttctct 109380
catccatgta cagtttagca ctgacttctt cagggacgag tgagaaaatg ccaccacttc 109440
acaatggtag agggtgggtg aaaaagttat tagccaggca ccaagaacca atctgaagcc 109500
aagaacagca atgcaaagcc aacaaactag ctctcttgta gacaccactc ccttccaatc 109560
ccattctcta ctaaggaaaa cccccaggtg agctggcatg gtcaaactac accttcaggt 109620
aggtaagaat ttttttaaa aaccaaaaat taaaaaaaga gacacaaaat gtagtcagct 109680
atttaattag gttcttaaga catttagaac accaatttgt gaggataaat tccattcgtc 109740
agagcaaaca cagatcgcag gtagccctgg agctgaggaa tagctttgat ttttggtaaa 109800
atttgtgagt ccacagcttt ctgatcaatc ttgcgctgct ccgtaatctc atatttctaa 109860
ataaagagaa aatcaaacat tttaaaacag gcacatacca aattacttgt aggtcaacta 109920
aggagtcctg tctcacaagt actaatcccc aagaatattt agaaaacatt aaagacaatt 109980
ttgacaatcc tttccttgga atgctgtgaa acacaaccca ttttttaatg taataaaagt 110040
agctcttaag cttttgtata ctttaggaca catcaaggat aagtaagggc acattcccaa 110100
tacgatggta gcagttaatt cccacacaat tccaccaaac tttaggattc taagttgagc 110160
tcccagactg ccaaaagaac tactcaattt agaagaatct ggaatactaa gtatctccca 110220
gcattcctca ttatttaacc tttcattttt cttcttttg tgcaacctgt ttcttttcac 110280
tcccaggtag aagggccagt gctaacacag gagatgacaa gtagaaactt acctcttttt 110340
ctgtgtcgaa gatctcacct tcctggtgtc tgggcttccg cagcttcttc ttcttgaagt 110400
aagcatcagt aagatgtttt gggattttta cattgctgat atcgattttg gttgaagtgg 110460
caatgacaaa tttctggtgt gttcttcgta gaggaactcg attgaggacc agaggtccta 110520
agggggaaaa attaatttag caaggaaaag ggggaagaat catcatcctg caatttaggt 110580
gaccattact tgttatgttg ctacacaaag aagaccactt gtctaaccca cttgcacaca 110640
aggcaatgaa atgggcctca gacacttgtg gcaataagtg tctaccatgt aggcagtagc 110700
aaacaaacgt gtatactgca agcatttaaa aatggaagtt tcacagaaca tcacaatcca 110760
aggattttct taccagtcac aagtaataag ccactagcca gctgcttcag gaaaaccacc 110820
ctctgtaagt taaaaagaaa ataattagtt ttctgcaatt aaaaactgac ttctgaattc 110880
```

-continued

```
ataaaatcac aggcatctaa atttgggtaa aggaaatttc tacatgtata tgtatacagc 110940
tcggcagttc tggaagcaac cacagcaagc tactaaggta gtactccaga cataaacacg 111000
tttttgagta aatgaacatg tgtaacataa tcaacagcag gaaatggcta ataaatcacc 111060
atggattaca cttcttattt gcaacaacta agttgtatct tgcagatcat ttccccttgc 111120
cccaaacata ggtaaataaa ggaaaagtac acctagcgtg caaacgcatt gccaccaggc 111180
accccaggca gctgcagtga agcgccccaa gcacaggtac tctcaccttg cccctgtggc 111240
gtccagtgag gatgatcaga atggtcccgg gggtaatgct ggctcgcagt tttctcacgt 111300
gctgactgaa gggtttttg ccgtggctca acagctttcg aggcacatct tcagtaggat 111360
aatatctagg ctgtggagag tccatagatc caacttattt aaataagcca ttcagattac 111420
tagaagcaag ctatgtcagc caaacttttg ctacagcctt tttattttaa agtataatac 111480
tgtatttata tgattccatt ttcatttctg ctaagtagac ttggaaaagg tcaattatgc 111540
ttctgcatcc tgtgtgcaaa aaaggagaca ccatttaatg aatgagatgt gtgctcaagc 111600
aaagaaagca tcaagcaagt cacctttgca atcttgagca aaaactaaac ctcagagatt 111660
acacgtgtga catgccacat tttgcagatt agggatacat ggcttgtttt ccaattcaag 111720
taaagtgtgt ccatatccta gccacttcat ctgatcctca cagcaacaag tcttactccc 111780
acttcatcca caaaggaaaa caaattgcat aaagccagac actaggactg gcagatcatt 111840
tattgcagaa gttagacacc atgcaagggc cattaaagac atgactacaa ataactcaca 111900
ataacctatt tccaactata ccatatcatt agtgcagtct cactttcacc acaaacatga 111960
tcacctaatg ggaaaacgag ttcacaaaac aactgtcatc ttccctctca tgcagtaatc 112020
ttcaactgtg aaactgtatg gtgttaactt atttgggaat gttcccataa tgaaaattac 112080
agagcaaatc ctgagattac attgggtctt gtgtgtggta aagggggcca agaaacactg 112140
ctctagtggg aaatgttcta tagaacaggc tatgtattat ttcatttaat ctccataaaa 112200
actctttgag gtaaaccctc attcccatct tatctttttt tgagatgaag cctccctctg 112260
tcgcccaggc tggagtgcag tagtgcaatc tctgcctccc gggttcaagc gattcttctg 112320
cctcagcctc cagagcagct gggactacag gcacgcaacc agctaatttg tatattttta 112380
ctagagatgt ggtttcacca tgttggccag gctggtcttg aactcctgac ctcaggtgat 112440
ctgctcgcct cagcctccca aagtgctggg attacaggca ttagccacca cactcagcct 112500
cattcccata ttatatgcaa aggaacaaag cacagacgag taatttaaat tacttaagat 112560
taacagtaaa tgttgaagcc aagttacaaa cccagagccc tttattttct atcagaaatt 112620
ctccggtatg cagaaactta cagtatctaa gtattcaaaa acatcttcac agtattcaag 112680
cataaacaga aaatccaatt tacagtcccc acatcttacc attttgcgaa gtttaaccac 112740
ccgggtaccg ccgttcttgt caccaccaac tggttttgta acagttgcga gaaccttctc 112800
cttctttttc ttttcaacct acaaggacac aaatgcatca acagtaagag aatgccaatt 112860
aaggttaaga cataatggtc cgtggtcctc ttcccttacc ttggatttag cggctgagta 112920
cttcctcttg tacatggcct ttctggaata catggcagat cgggaatacc tgccaattcc 112980
tctgacaagg acagggttgc ggctgcaatg gggcttcccc ttcttgggct ttttagcttt 113040
gaggttaccc tttttcacct tgccaccagc atcaaccttc ttggcttcgg gtttcttctc 113100
tttagtatct ggcttctcaa ctttttcacc cgccatctaa aaatattttt ttgtagataa 113160
aaaaaggcat ttcaccagtc atctctctaa caagacaata atgaacctgt acatgaatgg 113220
gctgggctcc ccagactaca atccctcccc cggtaagata caggccttcc tctcaaactc 113280
```

-continued

```
tacccattct actccaacct tcactatgac tcatttgggg tttgtctccc caatacacta 113340
taaacttttt ttttgagaat ttgaaactac ctcacaccta ttaggttttt tgccaaatac 113400
tgagcggtca gaagtccgta caaccattat tttttattac tgttttgcga attagaaaac 113460
ttagatgcag aatgtgtcca caggttagaa gcaccaagac cagaacttga aatcccttac 113520
tttcagtacc tttcgtctta acccttaaga ccagtgtctc ttttcaagaa actcgattta 113580
ggaattgcgg acacaaacgg aatcagccca aattgagcca gagaaaaaga tcgcaaagac 113640
caagaggcga cttccggtcg gggacgctgg gagacgcgaa accttttggc ttcagtgcgg 113700
aaccccaacg tggctgcgac aggctcagtg tcatcctctg gaacccagga ccaggaacac 113760
agtgcacgcg ccgtctcccc gcttcctcta acacccacca gtctgctacg ggtccccgaa 113820
agggcctcgt tcccccagcc caagagagtg gcgaagaacc ggagggagcc actacggcat 113880
tctacctcac cctctttgtg ccctgccgca aacccaaaca acaaaaatga agcgtctgga 113940
aggcctctca gttagccttg gacatgtccg accccctgtag gtgtcgactg gatgccctcc 114000
aggttcggat ggcgaaggat tgggagtcct gaactcaagt cttgcagaca ggcccgcgat 114060
tcttaccttg caagatggga aagagaatta aggtcccggc ttccggtcta taagcaatca 114120
tgggaagtgc gagtctcact tccttccgga tctggggcat catggggaat gtagtatttc 114180
cccgttaaga aaaaagtagt aaatcctagg ccgggtgcgg tggctcacgc ctgtaatccc 114240
agccctttgg gaggccgagg caggaggatc ctctgaggtt ggcagttcga gaccagcctg 114300
gccaacatgg tgaaatcccg tctctactaa aaatacaaaa ggtagccggg cgtgggtggt 114360
gcgtgtctgt aatgacagcc agtcgaggcg cggaggcagg agaatcactt gaatctggag 114420
gtggagattg cagtgagcca agatcgcgac actgcgctct aggcaacaga gcaagattct 114480
caaaaaagaa aaaaaaaaaa aaaagggccg gacacggtgg ctcacgcctg taatcccagc 114540
actccaaaga tcgtgccact gcgtgccacc gcactccagc ctgggaaata gagccagact 114600
cagtctcaaa acaataacaa caacaaaaaa aagaaaaaaa gaaaaaaaat tagccgagtg 114660
tggttgttag tgcctgtagt cccagctatt cgggaggcta aggcgggagg atcacttgag 114720
tcttggaggt ctgggctgca gtgcagtgaa ctctaatctt gtcacttgag attaggtcag 114780
tggtcccctc ttcccttacc ttggatttag cggctgacta cttcctcttg tacatggcct 114840
ttctcattcc cgtcctccgg cctggcctac agaatgagac tctgtcttaa aaaaagtaaa 114900
aaaaaattaa agtgaggata acaatagtaa cttacttcat aaggatgttg ggaacattaa 114960
ataatatata caacagtact gagaagcata tttgattatt tgatggatgg taaatgctac 115020
ataagtgtta gctctttttt tttttttttt tttttttttt tttttttttt tgagatggag 115080
tctcgctctg tcacccaggc tggagtgtgg tggcacgatc ttggctcacg gcaacctctg 115140
cctcctgggt tcaagtgatt ctcctgcctc agcctcccaa gtagcaggga ttacaggcgc 115200
acaccaccat gcccagctaa ttttttgtat ttttagtaga gacagagttt caccatgatg 115260
gccaagctgg ttttgaactc ctgacctcaa gtaatccacc cgcctcagcc tcccaaagtg 115320
ctaggattac aggcgtgagc caccgcacct ggcgaactgt tagctcttgt tattgtcacc 115380
atcaccacta caatcatctg atcatcaaca tcctagttgt tgtcaagtat tctgctaaag 115440
tttatgcatg ggagataata ggcaatattg catacaatgt gccttgcttt atttcattta 115500
attctcccaa caacctgtga atgatactat tatgaggaaa ctgagtctca aggacattaa 115560
gtaacttgct cacagcatag atctgattcc aaagattgca ctcttaacca ttaggctgca 115620
```

-continued

```
agattaaaga gatgattaat gaagatgcat gagagttttg ctcatgttag aattaaaaat 115680
aagaatattt attatctttt acaaaataca caacacagta tatgtgatag ttctttactg 115740
cttcaaagcc cttaagccaa catgtacaca tttgtaatac cttctagctt gcgttttcca 115800
ttttcctcca ttcgtttctt tctggttgct agagcttttc accttgattt tttcagatcg 115860
aaaccacctg cttcatggct gtgtctctgg gaatcattta gccttttct ggttctgatt 115920
cactgaggat acaaatacaa tgatcagatg aacactgccc tttttttga gaatgggaat 115980
gtcagcagct ttatttgttt agcttcctca gcaaagcacc tcttagaaac ttcaactgca 116040
gaaaatgtac cacaatgaat gaatgagatg cacagttgct tacgtgggcc cctcaaaatt 116100
gctggcaatc tcagataatt tcacctagtg aacgccccaa aatatgtgtt gaatgacctg 116160
tcattaaaat aaaaacgtag atgaaccccc tcttgtgttt tgttgcggta ttgcaaaatt 116220
tacaattcat tagttgggca aaataccatg ttagttataa agtaaatgtt tttattaagt 116280
ttagttttgc catatataaa attctctgaa atttgtgcag cactttaatc acaaagcaga 116340
catttttgca gacacttaat cttttttttt tttttctgag atggagtctt gctctgtcgc 116400
ccaggctgga gtgcagtgcc gtgatcttgg ctcactgcaa cctctgcctc ctgggttcaa 116460
gccattctcc tgcctcagcc tcttgagtag ctgggattac aggtgcccgc taccacacct 116520
ggctaatttt ttttttgaa acagagtctt gctcttttgc ccaggctgga gcgcggtggc 116580
atgatctcgg ctcactgcaa ccttcgcctc ccgggttcac gccattctcc tgcctcagcc 116640
tcccgagtag ctgggactac aggcgcccgc caccatgcct gactaatttt ttgtattttt 116700
agtagaggtg gggtttcact gtgttagcca ggatggtctc gatctcctga cctcgtgatc 116760
tgcccgcctc gacctcccaa agtgctggga ttacaggcct gagccacctt gcccggccaa 116820
ttttttgtgt ttttattgga gacaggattt caccatgttg gccaggctgg ttttgaactc 116880
ctgacctcag gtgatctgct cacctcggcc tcccaaagtg ctgggattac aggcgtgagc 116940
cacctcgccc agcctaattt tttttttttt ttggagacag agtctcgctc tgtcgcccag 117000
gctggaatgc aaggtgagat catggctcac tgcagccttg acctcctggg ttcaagcaat 117060
cctcccacct cagccccctg agtagctggg agtacagtgc acaccaccat acctggctaa 117120
ttttttaca ttttttgtag agacagggtc tcacaatgtt gcctcagctg tattttttgt 117180
ttgtttgtta ggcagtaaat cttttaaagc ctggccaaca tggtgaaacc ccatctctgc 117240
taaaaataca aaaattagcc aggcatggtg gtgcatgcct gtaattccag ctacttggga 117300
ggctgaggca cgagaatcac ttgaacccgg gaggcagagg ttgcagtgag ccgagattgt 117360
gccactgcac tccagcctgg gccacacagt gagactctgt ctcaaataaa taaataaata 117420
aataaataaa taaataaata gaaaaatatc tttatatgtg ttatgtatgt gtgtgagcct 117480
gtgtatggga tgagtttgtg tgtttgtata tgtataaagt gtggaaagac atacaccaaa 117540
ccattaacac tgctggggat tgggatatgg agtacgtatg catcaaggaa cagagaaaat 117600
tactgtttgt tatttagttt gttgcaagga acttgtattg cttttgtaat tgagaaagaa 117660
attcaaataa agtaatggct attatctgaa ttaatctcta aatgaatata tctttttaaa 117720
attaagatgg agttggccgg gtgcggtggc tcacgcctgt aatcccagca ctttgggaag 117780
ccaaggcagg tggatcacga agtcaggaga tcgagaccat cctggctaac acggcgaaac 117840
cccgtctcta ctaaaaaata caaaaaaatt agccgggcat ggtggcgggt gcctgtagtc 117900
ccagctactc gggaggctga ggcaggagaa tggtgtgaac ccggaaggca gagtttgcag 117960
tgagccgaga ttgtgccact gcactccagc ctgggcgaca gagtgaagac tccatcttaa 118020
```

-continued aaagtaaata aataataata ataaaataat tcagattgag gttttttgt tttgttttgt 118080 tttgttttgt ttttgctatg ttgcccaggc tgccagtctg gtctcaaact cctgtctcaa 118140
gagatcctcc tgttagctac catgcccggc catataaatg aatatgccag gcactactcc 118200
aggcatataa agatgggaag accggccgga catggtagct catgcctgta atcctagcac 118260
tttgggaggc ggaggcagga tgattgtttg agcccagggg ttttagacca atctgggtaa 118320
catggcaaaa ccctgtctgt attaaaaaaa aaaaaaaagg aagacaatga ctttgtctta 118380
aaaggagatc ataatctaaa gaaagacaca gaacaacaat gacagaaccc acaatgatgt 118440
tgaaatgtgt taggtgctga tagaagcatg aagaggcagc cccaggagca taggaaagga 118500
gtctctcttt tattctcaaa aagtgaaaga atgttttctg gaggagctgc ttaagttgga 118560
gtttaacctt gcatgactgt tttccaggtg gagaagggtt tgaagagtat tccaggcagt 118620
aggaactaaa ttttggaaga cagggatgca agaaacagct agaagccttt agaaactgct 118680
agattatgtg agggtgttgg cacaggccat atctagaacg gactgatgtg ctaagggaag 118740
gagttcaact taatgctaga gggtttgaac ctccttcata caacagggga ggggagtgac 118800
gtgattagat ttgtattttt aaaagattat tcattctagc tgcagagtgt gcagaatata 118860
ggaaacacta ggaaggtagt agttcctgca ctcaaagagc taatagttta ctttggaaaa 118920
gagacaaatg atagccagct tttatcaagt gctgactttg ccagacactg ttctgagtat 118980
ttcacaaacc tatcctatgg taggattttg attcctactt tgcagagaag gaaacagaca 119040
cagaggagtc aaatgacttg cttatagaca cccaggcagc tagatcaaga acttaattgg 119100
cagccaggcg ccgtggctca cgcctgtaat tccagcactt tgggaggccg agtcgggtgg 119160
atcacgaggt caggagatca agaccatcct ggctaatgcg gtgaaaccct gtctctacta 119220
aaaaaataca aaaaattagc cgggcgtggt ggcaggtacc tgtagtccca gctacttggg 119280
aggctgaggc aagagaatgg cgtgaaccca ggaggcggtg cttgcagtga gtcgagatca 119340
cgccactgca ctccagcctg ggagacagag tgagactgtc taaaaaaaaa aacaaaaacaa 119400 aaaaaaccca caaaacttaa ttggatgctt cctatatgat acggctctta gatttatagt 119460
gtagcatgtt aggttctaag gataggtgtc ttggtgacca tctgacctgc actagagaat 119520
cgggtgaggc ttgtattcca gaggaagtgg ctcctagcct gagatcagag gcatagagtt 119580
gatgtggagg acagtcagga agaaccctct ggggaaagaa agcagattgt taaaaggctc 119640
tacgctggga aagaatatgg catattgagg ggagctgaaa gtcattcagc atggctgggt 119700
catagagaat gaagcgagta gtggggagac ggggtggtga agtgattggg gaccagagtt 119760
aaaaaaactc tggtgcattg ctcacgcctg taaatccaag gccttgggag gtcaaagtgg 119820
gaggactgct tgaggccagg agttcaaggc cagcctgggc aacatagcaa gaccttgggt 119880
ctaaaaaaat ttttttaaac tttttttttgg gccgggcatg gtggctcacg cctgtaatcc 119940
cagcactttg ggaggctgag gtgggtggat cacttgaggt caggagttgg agaccagcct 120000
ggccaacatg gcgaaaccct gtctctacta aagatacaaa aaaaattagc tgggcatggt 120060
tgtgcgtgcc tgtaatccca gctacttggg aggctcaggc aggagaattg cttgaatctg 120120
ggaggtggag tttgcagtga gccgggattg cgccactgca ctccagcctg ggtaacagaa 120180
tgagactcca actcaaacaa aacaaaaaac tttttttttt ttgtagggac aggggtctta 120240
ctctgttgcc caggctgttc ttgaactctt tgggctcaag aaatcctccc acctaggagt 120300
cccaaaacac tgggattaca gaggtgagcc accacatcca gggggataaa cctttttttt 120360

-continued

```
ttttttttgg acttcattct aaaatcaagg agaagccatt ggtgaattca atgtagggag 120420
tgactagttt tgcagttttt tttttttttt tttttgagat ggagtctcgc tccgacgccc 120480
aggtgggagt gcagtggcgc aatcttggct cactgcaagc accacttcct gggttcaagc 120540
aattctcttg cctcagcctc ctgagtagct gggactacag gtgcctgcca ctgcacccag 120600
ctaaattttg tatttttttt tttttttttt ttttttgaga cagagtctcg ctctgttgcc 120660
caggctggag tgcagtggtg tgatcttggc tcactgcaag ctccacctcc tgggttcacg 120720
ccattctcct gcctcagcct cccgagcagc tgggactaca ggtgcccacc accacgccca 120780
gctaatcttt tgtattttta gtagagatgg ggtttcactg tgttagccag gatggtctcg 120840
atctcctgac ctcgtgatcc gcccgcctca gcctcccaaa gtgctgggat tacaggcgtg 120900
agccaccgcg cccagcccta aattttgtat ttttagtaga gattgtgttt gaccatgttg 120960
gccaggctgg tctcaaactc ctgacctcag gtgatccacc caccttggcc tcccaaagtg 121020
ctgggattac aggtgtaagc caccgcactt ggccacagtt aattgtattt ttagtagaga 121080
cgagggttca ccatgttggc cagactggcc tcaaactcct gacctcaggt gatccacctg 121140
ccttggcctc ccaaagtgct gggattacag gcatgagcta ccgcgccccg agtgacccgc 121200
ctagttttgt agtttagatt actctggcta ctatgtggag attggattag gaagtttagg 121260
cctgcaggcc tgagatcagt taaaatgtag cttgtcatct agctggccag gatttaggga 121320
gagggacaac tgcttgttaa atggctctta tgtgaattaa attggcatat attaaaggtg 121380
atctttgtaa ggagcacatg atgctgaagc agttagcaca cagtatgaga ctcacttgta 121440
tatgaatgaa atgggcaagc attaaaaaaa tgaggatttt ggagctatac agatatgggt 121500
taaacttatg gctctgccat tcactagatc tgtagccttt atttatttat ttttgagaaa 121560
gagtctcacc ctgtcaccca ggctggagcg cagtggtgca gtctgggctc actgcaacct 121620
ctgcctgtcc ggttcaagca attctcccac ctcagcctcc ggagtagctg ggactacagg 121680
tgtgcgccac caagcccgac taatctttgt atttttagtt gagacggggt ctcaccatgt 121740
tggccaggct ggtcttgaac tcctgacctc aagtgatctg ctctccttgg cctcccaaag 121800
tgctgggatt acaggcgtga gccaccacgc tcagctagat ctgtagcctt caatgagtca 121860
tatgcgcatc aatcaagtaa aagctctact cttctcaatc tggtctgagc taccattatt 121920
cccagaccag aatactatag tattccgtat tttgactggc ttctctgttt ctggccttgc 121980
tctcttgctc gagcttcaca gagtgtccaa agtaatactt ccgtaccacc cggcccggct 122040
tttttttttt tttttttttt tttttttaag agacatggtc gcaccatgtt gcccaggctg 122100
gtcttgaact cctaggctca agcaatcctc ctgcctcagc ctcccaaagt tctgggatga 122160
aggcgtgagc caccatacct ggcctgagtg cagtggcgcg atctcggctt tcagcagcct 122220
cgaccttcca ggctcaagca atcctctcac ctcagcctcc cgagtagctg ggactacagg 122280
cgcgcgccac cacgcccggc taatttttgt atttttttgta gagatgggat ttcactattt 122340
tgcccgggct ggttcccaac tcctggactc aagcgattcg cccgcctcag cctcccaaag 122400
ggaagtgctg ggatttcagg cgtgtgccac cgctcccacc ccaaagtagt atttattgta 122460
attattatta ttattttgag acggagtctc gctctattgc caggctggag tgcagtggcg 122520
cgatctcggc tcaatgcaac ctctgcctcc cgggttcaag cgattctcct gcttcagact 122580
cccaagcagc tgggactaca ggcgcccccc accacgccag gctaattctt gaatttttag 122640
tggagacggg gtttcaccat gttggccagg atggtctcga tctcttgacc tcgtgatccg 122700
cccacctcgg cctcccaaag tgctgggatt acaggcgtga gccaccgcgc ccagcctatt 122760
```

attatttttt taggcagtgt cttgccctgt cgctcagggt gtagtgcagt ggcgtgatca 122820
cgactcactg cagccccgac ttctcgggct taagttatct tcccgccgca gcctccacgc 122880
ccggttagtt ttttgcattt tttgtagaga tgaggtcttg ctttttttgcc caggctggcc 122940 tcgaactcct tggcttaagc gaacctcttg ccgcagcctc ccaaagtgtt gggattacgg 123000
gcgtgaacca ccgcgcccag cctactatct ttatcttaca gaaagaaaag aatggaggaa 123060
accgaggctc ggagacagta ggtaatttcc ccaaggttcc acagctaatg agtggagcgg 123120
cgatttgtgg aacgaaatga atgaaatcga tgtggcagcg ggcccggacg ggtcggtggc 123180
gtagacgcgg agcgcgcagc tcacacctgg cggccgcggt ttccaggagg aagcaaggat 123240
gctttggaca ctgtgcgtgg cgcctccgcg gagcccccgc gctgccattc ccggccgtcg 123300
ctcggtcctc cgctgacggg aagcaggaag tggcggcggg cgtcgcgagc ggtgacatca 123360
cgggggcgac ggcggcgaag ggcgggggcg gaggaggagc gagccgggcc ggggggcagc 123420
tgcacagtct ccgggatccc caggcctgga ggggggtctg tgcgcggccg gctggctctg 123480
ccccgcgtcc ggtcccgagc gggcctccct cgggccagcc cgatgtgacc gagcccagcg 123540
gagcctgagc aaggagcggg tccgtcgcgg agccggaggg cgggaggaac atgacatcgc 123600
ggaggtgagg agccccgagg ggcccggcgc gggcctcggc ccggccaccg ccgcgttcgg 123660
ttagccccgt ccggaagggg gcgcccggc cgggcttcgg gctcccgccc cgggtcgggg 123720
ttgggggccg gttccctcct cgtcccctcg ccctccaggg gccgggggcc ggccccaccg 123780
cgcccccacc cctcgggtcc ccattcattt cctgcctccc cgagttccgg ctgcggcagc 123840
cccggggatg cccgtcaggc ccggggcagg tagagccgcc gagggaacca cgggtgccag 123900
cggccaggct cagcgccgca ttcctgaccc attgcctcat gagaattgcc tcatggtgat 123960
tccgaaataa ccctgctcac ttggggaggc tccttgggac acgagagggg agttgcgcgg 124020
ggccgggccc ccagtggtct agtcgttctg gctcactgtg ccactttcgt gcatttgggg 124080
acttcacgca ggacccctga ccctttata tgcctctttg tgtcttcttt tcctcctacc 124140
cctcacgtgc cagaaatgga aaaactgact gtatctgcag ccactagaag tatttccttc 124200
ctctgcgatc ttcgctttgg gagatggaaa ggaagggagc cgcatctcgt tatttaatcc 124260
ttcactgcaa ccttaacagt caggtcactt tactggtacc cgttttatgg atgaggaaac 124320
cgaggcccag aagcaacatg ctagtaaatg acaagatttg aaacttagga ggattagtga 124380
gttaatgaga tcctttgaaa ggtcagggta atactactac taatagctaa catttgctta 124440
gttctgacca cagccctatc agatggctac tattatcccc attgtaaaga tgagtaaacc 124500
gagtttcaga ggttaagtaa attgcctaac ctcacagcta gtaggtggtg gagacagaat 124560
ccctactttt aatcactatg ttgcttctat tattttgtaa ctattgctaa ccatttgtaa 124620
gccttaattt tgttgtcaaa cagtagtgtg acctgttgtt ttcagatagt gatcctgcta 124680
ttttgtatag tcactctata taccactcac acttaagacc cattgtctat tcttttccat 124740
gattgttcaa ttatggtcac tgtctcagac atttaaaaaa cgattcaagc tattgaggct 124800
atttgaatga gattttcttt tcttttttc tttttttttt tggagacgga ggctcactct 124860
gttgcccagg ctggagtgca gtggcgcaat ctcggctcac cacaatctcc gcctcctagg 124920
ttcaagcgat tctcctgcct cagcctccca agtaactagg actacaggcg caccactatg 124980
cccggctaat tttgtattt ttagtagaga cagggtttca ctatgttggc caggctggtc 125040
tcaaactcct gacctcgtga tccgcccgcc ttggcctccc aaagtgctgg aattacaggc 125100

-continued gtgagccacc gtacccagcc tgaatgagat ttttcaaaat attaggaatg tctcctccaa 125160
acacacctgg catgttattc atacatggat ctggaattta aaaaggggag aaaaagaaaa 125220
ctgagaactc gtaggaagtg agtgacttgg acaggtcggt tggcaagtgc ttacagatct 125280
gggtaatata taactgcatt tcaacagaac agtgtatagc ctcaaatgtt ctaattcttt 125340
agggagcttt taaataaaca gttgtctatt ctttaatctg tcaaatagtc attgagcctt 125400
ttgttcctgg tgtctgctct tccagacaag taaggatctg ctgctttagg agacatcaga 125460
cggggctggg ggttgggaaa aggtctgggt agtaatagac cctacattgt ccagtttgtt 125520
catttagaag catagaagtg tgggcatagt caaagtagca agtggtaaag atgacagttt 125580
gaaatggagt aattccttct cccctccagc cctggtatta tgcaccaccc aaaaagccgg 125640
gttatgaaca taatacacat aattttgaat gattcattat tttttggatt ataagcctgt 125700
tttatttgtt aaccagcctt aatgaggtat aaatgacatg caattaattg catatattta 125760
aatgtacaat ttgatcagtt ttgacataca tatacacttg ggaaaccacc accatagtca 125820
agataatgaa cacatctatc acccctggta attttgcctt atgttcttta taatccttcc 125880
tttgttctta ggcagccact attctgcttt ctgtcactat gtattagttt gcatttccta 125940
gaattttatt tttaaaaatt ttaaaattgt ttgaatagag atggggtctc actgtgttgc 126000
ccagggcagt ctcaaactcc tgggttcaag tgatcctctc accttggcct cctgaagtgt 126060
tgggattata ggcatgagac accctgccca gccctagaat tttattatta ttgttattat 126120
tgtgtttttt tgagataggg tctcactttg ttgcccaggc tggagtgcag tggtgcaatc 126180
actgcagcct tgttttccta ggctcaatcc atcccccctc ctcagctttc cggttactgg 126240
ggctacaggt gtgcaccacc acacccggct aatttttgta ttttttttata gagacagggt 126300 tttgccatgt tggccaggct ggtctcaaac tcccgggctc aagcgatctt cctgcctcgg 126360
cctcccaaag tgctgggatt acaggcatga gctattgcgt cccgccttca aattacttta 126420
acctagtatt aattcattca acaggaagtt aatgagccag gcaggataaa gcagtaagat 126480
aggaaaatat tgctattttc atggctgaga gagagcagac aaacacatga ctaaataggg 126540
caatttcagg tagtaataaa ttctaggagg gaaaaaatcc cacagaaatg tgaggatggg 126600
agaatgcagt tagttttgat aggtggttta gagaaggtga tcgtgtgagc tgacacctga 126660
atgacaatta gtagtctgaa ttttgttttg cttaattatc aaaataactc ctcttgggtt 126720
cggcttttat atgcatccag taattaaaat gtaagtatat tcaatgtact gatatctctc 126780
agcatcatag gtaggaaaac taaggcattc agcaattaag tgactcctcc cttgatcatg 126840
tagcagtgat agtactggat ttagattttg aggttgcttc tctgcccttt tctgcctttg 126900
tgaaaccaac aaagctgcct gtattttcca actcttcctt cagcatgtgg tacctccttt 126960
acatctgttt ttgttgctct gaaatccata cgcgacgatg agctgagagg ggcagaaaat 127020
tgagcttgtt ctgagactgg aggcttttgg tttatctctt gcaggtcaag tacattttgt 127080
cctgggctct ccctggtggc cacgtttgtt tatctcctgc gggagtaaat aaacttgcct 127140
tgctgaaaaa taacagttct gtgtctttgc agtggaaact gggatgtctt tattaacgtt 127200
aggtcctgat gtaaggccaa gtttttggtt agagttgctc aagtgcagag gccactgcta 127260
agatgactta cccctcgtgt ccatggtcaa tgtggagact gttatgagtg gcacatgatg 127320
ctggaaaagc agagccaact catgtttgta attgtcctag caggccgtgg tgtactttgt 127380
taggcagcca cagaacaata gagaaactca gcttattccc cttccctctg ggaaacacag 127440
acagtacttg ccatccaacg ccaatgtttt taaggaagaa agaggcaaaa agtgatgttg 127500
gcaaggtctc tgggagttgt ggaccccaac caaggattgg agaccctgaa atggattcag 127560
atgccctaaa atgcagccca gttcattact atgaattttg gaggactttg tgccttgagc 127620
aaatgtgtat atgtgacgct ctttgacaac actgaaatag gaaaaatact atccatgttc 127680
gcgaggagca ctgaatttag agagggagac agacttttat gccagcatca aatgaatttg 127740
ataaagctag taccaaaatg aaatttgaaa ttttttttt ttgaaataga gtcttactca 127800
gtcacccagg ctggagtgca gtgatacaat attggctcac tgcaacctcc acctcttggg 127860
ttcaaacaat tcttgtgcct cagtctcctg agtagctggg attacaggtg cgtgccacca 127920
tgtctggcta atttttatat ttttagtagg gatggggttt caccatgttg gccaggccgg 127980
tcttgaactc ctggcctcaa gtgatctgcc caccttggcc ttccaaagtg ctgggattat 128040
aggcatgagc taccacacaa gcctgaaatt tgaaatgtat tggtatagaa tatactgttt 128100
agaatgtatg tgtatatatg tatatttgta tactcatata aacacaaata cacattgtat 128160
gtgtttctgt aatatgtata tctgtctaca catacatgta tatacacaca tacaatgtct 128220 ttttttttt ttttttttt tgagacaggg tcttaccctg ttgcccaggc tggagactgc 128280
agtggcataa tcttggctca ctgcagcctc gacctcctgg gctcaagtga tcctcccatc 128340
tcagcctcct gagtagctgg gactgactac aggcacgtgg catcaaactt gtccaatttt 128400
tctatttttt tgtagagtta gggtcttgct ctgttgccca ggctggtctc aaattcctgg 128460
gctcaagctg tctgcctgcc tcggccttcc aaagtactag gattacagat gtgaaccact 128520
gtacctggcc tttacaatgt ctattttaaa gataatggtt caagttttta tcatccccact 128580 ggcctactct aatgaaacat ctatccattc attgaagaat tatttatggt gggataactc 128640
tgtgccaggt accgtgctag gcattgagta ttccaggttt taggaaacag cacatgcaaa 128700
agtgctgaag tgggagaaga tctcggagtg attgaaggct aggagagagc aagtgtggga 128760
gctgtgaggc tgggaaggtg ggaggtaggt gggagcagac cacataggga ttcttaatgt 128820
ctttagtgtc atgtggacca tggagaggag tgtagattgt atttttagag caatgcaaaa 128880
tcatagaagg atgtgatcgg gggagtggca tgagctgatc tatttaaaaa tatttctctg 128940
gctgctgtga aggaaggatt gtaggaggca ggagtagatt cagggagatg agacaagtga 129000
tgagagaggc tttgaacttg ggtaaaagta gtttgtggaa agtctttttt ggaggtagtt 129060
tttgtttatt gccttgtcat caaagcagag atgctgacca atgaaactcc atgagaaaat 129120
agtgatttat aaagacatat ctatgcactg ccattaaaaa gctgcttgga aaaaaaggat 129180
aaaaagctgc tttaacaact tttttttttg agatggggtc ttactctgtc acccaggctc 129240
acgacctcag ctcactgcaa cctctgcctc ccaggctcaa gcattctccc acctcagcct 129300
cccgagtggc tgggactgca ggcacacgcc accatgtcag gctaattgtg tgtgtgtgtg 129360
tgtgtgtgta tgtgtgtgtg tgtgtgtgtg tgtgtgtgct gggactgcag gcacacacca 129420
ccatgtcagg ctaattgtgt gtgtgtgtgt gtgtgtgtgt gtgtgtgtgt gtgtgtgtgt 129480
gtgtgtgtat gtagagatgg ggttttgcca tgttgcccag gctggtctca aaatgttgcc 129540
caggctggtc tcaaactcct gagctcaggt gatccacccg cctcggcctc caaagtgctg 129600
gagattacag acgtgagcca ctgtgcccac ctaacaactt taaaaaaatt ttgacattta 129660
gtaggatatt tattgcatta ttgttgagat ggcaaaatat tggagacaac tgaaatgttc 129720
atcagtgggg ggggctagtt aaatgaaata cagtgtagca tgcattagaa cacttttcaa 129780
gaatttaact ttttttgtag ccttttactt ataatgcttg tccctattga tgcctttttt 129840

-continued

```
ttcagcatga cttactcttt tactatagga tattaaaatt taattagatt agaaatgagg 129900
aatattcttg taatctgtag aaagtaacaa actataaact tattccccaa gaacaaatat 129960
aataattttt ctggagtagc aggtaagaaa gatataaatt tatatgtata caagaaactg 130020
aaattagact ttatacattt aaaggttaca agtgcagttt tattacatga atgtattatc 130080
cagcattgaa gtctgggctt ttagtgtaac cagcacctga ataacataca ttgtacccat 130140
taagtaattt ctcatccctc aaacccctcc caccctgaaa ttagactttg gatccctagt 130200
ttaaattcca cccctctctt tttttgagac aaggtctcac tctgtcaccc aggctggagg 130260
gcaatgttgc aatgatagct tactgtagcc tcaacctcct gggctcaagg gatacaccct 130320
cctcagcctc ctgagtagct ggaactgcag gcgtgcacca ccacattcag ctaatttttt 130380
gatttttttta tagagatgag gtcggaactc ctgggctcaa gcgattctcc ccaagtgctg 130440
gggttacaca catgggccac tgccccccagc ctaaacctcc tttctcagta tagcagcctt 130500
gagatgaagt tcctgaaatt actggccagc ttgactgttt ccccacatca ctggaggagg 130560
gggatgcata gataaaacaa aatattcagc atcattgtat tttctttttg tttcatcagc 130620
atcttttttt aaaactcact tgacataagt ccctagcctc aaagagtaaa gcctttgcag 130680
aatctgcatt cagatttcgg gtgtgatttc ctgacagata gttcaggttt gtaaactctt 130740
tttttttcct ttgagacaga gtttcactct tgtagcgcag gctggagtgc agtggcacca 130800
tcttgcctca ctgcaacttc tgccccccttg attcacgcga ttctcctgcc tcagcctcct 130860
gagtagctgg gattacaggc atgcgccacc acacctgggt aatttttgta tttttagtag 130920
agatggggtt tcaccatgtt ggccaggctg gttttgaact cctgacttca ggtgatctac 130980
ctgcctcagc ctcccaaagt gatgggatta caggtgtgag ccaccgcagc cggccaaaac 131040
tttgtttttt ttcctctttt tgttgctgag aaatgtaaac tcttacagac acaaattatg 131100
tctcccattt tttaaaaccc actcaacaca ggggtcatgt gtaataggcc ctggagctta 131160
ttttagacat tgatttgagg ctcttttccc caagtgctgg tttgtgtgtg tgtgtatgtg 131220
tgtgtaagtc tttctatgag atgagtggta cctacctggg ctgtgtgatc tttttttattt 131280
tatttatttt atttttgtag atacgaggtc tcactatgtt gctcaggctg gtcttgaact 131340
ctggggctca acctatcctc cctccttggc ctcctagagt gctgagatta caggtgtgag 131400
ccactgcacc tggccagcga tccttaataa atatagataa tggccgggcg tggtggctca 131460
cacctataat accagtactt tgaggggccg aggctggcag gtcacctgag ctgaggagtt 131520
tgagaccagc ctgggtaacg tgggtgaaac cctgtctcta cagaaaatag aaaaattagc 131580
caggtgtggt ggtgcatgcc tgtagtcaca gctacttggg aggttgagac aggagaattg 131640
cttgaacctg gaaggtggag gttgcagtga gccgagatcg tgtctttgaa ctccagcctg 131700
ggtgacagag tgagaccttg tctcaaaaaa aaatatagat ataggctggg cgtggtggct 131760
cacacctgta atcccagcac tttgggaggc cgaggcgggt ggatcaggag gtcaggagat 131820
cgagaccatc ctagctaaca tggtgaaacc ctgtctctac taaaaataca aacaattagc 131880
caggcctggt ggtgggtgcc tgtagtccca gctactcggg aggctgaggc aggagaatgg 131940
cgtgaacccg ggaggtggag gttgcagtga gccgagactg tgccactgcc ctccagcctg 132000
ggcgacagag cgagactctg tctcaaaaaa aaaaaatcta tatatctata tatctatatc 132060
tatatagata tagatataga taatgccaga tgatggctgg ttagaaggga ttgtcagggg 132120
ctggcaggtt ttgcaggtgt tagaatgagc aagatgagga gaaggatgct tacttccctc 132180
tccttgtaac tctctacccc ctcccctcag tgttttttta tttttatttt tatttattta 132240
```

-continued

```
ttttttttga gacaaggtct tgctctgtca cccacactgg attgcagtga tgcaatcata 132300
gctcattgaa gcccaaactc ctgggctcaa gtgatcctct tgcctcagcc tcccaagtaa 132360
ctgggaccac aggtgcgtac aactatgccc agttaagttt ttcatttttt atacagacgg 132420
ggtcttgcta tgctgtccag gctggacttg cacttctggc ttcaagtgat tctcttgcct 132480
cagtttccca aagtgctggc attatgggca taagccactg tgcctagccc atcagtgtct 132540
ttttatcctt tactcctatc aaaattcatt cactcagcag ccattgatca agtgcctact 132600
atatacatgt tgaggactgg aaatttattt gtctcttctc atcttatctg gaccctctgt 132660
gttaattgta attaactgta atcattctgt attaattgta ataaacttgt tgataaactc 132720
aaatgaggcc ataccgtttt gccacttccc ctccttccag gttatatgga tgtacttaca 132780
ttgcaggttt catttgttgg ttcagttttt aaactaagcc ctattgtgtc aaattatgct 132840
aggtgtgaga tggggagttc aagctgtgtg ttgtcttttt tttttttttt tttttgcct 132900
cacttactaa tatacaagcg cttataacct ttgaggctgg ccctatacat taagattttt 132960
attaattcca ctgttcttta tcttctctta ctaagttctc agggtcgaat gaactctaac 133020
tgctccttgc tagtgataag caagttgcaa attacagaat tgtcagtgat tgaatacacg 133080
tattaaacct gtaactggga agcatttttg gtaattatga atacttttgg aaaaaaaaaa 133140
gctatggaag gaaagtttaa aatctacgaa agctcaagta gatggtcatg gaatagctat 133200
ttcaatttct aactatatat tacttattta tttatttatt tttgagacgg agtttagctc 133260
ttgttgccca ggctggagtg cagtggcacc atctcggctc actgcaacct ctgcctcctg 133320
agttcaagtg attcttgtgc ctcagcctct caagtagctg ggattacagg tgtgtgccac 133380
cacactcggc tattttttgc atttttagta gagatggggc tggtcttgaa ctcccagcct 133440
caggtgatct gcctgcctca gcctcccaaa gtgctgagat tacaggtgtg agccacagcg 133500
cctggccata tattgctttt ttcttattat cagagccagt tcataattgt ggaaaaatag 133560
tgtttgtaac aatgtaagta tggtgatgaa ctacttgcnn nnnnnnnnnn nnnnnnnnnn 133620
nnnnnnnnnn nnnnnnnnnn nnnnnnnnnn nnnnnnnnnn nnnnnnnnnn nnnnnnnnnn 133680
nnnnnnnnnn nnnnnnnncc tgaaaaatta cacgtttgtt ctaggttttc tgacttattt 133740
ccacaacttt ttagtctttc cccctggaat catgcccctt tgcataaaca ggactctgat 133800
gtacctgaag tattttcaca cttcgggtgg actttctgtt tctgggggtg gttttagagc 133860
aattttaggc ctgccactag ctaccctgtt ctctacacca tgctgttttt ctcagaatgc 133920
tcttcttttg cacaaaggct tggagtagga ggttgagcag tcactcactg acgtttggta 133980
tattttcttt tttttgctta caggtactct ggaagtttgg gcattctctt taagttgagg 134040
gtgtggtttt catgtcattt tatttgttta ttgttttctt gtgtgtgttt cttagagaca 134100
gggtcccact cttgccctgg ctgaagtgca gtggtgatct gggctcactg caagctccgc 134160
ctactgggtt cacgccattc tcctgcctca gcctcccgag tagctgggat tacaggcaca 134220
tgccaccacg cctggctaat ttttttgcat ttttagtaga gagggggttt cactgtgtta 134280
gccaggatgg tctcgatctc ctgaccttgt gattctcctg cctcagcctc cttagtagct 134340
gggactatag gcacacacca ccatgcatgg ctaattttta tattttttttg tagagactgg 134400
gtttcgccat gttgcccaag ctggtcttga actcctgggc tcaagtgatc cacctgcctt 134460
ggcctcccaa aatgctagga ttacaggtgt aagccactgc gcctggccct aatttttgca 134520
tttttgtag agatggggtt tcactatatt gcccaggctg gtcttgaact cctgggctca 134580
```

-continued agtgatcttc ccatcacagc cccctaaagt gctgggatta taggcgtgaa ccactgtgcc 134640
tggctgagga ttaagtttca acctcagggg agcggcattc aaactatagc attgtccttt 134700
agtgactggc ttagttcact tagaatgttt gtctattcat ccatctatag acactgtttt 134760
ctttcacctt ttggctttgc aaataatgct gctgtgaata tgagttatag aaaaatacca 134820
atttgaatcc gtgttttcaa ttactttgag tatatacctg gaagtggaat ttctggatca 134880
tatggtactt ccaagttttt ttttttctt ttttgagaca aggtctcact ctgtcaccca 134940
ggctggagtg tagtggcacg atcttggctc actgcaacct ccgcctcccg ggttcaagcg 135000
attctcctgc ctcagcctct caagtagctg ggattacagg cacgcgccac cacgcccaac 135060
taattttgta tttttagtag agatgggttt ctccatgttg gtcaggctgc tcccgaactc 135120
ccgacctcag gtgatctgcc tgcctcagcc tcccaaaatt ctgggattac aggtgtgagc 135180
caccgcacct ggcctccatg tttcaatttt taaacaaaca attagttaaa aaaataggaa 135240
actaagagaa tgaactattt cctgttttat tcagtgggtt ataatctgtt actatcattg 135300
tttattttga ggtacaaatt gtccctactt tggccagcag aggatcctgc agtttgtctc 135360
ctgtgtcctt ttcatagctc cttgttggaa ctcttactgg cccacaatag gatgttccaa 135420
gttcatcttc ttacttttac tgccccaacg ctgggatcag ccatttcttc aaggaggcca 135480
gttcctttca ttggagaatg gaaaacccaa tatgtagaaa ccaagataga ggtgttaggt 135540
gtgattgcta ctggagtgtc attgcttcca aaccctttca gaagagacct aggaaatgtg 135600
tgtgtgtgtg tatatatata tgtgtgtgtg tgtgtgtatt cataaaagca catacacata 135660
cacatacccc gaagcatgta tttctgtatt attattattt ttttgagatg gagtcttgct 135720
ctgtcgccca ggctggagta cagtggcacg atcatggctc actgcaacct ctgcctcctg 135780
gattcaagca attctcctgt ctcagcctcc tgagtagctg ggattacagg tgtccaccac 135840
cacgcccacc taatttttgt atttttagta gagatggggt ttcaccacat tggccaggat 135900
ggtcttgaac tcctgacgtc aagtgatctg cccgcctcgg cctcccaaag tgctgggatt 135960
ataggcgtga gccactgttc ccatccagaa gcatacatat ctatttctat atctacattt 136020
ctgtctttac atgtatatat taaaaattac agtttgcact aatacctcca attacaatct 136080
aacatcatgg gatttattct ggctttctcc cttctcatat ttgtgtctcc ccaacagtga 136140
gaaacctggc ttgctatcct caacatggta acttatttat taagaaactt attctttttt 136200
tttttttttt tctgagattg agtttcgctc ttgttgccca agctggagtg cagtggtgtg 136260
atcttggctc accgcaacct ctgcctcctg ggttcaagcg attctcctgc ctcagcttct 136320
caagtagctg ggattacagg catgcaccac catgcccagc taatttcgta tttttagtag 136380
agatgggttt ctccatgttg gtcaggctgc tctggaactc ccgaccccag ctgatctgcc 136440
tgcctcggcc tcccaaagtc ctgggattac aggcgtgagc caccgtgccc tgcctctagt 136500
ttatttattt ttattccatg tgctcagtct tgcgagcacg tggtctgttt tcttgggcct 136560
ggccccctca gtgcactgtc ttaataccct agcccccagt ccctctgatc atatccccag 136620
acacccctac tgaatcccag gtctctacca agggaaaggc agggaggagg cattgaccaa 136680
ggagaagagg gggaagggac agggaaggtc ttgatttgta ttttctaaaa ttttctactc 136740
tgctcataat gcgtcttagc tgtgttgttg tggaaagtag tgctgacagt gtcttgtttt 136800
tttattactt actttgtctt tctttttaag atggtttcac ccaaatatca ctggtgtgga 136860
ggcagaaaac ctactgttga caagaggagt tgatggcagt tttttggcaa ggcctagtaa 136920
aagtaaccct ggagacttca cactttccgt taggtaagtt ggaatgaaaa gagaggatcc 136980

-continued

```
tgagagtgtt ttctaggtag gaagtggtaa aaccatgctt ggatagcttg ctgcctgcat 137040
ttcgagtttg aaggccttat ctgagccctg ggctgccttc agggtttggg gagtggcctc 137100
ctggacattt agcagaagag gagtaaggag ggcccttctt ctccctctga gacctcatgg 137160
aaggtgagtt ggagcaggtc atagaagttc ttaagccctc cagtgcttga gacttgttcc 137220
acacatcttg aacctggttt ctgcattttt cttttccttc ctgttgattt atttaaaaat 137280
tttatttctt ttcaattttt tttttttttt aaatagaggt gggatcttcc aatgttggcc 137340
aggttggcct tgaacttctg gcctcaagca atcctgcctc ggcctcccaa agtgttagga 137400
ttacaggcgt gagccactat gcctggcctt cttttttga gacaagctgt tgctctgttg 137460
cccaggctgg agtgcagtgg tacgatcaca gcttacagca gccttgaact cctgggctta 137520
agtgatcctc ccgcctcagc ctcccgggta gctgggactc caggcttgtg ccaccatgct 137580
cagcattttt aaaaaatatt ttttgtagag atgaggtctc actgtattac caaggctgat 137640
ctttaactct tagcctcaag tgatcctcct gcctcagcct cccaaagtgt tgggattaca 137700
ggcatgagcc accacactca gactttgttg acttcttaat aagaaaaata cttgttaaga 137760
gtttcttcag atcactttcc tttatcaaca agtaaaacat gactgaggaa gttgtggtcc 137820
cctttgcttc cctgcccagg cccgtttccc tccctctttc cccagaggaa accaccaaga 137880
ggttggcata tattcttcct gaacgtgttt ttatagttgt actgcacttg tactgtgtat 137940
gaacaatata aagttggttt gtgtgtttaa aaaattcaca tacatggatt tataatgtat 138000
gtatcatttt gcaacttaaa aatttttttt tgagctccat gctgattgat aacgatctat 138060
tttttttttt tgagatggag tttcagtctt attgcccagg ctgaagtgca atggcgtgat 138120
ctcagctcac tgcaacctca gcctcctggg ttcaagctat tctcctgtct cagcctccgg 138180
agtggctggg attacaggtg catgccacca tgcccagcta atttttgtat ttttagtaga 138240
gatggggttt caccatgtcg accaggctgg tctcaaactc ctgacctcag gtgatctgcc 138300
tgccttggcc tcccaaagtg ctggaattac aggcatgagc taccatgcct ggcctttttt 138360
tttttttttt tttgagacaa agtcttgctc tttttcccag gctggagtgc agtggccaca 138420
atcttggctc actgcaacct ctgcctcctg agttcaagca gttctcctgc ctcagcctcc 138480
tgagtagctg ggattacaga catgtaccac catgccaagt taatttttgt atttttttgta 138540
gagactaggt tttaccatgt tggccaggct ggtcctgaac tcctgactta aagtgatcca 138600
tctgccttgg cttcccaaag tgctggggtt acaggcatga gctatcgcgc ctggcctgag 138660
aaatctcatt cttactccta ctcccttgca cactatctcc attctgtagg tagccatttc 138720
tattaatttc ttgtttaccc ttctgtgttt ctttcattct ttttcttttt ttcttttttt 138780
tttttgagac aatcttgctc tgttgcccag actggagtgc agtggtgtga tcttggctca 138840
ccgcaacctc cacctcctgg gttcaagtga ttttcatgac tcagccacct aagtagttgg 138900
gattacagcg cctggtgtac actaccacac ccagctaatt tgtgtatttt tagtagagat 138960
ggggtttcac catgttgtcc aggctaatct ccaactcttg gcctcaaggg atctgcctgt 139020
ctcagcctcc caaagtgctg ggattatagg catgagccac catgcctggc cctatgtttc 139080
tttttataaa aataagcaaa ttaatatttt tattactatt ttccttttat ttttacacat 139140
caagtagaac attaaatata tttctctgta atttttttca gttacctaaa tcttttagtg 139200
atctctctca tctttttaat cagctggatc gcattctatc atgtgaatat tttataactt 139260
ctatatactg tcaccagcag gtagcgattt agttgtgtct aatattttaa aatgatatat 139320
```

-continued aatgcctcaa tgaatatagt aaccttttgc atatattgtt ttgtgctttg ggataacact 139380
acctcgtatt ggaaactgtg tcattacatg tgtctttaaa attacatgtg tctttttatt 139440
tttattttta ttttttttga gtgggagttt cactcttgtt gcccaggctg gagtgcagtg 139500
gtgagatctc ggccgactgc aacttccgcc tcccgggttc aagcgattct cctgcctcag 139560
cctcccgagt agctgggatt atagacatgt gccaccacgc caggctaatt ttgtattttt 139620
agtagagacg gggtttctcc acattggtca ggctggtctc gaactcccaa cctcagctga 139680
tccgcctgcc tcggcctccc aaagtgctgg gattacaggc gtgagccacc gcgtccggcc 139740
tcttaactat tgtttgaaat aatgtagaga cagctccaga gccatgaaga agtgtatgaa 139800
gaagcagtgt tagcttaaat gacatacatg tcacaattgc ctatgtgaaa ctatcataat 139860
tatgcatgag aagtatctat cctgcataac ctccaccaat aataataatg ttaataatag 139920
tgaaaactaa tgtttattaa gtccttactg tctccagcct ctgtgctaaa tactggttac 139980
taagtttccc tgaaaatact attctcatct gtttgttctt aataacagga tagcataatt 140040
gtaagttgta aatgaaataa tacagtgtat gtaataaaag gtacggttag taacgtcggc 140100
aagtgatccg tatnnnnnnn nnnnnnnnnn nnnnnnnnnn nnnnnnnnnn nnnnnnnnnn 140160
nnnnnnnnnn nnnnnnnnnn nnnnnnnnnn nnnnnnnnnn nnnnnnnnnn nnnccggtag 140220
ttgttttgtt tagccaacac tgcaaggcgg tgcagtagtt catcaacgga gtcttgctct 140280
gttgcccagg ctggagtgcg gtgatgcgat ctcggctcac tgcaagctcc gcctcctagg 140340
gttcacgcca ttctcctgcc tcagcctccc tagtagctgg gactacaggc gcccgccacc 140400
acgcccggct aatttttttgt atttttagta gagacggcgt ttcaccatgt tagccaggat 140460
ggtctcgatc tgaccttttg atccgcccgt ctcggcctcc caaagtgctg ggattacagg 140520
cgtgagccac tgagcctggc ctatattttt gtttttttatt atactttaag ttctgagata 140580
catgtgcaga acttgcaggt ttcttacata ggtacacatg tgccatagtg gtttgctgca 140640
cacatcaacc catcttctag gttttaagcc ccacatgcat tagttatttg tcctaatgct 140700
atccctcccc ttgccctcaa ctccctgaca ggccccagtg tttgatgttc ccctccctcc 140760
tgtgtccatg tgttcttttt tttttttttt ttgttgagac cgagtctccc tctgtcgccc 140820
aggctggagt gcagtggcgc aatctcggct cactgcaacc tccgcctcct gggttcacga 140880
cattctcctg cctcagcctc ccgagtagct gggactatag gcgcccgcta ccacgcccgg 140940
ctaatttttt gtatttgtgg tagagatggg tttcaccgtg ttagccagga tggtctcaat 141000
ctcctgacct cgtgatctgc ccgcctcagc cttccaaagt gctgggatta caggcgtgag 141060
ccactgcgcc tggccctgtc catgtgttct cattgttcag ctcccactta tgagtgagaa 141120
catgtggtgt ttggttttct gttcctgtgt tagtttgctg agaatgatgg tttccagctt 141180
catccatgtc cctacaaagg acatgaactc attctttttt atggctgcat agtattccat 141240
ggtgtatatg tgccacattt tctttatcca gtctatcatt gaagggcatc tgggttggtg 141300
ccaagtcctt gctattgtga atagtgctgc aataaacata cgtgtgcatg tgtctttata 141360
gtagaatgat atataatcct ctgggtatat acccagtaat gggattgctg ggtcaaatgg 141420
tatttctggt tctagaatct tgaggaatcg ccacactgtc ttccacaatg gttcaactaa 141480
tttacactcc caccaacagt gtaaaagcat tcctatttct ccacatcctc ttcagcatct 141540
gttgtttcct gattttttaa tgatcatcat tctaactggc atgggatgat tacctcattg 141600
tagttttgat tcgcatttct ctaatgacca gtgatgatga gcttttttttc ataagtttgt 141660 tggctgcata aatgtcttct tttgagaact gtctgttcat atccttcact cactttttga 141720

-continued

```
tgggattgtt tatttttttc ttgtaaattt gtttaagttc cttgtagatt ctggacatta 141780
aagctttgtc agccgggcac ggtggctcac gcctgtaatc ccagcagttt gggaggctga 141840
tgtgggcgga tcacgaggtc aggagatcga gaccatcctg gctaacacgg tgaaacccca 141900
tctctactaa aagtacaaaa aattagccgg gcgtggtggc gggggcctgt agtcccagct 141960
actcgggagg ctgaggcagg agaatagcgt gaacccggcg ggtggagctt gcaatgagca 142020
gagatcgcgc cactgcactc tagcctgggt gacagagcga gactccgtct caaaaaaaaa 142080
aagctttgtc agatgtacag attgcaaaaa ttttctccca ttctgtaggt tgcctattca 142140
ctctgatgat agtttctttt gctgtgcaga agctctttag tttaattaga tcccatttgt 142200
caattttggc ttgagaatgg cgtgaacccg ggaggcggag gttgcagtga gctgagatcg 142260
caccactgca ctccagcctg ggcaacagag cgagattctg tctcaaaaaa aaaaaaaaaa 142320
aaatttccct ccaaacactt ctttagctgt gtcccagaga ttctggtaca ttgtgttttt 142380
gttctcattg gtttcaaaga acttatttat ttctgcctta attttgttat ttacccagta 142440
atcatacagg agcaggttgt tcagtttcca tgtagttgtg tggttttgag tgagtttctt 142500
aatcctgagt tctaatttga ttgcactgtg ttctgagaga ctgttatgat ttccattctt 142560
tttcatttgc tgaggagtgt tttacttcta attatgtggt caattttaga ataagtgcta 142620
tgtggtgctg agaagaatgt atattctgtt gattttgggt ggaaagttct gtagatgtct 142680
attaggtcca cttggttcag agctgagttc aagtcctgaa tatccttgtt aattttcttt 142740
ctcattgatc tgtctaatat tgacaatggg gtgttaaagt ctcccactat tattgtgtga 142800
gagtctaagt atctttgtag atctctaaga atttgcatta tgaatctgtg tgctcctgta 142860
ctgggtgcat atatatttag gagagttagc tcttcttgat gcattgatcc ctttaccatt 142920
atgtaatgcc cttctttttc ttttttgatc ttggttggtt taaagtcatt tctattggag 142980
actaggattg cagcctctgc tttttttttg ctttccattt gcttagtaaa tattccccca 143040
tccctttatt ttgagcctat gtgtgtcttt gcatgtgaga tgggtctcct gaatacagca 143100
cactgatggg tcttgactct ttatccaatt tgccagtcta tgtctttttt ttcttttccc 143160
gagatggagt cttgctctgt tccccagact ggagtgcagt ggcacaatct tggctcacta 143220
caacctccgc ctcccaggtt caagcaattc tcctgcctcg gcctcctgag tagctgggat 143280
tacaggtgtg agccaccaca cccggctatt tttttgtat ttttagtaga gatggagttt 143340
caccatgtca gccagggttg tctcaaactc ctgaccttgt gaaccacccg cttcggcctc 143400
ccaaagtgct gagattacag gtgtaagcca ccatgcccag cccagtctgt gtcttttctt 143460
ttttttttga gatggagtct cactctgtca ctcaggctgt agtgcagtgg cacaatcttg 143520
gctcactgca agctccgcct cccatgttca cgccattctg ctgccttagc ctcctgagta 143580
gctgggacta caggcgcctg ccaccatgcc tggctaattt tttgtgtttc tagtagagac 143640
ggggtttcac cgtgttagcc aggatggtct cgatctcccg acctcgtgat ctgcctgcct 143700
cggcctccca aagtgctgag attacaggca tgagccatgg cgcctagccc agtcagtgtc 143760
ttttaattgg agcatttagc ccatttacat ttaaggttaa tattgttatg tgtgaatttg 143820
atcctattgt catgatgcta gctggttatt ttgcacatta gttgatacag tttcttcata 143880
gtgtcattgt tctttatatt ttggtatgtt tttgctgtgg ctggtaccag ttgttccttt 143940
ccatatttag tgcttccttc aggagctctt ttaaggcagg cctggtgggg acaaaatcct 144000
tcagcatttg cttgtctgta aaggatttta tttctcctcc acgatgaagc ttagtttagc 144060
```

-continued

```
tggatatgaa attctgggtt gaaaattctt ttcattaaga atgttgaata ttggccccca 144120
ctctcttctg gctcataggg tttctgcaga gagatccgct attagtctga tgggcttccc 144180
tttgtaggga acctgacctt tctctctggc tgcacttaac attttttcct tcagttcaac 144240
cttggtgaat ctgatgatta cgtgtctttg ggttgttctt atcaaggagt atcttagtag 144300
tgttctctgt atttcctgaa tttgaatgtt ggcctgtctt gttaggttgg ggaagttctc 144360
ctggataata tcctgaagtg tgttttctaa cttggttcca ttctccccat cactttcagg 144420
tacaccaatc aattgcaggt ttggtctttt cacatagtcg tatatttctt ggaggctttg 144480
ttcattcctt tttattattt tttctctaat cttgtcttcc cgctttattt tattaagttg 144540
atcttttctt tctttctttc ttttttgag acagagtttc attcttgttg cgcaggctgg 144600
agtgcaatgg tgcaatctcg gctcaccgca aacaccacct cccaggttca agcgattctc 144660
ctgcctcagc ctcccgagta gctaggatta caggcatgtg ccaccatgcc ctgctaattt 144720
tgtattttta gtagagatag tatttcccca tgttggccag gctggtctcg aactcctgac 144780
ctcaggtgat ccgcccgcct cggcctccca aagtgctggg attacaggcg tgagccactg 144840
cacccagcct ctatgtttaa tttttaaagg aactgccata ctgctttcaa cattaaagta 144900
aatacttttt tttttttttt tttttttcc tgagacagag tctcactctg tcacccaggc 144960
tggactgcag tagggtgatc tcagctcact gcaacctctg cctcccaggt tcaagcgata 145020
cttgtgtctc agcctcctga gtagctagct gggattacag gtgcacacca accatgccca 145080
gctaattttt ttttctttct ttctttcttt tgagacagag tttgctcttt cgcccaggca 145140
ggagtgaagt gactcaatct tggcttactg taacttctgc ctcccaggtt caagtgattc 145200
ttctgcctca gcctcccaag tagctgggat cataggcgcc ctgccaccat gtctggctaa 145260
gttttgtatt tttagtagag atggggtttc accatgttgg ccaggctggt ctcaaactcc 145320
tgatgttcgg tgatccacct gcctcagcct tccaaagtgc taggattaca ggcgtgagcc 145380
accgtgctca tccgcccagc taatgttttt gtatttttag tagagatggg gtttcaccat 145440
gctggccagg ctggtctgta actcctgacc tcaagtgatc cacctgtctt ggcctcccaa 145500
agtgctggga ttacaggcat gagccactac acccagccta aagtatatac ttttaactca 145560
ctttatacta ccacagttgg aggcatttat gaatgggaaa gaagtacctg aggctgggta 145620
attttgttta tttgatattt tttttgagat aacgtctcac tctgtcaccc aagctggagt 145680
gcagtgggtc catcacagct ccctgcagcc tcagctttct gggctcaagc gatcctcctg 145740
cttttcagcc tcctgagtag ctgggactat aggcatgcac cacaaagtcc agctaatttc 145800
tatttttttt ttctttttgt agagataggt ttcaccatgt tgcctgggct ggtcttgaac 145860
tccttggctc aagtgatctg cccacctcag cttcccaaaa gtgctggggc tataggtgtg 145920
agccaccaca cctggccaag gctaagtaat ttataaagag agagtgttta ttttggctca 145980
cagttctgca ggctgtacag gaagcgtgga attaacatca gcttctggtg aaagcttcag 146040
gaaggttaca atcatggtgg aaggtgaagg ggagcagtgt atcaaatggc aagagagaga 146100
gtaagaggtg gggagaggtc ctagaatttt taacaaccag atctagtata aactgagtga 146160
gaacttaatt atcatcaagg gtgctaaagc attcacgagg catcttcccc atgatccaat 146220
cacctcccac caggccccac ctccaacact ggaaatcata tttttcatat ctctttttgt 146280
tgttgttttt gttttgtttg agacggagtc ttgctctgtc acccaggctg aattgcagtg 146340
gcgcgatctt ggctcactgc aacctccacc ttctgggttc aagcaattct cctgtctcag 146400
cctctcgagt agctggaact acagacacat gccaccacgt caggctaatt tttgtatttt 146460
```

-continued

```
tagtagagac agggtttcac catattgctc aggctgttct tgaattcctg acctcaggtg 146520
atccacccgc ctcagcctcc caaagtgctg agattacagg catgagccac cacacccaga 146580
ggttttttga tcgttttttt gagatagagt gtctctctgt tgcccaagct ggagtgcagt 146640
ggcgcaatct cagctcactg caacctctgt ctcccaggtt caagtgattc tcgtgcctca 146700
gcctcccaag tagctgggat tacaggcgcc tgccaccaag accagctaat ttttgtattt 146760
ttagtacaga cagggtttca ccatgttagc aaggctggtc ttgaattctt gaccttaagt 146820
gatctgtccg cctcagcctc ccaaagtgct gggattacag gtgtgagcca ctgtgcccga 146880
ccccgggaat catatttcaa catgagacat aaaaggaata aacatccaaa ccatatacat 146940
ttgattgcag ttaagataag tactactatg aaaagaaata gtgtgcaaaa atgactgaga 147000
aacaggagga cctattgtgt ttgggggaat cagatgtcct ctacgaggaa gctgataact 147060
ggagaatagg taggagtttg ccaagtgaag caggtggcga agggcattct ggcaggggga 147120
acagcaagtg caaaggccta gaggtaggaa aatggtacaa ttgttaaaga aactgcaagc 147180
agtcagggtg gcttgctgag atgaagatgg gcattgtatg cctaagatct cagaagcaca 147240
gacaacaaaa acagacaaac aggacttaaa ccaaaaagct tctgtacagc aaaagaaata 147300
atcaagataa tgaaccaaca acacacacaa tgaaagaaaa tatctgtggg ccaggcacag 147360
tagctcacac ttgtaatccc agcattttgg gaggccaagg tgggcagatc acctgaggtc 147420
aggagcttga gaccagcctg gccaacatgg taaaacccca tctctactaa aaatgtaaaa 147480
attagctggg tgtggtggca tgtacctgta atcccagcta cttgggaggc tgaggcacga 147540
gagttgcttg aaccccggag atggatgttt cagtgagcca agattgcacc actgcactcc 147600
agcctgggag acagagtgag actgtctcaa aaaaaaatca atacataaaa aacccacaaa 147660
acttaattgg gatgcttcct atatgatacg gctcttagat ttatagtgta gcatgttagg 147720
ttctaaggat aggtgtcttg gtgaccatct gacctgcact agagaatnnn nnnnnnnnnn 147780
nnnnnnnnnn nnnnnnnnnn nnnnnnnnnn nnnnnnnnnn nnnnnnnnnn nnnnnnnnnn 147840
nnnnnnnnnn nnnnnnnnnn nnnnnnngca agtagttcat caatatatat aaaaagagag 147900
agagagagag gagagagagt aaacatggta caggttgagt atcccaaatc taaaatgctg 147960
caaaatccat ggccaggcgc ggtggttcac tcctgtaatc ccagcacttt gggaggcgga 148020
ggcaggtgga ccacctgagg tcaggagttc gagaccagcc tggccaacac ggtgaaaccc 148080
tgtctctact aaaaatacaa aaattagccg gccgtggtgg caagcgccta tagtcccaac 148140
tactcagggg gctgaggcag gagaatcact tgaacccaga aggtgaagtt tgcaataagc 148200
caagatcgct cactgcactc cagcctgggt gatggagcaa tactccatct caaaaaaataa 148260
attaattaaa taaatttaaa aagtgcccac ataacactca aaggaaatgc tcatcatagc 148320
atttcagata tttcagattt gagatttggg gattagagat gcttaagtat ataataaaaa 148380
tattccaaaa ttcgaaaaaa tctgaaatcc aaaacacttc tggtcccaag cattttggat 148440
aagggatact caacctgtat aaggttgact tgtaaatctg gatgaaaagt taacacgaat 148500
tatttgtact attttgcaac tcttatttaa atttgaaatt atttcaaaat aaaatgtttt 148560
ttaaaaccca taaatgatga aatccatcat gaatggcatc tgcttcagag gagtcctctc 148620
tagttaccag caaaaagata ttcttgggca ggcgcggtgg ctcacgcctg taatcccagc 148680
actttgggag gccgaggcgg gcggatcaca aggtcaggag atcgagacca tcctggctaa 148740
cacagtgaaa ccccctctct actaaaaatg caaaaaaatt agccaggcgt ggtggcatgt 148800
```

-continued gcctgtaatc ccagctactc gggaggctga ggcaggagaa tggcgtgaac ccagtaggcg 148860
gagcttgcag tgagcccaga tcaccactgc actccagcct gggcgacaga gtgagactcc 148920
gtctcaaaaa aaaaaaaaag atattcttca tggatttcaa aagtcattga gattcatggt 148980
aacagtaact tctaaagtca aattatcctg gacctttcta agctaataga atgctctgaa 149040
atgctcccag gaatatgtca atattaaatg tagagttcta gtactgacaa tcaagtgaac 149100
ttttaagaga cttctccaca aatattgacc caattcaagt atcttacaac agtgaaggag 149160
accaggcaca gtggctcaca cctgtaatcc cagcactttg ggaggccaag gtgggaggat 149220
cacctgaggt caggagttca agaccagcct gggcaaaatg gcaaaaccct gtctctacaa 149280
aaaaatacga acattagcca ggtgtggtgg catatgcctg tagtcccagc tactcaggag 149340
gctaaggtgg gaggattgct tgagtctggg aggcagagaa tgcagtgagc agagatcgca 149400
ccactgcact ccagcctagg caatcgagca agacctcttc tcagatttaa aaaaaaaagg 149460
ctgggcaagg tggctcatgc ttgtaatccc agcactttgg gaggccgagg caggtggatc 149520
acctgaggtc gggagcttaa gaccagcctg accaacatgg agaaaccctg tccctactaa 149580
aaatacaaaa tcagccgggc atggtggcgc atgcctgtaa tcccagttac tcaggaggct 149640
gaggcagaag aatcgcttga acccgggaag cggagggtgc ggtgagccaa gatcgccacc 149700
actgcactct agcctgggca acaacgcaaa actccatctc aaaaaaaaaa aaaaaagaaa 149760
agaaaagaaa aatcgtaaag ctcagatcaa aataatgaaa tattcatttg ctttttactc 149820
tctctgagag cttgtcagaa gattgagtct gggcccggtg actcatgcct ataatcccag 149880
cactttggga agagctgagg caggaggatt acctgaggtc aggagtttga ggccagcctg 149940
ggcaacatgg caaaacctca tctgtactaa aaatacaaaa attagccagg catggtggca 150000
cacatctgta atctcagata ctcgggaggc tgaggcagga gaatcacttg aacccgggag 150060
gcggaggttg caataagctg agatcatgcc actgcgctcc agcctaggca acaaagcgag 150120
actctgtctt aaaaaaaaaa aaaaaaaaaa aaaaaaaagg ccaggcacag tggctcacgc 150180
ctgtaatccc ggcactttgg gaggccgagg caggcggatc acgaggtcag gagattgaga 150240
ccatcctggg aaaccccgtc tctactaaaa atacaaaaaa attagctggg tgttgtggca 150300
ggcccctgta atcccagcta ctcgggaggc tgaggcagga aaatggcatg aacccaggag 150360
gtggagcttg cagtgagccg agatcatgcc actgcactcc agcctgggcg acagagcaag 150420
attccgtctc aaaaaaaaag gaaaattgag acagaataga atttcacccg ggaaaacgtc 150480
aacctcaatt tatgtgatac ctattattct agcatccaat acttttgcat tcagaatggt 150540
taaactattc cgttaagaaa aaaaatcctt ccttgcagct tctttcatct gtggttccag 150600
atgaaagatg cccagaattc taaggaatca aaaagtaatg acaactggct tctagctatt 150660
tatagttttt caaaaaggta taatgaaact cttacattag gcctcaattt gtctacctac 150720
ataagctaat taaaatgtca actctctttt gcttttggct gcaaaacaat tatgttaatt 150780
gggtgtggca actggaaact gagtggcata tgtgccttct accaagagga aaaaaatgga 150840
aaaactaatt attatataac acaggtgtgg agaccaaatc tttcagaata ttgggtttat 150900
ggtttgggtt tttttttttg tttttgtttt ttttttttaaa aaaggacaat ccagccatgc 150960
atggtggctc acacctgtaa tcccagcact ttggaaggcc aaggcaggta gatcacctga 151020
ggtcaggagt tcgagaccag cctggccaac atagtgaaac cccgtctcta ctaaaaatac 151080
aaaaaattag ccaagtatgg tggtgcgcgc ctatagtccc agctactccg gaggctgagg 151140
caggagaatc acctgaaccc aggagacgaa ggttacagag agccgagatc acagcactgc 151200

-continued actccagcct gaacaaaaga gcgagactcc gtctcaaata ataataataa taatacaaaa 151260
attagctggg catggtggct ggcaactgta atcccagcta cttgggaggc tgaggcatga 151320
gaatcacttg aaccccagag gcagaggtta cagtgagctg aaatcacacc actccactcc 151380
agcctcggca aaagagggag actctgtctc aaaaatataa taaaataaga ataaattttt 151440
taaaaagttt aaaaaaaagg gcaatcccct ccccaaatga caggctgaga atcactaaca 151500
catggtggca aagccttagg ggtagccaca tagactctgg tgccagattg tcttggtctg 151560
aagcccagct ctctgtgacc ctgggctaca tatttaacct ctctgttaag tcctataaaa 151620
tggaaggtgt aacagtaccc atgtcatagt gttgttgaga ggataaaatg agttaatatt 151680
tataaagtat ctagaagagt gcctggactt tcaggtagcc aaggacaacg atgattgcct 151740
aaatccatct ctccccatac atccttcaaa aacaacatag aattaaaaac aaaacaagcc 151800
aggcacaatg gttcatgcct gtaaatccca gtgttttggc aggctagggt gggaggattg 151860
cttaaggcca ggtgttcaag accagcctgg gcaacatagc aagatcccat ctctacaaaa 151920
aaattaaaaa ttagccaggg accaggcaca gtggctcaag cctgtaatcc cagcactttg 151980
ggaggccaag gtgggtggat cacttgaggt caagagtttg agaccagcct agccaacatg 152040
gtgaaaccct gtttctacta aaaaatacaa aaattagccg ggtatggtgg catgcacctg 152100
cagtctcagc tactcgggag gctgaggtga gagaatcgct tgaacccggg aggcagaggt 152160
tgcagtgagc cgagattgca ccactacact ccaatctggg ggacagagca agacttcgtc 152220
tcaaaaaaaa aaaaattagg tatggtggtg tgctcctgta gtcccagcta ctcaggaggc 152280
tgaggtggga ggttcatcta agcccagcag cttgaggatg cagtaagcta tgatcaagac 152340
gccactgcac tccagccagg gcaagagtgg gaccctgtct ctaagaaaca cacacaagaa 152400
aacaataaac aaataaaatg acatgaaaac cacaccctca acttaaagag aatgcccaaa 152460
cttccagatt acctgtaagc aaaaaaaaga aaatatacca aacgtcagtg agtgactgct 152520
caacctccta ctccaagcct ttgtgcaaaa gaagagcatt ctgagaaaaa cagcatggtg 152580
tagagaacag ggtagctagt ggcaggccta aaattgctct aaaaccaccc ccagaaacag 152640
aaagtccacc cgaagtgtga aaatacttca ggtacatcag agtcctgttt atggaaaggg 152700
gcatgattcc agggggaaag actaaaaagt tgtggaaata agtcagaaaa cctagaacaa 152760
acgtgtaatt tttcagggaa atgcagtcta caaaaattaa cccattagag taagaaaact 152820
taggcagacc aacttgtatt aaaaaaaata gagggagcct ctctgaacct attctggttc 152880
agaggctacc tgattaaaaa taagaaaaaa tagggaaaac aattaaggaa ctaccgcaca 152940
gaaaatcacc aggcccagat ggattcccaa tggacttcta ccaaaccttc aaagaccaaa 153000
tagtctcaat tcttaaaatc attcctgagt actaaaaaga aaggaaaact tccaacttcc 153060
ttttacaaac taaatataac actgatacct ataccaataa agatggcaca agaaaaacaa 153120
cagagaccaa tggtactcat gaatattgat gcagaacttc taaacaaaat ataaaagaat 153180
ccaataccac atttagaaaa taatgcaccg taacaaagta gttagaacca tacatcatat 153240
cacatatcag aataaatttt aggccgggca cggtggctca tgcctgtaat cccagcactt 153300
tgggaggcca aggcgggtgg atcacttaag gtcaggagtt cgagaccagc ctggccaaca 153360
gcaaaacccc atctgtacta aaaaaaaaat acaaaaatta gccaggcgcg gtggcaggtg 153420
cctgtaatcc cagctacttg ggaggccgag gcagcagaat cgcttgaacc cgggaggcgg 153480
gaggcagagg ctgcagtgag ccaagatcat tccactgcac tccagcctga gtgacacagt 153540

-continued

```
gagaccctgt ctcaaaaaaa taaaataaaa taaataataa acgtaaaaga tgaaacaatg 153600
caatactaga ggaaaacatg ggtgaatgtc ttgttaacct tagaataagg aaaggctttc 153660
tatgactcaa aatccagggg caataaaaaa aagattgata aatctgggat aattttaaca 153720
tcacctttca tcaacaattc aattgctttt taagaaaaat tcattaaatg gtaaaattta 153780
ttaccatttt taccatttat taccatttat taccataaat ttaattattc attaaatggt 153840
aaaaaacctc aaggactgaa gtcagttcta acttgcaatt tgagggtctt taaatcaatc 153900
attctttgga aaccaagaaa cttaaattca actccattca gaggcggaca acttacaacc 153960
cacagtccct cccactgagt tcagtgctat tctcagccaa aaaaaaaaaa aagccttcat 154020
ttctattata aaagcaatga aatgccaagg ctcagaaaaa cagacatact attaaatctg 154080
gatgcatatt ttgctcttct agcacttact catgtttttc aacccaaaag actaacaccc 154140
atgtaagggg agaagtatca ggaaaatgct tctgaaaaac atattttaaa aatctgattt 154200
gaagcatctc ttggttattg aagcaaccta cagagccaaa ccactgtctc aaatcccaga 154260
atgccacatc tcctgggcaa gctaattaat ctctctgctt cggtttttac atctgtaaaa 154320
tgtggataat aatagtgttt acctcatagg aaatgagaat taatgaatta atgcacataa 154380
aagaactata aagcatataa agcatttaaa actattaaag cttgtttgct tgttgttacc 154440
ttaatgaata cataaaacaa ttattgacta taatatctct accatagatt atgtttcatt 154500
aatatgcaat tactctagta ttaactaact tattatttaa taatctttat cttgaatgct 154560
acttagcccg atattggtac cacctgaatc tcttttgccc atgtttgttt tatttattct 154620
ttgacattct gtgccaattt gtctttttaa agcagaacac aactgaattt ttttttcttt 154680
tttcaaaata tttttataaa atagagatgg ggtcccacta tgttgttcag gctggtctca 154740
aactcctgga ctcaagtgat cctcccacct cagcctccca aagtgctggg attacaggtg 154800
tgagccacca tgcccggcct ggattttttc ttttaattcc atctggctca gccattattg 154860
aaggacttaa tccattatca ctgacagctc atgtttggta tcatatctgc tgattgtttc 154920
ctactttcaa ttttttttct gtcttttgcc acttagtgac ttcagtgact gtctacttca 154980
ggcagacacc tatttcttac tcaaatagaa ttctaatcat ttttaaatta tactggtagt 155040
catattgtag tatttaaaaa aaaaaaaaaa aaaaccttaa tcctacagtc ccaggttatt 155100
gaagggaaaa taacttttgc ctctcttaga tggaaagtga agaatttctg gctgttgttt 155160
tactagtctc cattaaatga aatacagcag gctcagcggt tgcttcattt taaacaccag 155220
ttagacagcc tagaccccca caatctacct gcttatctgt tccctgactg tcaccactgt 155280
catctcttct ttttttaaaa tagattctaa aagaatttct cacacttgtc cttgacctca 155340
cccctgtgat ggcagcctca aacatagtat tattaactgc ttttatgcag atctttgtac 155400
agggcagggc aaggtggctc acacctgtaa tcgcagcact ttgggaggct gaggtgggag 155460
gattgcttga gaccaggagt tcaagatcag cctgggcaac gtagggaaac cccatctcta 155520
caaaaaaatta aaaaattggt ggggcattga tggcacacac ctgtagtccc agttacttgg 155580
gaagctaaga cggaaagatt gcctgagcct gggacgtcgg ggttgcagtg agctgcgatt 155640
gtgccactga gctccagcct gggcaacagc actttcggag gccaaggcgg gcagagcact 155700
tgaggccagg agttccagac cagcctgggt gatgaactat tgnnnnnnnn nnnnnnnnnn 155760
nnnnnnnnnn nnnnnnnnnn nnnnnnnnnn nnnnnnnnnn nnnnnnnnnn nnnnnnnnnn 155820
nnnnnnnnnn nnnnnnnnnn nnttaatcgc agatggaacc agaaaggttt ccccaatggg 155880
aaaacggggg cacattagac ccaaagcaaa ttcaattggg agttagccca aaccaattag 155940
```

-continued gcaccccaa gaggctttaa acctttaaag cttttcggta tcgtatatcc tgtgtgggaa 156000
attggggacc tgaataacaa ttttaaccca gggaaaccag gttatggccc atggatacgg 156060
cggtacagtt agtttaacaa tttcacccag caacataaaa ttaaattaat tccaaccggc 156120
aatttttcct tttgtttccc ctttgccttt ttcaacatgt cctaacaatg ggcaatttta 156180
aagattaagc aaaagcttca ctctgcatcc tttttttttg ttttgttttg gagatggagt 156240
ctcgctatgt tgcccaggct ggagtgcagt gacgcgatct cagctcactg caagctccgc 156300
ctcccgggtt cacaccattc tcctgcctca gcctcccgag tagctgggac tacaagcgcc 156360
cgccaccacg cccggctaat tttttgtatt tttttttta gtagagacgg ggtttcactg 156420
tgttagccag gatggtctca atctcctgac cttgtgattc gcccgtcttg gtctcccaaa 156480
ttgctgggat tacaggcatg agccactgcg accggcgtaa aattctaaga cgtctattgc 156540
actcttctgc agtaaggttg ccagtcataa ttagtcaact tgagtcccgt tcctcataat 156600
ccgaaagtgt taactgaagg attctatata ttataaaact ctgtggaaaa tggccattat 156660
tcacccagat gtccactgga aggagaggct tgaaacactg tatttcatag gtgtggtggt 156720
atttcaaaag atagctttta aaaaattaat aaaccggcca gacgctgtgg ctcacgcctg 156780
taatcccaga actttgggag gccgaggcgg gaggatcaca aggtcaggag attgagacca 156840
tcctggctaa catggtgaaa ccccgtctct actaaaaata caaaaattag ctgggtgtgg 156900
cggcatgcgc ctgtagtccc agctgctggg gaggctgagg caggagaatg gtgtgaaccc 156960
aggaggcgga gcttgcagtg agctgagatt gtgccactgc actccagcct gggcgacaga 157020
gcaagactcc gtctcaaaaa aaaaaaccaa aaattaatag accacgaatc ttcctcaaat 157080
atgaaaaaga aacagttact aaaagaaaat agagattctt ccttctgtag ccagttatga 157140
aatttaaaat aattgcaaat aaaaatacta tacatgcatg gaggcaataa aatattatga 157200
tgaggagcag atgtgcagtg aacagaacta ggttaacgtg caagctcttc atgtgctctt 157260
gaacaagtcg aatacctact ctgcacttcc ttcatctgta caatgagtgc aatatttcca 157320
attgttaggc tcttttgaga atttaataaa ataatgcctg acatgtagga tacatttaat 157380
caatattatt aagtaattaa atatgtgctg ggcatggtgg ctcatgcctg taatcccagc 157440
actttgggag gccaaggcag gcggatcacc tgaggtcagg agttcgagac ttgcctggcc 157500
aacatggcaa aaccttgtct ctactaaaaa tacaaaaatt agcccggcat ggtggtgtat 157560
gcctgtaatc ccagctactt gggaggctga ggcaggaaaa ttgcctcaac ccgggaggtg 157620
gaggttgcag tgagctgaga tggagccact gcactctagc ctgggcaaca gagagagacc 157680
ctgtctcaaa ataaaaaata aaaagatttt ttatatatat atatatatat gtggatacac 157740
ccacacaaac acaaatctaa tagccacaaa aacattctta gctatctatt tctcctgata 157800
ccatggagcc tgtataacat ggaaagaatg aaacaagtta ttcactacta ccagtcataa 157860
atgtttatca cccatacaca tactagttgc tgagaaatca gaccataaat ttaaaaagca 157920
attaaaaaaa aaaatctagc aggccagaga ggttctttcc tttgaaaacc attcttctgt 157980
ggaaatagct gacaaattca cgcaatacat ttataaacat tttaggaaaa ccaacatcac 158040
agatatttta actaatccta ctctttctaa tcctaaaaat aaactacata aatgacatat 158100
atgtataaat tttggttctg tgaacttgga ttagtcttta agaaacaaag agcataggca 158160
cggcatagtg gctcacgcct gtaatctcag cactttggga agccaaggca ggcagatcac 158220
ttgaggtcag gagttcgaga ccagcctggc caacatggtg aaaccctgtc tctactaaaa 158280

-continued

```
atacaaaaat tagccaggca tggtggcgcg tgcctgtaat cccagcaact cgggaggcag 158340
aggcaggaga atcgtttgaa tccgggaggc agaggctgca gtgggctgag atcgcgccac 158400
tgcactccag cctgggcgac agagcaagac tcggtctcgg gggaaaaaaa agaaaagaaa 158460
gaaacaaaga gcatccactt tccacctttc acacacaaca cagccaatta aatcaaaaga 158520
ttccactatc atagcataat accccttgag ttttcaggca gataagacac tcagacacac 158580
cttgcttgtt atagaacagg cccaaatgag acacaataaa acgatgattc catgttagga 158640
attccctacc aaccatatcc tcctcttttt ggtgactaga ttgtaaaata agtcaattaa 158700
gagttcataa cggaagtgct gaagcaaccg caaatccaga cacaaaaata cagtggaacg 158760
tattcgcatc tcaagcacgt ccaaatgtct cggccaatgt gatccgatca ctgccgtttc 158820
cagaaacaca cagtaatggc ttttaattca tttctataaa tgttcgttgt gcgtaaagcc 158880
aaactgcacg caaaaccgca aaacacaaaa gatccctcgc atgccgttta tagccagaag 158940
ataggccatc ctctctgcgc cctaccccag aaagctctcc ttacggcagt aaaaatttga 159000
tgacacccca tgctacctac acatcaaaat gtcatcccac aaagtggaag gggagcagtg 159060
tcagcatccg ttggcctcca tgaaacgaca ctgccagtat tcccacctct aggcaaacac 159120
gaacccaagt gaagtcgatg gaaagttccc accaaccagg catatttggt tcccttctgc 159180
ccccaaggcc aagcagctca actgatgaga tctgctgttg cacctgccac ggctctgaac 159240
ccgggatgct tggcgacccc cggggcacac aaaaaggccc tgcggcctaa cgcgccagtg 159300
acccttcccc gagagtgcat ggagggccgc tggagcatcc ctctcgctgt ccacagcgcc 159360
cgcttccctg acaaaggccc cgtgtcaatc catccgagac acaacacaga gaagttgctg 159420
gattgcccat cgcggacccg cagctgccac taccctctcc cggaaaaaaa ccaaaccaaa 159480
ccaaacaaaa aaaacagaac tagggaagaa aaggatggga gggtacacag cgtgaaaatc 159540
aaaatgttcc caaagctaag caacctgggt gtgccctgga agtgggtcct gggggcccgt 159600
gggggagggg agggagggcc cggtggtggg cggtggctcc tctggggcat gaaggccgag 159660
ccaggcgcta gcctaataaa atgccgggtg tcggaacgct caaaagaaaa ccacaaatga 159720
aatcccctgc gggcgccagg ccccgaggag ggagggaggg agagcggggc gggcggtccg 159780
cagacctgcg gccgcggccc cacctgcccg ccccgcgccc acacacacct gccccggcag 159840
ccgccgggag gcgaggccgc ggctgaggcg aggagggggc ccgacccggg ggtgccgggc 159900
gagtgggtca gtccgatggc gggggccggg ggccgcctcg ctcacctcca ggtcggtgtc 159960
cgcggcctct ggggccccga ggatctcgct gggcagctcg gccaggtcgg tgacccggat 160020
cagcccgtcg tgcaggaaga tggtctcttc cttcaccgag agccactgcg ccgagtcagc 160080
ggccgccgcc gccgccgccg ccgcggccgc cgacgagccc atggccccgg ctgaaggctt 160140
ggcgctgagg agcagacgcc cggccggggg aaacggagca ggagccgccg cgatcaccag 160200
tccatggcag cggccgccgc gcccgccagc ggcgccccac ttgctgcctc gcccgtgcaa 160260
ctccgcccta ggcggtccga gtcgccatac ccccgacccc ggcccgggag accccggccc 160320
tgccgccgcc gccgccgccg ccgccgccgc cgccctcagg agcaggatcc gcctctgccg 160380
ctcggcaacc aactgtcagt gagacgccat gttgggggcg gggctcccgg catgcctcgc 160440
ggagcggaca atacaggccc cgcccgccgc tccgcccacc gctccgcgga cgaggccacc 160500
cgggtggcct ggacgtccgc ctagcccttc gctgccgcct gccctcggcc tgacctccgc 160560
cggccccttc tccccctggc cattcagggt agccctggct ttgcagcgcg ccagggaaga 160620
ggacgccgct tcccccgtcc tgtccctact caggtgtgca ccccttgctc gggcccgcgc 160680
```

-continued ccccaccctg ggcagagcat agagatcact ccttgttttc acgtttaaat gagatgcaag 160740
caaaaggctg gcgcagaata ggcgctgcac acttgttcat aagcacttgg tagaatcaca 160800
tagtagatga ttaatattga ctgaaaagtc tagtacccag taagcactca aaacctggtg 160860
aaaataaagc gtctgtccac aatgcttggt gctcaatgcc cgacacttaa tatgtgctcc 160920
atgagtggca attctaatta ttgctatgtt cgttccatca gtgttccaca ctaattgaca 160980
tacaccttaa aaatatgctc actaggccgg gtgcggtggc tcacacctgt aatcccagca 161040
cggaggtcaa ggcagaagga ctgcttgagc ccagaagttt gaggccagcc tgggcaacat 161100
agggagaccc catctctaca aaaaataaaa attagcgggg cagggtggca agcgtctgta 161160
gtcctgctac tcgggaggct gaggcaagag gatctcttga actcaggagg tggaggctgc 161220
agtgagctat tatcttgcca ctgcactcca gcccgggcga cagagggaga ccccatccct 161280
ccctccccac caaaaatata tatatgccca ccagtgccat tttataaaaa caagaaagga 161340
aaactatatg tataaagaac aatgcatgaa caaatacaca ccagatgttt aaggtgagtt 161400
gccatgggag tgtggggctg gtctggaact actgagatga gattgttctc tattacttgt 161460
atatttttat cacttaaaaa ataataaaac aggccgggca cagtggctta cacctgtaat 161520
cccagcactt tgggaggcca aggtgggcag atcacctgag gtcaggagtt cgagaccagc 161580
ctggtcaaca tgatgaaacc ctgtctctgc taaaaaaaat acacaaatta gccaggaatg 161640
gttgcacatg cctgtagtcc cagatactca ggaggctgag gcaggagaat agctggaacc 161700
caggaggcgg aggttgcagt gagccgagat catgccactg cactccagcc tgggcaacag 161760
agcaagactc catctcaata ataataataa taataataat aacaataaca ataacaggag 161820
aacattaagg tgcataccct ttgatccagc aattcaactt tgaggaagtt gtctgaagga 161880
aataatcaga ctcgtagtca aggatggata tacagggttg tgtagctcaa tattgtttac 161940
aaaaggaaaa acttatcaat ctagatgtcc aacaatatgg ggctggttaa ctaaaatatg 162000
atatatccat aagatggaat attatggccg ggcacagtgg ctcacgtggg taatcccaac 162060
actttgggag gccaaggctg gcagatctct tgagcccaga agctcgagac cccccttgggc 162120
aacatgacaa aaccccgtca ctacaaaaaa tacaaaaatt agccaggcgt ggtggtgcac 162180
acccatagtc ccagctactc aggaggctga agcaggaaga tcgtttgagc ccagaaggca 162240
gaagttgcag tgattcagct aagattatgc cactgcactc cagcctgggc aacagagtaa 162300
gaccctgtct caaaaaagaa gaaaagaaga ggaagaggag gaagaagaga acaataaatc 162360
cagcagttca gagttgatca gaaccatgga aacaataaaa caggcaagtg taatggaatg 162420
gccatttcat caaatcctcc caaatgtctg agagggggag tattattatt cctactttca 162480
gctgggaagt caagactcag ttagatactt tgctcaatgt cacaaagcca gtaaacatca 162540
aagctcagat gtaaacccag gtctgtccga ttttacaact tcagcttcct tattttgact 162600
gtaagaaaac tccttcattc cttttttttt tttttttgag acggagtctt gctctgtcac 162660
ccaggctgga gtgcaatggc atgatctcgg ctcactgcaa cctcttggct cactgcaacc 162720
tccatctcct gggttcaagt gattctcctg cctcagcctc ccgagtagct gggattacag 162780
gcatgtacca ccacgctcgg ccaattttgt atttttagta gaggcggggt ttcaccatgt 162840
tggtcaggct ggtctcaaag tcctgacctc aggtgatcca cccacctcgg cctcccaaag 162900
tgctgggatt acaggcatga gccactgcgc ctggcccatt ttattttatt tatttatttc 162960
gagatggagt ttcactctgt cacccaggct ggagtgcaat ggctagatct tggctcactg 163020

-continued caacctccgc ctcccgggtt caagtgattc tcctggttca gcctcccgag tagttgggat 163080
tacaggcacc caccaccaca cccggctaac ttttgtacgt ttagtagaga tggggtttca 163140
ccatgttggc caggctggta ttttttcatt tttaaaaaaa tttttttaga gatgggctct 163200
gcctgtgttg cctaggctga tctccaactc ctagcctcac gtgatattca caccttggcc 163260
tccccaaagc actgggatta caggcatgag ccactatgac cggcccatca caatttttaa 163320
atgcttagat tcaggactct aaccatctta aatagttcag ataaaatttc ttctatactt 163380
agtcttattt cttctactct taatgatgtt ttaagatcag gagtcaaggt gcccaggaac 163440
tcttgtcctt cagcctaagt gatgaaaaca gcacagatct agggcttaaa gtctttagac 163500
tgcataatga atagttattt aatattttag caacagtaat taattagtca taggactgca 163560
tggctgccac tgcaccatga tgaggcagct gatgaattaa tatttataga accccctccg 163620
gaaaggagac catttagtag ggatttctag aacagatcag caagacaaag aaaatgcctg 163680
gtcaaaagaa ctttaggttg gaagctacga ggaagagaat ctgtatctag tctagacaac 163740
acacacatac acacacaaga cattcattta taggaaggaa agatttatgg cttatgactt 163800
cttttctttg gaatcgtcat ttctactctt ctattcaaga atgggggatc aggatgggaa 163860
aaggagcaag agaaagtgtt ggctgggcaa ccctaagtta gaagcagaga agaaatatga 163920
ggaaaatagg aagaatagct atgactaggt tggacctcag ttactcctgg gaggcatctc 163980
cccaagaggg agcagcaggc ttgttgatgg agatcatctc cctcctgccc cagctgctga 164040
cgtgatactc gctagccctg gctcaagctg ggcccctct gggattttgc aatatctctc 164100
ccttctgctg gttttctata ccagctgact gtctaaaatg acttcgtaat ccttcctggg 164160
tccaaaaata tgtgagtgtg gtgtgaagat aagtggtcct tgataaactt tattagagct 164220
taaaggtggt tttagatgag gcagccatgt taatttttaa ggcctttcaa aacaccaagg 164280
aaaaaataca cacacacaca cacacacaca cacacagaac ctatggggga gattgattat 164340
ttccgtctta ctaattacag tctcaaagag gaaacacaca cacctactca aaatcttttt 164400
tccaagtgtt ctggtaggcc ctgttcatat ttttatttca aagaagatta ttttggctca 164460
tgggtggatc tatgtggtaa cagggaaaag aaatcagatg aaagagatat ttgaaaacga 164520
ggagggggaa attctccttg gagcaccact gaattgctaa aactaaagga cgggtctcca 164580
cattgatgaa aagccagaag atgaagcagc attaaatgcc tttctcattt gaaaagatca 164640
tcagcagcag ggagctctga aagatgctat gtcctccatc gccaccttgt gtgcatcaca 164700
ggccttgctg cactgggatt tgtagttcag acttggaaat ttgctaacat tcgtctcctg 164760
caaaaaaatt agattaagaa aaagttgtgg ccgggcgcgg tggctcacgc ctgtaatccc 164820
agcactttgg aaggccgagg cgggtggatc acgaggtcag gagatagaga ccatcctggc 164880
taacacggtg aaaccccgtc tctactaaaa atactagccg tgcgcggtgg caggcgcctg 164940
tagtcccagc tactcgggag gctgaggcgg gagaatggcg tgaacccagg aggcggagct 165000
tgcggtgagc cgagatcgcg ccactgcact ccagtctggg caacagagcg agactccgtc 165060
tcacaaaaac acaaaaaaac aaaaacaaaa agttatggct catgcctgta atcccagcac 165120
tttgggaagc cgaggtgggc ggatcacctg aagtcaggag ttcgagacca gcctggccaa 165180
cagggcaaaa ccccatctct actaaaatta caaaattagc caggtgtggt ggtgcgcgcc 165240
tgtaatccca gttacccagt taccaggagg ctgaggcatg agaatcactt gaacccggga 165300
gatgaatgtt gcagcgagcc gagattacgc cactgcactc cagcctgggc aacctaacga 165360
gtccatctca aaaaataaaa ataaaaataa aaataaaaaa gttgttagca caaaggaaaa 165420

-continued gtggacaaaa gatattattg aagagttttc actcaaggaa aagcaaacac tgtacgtttt 165480
tgttccttca gtattcatta aatgcctact ctgtgccagg cagagttagg tttgaggatc 165540
gagttcccaa ggagactggc agcttccctt tctcatgaaa gacagggagg ctgcttgaag 165600
gaatcattcc aacggggatg agaagtccgg gcacctagtc tgggggtgag gttcccggaa 165660
gatgttgagt ttaaagctgg taactgctac gtatgagtta atgaatgtga ggatggtggg 165720
ggaaacttca atactattat tcaccaaaaa aagcacatgc aatgcagtgt ggtgtttgaa 165780
tcatggactg cttggatttg gtcccagatc ttttgcatgt taccatgaag aagtaattcc 165840
acctacctgt ttcccagttt tctgggatga tggtggtggt atctaccttc ataagtaagc 165900
aaggttggtt ccttctgagg attttttgtt tgtttctttg tttgtttgtt tgagacaggg 165960
tctcagtctg tttcccaggc tggagtgcag tggtgcgatc tcaactcact gcaacttctg 166020
cctcccaggc tcaagtgatc ctcccgcctc agccttctga gtagctggga ccatgggcat 166080
gcaccaccat gcctggctaa tttttgtatt tttttgtaga gacagggttt cgccatgttg 166140
ctcaggctag tctcgaactc ctgagctcaa gcaactgccc acctctgcct cccaaagtga 166200
taggattaga ggtgtgagcc accacacctg gcccttctga gagttttgaa agaagaatct 166260
attccagacc tctctccatg gcttgtagat gaccatagtc ttcctatgtc tctgtatatt 166320
gtcttccctt ggtgtgtgtc tgtgtccaaa tttgttcgtc tctctctttt tttttttttt 166380
tttttgagac aaggtctcac tttgttgctg gagtgcagtg gcacgatcac ggctcactgc 166440
agtctcagcc tgctaggctc aagtgaacct ccctcttcag cctccctagt agccgggact 166500
acaggcatgt gccaccacac ctggctaatt tttttttttt aaagatgggg tcttgctgtg 166560
ttgcccaggc ttgcctacaa ctgctggact caagaagtcc tcccgccttg acctcccaaa 166620
gtgctgggat tacaagcatg agtcaccaca cctggcccaa attttctctt tttacaagaa 166680
cattagtcat attggattgg gccccccatct taaggacttc attttaactt gattctctct 166740
ctctctgaag accctgtctc caaataacat tacatcctga ggtactgagg gttaggactt 166800
catcatgtaa attttcaaag ggacacagtt cagcccataa cagaaatgga gctatgattc 166860
cctgagatag gaagtattag ggaagaaaca tgtggggaag gagggcagag aaccaagaat 166920
tggaaagaaa aacagttaaa gtcatgagac tattcattta taatgattta cattttatgg 166980
gatctaatta cactaaagag cttctgcaca gcaaaagaaa ctaccatcag agtgaacagg 167040
caacctacag aatgggagaa aatttttgca atctactcat ctgacaaagg gctaatatcc 167100
agagtctaca aagaactcaa acaaatttac aagaaaaaaa caaccccatc aacaagtggg 167160
cgaaggatat gaacagacag ttctcaaaag aagacattta tgcagccaac agacacatga 167220
aaaaaggctc atcatcactg gccatcagag aaacgcaaat taaaaccaca atgagatacc 167280
atctcacacc agttagaatg gcgatcatta aaaagtcagg aaacaacagg tgctggagag 167340
gatgtggaga aataggaaca cttttacact gttggtggga ctgtaaacta gtttgaccat 167400
tgtggaagac agtgtagtga ttcctcaggg atctagaact agaaatacca tttgacccag 167460
ccatcccatt actgggtata tacccaaagg attataagtc atgctgctat aaagacacat 167520
gcacacgtat gtttgttgtg gcactattca caatagcaaa gacttggaac caacccaaat 167580
gcccatcaat gatagactgg attaagaaaa tgtggcacat atacaccatg gaatactatg 167640
cagccataaa aaatgatgag ttcatgtcct ttgtagggat atggatgaag ctggaaacca 167700
tcattctcag caaactatca caaggacaaa aaccaaaaca ccacatgttc tcactcatag 167760

-continued gtgggaattg aacaatgaga acacttggac acaggaaggg gaacatcaca caccggggcc 167820
tgttgtgggg tggggggagg ggggaggggg gagggatagc attaggagac atacccaatg 167880
taaatggtga gttaatgggt gcagcacacc aacatggcaa atgtatacat atgtaacaaa 167940
cctgcacgtt gtgcacatgt accctagaac ttaaagtata attaaaaaaa aaaaaaaaat 168000
atatatatat ataaagattt acattttaaa ataaaatagg ctggctgtgg tggctcaagc 168060
ctgtaatccc agcactttgg gaggctgagg tgggcggatc acttaggcca ggagtttgag 168120
accagcctgg ccaacatgat gaaaccccgc ctatactaaa aaaaaataca aaaattagcc 168180
gggcatggtg gcggacccct gtaatcccag ctgcttagga ggctgaggca ctagaatcac 168240
tccaacccag gaggtggagg ttgcagtgag cggagatcgt gccactgcac tccagcctgg 168300
tcgacagaat gaggctcggt ctcagaaaaa taaataaatc aaacaaaaac aaaacaaaaa 168360
ataatttgca ttgtatactc tcacttgtca cctgcttcag gtcatctcag gccagtgccc 168420
atctttatat gcatataaaa acatagatat ataaagacat atatatatat atatatatat 168480
atataaagac ggatatgaag aactactcnn nnnnnnnnnn nnnnnnnnnn nnnnnnnnnn 168540
nnnnnnnnnn nnnnnnnnnn nnnnnnnnnn nnnnnnnnnn nnnnnnnnnn nnnnnnnnnn 168600
nnnnnnnngt ctgagcaaac atggtgaaac ctcgtctcta cagaagatat aaaattagct 168660
gggtgtggtg tacacaacct gtagtcccag ctgcttgaga ggctgaggga ggaggattgc 168720
atgagcccag gaggcagaca ttgcagtggg ccaagattgc gccattgcac tccagcctgg 168780
gagacagcga gactctgtct caaaaaaaca ataaaaataa aaataaaaat aaaataaaat 168840
gtgccattct atttcattat ataaagattt attcaatcac attgtgtgga tgatatcaca 168900
gatgcgaaca gtattaggaa gcaaaaagca atcccttcac ctttcttaat actcaaataa 168960
ttttttttta atttgccaaa atgaaatcta gtaagtcaaa gggatcttat ttctaaggac 169020
tcttggatta taaacagaat ttctagcggg gtgataactg gggagagtca cttggctcag 169080
tcactgacct tcctttatcc ttaaattgag agtggcaatt tcatgaccct gaatagtata 169140
aaaaatatgt ccctcaaacg tataagcacc atatgaagct aatagccttt gaaggtctat 169200
atttactgtg tcatagataa gctcaactac aattcgattt gattaaaaaa tcagtacagt 169260
gatactctaa tccaaaaaat atcaaatgat tgctaaaaat aaaggggata ttgtaaatgg 169320
cataaattgc atcaaaatgg gaatgaacac taaataatta cagctatata tgttctaaaa 169380
actaatgaca aaagaaagct gaaaaatccc cagtaacttc tcattagatc ttttccgtct 169440
cactctcttt ctggtgtgtg ttttttgttt gtttgttttt ttgtttttttg tttttagaaa 169500
gacagggttg ggctgtcacc cagggtggag tgcagtggca tgatcttggc tcactgcaac 169560
ctccatttcc caggctcaaa ccatccatcc acctcagcct cccaagtagc tgggactaca 169620
ggcgtgcacc accatgccca gctaattttt gtattttggt agagacaggg ttttgccatg 169680
ttgcctaggc tggtctcaaa ctcctgggct caagtgatcc tcccacctcg gcctcccaaa 169740
gtgctgggag gcatgagcca ccaggtcagg cccctttcct tttcttaacc aagaaggtaa 169800
catacaaaaa ctgccatgat atattcaaac acttatggat agggctagct accaaaaagt 169860
ttaaggttct tctgaacttt taggcttcct gattaaaaag aattataaaa agttccttca 169920
acctttctga gctaggggtt taggcactat aagtctctaa atgtttactc tctgtttttg 169980
tacttatctt gtcattacat taacagacag ttcgtggtat gtggaccata ctttgagagg 170040
cattgttctg tacggaacat actttatttt ccagagtaat ttaaaaagcc tccaagttca 170100
cagtaatgac caaaatagac caaaggaact cagtgttttc tgaaaaaaag caggactaaa 170160

-continued tgatttcaag atccttttca gccccacaag ttctatgatc ctaaagctaa agatgtgatt 170220
tgactggtaa gtaaaacgct cattgcctaa tgataggcat ttctgtcaca ccaacagagt 170280
agctaaaaga ggaaaagtca taataaaaaa aaagtggggg ttggggggaa taagctcaga 170340
gaagagaaag aatttaactg tgaagtagac acggacagtg aggagatgta gctcagtaag 170400
acagataaaa cgccaatagg ctgaacaaca tggtgaaacc ccatctgccc agctactggg 170460
tggggggcta aggtgggaag atagcttgag tctgggaggt tgaggttgca gtgagctgtg 170520
atgataagga gggtgggagg aaggatagag aaaacaaaca aacaaactac taaagcagtt 170580
acttccactc agggtaggag atgcagttct cacaaattag cctctgaaaa ttggccattt 170640
taataattaa gcctaagtca tgaaagaaag gttaaattat ctttaagaac cttgtttacc 170700
aaagcaaaga agtatgtaat acataaaaga cttatatcac aaagattaca tagcattcaa 170760
aaaagactcc tagattcatt atttcagaat ctttattata cagtattagt tttatgttac 170820
ttacaaaatg ctaatgtatg gtatgaatgg cattaatcca attctaggct tctagtagga 170880
gctcaataaa ctgctactac catgtatttt attctttaac tgcagaagcc tccatgttct 170940
catatctaaa agataattct ggccaggccc agtggctcat gcctgtcatc ccagcacttt 171000
gggaagccga ggcaggcgga tcacttgagg tgaggagttt gagaccagcc tggccaacat 171060
ggtgaaaccc tgtctctact aaaaatacaa aaattagctg gacatggtgg caggcacctg 171120
taatcccagc tattccagag gttgaggcac aagaaattgc ttgaacctgg gaggcgtagg 171180
ttgcaatgag ccaacatcac gccactgcac ttcagcctgg tgatagagca agattctgtc 171240
tcaaaaaaaa taaaaaataa ttcctattgt atctatccca caagtttatt tttagaggaa 171300
taaaataatg tggtcagtta aaatatgatt catccataaa ataaaatatt ataacctact 171360
aaaaagtatt aagagctggg tacagtggca cacacctgaa atcccagcta ttcaggagcc 171420
cgaagcaggg ggatcacttc agcccaggag ttcaagacca gcttgaacaa catagcaaaa 171480
cctcatttca aaaagaaaaa aaatcaaaaa aagcattatg taaattttat gttatgaata 171540
tgaaaaatat ccttacacat attgtttagt ataaggtaca aatagcatat atagtatgat 171600
ctcaatgaca gaatattatt caggggtagt aataaatgtg cctatctgtc tatgaccata 171660
gacagattat gatcaaagaa aggaggatta aactaacatt tcgaatcata attgacgaca 171720
ccaaaaagat tcattcaaaa catgtatcaa gaaaatttag aggagatact gtttctcagt 171780
tgtaaataat gccagaaaaa ctcataaggc tacaagagac agagatccaa agctacattt 171840
gctaaaaaga aatttgtgtc actgtcaaca tagtaagaaa gacgcttact ctcaacaaac 171900
acacattcta gatcctgtag tataagaacg gccggccggg cgcggtggct catgcctata 171960
atcccagcac tttgggaggc cgaggcaggt agatcacgag gtcaggagat caagaccatc 172020
ctggctaaca cagtgaaacc tcgtctctac taaaaataca aaaaaattag ccaggtgtgg 172080
tggcggatgc ctgtagtccc agctactagg gaggctgagg caggagaatg gcgtgaatgc 172140
gggaggcaga ggctgcaatg agtcgagatg ggccactgca ctcctgcact ccagcctggg 172200
caacagagca agactccgtc tcaaaaaaaa aaaaagaact gccactcagg tgtggacctg 172260
ggccctcagc atcatcagca ttacctggga cctagttaga aatggagaat cttctctacc 172320
atgtgaatca tgcttttttt tttttaaagg aataaatataa acgaacaaaa aagaaatgcc 172380
aaaaaaaaat tgcaaactct caggaccacc cccctcccca gcaaccacta catcagactc 172440
tatgtctaca tattacttta ttatgtattt tatttttgag acggagtctc actctgtcgc 172500

-continued

```
ccacactgga gtgcagggga gtgatctcag ctcattgcaa cctctgcctc ccggattcaa 172560
atgattcttg tgcttcagct tctgagtagc tgggattaca ggtgcctgcc accatgtcca 172620
gctacttttt atatttttag tagagatggg gtttcaccat tttggccagg ctggtcttca 172680
acttctggcc tccagtaatc cactcacctt ggcctcccaa agtgctggga ttacaggcgt 172740
gagccaccgc gcctggccta catttttttt ttttaataga caagatctct gtcgtcaggc 172800
tgagtgcagc agcatgatga tagctcactg caaacttgaa cttctgggct caactgatcc 172860
tcctgcctca gcttcccaaa gtgctgagac tacaggcata agctaccacg cccagcctta 172920
ctctacattt taacaaaacc tccaggtggt acgcacatta aagtttaaga agagctgcta 172980
caaagcccaa agagaattaa gagggaggaa tacgcacagg tgcaacaatg gacttttccc 173040
aattgatgca acagagatat cttctggttt ggatgacaat cacatggaca agaagttaca 173100
atgatctttc caccactgtc tagaaagtat ttttcttggt aactagaaga aagctagagt 173160
atttctagaa agtatctagg tataggttta aacacataaa agtagcaaaa gagtcagggg 173220
cagtagcatg cacctatagt cccagctact tgggaggctg gggcaggagg atcgcttgag 173280
gccaggagtc tggggctgca gtgtgcaatg attgtacctg tgaatagcca ctgcactcta 173340
gcctgggcaa cagagtgaga ccctgtctct aagtaaataa atgaataaaa tgtataaagt 173400
agcaaaatac tattcttacc attcacaaat ttttccatca tcaaagaagt tatatatcaa 173460
aagggtttcc attggaagca tccatcatcc caagaataaa gttttccttg aggggcagtt 173520
ctcaagaact aagtaccttg atcttatatc tctaacaaag tgaaaaaata aaacagaaat 173580
atagagaaag gaaagtatta aaatatatac cagaaaatgt atcattaaga tgcacttttg 173640
caaaaatgtt ttaaattcaa tctagggaaa taaattatac ctgatcccat atatctctag 173700
caaaaataac caacaacatt atttctgtta aaggtaagat tggccggggg cggtggctca 173760
cgcctgtaat tccagcactt tgggaggctg aggcaggtgg atcacctgag gtcaggagtt 173820
cgagaccagc ctggtcgaca tggtgaaacc ccatctctac taaaaataca aaaattagct 173880
gggcatggtg gcatgcacct gtaatcccag ttacttggga ggctgaggca ggagaatcgc 173940
ttgaacccag gaggcacagg ttgcagtgag ctgagatcgc gccattgcac tccagcctgg 174000
tgaacaagag agaaactccg tctcaaaaaa aaaaaaaaaa ggtaagatca aaacagtatt 174060
attagtcaac tacattaata aagacaagga tctaattttt tccagctttt aaaaacctga 174120
aagataatgt ctgttcatcc gcgacaatac acgattttag aatggaacac accaacaaaa 174180
acttgaggga cccaatactt gaattataac aggtatttta accacaaagc tcttctccca 174240
tccatatttt cttcattatt atatgtcata tgtcagttgc tattctgggt gtgttacccc 174300
atttatctca tttagtcttc ttatttaccc tttttttca gacagagtct cactctgtcg 174360
cccaggcttg agtgcagtgg tgcaatcaca gcctcaacct ctaggctcaa gcgatcctcc 174420
cacctcagcc tcccaagtag ctgggactac aggtgcatga caccacacct ggctaatttt 174480
ctaattttat ttttgtagag atagggtctc actacattgc ccaggcttgc tttgcattcc 174540
tggggtcaag caatcctccc acctcagcct cccaaatgct aagattacag gtgtgagtca 174600
acatacccgg cccttattta cccttgaagg ggggcatttt ataaccaaga aattgaaatt 174660
ctgataggtg gtagaactga actaacagct ggcgagatgt gtcaatgcca aagcctacag 174720
tcttaaccac taggctcact ctgtgttcat aaggatcccc tgaaggaccc tgcattttaa 174780
agtcccaggt tatttgtcac tgactccata taccatcctc ctttaaatcc cacagggcac 174840
aatattctgt atggccctga atgttaacgt gtattccaaa aacaacaaaa aactctacaa 174900
```

-continued tatagtactt tacatacatt taaaaaccag tcatgtgcaa gatatatact tattttttgt 174960
gtaagtacct gcttaactcc agaagcagga agaaggacat tgaagcacca aatagaacta 175020
cttggagaaa gatgaaataa accggtagga tcagaatttg ggagcactct tctagttaac 175080
actataggtt cccaattaca atgtatgtag gaattgtcaa acagacttgc aaccagaggg 175140
cctttgaatt cattacaagt cctctgtctc tattgctgtg atacttaagt atctatctgt 175200
actcaatggg actgtgctta tgtacacaac tgtatatatc tgtttgaaaa gatttccgtt 175260
tcagttgttt caaagctgtc cccattgatc tgctaacaga gctgaagctg ccctgggtga 175320
tatccttgct ttttgtttc ttttgttttt ctaacatgtt aagtttctaa gtacttcata 175380
ctttaatatt ctcaaaaata ccaccttcat cacctggtgg actattgcct tatggaagtc 175440
aatattctcc agagtgaaca gtaagggctc tgtggaagcc aacctgcagg cctcctctat 175500
gggaacacaa ggaagctatg gagactgcag tggagtgatg ggagggaggg gagcacatca 175560
ggagaccagg tcagagagga atctgcctac gcatcactca tacgtgcact cactacctct 175620
ggggagcatc taagtaacta ctaatactgg ctgctgctgg gaagttggtg gtggtggagg 175680
caggtgggga gcgttatgtt agcaaggaga catttccctg tattctctct tgaactaatt 175740
ctaaaatttt tttttttttt tgagatgggg tctcattctg tcaaccaggc tggagtgcac 175800
tggcaaaatc agctcactgc agcctcaaac ttccaggctc aatcagtcct cctgcctgag 175860
cctctagagt agcagggact acaggcacac atcaccatgc ccggctaatt tttgtatatt 175920
tagtagagac ggggttccac catgtttgcc aggctggtct cgaattcccg acctcatgtg 175980
gtccaactgt ctgggcctcc ccaagtactg ggattacagg catgagccac tgcgcccagc 176040
ctcccttatg cttttctaca tcttctaaat tttcaaaaat tcctctaaca ttttaatttt 176100
tttaaatttt aagcattttg taatgtttta aataaattat aatcaatagt tttattacgc 176160
taatcagtaa ttagattata ttaaatctta aaacttctgt aacagttcca ttcttttta 176220 attttttaaa atttatatat aacatgtaat atgtattcat gtgtatataa aatttatata 176280
tgtgtgtata cacacaagca tacacacact ctctctctct ctcttatata taaagatgag 176340
gtcttgttgt gttgcccagg ctggtctcct gagctcaagc aatcctccca tctcggcctc 176400
ccagagtgct gggattacag gcatgagcca ccttgtccgg cccagttttc aaggtactgc 176460
tactcaataa aagtggctta atggacatag aataggttta ctaaaaacct aaaaatgtgc 176520
aaaataaata gaatagtgct caagttcact acttgatcat agaacaacta agttaagcaa 176580
aaaattcatt caaagtcatt aatattttta gaacgatgat caaagcaaca tattttcaat 176640
taactccatc taactagcta ttttcagaaa tctctctgga attcattatt ctctacataa 176700
aatgcactat gctctataca aaaatcaaag gtcaggccag gtacagtggc tcaggcctgt 176760
aatcccagca ctttgggagg ccgaggcagg tggatcacga ggtcaggagt tcaagaccag 176820
cctgggcaac atggtgaaac cccatctcta ctaaaaataa aaaaattaac caggcagtgg 176880
tggcgtgcgc ctgcaatcct agctactcag gaggctgagg caggagaatt gcttgaacct 176940
gggaggtaga ggttgcagtg agcagaggtt gcagtaagcc gagatcgtac ccctgcactc 177000
cagcctggat gacagagcaa gactcaatct ccaaaaaaaa aaaaaaaaaa aaaaaaatca 177060
aaggtcgtga ccccacatta cttatctagg ttccaatatt aaaaatatta ataatattac 177120
aactgttgag aagtgtttcc ttcttatcta aaatgcaaaa tgggctgggc acggtggctc 177180
acgcctgtaa tcccagcagt ttgggaggct aagacaggtg aatcacctga ggtcaggagt 177240

-continued tcgagaccag cctggccaac atatagtaaa accccatctc tacaaaaaat acaaaaatta 177300
gctggacata gtgccacaca tctgtagtcc cagatacttg ggaagctgag gcaggagaat 177360
cacttgaacc tgggaggcgg agcttgcagt gagccgagat tacgccactg cactccagcc 177420
tgggtgacag agcaagactc tctctctcaa aaaaaaaaaa aaataaataa ataaaaggca 177480
aaatgtatgc caggagcagc agctcaggct tgtaatgcca gcaccctgga aggccaaggc 177540
agatagatag cttcagccca ggagtttgag accagcctga acaacatgat gaaaccccat 177600
ctctacaaaa acacaaaaat tagccagccg tggtggcatg ggcctgtagc cccagctact 177660
ctagaggctg aggcacttga atcaattgag cccgggaggt ccagactgca gtgagccgtg 177720
actgcgcgcc actgccctcc agccatggac aacaaagcga gaccctgtct caataaaaaa 177780
ataaaaattt taaaaataaa aagtgtaact gcaattaaaa ttcctagagt ctcatgtgaa 177840
ctactttagt tcatcaaaaa taactaccta ttcttatttt attctccatt agtgaatttt 177900
tcctgacctg tgtcctcaac ttatgatctt atttgatcac agagccctag aaggcttgtg 177960
gggcataaga tcttgtcaca actactcaat tctgctttgt agcatgaagg cagacaatat 178020
gtaaacaaat aggctgatta tgttccaata aaactttatt tatgaaaaca gctagttggc 178080
tggatatgac cctgaaagcc agtttactga cctctatcta aaaagcgtta tctaacagaa 178140
atacataaaa cacatatgta atttaatatt ttccagaagc catgttaaaa aaggtaaaaa 178200
taaacagata aaattaattc tagtattttt aatttaaata tattttactt aacccattat 178260
atatacaaat catcatttca acatttaatc aatatggatt attactagcc gggtgtggtg 178320
gcatatgcct atagtcctag ctgctgggga ggctgagccc aggagttcaa ggttacagtg 178380
agctacgata gtgccactgc actctggcct aggtgacaga gtgagaccct gtctctaaaa 178440
atgtaaatta aaattaaaaa taaaatatta ccactgagtt cttttaaaat ttttttttgca 178500
tgaagccttc acaaatctga tgtgtattat actttcagca catttcactt ctgaccagcc 178560
acattcaact gctcaatagc cacatgtggg tggtggctac caactggaca gtgcagttct 178620
ggaggctatt taagtaaaac tcctgaacct tgacaatact aatgtaaaac aacaatctga 178680
acaacaaaag aaactgcagg catataattg tactctataa gtggacagaa gcaaaaatgc 178740
atttagattt taaaaacaat gtttctcttg ggatagcaac tgttactgct gcttctttgt 178800
gttttttttt tgtttttttt tttttttttg agacagggtc tccctgtgtt gcccaggctg 178860
gagtgcagtg gagcgatctc ggctgattca ctgcaacctc tgccttctgg gctcaagtga 178920
tcctcccacc tcagcctccc gagtacctgg gacttgggtg tataccacca cgcccagcta 178980
attttttgta tttttagtag agaccgggtt tcaccatgtt gcccgggctg gtctcaaacc 179040
cctgggctca ggcgatccac ccgcctcagc ctcccaaagt gctgggatta taggcaacag 179100
ttaccgtttg aggttacctg tttaaaatga ttagcagtat aagataccaa tactaacaaa 179160
attttattaa attttattcg catactttca gctgaccaac attctccctc agacaagagg 179220
ggaaaaaccc aaaatacctg gtgaacaaaa aaaaattgtt ccattttggc agagcacagt 179280
ggctcacatc taatcccagc actttgggag gccaaggtgg gtagacaact tgagctcagg 179340
agttcaagac aagcctgggc aacgtagtga gacccccatg tctacaaaaa aattttttttt 179400
aaataaaaaa ttagtaaggc atggtggtgt gagcctatag tcccagctac ttgggaagct 179460
gagatggcgg gattgcttga gctcaggaaa ttgaggtggc agtgagctat gattatgctg 179520
ctgtactcag cctggacaac aaagtgagac cgtgtctctt aaaaaagaca ttgttctttt 179580
ttgaaaaaat tgcctgttgc tgggcgcaac attcttaatt atttcaacat taaaaaaaag 179640
aagaagaaaa aaaagagcgc ctgtaattcc agcactttgg gaacccaagg tgggcagatc 179700
acctgaggtc aggagttaga gaccagcctg gccaacatgg tgaaacccca tctctactaa 179760
aaatacaaaa attagccaga catggtgatg ggcacctgta ataccagcta cttggaggct 179820
aaggcaggag aatcgcttga acccaggagg cggaggttgc agtgagctga gatcgcgcca 179880
ttgcacttca gcctgggcaa caagagtgaa actctgtctc aaaaaaaaaa aaaaaagaaa 179940
gaaaaagaaa aagaaaaaat tgcttgttac tatttttttt ttgtatcgta catgtgggta 180000
cactgccaat actacttggg tttgttgact gccttcagag ggagaaaatg ctaaattttg 180060
gctgggtgta gtggctcacg catgtaatcc cagcactttg ggaagccgag gcaagcagat 180120
tacttgaggt caggagtacg agacccgtct ggccaacatg gtgaaacccc atctccacca 180180
aaaatacaaa aattagccag gtgtggtggc gcacacctgt aatcccagtt tcttgggagg 180240
ctgaggcaga atcacttgaa ccggggaggt agaggttgca gtgagccgag attgtgccac 180300
tgcactccag cctgggtgac agagtaagac ttggtctcaa aaaaaaaaag aaagaaagaa 180360
agaaagaaag aaagaaagaa agaaagaaaa caaaacaaaa ggctgaattt cagctaaagg 180420
tatgtgaaaa taaagataca tattttcttt cccatccaag gtcacagatg ccatgaattc 180480
tattcatgga tcccatgcat ctctgaatcc tatttaggtt cagaacccct gagggaaagg 180540
aaagtttatt tataaactca actgaaaaaa tgcttccggc agggcccagt ggctcacgcc 180600
tgtaattcca gcactttggg aggtggaggt gggtggatca tctgaggtca ggagttcaag 180660
accagcctgg ccaacatggt gaaaccccat ctctaataaa aatacaaaaa tttagctggg 180720
tgtggtggca tgcacctgta atcccagtta cttgggaggc tgaggcagga gaatcgcttg 180780
aacccgggag gcagaggttg cagtgagcca agatcttgcc attgcactcc agcctgggca 180840
acagagggag actccatctc aaaaaaaaaa aaaaaaaaaa aaaaaaaacg ctaacacgtc 180900
atagagatag aaggtccaga ttttctactc tgccccataa atagctacat ctattgtatt 180960
agactttaca cagtagaaat cataacacaa actacagagc acaaagcaaa tatagtaaac 181020
attgaaaaga tccattacaa atacaaactg aatgttaata ttttgttagt ataaaaccac 181080
tacttgaatg ccgaatctgt agttattagc attactaaac ctacaatttg cataaaatac 181140
tttgcaaatt atgcatctta ttgttaatct aaaattgcta cacactgtgc tctgacctag 181200
taattcagcc aactgcaggt tttagtaaaa gcgctaggga tccaaatgtg tccactccaa 181260
agtgtcccat catggaacat taattattca ccaaatgtgc ttaatagcac tttctaaact 181320
acaagctcca tgcaaatatt caacattatt gggagaggat tcatacagca ctattaaaat 181380
ccctcgaaat tataaagtag taacagtaat aagtcacaga aacactttaa aaatcactac 181440
aaatttataa tttaccaaac tatcaaacag ataacacttt aaatactgaa aattatttcg 181500
cttcctataa attgatatta tctttaaata gtagattatc tttaaaatag cagatttaaa 181560
gaaacagcag aagacaatta tagtatatcc acaaattact atgcagacat taaaaattat 181620
atctttaaat cttattcaaa atgttcccag taagtaatca caggatccaa aactgcaaat 181680
agcatataat cccaatttta tctatataaa aatatgagct gaagaagcaa ataataaaaa 181740
attaatttcg ttctggtgga atggtgtaat cccagggtat ttattgtctc tcttatactt 181800
ttagatgttt tctctatttt caacaacatc cctgtattat ttacttataa tcaaaaaggt 181860
tttacatagc ataaaaatac aatccactta atataggtat ttttcacata ggtaaaaaaa 181920
atgtggaatc actcatgtta ttagcatgta agagagaaaa ttttcagggg ctctaagtcc 181980

-continued aaataatctc cctcacaact gctgtgcatt ctgagcacac ttcgggagcc aatgcttctc 182040
ttcccggtat gtgcagctcc ctcgctctcc tggtctctgg cactatccac aaaccatcac 182100
ggagtaagga gtcattgttt ccctcctgcc tatatataga catggtctct gtattaaccg 182160
gattactgac caaaatgagc ctatgccggg acaagaaggc tatcaagcca caagagaggt 182220
gctctgaagt gaactcataa gagctggatg gcactgacag aaaactctgg cttctttggc 182280
tgaccagggt tcagcgtgca tttctaggta cccaattaca tccattggat gcatcttttg 182340
gagcgaaagt tattgcctta ttaagcaaac ctaggatttc tttttttttt tttttttttg 182400
agacagagtc tcgctctgtc atccagactg aagtgcagtg gtgtgatctt ggctcactac 182460
aacctccgcc tctgaggtgc aaacaattct cctgcctcag cctcccaagt agctgggatt 182520
acaggcaccc accaccacgc ccagctaatt tttaaaacat tttttgtaga gatggggttt 182580
tcccatgttg gccaggctgg actcgaactc ctgacctcaa gtgatccacc tgcctcagcc 182640
ttccaaaatg ctgggattac agtgtgagcc acctcaccca gccaaattaa gcaaacctat 182700
gagttctaaa atggcctctg agagggtgtg cggaaaagag gtcctatcaa acactaatac 182760
cgggactata attggtaatc acacaggagg gcaatttggt agtatctatt aaaattaatt 182820
tgtcaccaat gacccagcaa ttccacttac cctagcgaaa taatctcagg tgtgcatgag 182880
caggcatgca agaatctgta ctgaaggact gtttttaaga gtgaaaaact gaaaacaacc 182940
aaaataccca tcgtgctcaa ctgaataatg gcgtccacca aaatgtccac ctactaatcc 183000
ttggaacctg taaatgtgac cttagatggc aaaagggact ttgcagatgt gattaagtta 183060
aagatcttga gatggaggga ttatcctgta ttatctgggt gggccctaaa tgtactcaca 183120
agggtgctta taaaagggat gtgggaagag tgggtcagag gagaaggcga tgtgatgaca 183180
gatgagagac tgcagtaaca tactctgaag atggaggaaa cagcaacaag ccaagaaata 183240
caagtggcca caagaagctg tggaaaaggc atgggaacag attctcccct agagcctgca 183300
gaaggaacca gacctaccaa tgcttgactt ttagcccagt gagactcatt tcaaactttt 183360
gacttccaaa aatgtgagaa taaatccatg ttgccttaag ccacgaaatt tgtgataatc 183420
tgttaacatg gcaacaggaa actaagatac tcatcaatag ggaatgtcta aataaaactg 183480
tggcatttct agagtcttgt gcagcactta aaaataatgt ggtagatata tatatggaga 183540
cacagaatga tcaaaacata tccttgagtt taaaaagaaa gcaagttaca gaaagatatg 183600
tctagtatga catctttatg taaaaaagaa aaaaatagaa tgtgttatat acacaccaaa 183660
attttaaaat ggtcttgaag aatatacacg aaaaaatttt cactaattta gccagggcaa 183720
gaaggacaca gagatccaaa ttagagatgg tgcttaaaag ggacttcagt tttacctgtt 183780
atttccgttt tgtcaagaat gtattcatgt actactcata gttttttttt taattaatag 183840
atacataagc tgtgcttaaa atacaggatc aaaataaaag ttacacaatt tctgcaattt 183900
ctctcctatg catttgtccc atagttgatc acctgctgtt atttacattt gtctacaact 183960
attgactaaa catcttgtaa agcagactac actccttgtg ttcaccccac aaccactgtt 184020
gtaaaacaag agggaaaggt ggggagggga aagcatgggg cactttcggc aattgacagt 184080
actttcataa ttaacaccac agttaccttc agacctagga aagaagagat gtatgaccac 184140
ccacccagca gctcgagcca acaggtagta ttttatgaca gtaaagatgg aagccaagaa 184200
gacagataat aatcaaagct gatttattta gcaagacctt aggtatacaa ttggagaaaa 184260
actgaaacag agactatcta ttatctcatc tgcctagcca cactgcaaac aaattgagaa 184320
ggaagaaaat tccagccagg cgcggtggtt cacacctgta atcccagcac tctggaaggc 184380

-continued

```
cgaggtgggt ggagcacctg aggtcaggag ttcaagagca gcctgaccaa cgtagtgaaa 184440
ccccatctct tctaaaaata caaagctagc tgggcatggt ggcacatgcc tgtaatctca 184500
gctacttggg aggccgaggc agaagaatag cttgaaccca agaggcggag gttttagtga 184560
gccgagatca cgccattgca ctccagcctg ggcaacaaaa gagaaactcc atctcaaaaa 184620
gaaaaaaaaa ggaaagaaaa ttccagccag gtacagtggc ttgtacctgt aatcccagca 184680
ctttgggagg ccaaggcaag cgagtcatct gaggtcagga gttcgagacc agcctgacca 184740
acatggagaa accccgtctc tactaaaact acaaaatgag ctgggcgtgg aggcgggcgc 184800
ctgtaatccc agctacttgg aaggctgagg caggagaatc gcttaaaccc gggaggcgga 184860
ggttgcggta agccgagatt gtgccgttgc actccagact gggcaacaag agtgaaactc 184920
tgtctcaaaa aaaaacacaa aaaaaacaag gaaaaagaaa attccgcagg gatcaccaac 184980
caaacaaaca aacaaaaaac gattccacta ctatagaaaa aattatgttg atgggatagt 185040
tttgctttca aatacaatag gcagctggct gaatatgcat aaaataacct ccaagcaaca 185100
tagcacctta taaagagagt caatacactt taaacataat cacatctttt ttttttttt 185160
tttaatattt tggtgtcagg gaatcactct gtcatgcagg ctggagtaca gtggcacaat 185220
catagcttac tgcctcttcc agctcctgga ctcaagtgat cctcccacct cagcctccca 185280
agtagccaac cacgccccgc taattttttt tattttttta agatggagtc tcgctttgtc 185340
gcccagtctg gagtgcagtg gcgcaatctc ggctcactgc aagctccgcc tcctgggttc 185400
acgccgttct cctgcctcag cctcccgagt agctgggact acaggtgccc gccaccatgc 185460
ccggctaatt ttttgtattt ttttagtaga gacggggttt caccgtgtta gcgaagatgg 185520
tctcgatctc ctgacctcgt gatccgccca cctgacctcg tgtgatccgc ccacctctgc 185580
ctcccaaagt gctgggatta caggcatgag ccactgcacc tggcccatgt ctagctaatt 185640
ttaaaatgtt ttgtagagat gggatcttgc tatgttgccc aggctggtct tgaactcctg 185700
gcctcaagca attctcctgc tttggcctct caagtgctgg aattacaggc atgagccacc 185760
acactcagcc cacatccatc ttattattat tattgttatt tttgtttggt ttttttgaga 185820
cagggtctgg ctctgtcacc caggctggag tacagtgaca gtcttcgcct actacaacct 185880
ttgcctccta ggctcaagta atttttcagc ctcagcctcc tgagtagctg ggactacaag 185940
tgcatgccac cacgcccagc taattttatt gtatttgttt gtagggagag agttttgcca 186000
tgttgtccag gctggtcttg aactccagtc cactccttgc cctcccatag tgctgagatt 186060
acaggcatga gacaccatat ctggccacct ccatcttttt aattctgaca ttagccctat 186120
cattatccca ctcttttaga tgatgatagt ataacataat agttcaagaa tatggactca 186180
gggctggaat cagacagacc tatttcagtc ttagctttgc cactaactat cttacctttg 186240
tcaagttact taacttttgt ctgtgccagt ttcctcattt ataaaataaa gataatcctt 186300
ggccaggcac ggtggctgac gcctgaaatt ccaacacttg ggaggccaag gagggtggat 186360
cacttgaggt caggagttag cctggccaac atggtgaaac cccgtctcta ctaaaaatac 186420
aaaaaatagc caggtgtggt ggcacgggag ttactcggga ggctgaggca gaagaatcac 186480
ttgaacccag gaggcggagg ttgcagtgag ccgagatcac gccactgcac tccagcctgg 186540
gcgacaaagt aagactccat ttcaaaacaa acaaaacaaa acaaaaataa taaaagtaaa 186600
gataatccag taccaacctc atgtttttg tgaggatcaa ataaaataat ggatgtgaag 186660
tacttagcac agaacatacc actcaatatg ctggcgctgt tgtcgtggga gtggtagaga 186720
```

-continued

```
tagtgacaat gatgactaag aagatgcacc agaagataac taggggctga gcgcagtggc 186780
tcacacatat aatcccagca ctttgggagg ctgaggtggg cagatcacca gaggtcagga 186840
gttccagacc agcctggcca acattgtgaa accctgtgtc tgctaaaaat ataaaattag 186900
ccaggcatgg tgatgcatgc ctgtaatccc aactactcgg gaggctgagg caggagaacc 186960
acttgaaccc gggaggcgaa ggttgcagtg agctgcgatc gtgctattgc gctccagcct 187020
aggtgacaga acgagactct gtctcaaaaa aaaaaaaaaa aaaaagtaac tagtgatttc 187080
tgaaggtatg gaatttggcc aggtgcagtg gctcacacct gtattcccag cactttggga 187140
gactgagaca ggaggattgc ttgaggccag gagttcacaa ccagcctgag caacacagca 187200
tgactccatc tctataaaac attaaaaaat tagtagcaca ccggtagtcc cagctactca 187260
ggaggctaag gtgggaagac cacttaaagc acaggagtgt gaggctgcag tgaactatga 187320
tcacaccact gctctccagc cagtgacaga gtgagaacct gtctctagaa aaatatgttt 187380
aaaaaaaggt atggaatttg cccaaggtca tacagcaagc aaggagcaga gctagaattt 187440
caatcccagt ttgactcttt aaacctgact ttaacttcaa ggcaatactg tctcccacag 187500
ccctcaaata cttcattctc attttacagc tcgagccaga caagcctgaa agcctgttgg 187560
gccttttgcc caagctcaca gaatactgca ccaagattca gtgactccta ttacagtgct 187620
cattaattgc atggtaatca acactactgg tgaacaaggg tagtttattc gcttattcat 187680
taactcatcc aaatctagaa ttctataaaa gtacataaac actttccaaa ggattttgcc 187740
caaaggatat ataggctagc agtgtcctcc taggagaata gaccaacata aatctaaata 187800
tcatctcaaa gatttcactt gagtgtatga taagtattta aagccttgat gatttcagct 187860
gatcaacttc aaacccaaat gccccttttc ttatctggca aaacaaaata ataaacaaaa 187920
accctttgca tctattaggt tccatttgtt aattaacata taattggcgt acagtaaact 187980
gcacatattt aaagtgtgtg atttaatgag ttttgacata catatacaaa tgtgaaacca 188040
tcaccacaat caaaataggg aaagagccat cgccccaaaa gtttcttcat gctcctttat 188100
actccgtccc tctcatcctt tcctgcctgc ctgcctctat ccccaggtaa ccactacaga 188160
ttagtctgca tttctagaat ttcatagaaa tggagtctta cagtatatac tcctgtttgt 188220
ctggtttctt ccactctgca taaatccatg ttgtgagtac caacggttca ttcgtttttg 188280
ttgctgagta atactccatt gtatggatgt accacatttg tttatccatt cacctgctga 188340
cggacatttg gattgtttcc agctttgggc aatcacaaat aaagctgact tgaacattca 188400
cgttcaagtc tttgtgtggt gtggggcggg gtggagaggg agtacttaaa agcaaacaca 188460
atgaaatatg agaagcacta accaaaatgc ttaaatttaa aatgaacttc aactgtggag 188520
taagaaatat cttagccacc ttgggtaagt caatcagctt ctctgtcaat actcttatat 188580
acgatgcctg cttgttccca accgcagttt gtaaagaaaa atggaatagg aagcagaatg 188640
cttttggaat tctcacaagt aagctattcc ttcttttccc cctcttaaat tccctttatc 188700
ttaaaaagaa taatgttcta tgaaatgcaa tgcaaaatgc aataacattt gagatgttat 188760
ttttgagtta ttgctttttt atttctctta aatgtatatt tatttcaaca ttttaaaaaa 188820
atttcctaag ccggtcgtgg tggctcacgt ctgtaatccc aaaactttga gaggtagagg 188880
cggctggatc acttgaggtc agcagttcaa gtccaccctg gccaatatgg cgaaaccgca 188940
tctctactaa aaatacaaaa aaaaaaaaaa aattagctgg ggtgagggtc gcttgtaatc 189000
ccagctactt ggcaggctga ggcaggagaa tcccttgaac ctgagaggca gaggttgcag 189060
tgaaccgaga tacagccatt gcaccctagg ttgggcaaca gagcaggact cctgtctaaa 189120
```

-continued aaaaaataat aataaaaatt cctatatgcc ttttgctttc caccagcaac ataaaattaa 189180
aataaataca aacggctatt ttttcttttt ttttctcttt gcctttttcc acatgttcta 189240
acaaatggct attttaaaga ataagcaaaa gcctcactct gcattctttt tttttgtttt 189300
gttttggaga tggagtctca ctctgtggcc caggctggag cgcagtggcc tgatctcggc 189360
tcactgcaag ctccgcctcc tgggttcacg ccattctcct gcctcagcct cccgagtagc 189420
tgggactaca ggcgcccgcc accacgcccg gctaattttt tgtattttta gtagagacgg 189480
ggtttcaccg tgttagccag gatggtctcg atctcctgac ctcgtgatct gcccgccgtg 189540
gcctcccaaa gtgctgggat tacaggcatg agccaccacg cccggccaca ctctgcattc 189600
ttaattcact catagtaaga tccaaagccc tcacctacaa ggatctactt gatttgtatc 189660
ccctgctccc catctctcct ctccccttta gcttactggg ctcagacctc caaatatgct 189720
gaggacgctt ccctctcaag gacttggctc ttgctgtcgt ctctgtatgg gatgttcttt 189780
cccatatggt atactccctc cctcccttca ggtctctgct caaaagccat cctgggcttt 189840
ccttttgtgt ccaccctata taaaacagga caggctgggt gcagtggctg acgcctgtaa 189900
tcccaactct ttgggaggcg gaggtgggca gatcacctga ggtccggagt tcaagaccag 189960
cctgaccaac atggtgaaac tcatctctac taaaaataca aaaattagcc aggcgtggtg 190020
gtgcgtgcct gtaatctcag ctcctcaggg ggctgaggct ggagaatcgc ctcaacccgg 190080
gaggtggagg ctgcagtgag cagagatggc actactgcat tccagcctgg gaaacagagc 190140
aagaatctct gtctcgaaca taaataatta aaaataagat aaaataaaac aggacagttg 190200
gctgagtgca gtgactcatg ctgagcactc tgggagtctc aggtgggaag atcacttgag 190260
gccaagagga attcaagacc agcctggaca atatagcaag gccccaactc taataaaaaa 190320
aaaaaataaa acaaaaaaac ggagccctct ttccaatgct ctccatctct ttactgagct 190380
atacttttct ctttagcact tatcatttgc ctctatgtca tgttacatat ttgtcattgt 190440
ctatatcatc ccactaaatt ataagctttt tgaggacaag gattttattt tatccactgc 190500
tatatcccca acatccagga cggttggccc agctcactct aaattccacc aatacttgtt 190560
gaatgaatta gttgattaaa cattatttat tgctttaaaa aaaaatctgt ttagaaattt 190620
actgggaaga ggccgggtgc ggtggctcac gcctgtaatc tcggcacttt gggaggctaa 190680
ggaaagcaga ttatttgagg ttaggagttc gagaccagcc tggccaacat ggtgaaaccc 190740
agtgtctact aaaaatacaa aattagctgg gcatggtggc acatgcctgt aatcccagct 190800
cctcaggggg ctgaggctgg agaatcgcct caacccggga ggtggaggct gcagtgagca 190860
gagatggcac tactgcattc cagcctgggc gacagagcaa gactccgtct caaaaaaaaa 190920
aaccaaaaat taatagacca cgaatcttcc tcaaatatga aaaagaaaca gttactaaaa 190980
gaaaatagag attcttcctt ctgtagccag ttatgaaatt taaaataatt gcaaataaaa 191040
atactataca tgcatggagg caataaaata ttatgatgag gagcagatgt gcagtgaaca 191100
gtactatgat gaacgtatnn nnnnnnnnnn nnnnnnnnnn nnnnnnnnnn nnnnnnnnnn 191160
nnnnnnnnnn nnnnnnnnnn nnnnnnnnnn nnnnnnnnnn nnnnnnnnnn nnnnnnnngg 191220
atcctcctgc ctcagcctcc caaagtgttg ggattacagg catgagccac cacactcaga 191280
ctttgttgac ttcttaataa gaaaaatact tgttaagagt ttcttcagat cactttcctt 191340
tatcaacaag taaaacatga ctgaggaagt tgtggtcccc tttgcttccc tgcccaggcc 191400
cgtttccctc cctctttccc cagaggaaac caccaagagg ttggcatata ttcttcctga 191460

-continued acgtgttttt atagttgtac tgcacttgta ctgtgtatga acaatataaa gttggtttgt 191520
gtgtttaaaa aattcacata catggattta taatgtatgt atcattttgc aacttaaaaa 191580
tttttttttg agctccatgc tgattgataa cgatctattt tttttttttg agatggagtt 191640
tcagtcttat tgcccaggct gaagtgcaat ggcgtgatct cagctcactg caacctcagc 191700
ctcctgggtt caagctattc tcctgtctca gcctccggag tggctgggat tacaggtgca 191760
tgccaccatg cccagctaat ttttgtattt ttagtagaga tggggtttca ccatgtcgac 191820
caggctggtc tcaaactcct gacctcaggt gatctgcctg ccttggcctc ccaaagtgct 191880
ggaattacag gcatgagcta ccatgcctgg cctttttttt tttttttttt tgagacaaag 191940
tcttgctctt tttcccaggc tggagtgcag tggccacaat cttggctcac tgcaacctct 192000
gcctcctgag ttcaagcagt tctcctgcct cagcctcctg agtagctggg attacagaca 192060
tgtaccacca tgccaagtta atttttgtat tttttgtaga gactaggttt taccatgttg 192120
gccaggctgg tcctgaactc ctgacttaaa gtgatccatc tgccttggct tcccaaagtg 192180
ctggggttac aggcatgagc tatcgcgcct ggcctgagaa atctcattct tactcctact 192240
cccttgcaca ctatctccat tctgtaggta gccatttcta ttaatttctt gtttaccctt 192300
ctgtgtttct ttcattcttt ttcttttttt cttttttttt tttgagacaa tcttgctctg 192360
ttgcccagac tggagtgcag tggtgtgatc ttggctcacc gcaacctcca cctcctgggt 192420
tcaagtgatt ttcatgactc agccacctaa gtagttggga ttacagcgcc tggtgtacac 192480
taccacaccc agctaatttg tgtattttta gtagagatgg ggtttcacca tgttgtccag 192540
gctaatctcc aactcttggc ctcaagggat ctgcctgtct cagcctccca aagtgctggg 192600
attataggca tgagccacca tgcctggccc tatgtttctt tttataaaaa taagcaaatt 192660
aatattttta ttactatttt ccttttattt ttacacatca agtagaacat taaatatatt 192720
tctctgtaat ttttttcagt tacctaaatc ttttagtgat ctctctcatc tttttaatca 192780
gctggatcgc attctatcat gtgaatattt tataacttct atatactgtc accagcaggt 192840
agcgatttag ttgtgtctaa tattttaaaa tgatatataa tgcctcaatg aatatagtaa 192900
ccttttgcat atattgtttt gtgctttggg ataacactac ctcgtattgg aaactgtgtc 192960
attacatgtg tctttaaaat tacatgtgtc tttttatttt tatttttatt ttttttgagt 193020
gggagtttca ctcttgttgc ccaggctgga gtgcagtggt gagatctcgg ccgactgcaa 193080
cttccgcctc ccgggttcaa gcgattctcc tgcctcagcc tccccagtag gtgagattac 193140
aggtgcctgc caccacgccc agctaatttt tgtattttta gtagggacgg ggtttcacca 193200
tgttggccag gctggtatcg gtctgctgac ctcaggtgat cctcccacct cagcctccca 193260
aagtgctggg attacagacg tgagccacca tgcctggcca tcactttttt tttttttctta 193320 attgctgcat agtggccggg cacagtggct cacgcctgta atcccagcac tttgggaggc 193380
caaggcaggc ggcggatcat gaggtcagga gaccaatacc atcctggcta acatggtgaa 193440
accccgtctc tactaaaaat acaaaaaaat ttagctgggc gtcgtggcgg gcgcctgtag 193500
tcccagctac ttgggaggtt gaggcaggag aatggtgtga acccgggacg tggagcttgc 193560
agtgagccaa gattgcacca ctgcactcca gcctgggtga tggagtgaga ctctgtctca 193620
aaaacaaaca aacaaacaaa aaaattgctg catagtattc cattgtatga gtagtaacac 193680
aacaattttt ataatgcata gtattccatt gtatgaatag taatgtagca ctatttgttt 193740
atacattttt atgattaaaa aacaaaatgt ttttctatta tgaataaagt ggcaatgaat 193800
atttttgtac aagtgttttg gtagctatac agttattgtc acttaatata tgcaattcga 193860

-continued taggccagtc attcaaaata gaagatatac aaggtaggcc gggcgtggtg gctcacgcct 193920
gtaatctcag cactttggga ggccgaggtg ggtggatcac ctgtggttag gagtttcaga 193980
ccagcctgac caacatggag aaacctcatc tctactaaaa atacaaaagt agctgagcgt 194040
ggtggcgcat tcctgtaatc ccagcttctt gggaggctga ggtaggagaa tcacttgaac 194100
ctggatttat aatgtatgta aatccaccgc gaaggttgcg gtgaaccgag atcacgtcat 194160
tgcactccag cctgggcaat aagagcgaaa ctccatctca aaaaaaaaaa aaaaagatat 194220
gcaaggtaaa gatactaata aagacctttg tgttgagttg gttgacatgt ggttatttca 194280
cccatcgtat ttcttatagg gaataggtaa attcgttcct tgggtttctt tcaacactta 194340
ggtaaaatcc gacgtggaag atgagatctg attttactgg tgtaactctt tatttgtccc 194400
cttgcctccc tttccaatgg actattttag aagaaatgga gctgtcaccc acatcaagat 194460
tcagaacact ggtgattact atgacctgta tggaggggag aaatttgcca ctttggctga 194520
gttggtccag tattacatgg aacatcacgg gcaattaaaa gagaagaatg gagatgtcat 194580
tgagcttaaa tatcctctga actgtgcaga tcctacctct gaaaggtcag taacatttta 194640
gtgaccacaa agtctgctgc tcccttgtgc cctgagtgtc agaaatgcat gacggtctgt 194700
gtatgactct ctgactccaa aggcttgtga ctgtttttttg agctgtaatc tttaaagaat 194760
tactaaagtg agactaatag catcaaatta ttttcagagt acctttttcc tgcaaaagtt 194820
ttaatcagtg ttacttacac tcatcctata ggggttgcat accattcctg catatacttg 194880
gtacgtgtat tagttttaag acttattgaa cttcagcaga taatctttga gagttattag 194940
aggaaaacaa atgataatgg agacaccaaa atagcagcag ttttctatgg tggctctcga 195000
ccagttattc agcaatgtca ccaacagatg tcagtttaag ctcagaagtg gaaaagcaga 195060
gagctcagag ggtcagcttt ttcatcagtt cttttaatgt tatcaccaca attatgtgag 195120
aatgaccttg cttagagaaa attatgttat tttcgagatc tttccccctg tgttggaact 195180
aggctgatga aagcatgggc ttgacttatt tattgattgt attcgttttg tacattccca 195240
atctcctctc tgacttggtg caaattcagg atctcttagt tagtttgtat attttgtgtc 195300
ttcaggtatg attttttcag cttatacctt tatgtcagtg ctattatgtg ctgataattt 195360
gtttctctag ctaccaccgt agcttcaggc aaaaggctgt cagccaactc tgtacagttt 195420
atttctaaat tttactgttt tcagttgagt atggatgaag aataactcaa agtttattct 195480
tttgatgatg agcccttaac accacctgcc atgatagtac ttgctttctg accaagatcc 195540
tgagggaaaa agccacttta ttattagaac tatgttaaga tgcttcccaa aaaacatgga 195600
gcagtattgt ctcaaagtct gtccttggat ggctttggat gcctacatca ggactgtctg 195660
atgtgctggt taaaatgcag attcctgggc ctcattcaga cttacatgta ttgatattgc 195720
tggttgtgga gcctgggaat tcatattttt agcaaaatcc ctcattttta ctccaagtct 195780
tatgtgcatt atacagtttg agatgatcac ccaggatata gtccaaagac actggaggct 195840
gttgaagtat aggttgtata tatggaaaag gttggaatgt ttgaattaat ttataatgaa 195900
gatccttttt aattgagtgt tcacatgcca aggcaaggac aaacattcaa aatgattttc 195960
tgtctctgtt acaacttttt ctttcttttt tttaatttat ttatttgaga tggagtctca 196020
ctctgtcacc caggctggag tcaagtgacg cgatctcggc tcactacaac ctccgcctcc 196080
cagattcaag taattctctt gcctcagcct cccgagtagc tgggactaca ggcatgtgcc 196140
accatgccca gttaattttt gtatttttag tagagacagg gttttgtcat gtttgccagg 196200

-continued

```
ctggtctcaa actcctgaac tcaggtgatc cgcccacctt gacctctcaa agtgctggga 196260
ttataggcgt gagccaccgt gcctgtctct attacaactt tttattacaa cttctttatt 196320
ttgactttat ttttacaaat tatttattta tttttttga gatggagttt cgctcgtcac 196380
ccaggctgga gtgcaatggt gcgatctcag ctcactgcaa cctccgcctc ccaggttcaa 196440
gtgattctcc tgcctcagcc tcctgagtag ctgggattac aggcacttgc caccacaccc 196500
ggccaatttt gtatttttag cagagacagg gtttcaccat gttggtcagg ctggtctcga 196560
attcttgacc tcaggtgatc cacctgcctc ggcctcccaa agtgttggga ttacaggcat 196620
gagccaccac gtccggccga cttttatttt tttttcttga gacagggtct tgctctgtca 196680
cccaagctgg agtgcggtgg catgatcata gcgcactgca gcctcgacct cctggactca 196740
agtgatcctc ctgcctcggc cttgtgtata gctgggatta caggcagttg ccaccatgcc 196800
aggctaattt ttaattgttt tgtgaagatg gggatttcac tgtgttgccc agactggtct 196860
tgaactcctg gcctcaagtg atcttcctgc cttggccttc caaagtgttg ggattacagg 196920
cataagccac tatgcatggc ctgtaacttc tttaaatggc tataattaaa cagttggtcc 196980
ttttaagatt gggcaatgga cgaatggcaa attgcatttt taaaagagga gggatttaaa 197040
aaaaaacagg aaagattggg gcatttgtct ctaaaggact gtggactcat ttaagaagtt 197100
tagtggtcat tcttaccatc tttgtggttt ttcctgcctg catgggatgc agattttctg 197160
tctcaggtgg gattgatcaa tcccttggag gaatgtgtct actttttaat tgtgtttagg 197220
agagctgact gtatacagta gttttgtgaa agaacaacat gaacccatag tagagctaaa 197280
ttctttttta tttttaaaa actttaggtg gtttcatgga catctctctg ggaaagaagc 197340
agagaaatta ttaactgaaa aaggaaaaca tggtagtttt cttgtacgag agagccagag 197400
ccaccctgga gattttgttc tttctgtgcg cactggtgat gacaaagggg agagcaatga 197460
cggcaagtct aaagtgaccc atgttatgat tcgctgtcag gtaaatctcc agttgaaaaa 197520
tgggtctggc aagatgttac ctttgggtga tttttctgct gacagaagac agacaccatt 197580
acattcaaag tcagattgtc ttttatttat ttatttattt atttatttat ttgagacagg 197640
gtcttgctct atcacctaca gatggggttt caccacgttg ggtctggtga cccaaatctt 197700
tgggtgattt ttctgctgga agaggacaaa caccattaca ttcaaagtca gattttctgt 197760
ttttttttt tttttgtttt tgttttttta atattcattt gtttattcat ttgagactgg 197820
gtcttgctct gtcacgcagg ctggagtgca acctccctgg gctcagttga tcttccctca 197880
gcctcttgag tagctgggac tacaggtgtg tgccaccatg cccagctagt gtttgtattt 197940
tttgtggaga tggtgttttg ccgcattgcc cagtgtggtc ttgaactagt gctcaagagg 198000
cctgcctcct tcaacctctc aaagtgttag gattacagat gtgaactact gtgcctgatc 198060
caaagtcaga ttttctttgc ttacttagtc aagttcgtct atgcttttat tatacttaat 198120
atattagtat agttactgta ttagtatatt agcatattta atatattatt atacttatca 198180
tacttgagta tattgagtat atttacactt ttagtatatt tgtatacaca caccacattt 198240
ttattattta tcttttttt gagacagagt ctccctctgt ctcccaggct gaagcacagt 198300
tggctcactg caacctctgc ctcttgggct caagtgattc tcgtgcctca ccctcctgag 198360
tagcagggat tacaggtgtc caccaccaag cctggctaat ttttgtattt ttagtggata 198420
tggggtttta ccatgttggc caggctggtc tcgaactcct gacctcaaat gatctgcccg 198480
ccttggcctc ccaaagtgct ggaattactg gcgtgagcca ctgcacccag cctattatct 198540
gtcttttgat ggacatttaa gttgtctcta tatactagct attgtgaata atgctgcagt 198600
```

-continued

```
gaacatgaga gtgcttgaaa acactaatgt aacataaagg taacaaataa taaatgtcat 198660
gtgtttatct tgaaaggaac tgaaatacga cgttggtgga ggagaacggt ttgattcttt 198720
gacagatctt gtggaacatt ataagaagaa tcctatggtg gaaacattgg gtacagtact 198780
acaactcaag caggtgagca gattggaaag ctcaagcttt ctccttaaaa acttaaaaca 198840
aatcctaata gagaatttg caaacataca gaggtagaca gaatagtatc atcagcctcc 198900
atgtacccat tgcagcttca actatcaaat cttttttttt ttttttttt ttgagacagt 198960
cttactctgt cacccagtct ggagtacagt gttgcaatct tggctcacta caacctctgc 199020
ttcctgggtt caagcgattc tcctgcctca gcctcctgag tagctgggac tacaggtgcc 199080
caccaccatg cccggctagt ttttgtgttt ttaatagaga tggggtttca ccatgttggc 199140
ctggctggtc ttgaattccc gacctcaggt tttctgcccg ccttggcctc ccgaagtttt 199200
gggattacag gcgtgagcta ccacgcccgg ccctaaatct tttcttatta tgattccact 199260
cactgactgc cgctatagta cttggaaaca tattccagat ttatattatt cccatattta 199320
tctgtaaaag gcattacaga ggttcttttt ttttttttt tttttgaga tggagttttg 199380
ctctgtcgcc caggctggag tgcagtggcg tgttcttggc tcactgcaac ctctgcgtcc 199440
cgggttcaag agcttctcct gcctcagcct cctgagtagc tgggattata ggtggtgcca 199500
ctacacccag ctaattttg tatttttagt agagatgggg tttcaccatg ttagccaggc 199560
tggtcttgaa ctcctgacct caagtgatct gcctgcctca gcctctcaaa gtgctgggat 199620
tataggcatg agccactgca tctggcctaa ggctgtacag agttttaaag caagttttca 199680
ttatagatcc acttctggtt acctttaggt aacctcactt attcactttg gcattgttgc 199740
tatttcaaat ttcaccttta tgatagtgga aaatgatata atctctctaa ataatgtggt 199800
ctattcataa agaaaaatag gcttgaattt atatcagcag agtaaagtgt atgtgaagac 199860
tgaagaaaga tacattttct ggctgaacag aaaacacggt gaaacgattt gaaaactttt 199920
attgtgaatt acagggtcct atgaaccctc tgtccgtgcc tttatgaata tcaacataga 199980
catgtttttt ttttttttt tgcattaaca ccgttttctg taatattttc tttattttac 200040
atcaactgct gtactcgatc agccccttaa cacgactcgt ataaatgctg ctgaaataga 200100
aagcagagtt cgagaactaa gcaaattagc tgagaccaca gataaagtca aacaaggctt 200160
ttgggaagaa tttgaggtaa gttattaaaa aactgttttt acgtgagttg ttatatccta 200220
tttttagtgg aggagaagtt gctcttgtgt ttggaattgg acctgagaga cttgaaactg 200280
acgtcctttt ttaattcggc cattgattga cacggagcaa gttgctgaga gggcttcttc 200340
gaaacagaag agcattgtgt tctgagggaa gggagttggc agtgagtagt caatggatgt 200400
gctagccgct ccatttggct cttttggttt ggactggtgg caaaatctca gagaaacaaa 200460
aggatctaat ttcttcgaaa gatttccagc atgcactggg gtctttagaa acaatctata 200520
gccttagtgc agcaaatgag tatgagtaaa agagaaacac cttgtggtgg cttttttttt 200580
tttttttttg agacagggtc tcgctctgtc gccgaagctg gagtgtagtg gcgtgatctc 200640
ggtttactgc agccccgtcc tccctgggct caagtgatct tcccatctca gcctactgag 200700
tagctgggac tacaggcaca tgcccctatg cctggctaat tttgtattt ttggtagaga 200760
tgaggttttg cagtgttgcc caggctggtc ttgaactctt gggctcaagt gatcctccta 200820
cttaagcttc ccgagtagct gggactacag gcacacgata ccatgcccat ctaattttg 200880
tatttttttg tagagatggg gttttgcagt gttgcccagg ctggtcttga actcttgggc 200940
```

-continued

```
tcaagtgatc ctccagcttt gacgtgccaa atgtggtggc tttaatttca gagttcaaat 201000
tgataactct ggtaagttaa gtgaactgat ttcttttttt tttaaattat ttttgttgat 201060
tatactttaa gttctgggat atatgtgcag aacgtgcagg tttgtacata ggtatacatg 201120
tgccatcatg gtttgctgca cacattaacc catcatttag gttttaagtc ctgcatgcat 201180
taggtgtttg tcctaatgct ctccctcccc tttaatgcat cagtgaaaaa gtgatgatag 201240
gctgggcgtg gtggctcact cctgtaatct cagcactttg agagggtgag gcaggtggac 201300
cacttgaatc caggagtttg cccccatccc cagacagtgt gtgtgatgtt cccctccctg 201360
tgtccatgtg ttctcattgt ttggttttct gttcctgtgt tagtttgctg agaatgatgg 201420
tttccagctt catccatgac cctgcaaagg acatgaactc attctttttt tatggctgca 201480
tagtattcca tggtgtgtat gtgccacatt ttctttatcc ggtctatcat tgatgggcat 201540
ttgggttggt tccaagtctt tgctattgta aatagtgctg caataaacat atgtgtgcat 201600
atgtctttat agtagaatgt tttataatcc tttgggtata tacccagtaa tgggattgct 201660
gggtcaaatg gtatttctgg ttctagatcc ttgaggagtc accacactgt cttccacaat 201720
ggttcaacta atttacactc ccaccaacag tgtaaaagca ttcctatttc tccacatctt 201780
ctccagcatc tgttgtttcc tgactttaag tgaactgatc tctttcctga aactaacttg 201840
ggttggagaa tgtccctgat gggaatgtgc tgtgttccca ttgcactctt ctatatcact 201900
tacccattga caatgtgatc tctttcattt tctcctcatc catttgacag aaaacttcaa 201960
aaacaaggat tctggcatat ttacctttgc agttgtcccc agcatgtagc acggtgccta 202020
gtacacagaa gaaactccat aaatgtttgt tgaatgagat ttacatttaa ctcatgttta 202080
catcatttta ttttcctgtt ctgttttatg ggaatgatta ttctatgctt tttgaggact 202140
acaatttata aatatttgtg gattgaatga ataagtgaat actgggcaaa taaagtcctt 202200
ttagccagag tatgtctgaa caacttgctg agatagatat gatttcccat tttccagctg 202260
aggggcctaa gggaggttaa gtaaattatt caatcttcat accacagttt ttgttttgtt 202320
ttgttttgtt ttttttcctc ctgagacaga gtctcacttt gctgccatac tggagtacag 202380
tggtgcaatc atagctcact gcagcgtcca acttctgggc tcacgccatc ctcccacctc 202440
agcctcctga gtagctggta ctacaggtgt gcaccaccat agccggctaa tttttcattt 202500
tttgtagata tggggtctca ctgtgttact caggttggtc ttgaacttct gagctcaaac 202560
aattctcctg tcttggcctc tcaaagtgtt gggattacag gtgtgagcca ctgtgcccgg 202620
cccataccac agatattgat tgaattccag cagtggggag gagtgtggaa tagaacattc 202680
tcagtccttg ctcaacatta ctgaacagag acttgaattt gagtttattc tctcatccca 202740
ggcttcgcgt taggctctga agacactagt gaacaagaca gacagggtta ctgcctttaa 202800
agggagcttt tagttgagag aaggaaaaca gtgatgaaaa gcatcagtga aaaagtgatg 202860
ataggctggg gcgtagtggc tactcctgta atctcagcac ttttagaggg tgaggcaggc 202920
agctcacttg attccaggag tttgagacca ggctgggcaa catggtaaaa ccccgtctct 202980
acaaaaaata caaaaagtag ctgggtgtgg gggtgcgcac ccacagtccc agctactctg 203040
ggggttgagg tgggaggatt gctcgagcct gggagattga ggctgcagtg agctgagatc 203100
acgtcactgc tctccagcct gagcaacaga gccagaacct gtcccaaaaa aaaaaaaaat 203160
tgatgataaa catagtgaga cagaattttg aaatctcagc ctcactgttg ccttccttgt 203220
cccctgcctg cctaaataat aaaaggcagc atttcagcag tcattcattt cattactttc 203280
acttcatttc accttcataa agcctcatga ggtaagatgg gaagatacag aagttttaga 203340
```

-continued aaccgctcat caaaattgaa tggaaagccg attgttccaa aactttttag tgtggaaaat 203400
ttctattata tgcaaaagta gagagaatgg gatagttata gcagtatacc tgacacccag 203460
cattaacaac tgttgataat atggccaatc tttttcgact ctgccccact cacttcccca 203520
gccctgactt gtcttgaagc aaatactttt tttttttttt tgagatagag ttttgttttg 203580
ttttgttttt tgtttttgag atggagtctc actctgtccc ccaagctgga gtgctgtggc 203640
ttgatcttgg ctcactacaa cctccgcctc ctgggttcaa gtgattcttg tgcctcagcc 203700
tcctgagtaa ctgggattac aggtgtgtac caccatgccc agctaatttt tgtattttta 203760
gtagggacag ggttttcact atgttggcca cgctggtctc aaactcctga cctcaggtga 203820
tccgcctgac ttggcctccg aaagtgctgg gattgtaggt gtgagccact gctcccggcc 203880
ttgaagcaaa tcttaacaca tcatttcgtc tgtaactatt ttatttcaaa aaattataac 203940
ctgaatagca ttatcatatc taaaactatt aacagtattt ccttaatatt aacacatatc 204000
agtcacattt tcctgattgc tacacacaca cacacacaca cacacacaca cacacttgca 204060
atttgtgttt ttttcttttt agatggatct cactctgttg cccaggctgg agtgcaatgg 204120
tgcattctca gctcactgca acctccacct cctgggctca actgattctc ttgcctcagc 204180
ctcctgagta gctgggacta caggtgccca ccacctcacc tggctagttt ttgtattttt 204240
agtagaggtg gggtttcacc atgttggcca ggttggtctc aaacttccga cctcaggtga 204300
tccacccacc ttggcctccc aaagtgctgg gattacaggc atgagccact gtgcccagca 204360
gcaatttgtt tgaattggga gtgctttctt ccaccttgat tatgaaaaaa tttcaaatgt 204420
gtataaaaca gattcatata aaggatcctg atatgccatt atcagcttta tcaattatcc 204480
ctgtcatcat atttttatt tataaatatt tcaatatttg tggaatcctt aaaaatgcat 204540
cacataaccc aacattgttc atattatacc aattgtctta taatttaaaa atattttgtt 204600
caatcatttt tcagataagc ttcacacact gtggttggct aagtctcata atatttctgt 204660
tgtaaaaatc ttaagtctgg gcgtggtggc acacggctgt cattccagca ctttgggagg 204720
ctgaggtggg cggatcacga ggtcaagaga tcgagaccat cctggccaac atggtgaaac 204780
ccggtctcta ctaaaaatac aaaaattagc tgggcgtggt agtgcgtgcc tgtagtccca 204840
gctactcggg aggctgaggc aggagaatcg cttgaaccca gaaggtggca gttgcagtga 204900
gccgagatcg cgccactgca ctccagccta gagacagagt gcggcttcat ctcaaaacga 204960
aacaaaacaa aacaatctta agtctcttag aatactttga tgccccttcc atctctcttt 205020
ttctgtcttc cttccccctc tccctgtctt ttctgctgtt gaagaaagca gatcatttgt 205080
cctgagagtt acttatagtc tgaattttgc tgagtgcctc tctgtggtgg acttaagcat 205140
gtatccatcc cttatatttc ttgtaagttg atatatctag agacttcatt ggatacaagt 205200
tttctttggc aagatagcat gtatggtggt gtatcaggag gtgtttatgt cctgttgttt 205260
cttctctgat tttcttagca gctcctgatc attattactt agatccatta attcataagg 205320
gactatatgg tagtgatatt gtaattttat cattcttctt catttgttag gttggcatat 205380
ttctataaaa agcttttcat cgccgagggt tgatttttc cttcttacta agcagttttc 205440
ttttcttttt cttttttttt tttttgaggt aggtctcact gtgttgctca ggctggtgtg 205500
cagtggcgca aacacacagt tgcgaactct tgggctgagg tgatcctcct gcctcagttt 205560
cctgtgtagt tgggaccaca ggtgcatgcc accatgcctg gctaattttt tgattctttt 205620
gtagagatga ggtctcactt tatttcccag gctggtcttg aatgtctggg ctcaagcaat 205680

-continued ctttctacct cagcctcctg agtagctggg actacaggca cataccacca tgcccagcta 205740
attttttaat ttttattttt agtagagatg tggtcgtatt atgttgctca ggatggtctc 205800
gaactgcaga gctcaagtga tcctcctgcc tcagcctccc agtgtgctgg gattataggt 205860
gtactacagg caagagccaa tgagcctggt cagatttttt tttcctgatt tgaaatctgt 205920
tatgggttca attgatactt ccaaatcaaa ctcagggttt caggattttt actaacctca 205980
ttgatcttac ccatgtatct cctttctcta atgccaaaaa tcctacttct tgaagccata 206040
ataagattat tcatttgttt tatcccacat tacacacaac aatcttagaa taatgacttc 206100
ccaataatat gattactgaa aacagtttaa tttttttttgc gcttttcaaa aaaatccttc 206160
agagatgtgt agtcaagtta ctgtattctg ctgggcacag tggctcacgc ctataatccc 206220
agtactttgg gaggacaaga agggaggatc gctggacctc aggagtttga gaccagccgg 206280
ggcaatatag tgagaccctg tctctacaaa agaaaattaa aaattaacca gacatggtgg 206340
catgtcccta tagtcccagc tattgagagg ctgtggcgag agtaggctta agcccaggag 206400
tttgaagctg cagtgagata cgattgtgac actgtactct agggtgacag agcagggacc 206460
ctgtttttaa aaaaaaaaaa tgaaaaaact tcctgtgcct tagactcatt tgtaatcgtc 206520
cttctctctg tgtggctata tgctaactgg gtatatggtt agtttatttg tttcatttaa 206580
aaaatctctt tctgttaagt tttatttata attacacaaa tactggcttt gatagtcaaa 206640
ttgaaaaaac aaagtgtatt caaagaagtc taccttctat ccttgtcctt tcctatgttt 206700
tagccatagt ataaaaagtt atggtttatc attatatttc aaaaatataa gaagatattc 206760
ccatatccca ctttttctta aacagtagca taactttaca tactttttttc taaccttgct 206820 tttttaaata tcctggacat cctggatatc cataatagtg tctagagata gtcttcattc 206880 ttttttttact gtatagtaat ccactgtgta cttgtaccat agtttattca acctattgat 206940
gggcatttgg gtagtttcca aatgtatcac agagaggatt acagtgaata gccttgtgta 207000
tgcatcctgc tttacttttg ctgactactg gtaatattaa catttttttat gttctgtatt 207060 taaaaaatgg tggttattat tcatctataa cttttattat acatgacttt ggttagcatg 207120
ctttaacctt ttagcataac atttgcaagc tacttgtttt aattaaaatt ttggttaaat 207180
gtaaaaaata gtgagctatt ttgtaatcta gattcaatag aatcttatac ttcctttaca 207240
aatgatagct gagttgatca tttgtgtaaa tgactgtgaa cttaaaaatt acagcatttt 207300
ttaaaataaa tttttttaac attttaaaat tatttaaaat aatagacaca caaagtaaaa 207360
agagaagaaa aaaaaaagag acagggtctt gctatgttgc ccaggctggt ctcaaactcc 207420
caggctcaaa tgatcctcct gccttggcct cctaaagtgt aagccaccac acttggcaaa 207480
aattagtttc tttaaaacaa aaacattaca ggttatctgg taccatggta gcttctttaa 207540
cactaggttc acttagaaca aagcttagga acaaagtcag actttcacaa agagcttgtg 207600
tggcaatggg gtatttttttg caaattccat tggtggggtc aagatgtgag tttagaagga 207660
actcttagcc tgactcttct ggccatggaa aaagatggtt gcttctaaat gctgacctgg 207720
tgattttaca ctgtcacatc tcaaattgtg gtcatctttt atacattatt aacaacaaaa 207780
gggaaaaatt gagttgactt taagaggaag tggaaaataa cgagatcaca tctgtactct 207840
acaggctctc cacagaggtc agactgaggt ggtaaaattg ttgtgcacta aattagggca 207900
ttaacgtttc atggaaactg aagctatatc taaatagctg atggcctgct ttctagatct 207960
cctatatacc tgcttctcaa attcagtctg ttttaaaaaa ttgccctttg aggttggaac 208020
cagcgaaata aggctgaaaa cagaataagc cattattgaa aaaattagga acttggaagc 208080

-continued

```
agatactcat aatctaaatc ctctgaagct aaagtttgat ccacaatagc aaagcattat 208140
cattttagtg attgtacctt agttgtttcc tggcaggtga taaatttggg atcactttct 208200
tcttacagtg tgctctgata gtctttaaaa caaaccagag ctctaaattg taatgccatt 208260
ggtaatttaa ctctgatttg tctctatgcc tgtctcctgg tgttctgtaa aattctacac 208320
gtcatttcag gtatcactat ccagaagacg ttacttttgc ctttgatgca ctttaaaatg 208380
tgaagtctct tgtgaagctc tttggttatt ttctcctttg ctgctgaaat aaattcaggt 208440
tgatgatttt cttgtaggat atgttgtgtg atctagacat tgcaaaccca agtctttgat 208500
ttttttttcc ctacagattg cctgtttctt ttttatttta atttttatta gttattatta 208560
tttttgagat ggagtctcac tctgtcaccc aggctggagt gcagaggtgt gatagctcac 208620
tgcaacctcc acctcccggg ttcttgtgcc tcagccaccc aggtagctgg gattacaggc 208680
acgtaccacc actctcagct aatttttttg tatttttagt agggatggga tttctccatg 208740
ttggccaggc tgatctcaaa ctcctgacct taagtgatct tcctgccttg gtctctgaaa 208800
gtgttgggat tacaggtgtg agccactgtg cctggccagt tattaatttt tttaaagaga 208860
tggggtctca ctatcttgcc caggctggag tgcagtggct ctttacaggc actgttgtag 208920
tgcactgcag ccttgaactc ctgggctcaa gtgatcctcc tgagaggctg gaattacagg 208980
cacacaccac tgtgtccaac agattgccca tttgtgatct gtgtaaatat ctctcacttc 209040
ctgcagtatc tctgctcaag aatgtaaaga gatggataat atttttagat ttgttgaaac 209100
aaagtaaagt tctgctcaaa tgagaatgac actaactaaa tgaaaaggcc ggttataatt 209160
ctgtaatttt gtgcctgcaa tgtgtgtgtt attgtacact tgaatcggcc ctgtgcattg 209220
tggcgaggtg catattgcat ggttgtattg aaaaggtgct tgggccgggc gtggtggctc 209280
acacctgtaa tcccagcaat ttgggaggct gaggcagctg gattacctga ggttaggagt 209340
tcaagaccag cctggccaac atggtgaaac cctgtttcta gtaaaaaaata caaaaaatta 209400
gctgggtgtg gtggtgggtg cctgtaatac cagctactag ggaggctaag gcagggagaa 209460
ttgcttaaac ctgggaggca gaggttgcag tgagctgaga ttgtgccact gcactccagc 209520
ctgagtgtat cacaaaaaaa aaaaaaaaag gtttttgccc tctctctgtg cctgctgctc 209580
cctgttgagt cctataggcc tgagctgcca gggggtactg tgggctgaga ctggacattg 209640
caaccgactg caaggcaccg tgggacccag gttgtggatg gactgtctct cgggctttct 209700
tctttccatt catcttcctc ctctaactcc cctctgtatc cagtatcctt gctctccata 209760
cacctgcttc attctttttc cttcagtaga tttttctgct tcttgactta caaaccctac 209820
ttctagcccc tttcagatat tgaaactagc aactttcagg ctttgtacca aagtctcaga 209880
gattctcatt gactcggatg ccatccatct ctagtccaaa gaacaatgtc aaggacatga 209940
acatgtggaa caaaagtgtc tgctgtggac acctttgggg agaaatagtt ttcagtgatg 210000
agggttgtag tgagttgggc agatatccca aaaatatctg ccaaaaacta tagacacttc 210060
tggttgcagt gacttattcc ttccttcatt cagcaaatac tgattgaaca ccgactgtat 210120
gtctggatct attctaggtt ttgggggtgg agcagtgaac aaatcagtct ttatctttat 210180
agagtgtaca gtcaagtggg agagacaggc agtaaacaaa gaaacagttc aatattcaat 210240
ctgtgagatg gtgataagtg ctacagagaa aacaaactag tgtaagataa aaagggtgtt 210300
ttgataggcc tttactattt aggtctcttt gataaggtgg catttgaaca aagctctgaa 210360
ggaaataatg gagccaacca tgcatataac ctcagggaga acattctagg tagagggaac 210420
```

-continued

```
agcaagtgca aaggccctga agtgggggtt tgtttacctt gttgcacaat ctgcacacag 210480
gccagtacaa ttggaatgga tgggaaatgt aaaagagaga agttgaaaag gccaggtgca 210540
gtggctcatg cctacaatcc cagcattttg ggaggctgaa gtgggaggaa tttgagatca 210600
gcctgggcaa cagaaccaga cctcgggcta atttttgtat tttagtaga gacagggttt 210660
caccatattg gccaggctga tctcaaactc ctgacctcag gtgatcctcc tgcctcagcc 210720
tcccaaagtg ctaggattac aggtgtgagc catggccccc agccgtatct ttgtcttaaa 210780
aagtaatctc tgtgcttggt aggccaagaa tttaaaatat aaaaaattta agaaagaaaa 210840
aaaataagta aagtaactat acaggttggt ctggccgtaa tggtgagtgt cattattttt 210900
cttccctagg tattttggct ctgttgctca gagcagtgca ggcgaaatgg tcattagggc 210960
atcgtcatgg tgcctgggga tgcctggctc agccagttta ttttctgtct gcctctctcc 211020
ttggtccttt tcctccactt tcattcatga aattctagtc aagagctggg tccagtggtt 211080
ttcaatccaa gggctttgga agcctctggg gtctattttg gtcattgcag tcactgggct 211140
gctgctcctg gcatttaggt tggcaggggt ctgggctggg aagcaggaat gttcagtggc 211200
cataaatgta agggttggtc ttacatttac ataagggaga caatgaaaac ttaactcctc 211260
cacagtagtg gagtagtgcc gttgggtact cacagtcagt agtgccgttg ggtactcaca 211320
tgtacaacat ggatcaggac attgactttc tgtggatacc ttttaatagt ttattagatg 211380
tgttaggctg ttttgcactg ctctaaagga atatctgagt ctaggtaatt tataaagaca 211440
agaggtttaa ttggctcatg gttctgaagg ctgtacaagc atggctccag catctgcttc 211500
tggtgagggc ctcaggaagc ttccggtcat agtggaaggc aaaaggaggg cagacgatca 211560
catggccgga gtggtggcaa gggtggggtg ggagccacgc tcttttttta attttatttt 211620
aatttgagac agtgtctcac tcttttgccc agcctggagt gcagtggcgt gatctcagct 211680
cactgcagcc tctgcctccc aggttcaagc aattctcctg cctcagcctc ctgagtagtt 211740
gggactacag gcgcgcatca caatgcccag ctgattttg tatttttagc agagacaggg 211800
tttcaccatg ttggccaggc tggtctcgga ctcctgatct caagtaatcc gcctgcctcg 211860
gcctcccaaa gtgctgggat tacaggcatg agccactgcg cacggccacc acactgtttt 211920
aaacaaccag attgcacgtg aacttagagt gagaactcac tgtgaggatg gcaccaaaac 211980
attcatgaag gatccaccac cttcctttag gccccacctc caacactgga ggtcatattt 212040
caacttgaga tttggagggg acagacatcc aaaccgtatc attaaattta atagttttat 212100
gcagtttttt tggctctaga tctgtttaga ctcctgcagt caggtgtctg taactagcct 212160
ctggtccttt ttgagagttc acagtttggt gcaaaccctt tggatgtatt atttgggaaa 212220
atgggatatc tggcagcctg tgtccctgct ttacattatc ctttttgctg cctgccccaa 212280
gcctcctcat tagcatccct gccaaggcca gtggagaagg atggagatgc ggtgacattc 212340
agcttgacag gtcattagca gcttttgtgc cctagggact gctggtggga gggaggttgt 212400
ggaagataaa ccctgacagg aatgtattct cctcgagggc agggtttatt tgatattttt 212460
ctggagctta gaaccataag cctggtgctg gggaggaagc gcccttagca tttggtagcc 212520
tctgtgggca gagcatggaa agtcacaact tctgaattgt ttgtattttc agtctcactc 212580
tagatggatg gcatcttctg ctatgggaaa tgaaatatgt ttaggcaact tgagtcccag 212640
gtgcagatga ggctgggcta attggtgcac tagggaagga gccgggggag agatgtgctg 212700
ttagctatta tcaatctgtg acaactgtca gctgctggca gttagcaccc acctgagcct 212760
gggatgcagg ggtgcctctc ctgtcctctg tggaagcctc tggacccagc agccatcttg 212820
```

-continued actgtgcact gttcaagccc caagtccgcc tggaagaggt gattgagaac ttactgcagg 212880
ataaggaaag cgcaggacag gtgcagtggc tcacgcctgt aatctcagtg ctttgggagg 212940
ctgaggccgg aggagggctg gagtccttga gtgcgagacc agcctgggca acatagtgag 213000
accctgtctt tacaaaaagg aaaagaatta gccagatgtg gtggtgcgtg cctgtagtcc 213060
cagccactca agaggctgag gtgcgaggat cacttgagcc caggagtttg aggttacagt 213120
gagctatgat cataccactg cattccagcc tgggtgagag agcatgactc tgtcccaaca 213180
acaaaaaaaa agattaaggg aagcctctgg cagacctgat gatgggtggc ccagccaaaa 213240
tgagtattga tgaggatttc cctggtctgg aactctgaat ttagtctggc aaagtattcc 213300
ctttgtgttg tgagatgatt cttggtgtta ccccatcacg gtaggtaaga tgaattagca 213360
aatgagaaag gctttctctt tttcatcctt atctagtccg tagatgaagc ctgaagaagg 213420
tctccatatg gtagtagtaa gtgtttaaca tctacctcta acacttgcct gtgtcttttt 213480
ttttttgcaa agcctcagga atgccccagt atctaggtag aatttgataa tatttcattt 213540
ttgttatatt ccctttctg tttaccttct atatacagca aaatgaaaaa atttttaaaa 213600
tttgtgcaag taagggcaat ttcttttttc tttttctttt tttttgagac agggtcttgc 213660
tctggcaccc aggctggagt gcagtgacac aatctcggct cactgcaacc tctgcttcct 213720
gggtttaagc gattctcctg cctcaggctt ccaagtagct gggattacag gtgcctgcca 213780
ccactcccag ctaattttca tatttttagt agagaccagg ttttgccatg ttgactgggc 213840
tggtcttgaa ctcctgacct caggtgatcc atccaccttg gcctcccaaa gtgctgggat 213900
tataggcttg agccactggg cctggctgag gcagtttctt tttgaaatat attttgtgaa 213960
ggagaaaaag aggagttcag tttaaagaaa caaatgacat aagaggtggt atgcagagat 214020
gccaaagcat cttgaaggtg cttttttttt tggaaacaga gtcttgcttc attgcccagt 214080
ctggtctgca gtggtgcaat catggttccc tgcagccttg accttctggg ctcaagtaat 214140
cctcccacct cagcctctca agtagctggg actacagatg catgccacta tgtctggcta 214200
atctttaaat tttttgtaga agccagctct caccatattg cccaggctgg tcttgacctc 214260
ctgtcctcga gcaaaaatac cgattttgat taagtctggg gtaggacctg gggctgggat 214320
tctaaccagc tcccaggtgg tgctaatgct gctggtctac agaccacacg tggagtagcc 214380
agtgtagagt tcatgtagca atagtgatgt catagaaata gccagtatct gtatacttgc 214440
tttgttgtat gtcacgcact gtatagtgat gtacatgcat ctcatttgac cctcaccccg 214500
cccctttggg ggtagaaagg attgtgctca tttcacactc aaggaaactg aggcacagac 214560
aggcaaagta gcttggcgaa acagaaagga acttagaggc aggccctgat tagctcagag 214620
actagaaggc cttgtgcgtc atcctgaaca gcttggactt gatcttgaag gtggagggag 214680
aaattgaagg gtaattaaac aggaactgta ggaaattcac cttgcatagt gattgctttg 214740
gccacgtgtg ccctgccacc gcccccccac ctcagtgaag tgtcatgcga agttgggttc 214800
gtaaatgaag gcccgaatgc tttcctgaca agtttgtttt aaatcaagct gctaattagt 214860
cccagtcccc ctcccccggt atgtattttt ttgttgatgt cgtttcactt catttagttg 214920
aagtgattga ttcagttcag tgtttgaact tctttttgaa cctcacctta ataacctgtc 214980
taaacatcaa ggttaaacct tcttgctaac acagcagtat tgcttggtaa gactggctca 215040
cagtccaagg aaatgcttgc ccagagaggg caaactgcct taactcctta acctgagctc 215100
attaaaaaaa attcaaatga ctgattcctt gtcacagttc tacctacatt gtttttattt 215160

-continued ttgtccaggt ttcagctagt taaatgcttt tgtgatgagc ttatgtccag gctgaaggtt 215220
gcattttgaa actgagcgtc aaataccaat ttaaagtcca gacctttaca cttgtgaaat 215280
tcagataaat gaaatggaaa taaaacaggg ctgctgtgtt gtgaaatatg actgtgtttt 215340
tccttgtagg actctttgag ggtagccatt ttggcatttt atatataaat tttcttttct 215400
tagcctacct tttactttct tgatttgcct atttgtgatt tcccattaaa cactaggctt 215460
tttgtaaacc aattatccct tgaaattgac tttttttttt tttgagacag gatcttgttt 215520
tgccacacag gctggagtgc cgtggctcca tcatatgata aacagaaaga gagagagaga 215580
gagagagaga gagagagaga gagaccctgt cttatttaaa acaaaaaaag aagaagaaaa 215640
aaagaatata gatcacagct gttatttgta tatgctacgc caatccttgt tgggtttcat 215700
tctttataat tgttattttt aaagattttt cttatgaata ttctattgtt tcattgtaga 215760
aaatttaagg gagaacacag tgggaaaaaa aaaacaagaa aaggacttca taatcctgct 215820
accctgggag aaaaaaaaaa tcaccattac ctatttggtt cttctcccac tttttttttt 215880
ttcgagatgg agtctccctt tgttacccag gctggagggc agggacgtga tcttggctct 215940
ctgcaacctc tgcctcctgg gttcaagcga ttctcgtgcc tcagcctccc gagtatctgg 216000
gattacaggg gtgtgccatc acacctggct aatttttgta tttttagtag agacggggtt 216060
ttgtcatgtt ggccaggctg gtttgttggc catgtctggt tttttgtcat attggccagt 216120
ctgtttgtca tgtcaggctg acatgttttg tcatgttggc caggctggtc tttaactcct 216180
gacttcaggt aatcctgaag tgctaggatt ataggcgtga gccattgcac ctggccttct 216240
gccttttttt taaagaaaaa aaattaaaac atttttttct ttttaagata gcgtctcatt 216300
ttgttgccca ggctggtctt gaactcctgg gctcaagtga tcctccagcc tcagcctctg 216360
gagtagctgg gactacagat gcacatcatg gtgtccttat gccatttctt ttgtacgtag 216420
gtgaatgcaa gtgtatgatt acatcatatg ctattttgga ggtttgactt tcttttcact 216480
ttcatcatct ttccaaggtg ttattttcct agtacatctt tttaaatgga catagaacat 216540
tcttttgtat gaacaaacaa tagttttatt taggcggtcc tttcctgttg gacatttata 216600
ttattttcag catttctcca cagttgttgc agcattcaga tgaaccttct tttttttttt 216660
ttttgagacg gagtctcgct ctttcgccca ggctggagtg cagtggcaca atctctcctc 216720
aagtgattcc tgtgtcaccc tcccacgtag ctgggattac aggtgcccat gtctggctaa 216780
tttttgtgtt tttggtagag ctgtggtttt accatgttgg ccaggctggt ttcgaactcc 216840
tgccctgaag tgatctgccc acctcagcct cccaaagtgt ggggattaca ggtgtaagcc 216900
atcacgcctg acccagatga acattcttgt agctatcgca cacaattctg aacatttcct 216960
aggatgaatt ccttaaagaa gtaatgctga tccaggcttt tttctttttc tgtgactctt 217020
tgacacgtaa taatattgac ttttctttct ttccagacac tacaacaaca ggagtgcaaa 217080
cttctctaca gccgaaaaga gggtcaaagg caagaaaaca aaaacaaaaa tagatataaa 217140
aacatcctgc cctgtaagta tcaatattcc gctcagtaat agtcactctt ggagattttg 217200
attcctagca cctctgtacc tttcctcagg gtcgtgtgct cttgttagca catcggaggc 217260
cttagcttct ttaattgcaa gcagtttcca aaataatcaa ccatggtggg tgttgatgac 217320
ttcattcact gagctcccgt gatgctgatt actgagtaaa gttgccacta ggtggctttg 217380
tctgtggttg gttccttctg ttaattaatt ttctgtctgc ccaagataga tcatctcaag 217440
gcttgggatc tctcagtgtc agggacctta gggtgccaga tttgtgtctt gactcctcct 217500
cactgggcct gtgagtcctg ggtaaggcct gcctcctttc tgggactcag ttcccttaag 217560

-continued

```
tgggaaacag acaaacacct cctgagggct cctagaactg ttctgcttgc tgatcccctg 217620
agctcaagtt actggagaaa gggtatatac ctaaactgct cagaagaaga ctttgtgggc 217680
cgggcgcagt ggctcacacc tgtaatccca gcactttcgg aggccgaggc aagcggatca 217740
cctctgatca ggagttcaag accagcctgg ccaacatggt gaaaccccat ctctactaaa 217800
aatacaaaaa ttagccatat gtggtggtgt gcgcctgtaa tcccagctac tcgggaggct 217860
gaggcgggaa attggttgaa cccaggagat ggaggttgca gtgagccgag atgtgccatt 217920
gcactccagc ctgggtgaca agagcaaaac tccgtctcaa aaaaaaaaaa ggaagacttt 217980
gtgaatattc gcaaagctgt aaagctgtac ctttcaattt tttttgaga catagtctca 218040
ctctgttgct cagggtgcag tcacagctca ctgtagcctc aacctcctgg gctcaagcga 218100
ttctcccacc tcagcctcct gattagctgg gacaataggc aggcaccagt acacctggtt 218160
gattttacag tttttctgta ggccggcgca gtggcttacg cctgtaatcc cagcaccctg 218220
ggaggccgag gtgggcggat cacctgaggt taggagttcg agagtagcct ggccaacatg 218280
gtgaaacccc atctctatta aaaattacaa aaattagctg ggcgtggtgg tggatgcctg 218340
taatcccagc tacttgggag gctgaggctg aggcaggaga atcgcttgaa cctgggaggc 218400
ggaggttgca atgagccgga ggtgctatgt gcaccactgc actccaggct gggcgacaga 218460
gtgagactct gtctcaaaac aaaaaacgat ttaaaaaata ataaaatttt ttctagggcg 218520
gggtctccct atgttgccca ggctggtctt gaactcctgg gctcaagtag tcctcctgcc 218580
tcagcctccc aaactgttgg gattaccagt gcaagccatt gtgcctggct gtaccttctg 218640
taacacccaa atgccacctg gcaaagccca agttgaatca tgaggaaaaa aggcctggaa 218700
ggatgtagac cttccttttt tctacttatt tatttattta tttttgagat agggtcttac 218760
tctgttgccc aggctggagt gcagtggcat gatcatgggt cactgcagcc tcaacctccc 218820
gggctcaagt ggtccttccc accccagcct gcaatgtagc tgggactaca ggcatgtgct 218880
accatgccca gctaattttt gtatttttg taattatttt ttttgtagag acagggtttc 218940
gtcatgttgc ctaggctggt ctcgaattcc tgggctcaaa cgatctgcct gcatcggcct 219000
cccaaagtgt tgggattaca ggtgtgaacc actgtgtctg gctatatctt ctgtaacacc 219060
caaatgccac caggcaaagc ccaagttgaa ccaggaggga aaaaggcctg gcaggatgta 219120
ggccttgcat gaggatctca gaaactgcac taaaccagtc acagttcctc tctcccgagg 219180
tctaactcta tgctgaactc tttgcatttt tatctcactt aatccatatc acatgcacag 219240
gaaggaagca ttcgtagtat cctggtttcc tagaccattt tagcaaggtt ataagtgaag 219300
gggagtgggt gggagaactg gcactagagc ccccaaagtc actgttctta gcaccactct 219360
aatgcatggg gttctccatt gatgtgctat gcaaggcagt gcactgagga gaaaggaagg 219420
aacatttaca acttctcttt atttatatcc tgtccctaaa aaaaaaagaa aaagaaaaat 219480
ttgtctgagg cctagattga ttgcagggag tgcataatgt tttattgatt gattgattga 219540
ttgtatatag agatgggggg tctcactata ttgcccaggc tgatctcgaa ctcctaggct 219600
caagcaatcc tcctgctttg gcttcccaaa gtgctgggat tacaggcatg agcgactgca 219660
cctggctatg catactatat ttatccaact tacaaataag gcttgcttgc ctgtagtgca 219720
tatgtgtata catttcagca tagaaaaact gtgtgattgg gggttgtgat caaatttgga 219780
gagcattgct ctcatgtctt atcaggtcag agtcattttg tcaaatcttg taaaccattc 219840
tttgtgtgtg tctatgcatg aaacatagtc tttctctttc tgcatgcata tgtacatata 219900
```

-continued

```
catggtatat atgtatatca tatctacatg gatattgtaa tgtatatgta tgaggatggg 219960
ggaaagtgga gacatttgta atactgagaa aaggcagtga ggaatttgca gagaagcagt 220020
ttgagctgta gcatggtact agtgaccttg aggaagcctt atcctttttt tttggaattt 220080
attttttcaa tttttagaaa tagacaagag tttctctatg ttgcccaggc tggtcttgac 220140
ctcctgggcc caaactatcc tcctgccttg gcttcccaaa gtgccaggat tacaggtgtg 220200
gaccaccatg cctggccacc ttgtcctttc tatgtctaag ttgtgacatc tgctcagggg 220260
tcaggtggta ttaaatggta taaaatgtat gggaaagtga agggatcaat ggtatgcagt 220320
atctaaatag aatatcgctt tttcctccct taaaggtctc attcagatgt ttcctctgat 220380
gaacatctca tttccttaaa gatgaggagt ctgaagcaaa aaagacatta ttcttttaag 220440
acacatggct gtcttactaa ttcccattgc aaaatatgtt gtttaggtag agcactcaga 220500
tttttatacg aataatagac ttttgtacag aatttggaca gttgatacta tcagagcctt 220560
gtgatattcc actgcattat gcttcactaa aaaatacctg gctgggtgcg gtggctcaca 220620
actgtaatcc cagcactttg ggaggctgag gtgggcagat cacctgaggt caggagttca 220680
agatcagcct ggctaacatg gcaaaacccc atctctacta aaaatacaaa aattagccag 220740
atgtggtggc acgctcctgt aatcccagtt actcaggagg ctgaggtatg agaattgctt 220800
gagcccagga ggcagaggtt gcagagagcc gagatagtgc tattgcactc caacctgggt 220860
gacagaggaa aaccctgtct caaaaaaataa atttaaaaca acaacaacaa caacaacaaa 220920
aacccctctt tattatggaa attttcaaat atattcaaga gcataaagaa cccacatgta 220980
cccatcaccc agcttcaaca attatcaact catgcccagt cttggtttca tctatactct 221040
gatccacatc tcctctctcc ttgaattatt ttgaagccca tctcagacat catgtcatat 221100
atgtatactt caatcttctt tttttttaaa actccccctc cccttttctt ttttcttgag 221160
actgtgtctc actctgtcat ccaggctgga gtgatcttgg ctcactgcaa tgtccgcctc 221220
tcgggttcaa gcgatttttg tacctcagcc tccctagtag ctaggattac agatgtggac 221280
caacatgcct ggctaatttt tgtattttta atagagacag ggttttgtca tgttggccag 221340
gctggtcttg acctcctgac ctcatatgat ccacctgcct tggcctccca aagtgctgaa 221400
attataggcc actgcgccca gcccaaaatt tcttggtttg aaataatttt ggaactcata 221460
agaagttaca catatagtag agagaatttt cttgtacctt ctctgagctt cctatatacc 221520
caatgataac atcctatata cccatagtat atgatcaaaa ctaggaaatt gtgaagatgg 221580
cattttgaga catcaggcag tgttcacgtt actgttttgc ttacctgggc tttaattttt 221640
atgtgttttt ttttcaatca ttgaatgaac aaaacttgga ctaggctggg gagtaactga 221700
tttgaactgt tttttcctga agcagtccag gacttatgtg accgtggtct ctttttcttc 221760
tagttgatca taccagggtt gtcctacacg atggtgatcc caatgagcct gtttcagatt 221820
acatcaatgc aaatatcatc atggtaagct ttgcttttca cagtgttttc tgaccataca 221880
tttctagcct atttttgtat tttaaatcct tcctcatgtc ctgaaagtaa ctttaaggtg 221940
tttgaaggat tttcttccta aatttctagc ctgaatttga aaccaagtgc aacaattcaa 222000
agcccaaaaa gagttacatt gccacacaag gctgcctgca aaacacggtg aatgactttt 222060
ggcggatggt gttccaagaa aactcccgag tgattgtcat gacaacgaaa gaagtggaga 222120
gaggaaaggt aaatcacaga aacttctttt ctgctaaact gtttttaaag tatcagacat 222180
gtcagattgg ccatgtttag gaattgaata aatgaattaa gcttactgta actgattctc 222240
tggaaaaaag ggactaggag aaatttgatt atgttattcc ttggtgtagt tttctttatg 222300
```

-continued

```
tttcttctgc ttgggatttg ttgagcttct tggctccatg gatttgtagt tttccttaaa 222360
tttggataat gttcagtctt agtttcttca gatacatatc ctgggctggg catggtggct 222420
catgcctgta gtcccagcac tgtggggtgt tgaggtgggc ggatcacttg aggtcaggag 222480
tttgagacca gcctgggcaa tgtagtaaga ccccatctct taaaaaaaaa aaatgtaccc 222540
tgcacaacct tgtcctagga cagcagtcat acgtgtatta gactacttga agttgtctca 222600
tagcccactg atacttggtt tattttattc agtttttttct ccccgtgttt catttcgaat 222660
agcttctttt gctatgtctc caagttaatc ttctgcaata tgtcatccgc tcttaatcct 222720
atccagagta tttttcatca cagacattgt atttttcatc tctagaagtg ttaatgtcat 222780
ctatagcttt ccttttaaca tgtgtagcat tttccttacc ttttgaatgt atggagtatt 222840
tctgttgttg ttttttgttt tgtagagaca gggtctcggt ctgttgccca ggccggagtg 222900
cagtggcatg atctcagctc actgcagcct ctgcctcccg gttcaaatga ttctcatgcc 222960
tcagcctccc aagtagctgg gactacaggt gcgtgccacc acgcctggct aatttttgta 223020
tttttagtag agatggggtt ttgccatgtt ggccaggctg gttttggaac ccctgagctt 223080
aggtgatcca ccttccttga cctcccaaag tgttgggatt ataggtgtga gccaccatgc 223140
ctggccatgt tgtctgtttt aattaactct gcctaactgt cctcccaaat ggttgctgca 223200
gtgctcactc ccaccagcag cacctgccta ggactcatta ctccatactc ttcaagacac 223260
ttcagattaa aaaaataaat tgtaacaccc cacacctaca gaagagcgga cagatcttat 223320
tgagtgacag ccctctgtgt tatctcaaag tgagcccacc atggtggttt tttttttaaa 223380
tatggaaaag ttctgtgttt ttgtttgtgt tctagtgaaa gttctttttt agatatcctt 223440
taattggttt atataagatt ttatgtggaa tgtagcagtc atacctataa attaaaccta 223500
aggcagatgg agaactttgg agttgagcct tcctactgta attttcatat tggatgtgaa 223560
gggcagtgtg attttcataa gactttcatt gttgtactcc tagttggtat acttctgaat 223620
acctttgagg ccagttctgg tcatcgtgaa acaaaggttt ccttcagcaa atgcctgtgg 223680
taacattagg tgttcttgaa ttaatggacc aatgaaaaca tctttgtagt ttctgcttca 223740
ggcaagggtt ttttgcccta aatgtggata ggaagaatga agcccttcat cctccttttt 223800
gcctgattat agctatagga ggttcacctg ttctcagaag acatgaggat tgtgaagaga 223860
ggggtcttgt gttgcttcag aggaatcagt atcagtccct ttcagaagct ctcctggata 223920
gacaggcatt agggccaaat cactctgccc cacccctcac caccatgtcc tactctctgc 223980
tccctgtctc attcttcctc tttactttgg tggtgccgag aggatgacat gatgggtatt 224040
gattctctcc acagaccttt ctgacatcct actttcagta tccccccagt gcacagaaga 224100
caagccagac tgtggactgt gtttgattcc tgggctctat tttaaaagac agtgtattag 224160
ttctcacatt ttagaatttg tttgccaagg tttccacggg agtttagaaa ctagggggag 224220
ggctgatgtt taaagttagc taaaatgttc ttttcagggt catgatttaa ttttatattc 224280
tctggtgagt tccctatagt gactgggagc agtcctcagt cttgattggc cagtgacagc 224340
atagagtaca attaatatta ggagtgctca tttggggaaa ctaaaatttg catcaaatct 224400
gtcagaggtg tttggatcta caaaataccg gagggaaagc tgaattgaga atcataataa 224460
ataaaagacc acatcgttct tttttttttt tttttttggg actgtatctt gctctgtcac 224520
tcaggctgca gtgcagtggc actatcttgg atcactgcag gctccgcctc ccggattcaa 224580
gcgattttcc tgcctcagtg cctgagtagc tgggattaca ggcgtgtgcc actacacctg 224640
```

-continued

```
gctaatttt gtaattttag tagagacagg tttcaccatg ttggccaggc tggtctcaaa 224700
ctcctggcct caagtgatcc acccggcttc ccaaagtgct gggattacag gcgtgagcca 224760
ctgcgcccaa ccaagaccac atccttttat tgaacgttcc tcctaccatg ttttcttttt 224820
tctttcaatt aatcattgac tcattgactc tcactgttga tgtctgtagc tgctctctta 224880
tttccagttt tatagctgta aatttctctg tcttcctaag atacaaggta aatttctctt 224940
gctgatattg gtggttttgg aaagtgagtg gtgtggatga ctgcccagaa aacaacagaa 225000
cacaaaagca ttctctgccc agaacacatc accaaataga tacaaactca tctcttactg 225060
agtgaaatag cttccttttt ggcagcaaga atgattttct tggtgccata tttttcaatc 225120
cgcctgctct tgaagccagc agctattgca gacttggcat tcccaggcac ccagttaagg 225180
gaaagtgacg tgtagaggag gtatcagatg ggtctggata tagaaaaagc agctggttca 225240
aaaccccatg ggctgccttt ctgtgataga gttattcaca cttgggttag ataaggcaca 225300
gagtcctcct acactggtgc ggaaatgaaa cagacagtct ggctcgttgg gcagcctagc 225360
ctcctccaga atctgtgctt gccttcccta tggagtgact ggtagatctt agaattcaga 225420
cctcagtggt tgctagccag cactctcaca ttggttggtc cttctctctg catctttgat 225480
tctttagaga tagataaacc aagcaccgac tctcctttga catgtgcttg gaacagacac 225540
ctgcacgagc tgcctttctc ctcccacttc tgcctggtct tccaaacacc tgcttttctt 225600
gtttgaactc ttcctttttt tttgagacag aacctctctc tgtcacccag gctggagtgc 225660
agtggcatga tctcagctca ctgcaacctc tgcctcccag gttcaaataa ttctcctgcc 225720
tcagcctccc aagtagctgg gattacaggt gcctgctatc acgcctggct aatttttgta 225780
tttttagtag agacacggtt tcaccatttg gccaggttgg tctcaaacct ctggtctcaa 225840
gtgatctgcc cgcctcggcc acccgaactg ctgggattac aggcatgagc cactgcgccc 225900
cagctgattc tttacagata aacaaacatt gactctgctt tgacatgtgc ttggatcagg 225960
taactgcacc agctgccttt ctcctcccac ttctgcctgg tcctccgaat gcctgctttt 226020
cttatttgaa ctcttctgtc cttttctgaa aacctaacag atgcgaaaca ggccattttc 226080
catgttggtg gttattaagc aagacttgaa catttgtttg ttgcttgttt aggcttttat 226140
ttcagagttc acagaattaa ctttcttttt ttctgatctc ttccagagta aatgtgtcaa 226200
atactggcct gatgagtatg ctctaaaaga atatggcgtc atgcgtgtta ggaacgtcaa 226260
agaaagcgcc gctcatgact atacgctaag agaacttaaa ctttcaaagg ttggacaagt 226320
aagtatattg tcgtattcta gagactttgg gaactgttga tggtgtgtag gaattcaggg 226380
tcttgccgtt actcatgttt gcatacatgc atgcattcgc tcactcattg attcagtagc 226440
catttattag cttccttcta tgtgccaggt acagtttaag cagtactggt acattgtgaa 226500
caaggcaggt agtgttcctg ccctcatcga gcctagggag atagacaatt taaaaacaaa 226560
taactggcca ggcgccgtgg ctcaggcctg taatcccagc actttgggag gctgaggtgg 226620
gtggatcgct tgagccgggg agttcgagac cagccctggg tgggagactg ggatagggtg 226680
acctgagtgg ctacaaggtc tgttaggagg cctccgcagg ggcctatgtt gatggcctcc 226740
tctccaagta tccacagact tcagcagttg ttcttttttg ttccttcctt tggaatggaa 226800
tattatataa aatggcagaa taaactggaa gagaagcagt agatgtgaga ggtgccgggg 226860
ggtgaagtct gcaggatgtg gggattgttt ggcttttgga ggaggaagga gggattcaag 226920
acacattgta gaggtttgag tctgagcgga cagtggtgct gtggcagaca ccacaaaagc 226980
tggaaggaga actgatgtgg gcagtgattt gttttcttct ggatgtgttc agctgggcat 227040
```

-continued

```
ctgaacagtc atgtggacat tcatctattc attcagagat atttgttcaa tgacctcttg 227100
gttcctggca ccatgctgct tgctggagat agagctgggg aacaaaacag atggaatccc 227160
tgcactccca agtgtacact atactggcca gtaatctacc agcccagtaa ttgcacatat 227220
aaatatatca ttataaactg taatcagggc tagaaagaaa aaatgcagga gtttagggtt 227280
catttggagg gggaagggac tttttttttt tttttttga aacagaatct tgttctgtca 227340
cccagactgg agtgcactgg tgcattcacg gctcactgca gccacaacct cctaagctca 227400
agtgatcctc tcacctcagc ctcccatgta gctgggggct acaggtgtgt gccaccatgc 227460
ccacccaatt gttaaatttt ttatagagac ggttgtctca ttatgttgcc caggctggtc 227520
ttgaactcct gggcttaagc gatcctgctg ccacatgcag cctcccaagg tgctggaatt 227580
acaggcgtga gccagcgcac ccggccaagg gaggggaggt tcttaaggca tagggaacaa 227640
tgtgtttgag tcagcaaagg aggttgtggg ggtttgtcct aagtgtggta agcagccaga 227700
gttggattta agtttttaag agattcccct ccaccctgta gagactggag ggggcaggag 227760
ttgttctagg gattaggacc aatttggagg tagtgcagcc gtcagagtaa aaaataatag 227820
ggattgaact aggccagtgc ccagggtgcc tgaaagaaga ggacccagta gagctgactg 227880
gaggcagaca tgcagggatt cagtgaagga gtgtaccaag ggcgagggtg gtgtgcaggg 227940
tgactggcaa ttttctagct tgagaaaggt ccggggggat ggcagtggag ttgaggaagc 228000
tgggaggatc aaggaccttt ttgtgaacac acaaagtttg agatgccttg gacacattga 228060
agtggagcgg tcagggaggc aagggtggag gtgggatgcg gaggggaggt gggatgcaga 228120
gcgtcgtgga tggatcagtt ttgctcgata gagggacatg tttttctgtg gcaacaggag 228180
ggcaaaagga gaaggtggcc acagatgccg gtagatgagc tgagagtgat tgtattccct 228240
atcctctcgg aagcttgagg caaggccatc aacagacaat cagagggaat aagaagagat 228300
agaatatatg aagaaaggga gaaaagatga aatcgtaatt gtgtagcagg gcaagaagtc 228360
cagaaatttc tgtgctgtgc caagttccca gttgaggcgg tgaacatgaa aatatactga 228420
tacccattgc ctggtttttc tccaaggaca cttggctcct agggcacaaa acagaaagta 228480
cgtggtttgt ccaggccgag ggctttgcat agttgcagtg gatggagagg aggtcaagga 228540
atggaggcac atggtagaga gagactgtcc ccagagcacg gggactcctg gccggatgag 228600
ggggacaggg gcaggaggag gcaggtggaa agtagaggga gggctcagtg gtctggaggc 228660
tacaggaagt gacgggggga ccagaaggag ctggaaacca gtgtggttgt ggcccagggt 228720
gggatgtttg gatttctgat gtcagagagg gtccagtcct tctgatgatg gggaggggtg 228780
gaggctgaat ctatggtaga gatagtgaga ggaactggaa caatgtagct gtcaagtgga 228840
aatgggagaa agggctgggc gtggtggctc acgcctgtaa tcccagcata ttgggaggct 228900
gaggcaagag gatcgtgtta gctcaggagt tctgggctgc attgagctgt gattgtgcca 228960
ctgcactcca gccttggcaa cagagtgccc agttaaaaat aaaaataaaa taaaataaaa 229020
aaattaaaaa aaaaagaaga agaaaaaaga gaaaagtgtc cttttacatc ccttttaaaa 229080
atgtcactta aggctgggca aagtggctca tgcctgtaat ccctgcactt tgggaggctg 229140
aagtgggtgg attacttgag gtcaggagta caagaccagc ctggccaaca tggcgaaact 229200
ccttctctac taaaattagc tggatgtggt acatgcctgt agtcccagct actcgggagt 229260
cgagtctgag gcccaagaat tgcttgaatc ggggaggcgt aggttgcagt gagctgtgat 229320
caggtcactg tgcaccagcc tggatgacag agtgagactc tgtctcaaaa aaaaaagtca 229380
```

-continued cttagcttag attgtctcta catatatagg aagaagatgt aggaatgaat ggtgctgcta 229440
caattacgtc atctggatag acccagaaac atgatacttt ttggttttct gtagccttgg 229500
tgccattgtt gatctttatt aattatcatt atcctcaaaa tagccataat gtgctgagtc 229560
tcttcctatt tgctgggcag aggctgagta tttcagcgag ctcactgagt ccttaaaatt 229620
gcattatgat agagagaaag agattattat ttgcattttg caaaatgaag aaattgaggt 229680
ttagagatac ccaagggcca cgtgagtgtg agtgcctgga attggagcct aaatctagtc 229740
atctgatagc aaagcctgtt ttcttatctg ctttgcatta aatataagtt taaaatagaa 229800
caatactggc caggctgggt ggctcacgcc tgtaatccca gcactttggg aggtcgaggc 229860
aggcagatca cctgaggtca ggagtttgca accagcctgg ccaatatggc gaaagaaacc 229920
ccatcgctac taaaaataca aaaattagcc aggcatggtg atgtgtgcct gtaatcccag 229980
ctacttggga ggctgaggca ggagaatggc ttgaacccgg gaggcagagg ttgcagtgag 230040
ccaagatcac gccactgcac tccagcctgg gcaacagagt aagactctgt cttggaaaaa 230100
aaaaaaaaaa agaatgatac tatagtctgt gtttatatgg tggggaaggt tgagtatcaa 230160
aaaaataaca aagaggaatg aatgtcttaa gtgaatgcct gtttccccat ctgcttcctc 230220
ttctgctggg aggagagacc tggatcccta gaggtttcag ttgcctccag agctgagtgc 230280
cacagggatg caggggaata gggatgttac ctgtcgctgg taattcagag agatgattca 230340
gggtatagtt acctgaaaga acaaattgcc atgccagacg tcttggttct tatgacagag 230400
gcaaagagtt gcctccagga ttgcccaaaa ggagacgagt tctgggaacc tcacgaagag 230460
gacctttcag tggaacctgg ggagattctc ttcctctcca ttggatttag gaaagcttag 230520
aaccgggtga ttcctcaacc tcttgattta tttaattctt ttctggtttt tcttggctct 230580
actccagggg aatacggaga gaacggtctg gcaataccac tttcggacct ggccggacca 230640
cggcgtgccc agcgaccctg gggcgtgct ggacttcctg gaggaggtgc accataagca 230700
ggagagcatc atggatgcag ggccggtcgt ggtgcactgc aggtgacagc tcctgctgcc 230760
cctctaggcc acagcctgtc cctgtctcct agcgcccagg gcttgctttt acctacccac 230820
tcctagctct ttaactgtag gaagaattta atatctgttt gaggcataga gcaactgcat 230880
tgagggacat tttgatccca aggcatattt ctcctagacc ctacagcact gccattggcc 230940
atggccatgg caacatgctc agttaaaaca gcaaagacta agtcagcatt atctctgagt 231000
ccaccagaag ttgtgcatta aacaacttca tcctggctct gcagtttctc cttattcttc 231060
atgatgtttg ctttgtagct gttgactgct ttgtaggtat tgaggtggtg ggggtgtggt 231120
ggaaataggc ctgactcttg aggatccctt aagtcatttt tgcttggttc tctttttcct 231180
tcttttcttc tactcttcta tgattcatct ctttgattgt gattctgttc tctctctctc 231240
tctctctttt tttttttcg tttttgagac agagtcttgt tttgttgccc aggctagagt 231300
gcagtggtgc catcttggct cactgcaacc tccgcctccc gggttcaggc cattctcctg 231360
cctcagcctc ccaagtagct gggattacag gcatctgaca ctacgcccgg ctaatttttg 231420
tattttaata gagacaaggt tttgtcatgt tggccaggct ggtctcgaac ccttgacctc 231480
aggtgatcca cctgccttgt ccttccaaag tgctgggatt acaggtatga gctaccatgc 231540
ccggcccatt ctgttctctt ctaccataaa tatatttctc ccctaacact atatttgttt 231600
gcttcacaag attccagctg cttttccacc aaggcctttg atggaagctg tgctgtgacc 231660
tctgtaatga gtctgtgggc tgctgattct ccagtttggg cttcatgatt atactgggga 231720
atattgggtt tcctaaatct cattcatttc ttgggcaagt agatatatgt gaaagtgttt 231780

-continued atttgtccag ttgttaaaga agctaccatt tattgagcca gcctctgagc acaatgtttt 231840
ttgttttgtt ttgtttttaa tttttaaaat tatttacttc ttctatttca ataactttat 231900
tattattatt ttttgagaca gagtctcact ctgtcaccca ggctagagtg caattgagcg 231960
atcttagctc actgcaacct ctgctttctg ggttcaagca attctcatgt ctcagcctcc 232020
cgagtagctg ggattactgg tacgtgacaa catgcctggc taattttgt gtttttagta 232080 gagacgaggt tttgctatgt tggccaggct ggtctggaac tcctggcccc aagtgatcct 232140
cctgcctcgg cctcccaaag tgctggtatt ataggtgaga gccactgcgc ccggccctct 232200
ttcagtaatt ttgatgtatt tttttgtata tgattcctgt ttcattctgt ccaaccagca 232260
ctctgtatgg tatgtgctgt tgtccccatt tcacagatgc agaaattaag ggtcagagag 232320
gttaagggac ttacctcagg cacgttgtac tggagaagct gaactccaag agcaggtttg 232380
ggctgactcc aaagccctat gctttttgcc aacatatttt caaacataaa tagacaattt 232440
tataaatagc tccaaagagt agacattgtt tctgttgata ttaatggctt ggttttgagt 232500
ctgaaacccc catgaatgat tctgttgtcc ctgcttttttg tccttctgcc cgcagtgctg 232560
gaattggccg gacagggacg ttcattgtga ttgatattct tattgacatc atcagagaga 232620
aaggtgggtc atctggtggg caagaagcga cagtttctgt ttttagttta tggaaggaaa 232680
gtgctcacga aaacagtctg gggaagagag gttgaatggg aaaattcttt cacaaaaatc 232740
tgggctgaag acttcagtgt gtctgcctga gaacagaagt gacactattt gagcttttgg 232800
cataaaatga agtctaggag ctgcagaacc cactgccatg gccttttgtt gcatacacag 232860
tggtggtctc tatccagcca cctgaccttg tttacagtat ggggtgattt gttggcaagt 232920
gagggaatcc tgacttctgc cacttcgtta tttatgtagt cttctgggat cattggtatt 232980
ggtcagaagt tcaacactgt agccattgca acatgctcag ttaaaacagc aaagactaaa 233040
ttagcattgt ctctgagtcc actaaaagtt gtgcattaaa caacttcatc ctggctctgc 233100
agtttctctt tattcttcat gatgtttcct tcgtaggtgt tgactgcgat attgacgttc 233160
ccaaaaccat ccagatggtg cggtctcaga ggtcagggat ggtccagaca gaagcacagt 233220
accgatttat ctatatggcg gtccagcatt atattgaaac actacagcgc aggattgaag 233280
aagagcaggt accagcctga gggctggcat gcggattctc attctcttgc taggcctctt 233340
ggatacgctc tccttttgag caggaggaca ggctctgata gacaactgtt tgatttcgga 233400
atgggaaaca aactcccaac taaaagggcc tctggaaact gtcaattatt ctccacttct 233460
cagctctgat tttcactgc agaggagctt agggaagggc accatcctat cagcctggcc 233520
tgccagattg aagaactgcc atgcagaaag gttctgatgt tctcaggctc atgtggcaag 233580
cgtaaaactc aaagccttga agtttctagc ctgttccagc cttgatccag gccatgttta 233640
tcctgattcc atcctttaaa acgaatgcct cactcttaat agcgcacggc agtttgaacc 233700
actaatttgg tcgagttgga aacagtgaaa tttcaatttt aataagctgt gcataatgaa 233760
gaggaatgtg gaattggagc ctttccatct gaagctattc ataacaggca caaagctgag 233820
ttaattagga atatgctgag atgaaggaaa tgaggagagc tgctcttttg ggggctgtgc 233880
ttctctcccc aacccctcaa ccccattgcc atgctgcaga tggggtggtg tctaaacatc 233940
agtggcgagt gcctgcatta ctctgctcgt tgccttccag agaactcagc ttctccaaat 234000
gctgagctct tttcagaatg ggacctgcca ccagtatttg aaagatttct agcctagcag 234060
aacagcagcc acgttatcaa agtttggttg gccaaaggaa ggtacttgct aattagttta 234120

-continued

```
gtaggttttc agtccgcaca gacatacggg attgttttat tgtacataga catcttcaga 234180
aacagtgtat gtatagaaat gtaaggtcaa aatttgaacc tcagtgcttt aaatctgaat 234240
ttgtattaac tgatatgaaa tatttagacg gttactttat tttatatctg tcttccatta 234300
tacttaattt ggctcaagaa tagttaggca aaaagttgcc caaagagaag gatctcctag 234360
taaatacaaa gagaatgtaa catagttgct acaagttgga gcatgttcag ggatgtcttt 234420
tttttttttt ttttttgaga gagaggtctc tctctgttgc ccaggctgga gtgcagtggt 234480
gtaatcatgg ctcactgcag cctcaatctc ccaggcttaa gcgatcctcc cacctcagcc 234540
tcccaagtag ctgggactat aggcatgcgc caccacacct agctaatttt cgcatttttt 234600
gtagtgtcac agtttcgcca tgttgcccag gctagtctcg aattcctagg ctcaagcagt 234660
gcttctgcct cagcctctct gagtagttag gactacaaat ttgtggctcc atgcccggct 234720
aattttttta tctttatttt gtagagacaa ggtctcactg tgttgcccag gctagtcttg 234780
aactcctggg ctcaaacaac cctcccactt tgggtttcca aagtgctggg attacaagtg 234840
tgagccactg agcccagtga cctctgggtt ttaaaaatgt gtaggcttca attatttatt 234900
ttaaaaaatg aaatcctgca atatatagtt ttctgcgttg tgtggtttga atcaatctgg 234960
gaactggctt gctggctgat tgtggtaaag taagaagtac ttaatttagt agaaagttta 235020
aatggcagac ataacattaa acccagctga tttataaatg aagcaaaaga acaaaactca 235080
ttcaggataa ttggttattc taaaatacag tcatttctaa aattatgaag tgttcaggac 235140
ctttgggagt gaaagaattt gctaaagaag gatcagtgaa aaaaaggaat gatgggtgaa 235200
gagctgtgga gaaggaagag aagaaacagc acaaggaagg aagaatataa aatcagatgt 235260
gggaatccag gggaaagtgc aaacgaagca agattgagaa aattctcaag tttttataaa 235320
cagttctcac actctgccag ttccttggag gtagactttt ttgttaactt ccaactacag 235380
tagtgaaaaa aaaaaaaaaa ccctcaaatt tgcaaaagca gtctgtggaa ttttctttac 235440
ccagctttcc tgactgttaa ctttttagca cacttaactt tatcattcgt ttattctctc 235500
tgtttaaaat taaaaatgta aattttaaaa agtaaaatgt ttgttggtta caaacattta 235560
taccccttttg tctctaaata tcatttcatt ttaaaaaatg aataatctaa gcctacacat 235620
tctaaaatgt gtatattttc taaaaataag ggcattctct tacataacca atgtcacaat 235680
tatttgatac agtgatcaaa atcaggaaac taacattgat ataacactat tatctaacct 235740
acagaccatc ttcaaatttt gtcctgctag tatcttttat gggtccaggg tcacacagtg 235800
catttggcta taatgtatct tttttctctt tttttgagac agggtctcac tttgttgccc 235860
aggttggagt gcagtggtgc aattatggct cacggcagcc ttgacctcct tgggctcagg 235920
tgatcctccc acctcagcct ctcgagtagc tggagaccac aggtgtgcac caccatgcct 235980
ggctaagttt tgtatttttt gtagagatgg agcttcgccg tgttgccccg gctggccttg 236040
aactcctggg ctcaagtgac cctcccgcct tggcctccca aagtgctggg attacaggcg 236100
tgagtcacca cacctggcca gttattagta tgtttagtct ctttaatctg gaacagtttc 236160
tcagtcattc tttatttttc atgacctgga tgtttttgaa gagtttaggc cagctattta 236220
gcagaatgcc tttcagtttg gatttgtcca gtgttttctc ttgactatat tctagtcatg 236280
catttttggc aggactgtca cagaaatgtt gttgtagtct tcttagtaca tcacatcagg 236340
tacacactgt tgatctgatt cattactagt ggtgttaact ttgatcactt gaataaggtg 236400
gtgtctgtca aatttgtcca ccgtaaagtt acttgagcaa aacgtagctg ggactacagg 236460
cgtagcaaaa aatgtagcaa aaagtagtat ttttgctaca tttttttttt aggaacaaag 236520
```

-continued

```
tatttttccc ttttaagtta atctcttgtc cataaagtta ttatttttcc cttttaagtt 236580
aatatcttgt gggtagatac tggagactgc gtaaattacc tatttctcat aatacttttt 236640
ttttttttga gatggagtct cgcaccgtct cccaggctgg agtgcagtgg tgcaatctcg 236700
ggtcactgca agctccacct cccgggttga cgccattctc ctgcctcagc ctcccaagta 236760
gttgggacta caggcgcccg ccatcacacc tggctaattt tttgtatttt tagtagagac 236820
ggggtctcac cgtgttagcc aggatggtct tgatctcctg accttgtgat ctgcccgcct 236880
tggcctccca aagtgctggg attacagatg tgagtcactg cgcccggctc tcataatact 236940
ttttgcctac taattttata ttcattgatt aaattcttgc ctgaaaaaat tattactgtg 237000
gtatttgcca aatggcaatt ttctgtttcc atcattgcct ttccccccgct tttaaaagta 237060
taagtgacaa agaaaaactg tatataaagt gtacaccatg atattttgat atatgtatac 237120
tttgtgaaat gattatcaaa attgagttaa ataatgcatc caacatctca gttacttttt 237180
tttttttttg agacagagtc ttggtttgtc actaaggctg gagtgcagtg ccacaatctc 237240
ggctcattac aacctccacc tcccaggttc aagtgattct cctgccttgg cctccccagt 237300
agctgggatt acaggtgccc accatcacac ccggctaatt tttgtatttt tagtagaggt 237360
ggggtttcac tacgttggcc aggctggtct cgaactcctg acctcaaatg atcctcccgt 237420
ctcagctttc caaagtggtg ggattacagg cgtgagccac tgtgcccggc cactcttagt 237480
aaattttaag tgtacatttt tttttttttt tttttgagat ggagtctcac tttgtcaccc 237540
tggctggagt gcagtggcat gatcttgcca cactggaacc tctgcctcct gggttcattc 237600
aggtgcttct cccacctcag cctcccaagt agctgagact acaggtaccc gccaccatgc 237660
ctggctaatt attgtatttt tagtagagat gggggttcac catgttagcc aggctggcct 237720
caaactcctg acctcaggtg atctacccac ctcggcctcc caaagtactg agattacagg 237780
catgagccac cacacccagc cacattacgt tagtattaac tataatcacc atgctgtaca 237840
ttagatctcc aaaatgtatt catcttatgt aacttcaagt ttgtaccctt tgaccaaagt 237900
ctccttgttt tccctacccc caacccctgg taatcactgc tttaatctca gtttttatga 237960
gtttgactgg tttagattcc acatacaaat gagatcaggc agtgatggtt tatttcactt 238020
agcataatgt catccatgtt cttgcaaatg acaggatttt cttcttttta aaactaatat 238080
ccatgctgga cacggtggct catgcctgta atcccagcac tttggaaggc tgaggagggt 238140
ggatcacttg aggtcaggag ttcgagacca gcctggccaa catggtgaaa ccccatctct 238200
accaaaaata taaaaaatta gctggatgtg gtggcgcaca cctgtgatcc cagctacttg 238260
ggacactgag gcaggaggat cgcttgaacc cgggaggcgg aggttgcagt gagccaagat 238320
ggtgccactg cactttagcc tggatgttga tgttgttcca cttgtttatt tttattttgt 238380
tccctgtgct tttggtatca aatcctaaaa accattgcca tgaccattgt catgttactt 238440
tccccatatg ctttcttcta gaacttttaa ggttcatcat tcccttttct gtttttagtt 238500
gcaagcctac tataaggaag ggcttttctt tcttccttat ttatttattc atgtctatca 238560
gaatgggcac cttactacta tttttgttgt tattgcttga attgacttga atttggctag 238620
tggaaacctt ttcagatcgg gtactctgtc cttttgatct ctttccattt tcaagcactt 238680
ctttagactt aagatggtct aggctcatct tctcctttcc cagccatttt tcaaaggaac 238740
ctgattcctt ttagtgaaga gcagtatttt gaaaccaaga tctgggcact gggtctactt 238800
gtttgtactg gtacagtgtt ctttgaattg ctaattagct gatcaattac tgctctattt 238860
```

-continued gagttccctc tttctaaaac ctcacatatg tgtacagacg gtccctgact tatgatggtt 238920
cgacttatga tttttgattt tatgatggtt tgagagcaat acatccattc tgtttttcac 238980
ttttcattca acactttatt ttaaaatagg gattgtgaga tgatattgcc cacgtgtagg 239040
ctaatgtaag tgttctgagc acgtttaaag taggctaggc taagctgtgg tgtttggtag 239100
gttagatatg ttaaatgcat tttcgactag tgatattttc aacttatgat gagtttattg 239160
ggatgtatcc ccataaagtc gaggagcatt atacatatct ctgtataaca gagtgagttc 239220
cttatacctt tcatccactt tcccctgaag ttaacatttt acctaaccat gatacattta 239280
tcaaaactaa aacattaaca tcaatacatt gctattaact aaactagagt ttaattggat 239340
tttgccagtt ttccaatgaa tatccttttt ctgttccttg atccaattca tggtcacaca 239400
ctgagtttgg tcacttgtca ctgtagtctt ctccaatctg cgacagcttc ttaggctttc 239460
cttgtttttc atgtactctt gacgattttt aagagtactg gtcagatatc ttgtaggata 239520
tcccacaact tgtgtttaat cttatgtttt ctcatgatta gacttgagta atggattttt 239580
gggaagaata ccacagaggt atattgttaa gtgttctcat cacttggagg taaatgttat 239640
caacatggcc tggtgatgtt aaacttgtca gtttgtttag ttagtatctg ccagattttt 239700
ctcactgcat aattacaaat cctccttaac ttatgatggg gttacagcct gataagccca 239760
tcataaattg aaaatatcat aagtcaaaaa tgcatttaat gcatctaaac tactaaacat 239820
cacagcttag cctagcctgc cttgaacgta ttcaggacac ttacattagc ctacagttgg 239880
gcaaaatcat ctcatgggaa gcctgtttta taatgtgttg catatcttat gtaatgtgtt 239940
gagtactgta ctcagaatga aaaacagaag ggttgtattg cttttgcacc atcataaaat 240000
caaaaaaacc ataaggcaaa ccatcatgaa gttggggact gcctgtactt ttttcctctt 240060
tccctgttca attccttgga agaaagtcat ttagttcaga ccatactcaa gaaaagggaa 240120
ataaagctcc atctcttgga gcttaattga aactggaatg actagtttct atatacatta 240180
tttagaatcc ttttgtaaga aagatttgtt ccttctctcc atttatttat tccattattt 240240
atattgatag agacgcatgt acatttattt tatactttgg gttataatct atttttcttg 240300
ctcaaattgt tacagctttg gtcactggga ggttcttcag attggctcct gtgtcatttg 240360
acatgtcccc accctctcgt ttctgagtac ttctctactt tggcattaca aaagatgttc 240420
caggctcctc ttatattttt ccctgccgca gccctagaat catccatttt tctatggtgc 240480
cctggttcct tttactttag atgggggttt agaaaccaat ctgggtgttg ggtgtgctca 240540
ttgctactgg aatcactgct tctaggccct ctcagcagat agagctagaa aacatatggc 240600
tgtatatgaa tccatggatt catatatatc tataattgtt ttctgtatct ggccatctat 240660
atatatatta agctaaacat gaattcatac tgatgtctca gactcgaatc cattgccgca 240720
gggctcattc ttgccttcct cttgcttatt tgtgacttct ttctctaaca gggagaaacc 240780
ccagtctcat tatcaccaac ctatctactc atttgttcaa ccctggtata ggtgtaaagt 240840
agtttcagaa ttactaacct atacccatgt gagaattgta tttgcacttc ttgtttgaag 240900
gaaatacata caacacaggt agcgtctcta cacttcagta tacagagatc tgaacagtgt 240960
tctctctgag tgaatcatat tgcaggacag aaattacttt taaaaattct gtaatgggtc 241020
aggcctataa tcctagcact ttgggaggct gaggtgggca gatcacctga ggtcaggagt 241080
tcgagaccag cctggccaaa atggtaaaac cccatctcta caaaaaatac aaaaattagc 241140
caggcgtagt ggtgtgtgcc tgtaatccca gctactcagg aggctgaggc acgagaatca 241200
cttgaacctg ggaggcagag cttgcagtga gctgagattg agccactgca ctccagtctg 241260

-continued

```
ggcgacagag cgagactctg tctcaaaaaa aaaaaaaaaa aaaaattcca taatgatagc 241320
agagctggaa tagaaatggg attgcacagg ctgaatctga gttgttgcaa cagtaaacga 241380
gcaagattta aactggcctt gtgtagcact tgctatttgg ctcctcatat tttattagac 241440
gcttattctt ttttgtttgg tgtcattcct ttgagaaata tttgagtgcc ttttctgttg 241500
cagacattga ttagatgctg aggttgtaac aatgaagaag atagccatcg ctgttgcctc 241560
atggaactga agttttacta gatgtaaaat ttgagttaac atgaggccgt gcccctatgt 241620
gccctattgt ttcttcacac agctcccttc atctccttgg tccaatgaaa aggttttttc 241680
atacttgttc attcattcct gcattaatta aagtaggttg tactgtgcca ggcactggga 241740
atatttaagt agttgtgttc ctgaattgga aatgaatcca gcatggttgg agtagaagga 241800
gctgggggc aatgtggagt gtgatgggga gattggaaaa gtaagctgag accagatttt 241860
tcagtttgga gggagaggtg ggccttgtag gccatattac agattgtaga ctttatttgg 241920
agggacatgg aagtcattga ggagtctgaa gcaggggaat gacataaaaa gatcctcatt 241980
ttaggccgga tgtggtggct cacgcctgta atcccagcac tttgggaggt tgaagtgggt 242040
ggattgcttg aggccaagag tttgagacta gcctgggcaa catggtgaaa ccctgtctct 242100
atcaaaaata caaaaattag ctgggcatgg tggctcacac ctgtagtccc agctacttgg 242160
gaggctgagg catgagaatc gcttgaaccc gggaggcaga gattgcagtg agccgagatt 242220
gtgccactgc attccagcct gggtgacaga gtgagacttc gtgtcaaaaa aaaaacaaaa 242280
aacccctcat tttgaaaggg aaccctggct tgagggtgaa gaatgggtgg gcactaggct 242340
agagcagctg cagggtcagt gaggagctgc cgcagtgctg cacgtgagaa cccgtcatgg 242400
tttggtcagg gtgggcagga ctgacagtga gcacagagcg aagtaaaacc agcaaaattt 242460
catgattgga tagtggaagg aatcatggtg tttgtagtct tcaaatgtga acccagagtg 242520
cactggacaa gtagtctagg ctgctctgta accaaggcaa gtgttttcat tttaccctct 242580
cttcctgctc ttggcctttg gattttttgt aatttaaggt ttatgaatgt aatcagttac 242640
ttaacatgga aagatactta ataccagatg attttggagt cttgtgatca ataccttctc 242700
tcaatcttgg gtgtgtgtca gttggcaagg ccataaaatt tgttataaac attgcagaag 242760
gcttggttac tgtgctgtga cgttgaattt gggtggagat agatcaattt cagttgattt 242820
tctaggcttc agaaacacat taccctctac tccacaaaca caaatcaaaa caaaacaatc 242880
cctattccct gagcatttct cttgatctat aacacagcct gggctgtcac agtactaaga 242940
caagcccatc tgatttgtga gtcagtttta tttcttggtc ttctacataa gctaaaaagt 243000
ttcaacattt taatgctttt ccttggattc ctttgagtca ttgaagtaat tcctgtttca 243060
tttgtactaa ttattccaca ctagaaaatt ctgttgtaat cactttatgt attaatagaa 243120
atactgattt ttattttcaa ggaagtattg agtagggagg gggaaatagg gatttgctgt 243180
tcaatgggta tagagtttca gtaatacaag acaaaaaact tcagagatct tctatacagc 243240
agtgggtata tagttaacaa tactgcacat ctaacagttt gttaagaggg tagatctcat 243300
gtcatgtgtt tttaaaaatt gcttttaaaa aaagtatcga gtaaaaaagc agttttactc 243360
ctcagtttct atttatattt aaaattttta tttaaaaagt gagttgagat ttttaaacct 243420
caggataagt tttatttttt aaaaaattta ttttttatta ttttttgaga tggagtctca 243480
ctccatctca agtcacccag gctggagtgc agtggtgtct tggctcactg cgacctctat 243540
ctcccaggtt caagtgtttc tgctgcttca gcctcctgag tagctgggat tacaggtctg 243600
```

-continued

```
caccaccacg cctggctaat ttttgtattt ttagtagaga tggggtgtca ccatgttggc 243660
caggtttgtc ttgaactcct aacctcaagt gaccacctgc cttggcctct caaagtgctg 243720
ggattacagg tatgagccac agtgcccggc gggataagtt ttaaaataat attctctgct 243780
ggctgggcat ggtggctcat gcctgtaaac ccagcacttt gggaggctga ggcaggagca 243840
tcactcgagg ccaagagttt gagaccagtc tgggcaacat aatgagaccc cctctctaca 243900
aaaaataaaa aaaatttggc tgagtgtggc atgttcctgt agctatcggg aggctgagat 243960
gggaggattg cttgagccca ggagtttgag gctgcagtga gctatgattg caccactgcg 244020
ctctagtctg ggtgacagtg tgagaccctg tctcttaaaa aaaaaaaaaa aaaaggccag 244080
gcacagtggc tcaggcctgt aaccccagca ctttgggagg ccgaggcggg tggatcactt 244140
gaggccagga atttgagacc aggctggcca acatgatgaa accccgtctc tactaaaaat 244200
acaaaaataa gctgggtgtt gtggtgcaca cctgtaatcc cagctacttg ggaggctgag 244260
ggagagaatt gcttgaacct gggaggcaga ggctacagtg agccgagatc acaccactgc 244320
actccagcct gggtgacaga gcaagactcc atctcaaaaa caacaacaac aaaaaaacca 244380
aatgttcttg ccaattcttc catttaatat ttaattttga attatattgt atctttctaa 244440
ggattgtttc ttatataagc aaagattttt cagtgctaaa catttacgac tgctattcag 244500
aaatggttat ttacaagtct ttttgtttta agaaaatggc tgttcaaaaa attaaaatag 244560
tatataaacc aaacaaaata tttttgcttt ggatgtctgt tttgcagctt cttccctaca 244620
ctataagttc ttactgactg ctttatcact taataaattg gtttggctac tttaacagag 244680
gcaaatagta tcaggcaaaa aattattttt tatttttatt ttttgagaca gtctcactcc 244740
atcacccagg ctgcagtgca gtggcctgat cttggctcac tgcaacctcc acctcccagg 244800
ttcaagcgat tctcatgcct cagcctcctg agtagctgga attataggca tgcaccacca 244860
cactcagcta atttttgtat ttttagtaga gacagggttt tgccatgttg accaggctag 244920
tcttgaactc ctgacctcaa gtgatccatc tgctttggcc tcccaaagtg ctgggataac 244980
aggcatgagc caccatgccc agccctattt tttatttttt agagatgggt ctcgcttttt 245040
agagatgggt cttgttgccc aggccagagt gcagtggtgc gatcatagct tactgcagcc 245100
ttgaattcct gggctcaagc aattctcctg cctcagcctc ccgagtagct gggactacag 245160
gcctgtgcca ccaggcctgg cttgtacatt agtatttgat atggctaccc taagggcaat 245220
cctatagtga agtcaacatt agataatgat gctcatctga tggattagat tttcagagtt 245280
ggctgtttcc aggtgcctat aggagtagaa aagggtgaca aacctcctaa ctagatgtcc 245340
taccaaatat agttcactcc acatctgaga tgagactgca tgactgctgg ttttctttgc 245400
cttttccccc ccagggtatc atcagaacca aaaataaagt tttaaaggtg ggtcaggtgt 245460
gtgttggctc atgcctgtaa tcctagcact ttgggaggct gaggcaggtg gatcatctga 245520
gctcaggagt tcaagaccag cctggctaat aacatggtta agccccatct ctactaaaat 245580
acaaaaagtt agctgggcat ggtggtgggc acctgtaatc ccagctactc aggaggctga 245640
ggcatgaaaa tcgcttgaac cccagaggcg ggggttgcag tgagccgaga tcatgccact 245700
gcacactagc ctgaacaaca gagcaaggct ctgtctccaa acaaacaaaa atggtgccag 245760
agtcttttcc agggctgagg ggagatacaa tgaagtgtgt tattttttct gataagagtg 245820
ctaccatctt tcattcttgt gtgccatttc tagttggggt gaatttgttt tcggagttcc 245880
tttcccagct gtttgcctga aaaaccatga aatgtgttcc acatgaacta tgaaatgatt 245940
agatgctaat gtggcaaaga aagtgtgaat tctcttgtag aaacagggac atttggttcg 246000
```

-continued gtacagtaag ttgttaatgc gtgactctgt gctttcaaat tctgtggttc aaaagtactt 246060
ttcactccta ctgtgtattt accttgagaa ggtgaatccc ctaacaattt ggtcaatgta 246120
tcagtattct caacccgtct atcaattttt ttttctttct ccctcttttt tctttttttg 246180
ggcaaaatac cttttttgct ttttatcccc ttaaaataac cattgtccct cacatgtgca 246240
ctcttccaaa tttcagaaaa gcaagaggaa agggcacgaa tatacaaata ttaagtattc 246300
tctagcggac cagacgagtg gagatcagag ccctctcccg ccttgtactc caacgccacc 246360
ctgtgcagag taagtagtgc tgaaggaaat tctttttacc tggtcatggt ggtttaaaaa 246420
ggtttaaaaa acaaaaacaa aaacaaaaca caagtttgta gcacatgcct ttcactggtg 246480
cacgttcctg ttgccctact gttagtgtat ctgtgactgg tgatatctat tgattgtgtt 246540
aatgctatct caaccacgtt ttaattttcc taagctggcc aggcacggtg gctaacgcct 246600
gtaatcccag tgctttggga ggccgaggtt catggattac tttgaagtca ggagttcgag 246660
accagcctgg ccaacatggt gaaaccctgt ctctactaaa aatacaaaaa ttagccgggc 246720
atggtggcgc atgcctgtaa tcccagctac tcaggaggct gaggcaggag aatcgcttga 246780
acccaggaaa cggatgttgc agtgagccga gatcatgcca ctgcactcca gcctgggcga 246840
tagagtgagc ctctgtctaa aaataaaata aaataaaata aattcctaaa ctgaaggctg 246900
actgctatgc tagctaggat tatatgggat tttaagtata tcaagtggtg gttctccaag 246960
aagaatctaa tttttctttt gatgggctgg ggattgtaac aaaggaaggt catatgtctt 247020
aatgatgtgt taaggctctt tgcaaaatca aagtaaataa attgaccact aatgtgtcag 247080
cccagccatg ttctgctcat ttgccaccag tcaacagaaa tctactttgg gtgtttaaac 247140
caggagtcag caaactacag ctcacaaggc cagatgtggg ccatggcctg ttactgtatg 247200
gcctgttaat ggttttaaag ggttgtaaaa caaaagaaca caaaacaaag acccaataac 247260
aaaacaaagc ccgaagaata atatgcgaca gagaccatgt atggcatata gagcctaaaa 247320
tactgactct caagcccttc ccagaaatcc ttcccgactc cttgttgaaa acacggtagg 247380
aaagcatttg tcaaattgag gatatgaata gcaattgtaa gttattattt ttctatatat 247440
tcgaaagtca cttgctagta taacatttac cttttatttt tccctaagaa tcttctctct 247500
gtttgctttc gacatggatt tttaaacccc tgcagatttt aatattctat ataaatgttt 247560
taggtggcat atatgaggtt tgtattaaca tttgctttct atttaacatt gaaatgaaat 247620
tatacagcag aggtattttc tcgtccaagt tgccacttct ttctatcttt tttcttttct 247680
ttcccagtgg actgcctggg aaaattgata ttttaaattg ctctctgcaa taatttgcaa 247740
tggaactgga atgccagggt tctgagtcct tgccagacag ctcgtccctc ctgttggcat 247800
gactgagtca gctgtcatga ttccctcagt accagtggca tgcctgtgac agacagcctg 247860
tctgcctttc attcccgtcg tctcccttgt agggttcaga tccaggatac actggtcctg 247920
gagcccctct cagcctggca cccacagctg ctgggttcct tactctcctg gactgctctg 247980
atgtcatctc cctgctcagc agaaagaagt ctgggatctt gatgctttgg ccctctgtcc 248040
taggccctaa accacccatt gcccttcaca taacctgagc tggggctaaa tagatctctc 248100
atcactgcct gcctgctcct gtattttccc ttcttggagc ttttgcctgt tcagatccct 248160
ctactggaaa ttaataggat ttcattctat gtgtgcattt ccaacctttc ttcacagtgc 248220
gatccaaatg cctcatccta caggcctcct taaaacaacc tgctttctgc cagaccccag 248280
ggagcaccag gacttgaggc ttttattgca cttctgttgt ttttttgaga tggagtctcg 248340

-continued

```
ctctgtcgcc caggctggag tgcagtggca cgatctctgc tcactgcaac ctccatctcc 248400
cgagttcaag agattcttct gcctcagcct ctcaagcagc tgggactaca ggcatgtgcc 248460
atgacacccg gataattttt gtatttttag tagagacggg gttcaccata ttggccaggc 248520
tggtctcaaa ctcctgacct cgtgatccac ccacctgggc ctcccaaagt tctgggatta 248580
caggcgtgag ccaccatgcc cagcgttatt tcacttctgc ctctgtaatt atattgctgt 248640
atggctatct cttctctccc tgggaatgtc aggtcctagg cacaggaact gtgtctgtac 248700
catatctggt gcccaaagaa tgtagtatgt gttttataga tatcatgtaa gcttaaacag 248760
cgtggtctac atttttgtaa atgtctttct ttttcttttc tctccagaat gagagaagac 248820
agtgctagag tctatgaaaa cgtgggcctg atgcaacagc agaaaagttt cagatgagaa 248880
aacctgccaa aacttcagca cagaaatagg tatttaaatg caagtgctct attggttaat 248940
tgtttatata attggcagta tttttaagca ggcaagcaat ttgggaatgt tttagcaaag 249000
tgtaccataa ttgagtttta caaaccaggc tcctttttcc tctccctgta cttctttttc 249060
caagatggtt ttagtttaga gttcattaaa cattaaaatc aaacacagaa ttaattctgc 249120
atgaggcaag gctagcactt attccagaga aatggctgat actggtggta gagtgcaggt 249180
atcactgttc ctgcaatttt tattagagtt ggttagccca ggctgtgctg ggggatgatc 249240
tgtagggatc tgggaagcat cgggactcag cactgggtgg ttgggagtca ggaagcctga 249300
gttctcattt cagtcagtct ctgaccaact gtgtggcatg gggtgctaga ccacttggct 249360
gccgactggg tcaccgacat cccttccagc tctgctgctg gaaattcatc tctcccatat 249420
gttgcctccc catcaattac gtttttttaag tgtgacccaa gtatatgatg tatgttttca 249480
tgataaatta gaaacttatc tgggcatggt ggctcatacc tgtaatccca gcactttggg 249540
aggctgaggt gggcggatca cctgaggtca ggagttcgag accagcctga ccaactaaaa 249600
tagtagagac caacccgtct ctactaaaaa tagaaaatta gctgagcatg gtggtgcatg 249660
cctataatcc cagctactca ggaggctgag gcaggagagg cagcggttgc agtgtgccaa 249720
gatcgcgcca ttgcactcca cctgggccac aagagtgaaa ctccatctca aaaaaaaaaa 249780
aaaaaaaaaa aaaactcagt gtcagtattt catgtcgaaa ttccacttca atgggtagtg 249840
tagttaaaag ctctaagtct accttaaaat cacctaatgc tttgttaagc ttttagatat 249900
atgttcctta aaaactctta acttatttct tccccagatg tggactttca ccctctccct 249960
aaaaagatca agaacagacg caagaaagtt tatgtgaaga cagaatttgg atttggaagg 250020
cttgcaatgt ggttgactac cttttgataa gcaaaatttg aaaccattta aagaccactg 250080
tattttaact caacaatacc tgcttcccaa ttactcattt cctcagataa gaagaaatca 250140
tctctacaat gtagacaaca ttatatttta tagaatttgt ttgaaattga ggaagcagtt 250200
aaattgtgcg ctgtattttg cagattatgg ggattcaaat tctagtaata ggctttttta 250260
tttttatttt tataccctta accagtttaa tttttttttt cctcattgtt ggggatgatg 250320
agaagaaatg atttgggaaa attaagtaac aacgacctag aaaagtgaga acaatctcat 250380
ttaccatcat gtatccagta gtggataatt cattttgatg gcttctattt ttggccaaat 250440
gagaattaag ccagtgcctg agactgtcag aagttgacct ttgcactggc attaaagagt 250500
catagaaaaa gaatcatgga tatttatgaa ttaaggtaag aggtgtggct tttttttttt 250560
tctttttcc agccgttgac caattatagt tcggctgttg actgagaagt ttgtggtggg 250620
aaaacgtttg ccatattttc tttgcatttg aataattgtc ttgtacttag aaaaaaggcg 250680
tctatgaatg accagtgttt ttggtcgcca aatgttgctg acaaacttat cccaaaactt 250740
```

-continued

```
tagtggctta aaaaaacctg cccccaactg ttagtcaatc tgagctgggc tcagctgggc 250800
tgttcttctg ccagcctgca ggtggccact catgtggtca gcaggtcggc ggagagactg 250860
ggatggctgg gcttctctct ctgcctgcag tcctgagtct ctccttcttc gtgtagtctc 250920
tttcagtggc ctggctggca gggtagctag acctctcaca tgcagctcag agctcccaag 250980
agctcaaaag cagaaatggc caggccttct gaaaacttaa gtccagaatt gtcacagtgt 251040
cccttctact tccctctatt gatgatgatg atgatgatga tgatgatgat gatgatgatg 251100
atgatggttt tttctaatca gaagaaagct ggggtatgcc ctctacttac taaacaagtc 251160
acaagcccag ctcagattca agaaaagggt gtgaagtaga ggtgcagtta agtgggggc 251220
cactagtcta acagacggtc acaaccagtg ccatggaaaa ccaaggatat tagcaaaagc 251280
agaagttgct agtgaccttg ggaagccgaa gctgcttaca gtagctggga caagctgaaa 251340
gtcagactaa gaaataaaga gagggccttc aagaagcttc ctgaatgatt tctgctagcc 251400
ctgagcctat ttttggaacc agcacttggg gaaactgatc ttgtgaggat ggatgtgttt 251460
agggacacag ggcttttgag agcagcacca ccccactggg gcatccccag acttgggaaa 251520
cgtgactctt tcttaatgcc actgggtttt agtcaggcca cagtgagaag gaacagccct 251580
aacaggcctc cagccaggtt gaatgagctc atttttgttg tagccaacca gtaagatttg 251640
ctaatgttct acattaagtg ccttctccaa agacatccct ctttgcctca tatgttgaat 251700
catccagtgc ggatatttca atgaaaatat cattggttga cttttgtgat ggtaataatg 251760
ctatggcatc tttgccatga agttgtggcc tccttggatt cttctgactt tggcttctga 251820
aaggaaggcc tagatccagc cctggtggta gttcctttct gaggtctctc agtcccttga 251880
gactttgggg tagtttggct gccattctca ctgacaaaat gtatatcagc ccccacctcc 251940
accccccaat attccttgaa ctttgaattg cttcagaaca caggtgtggc ctgaaggtat 252000
tcccttatta gggaagtgtc actgctgtct tctagtcaaa cttgtaaaga aaaagattcc 252060
agttcagtat ttgcagcaag aagcttgaat gctgttcttt ttatcgcatt gttacatcga 252120
ctcattctcc attttgcttt ggttttgtct tgacttgact tgactttggg ggtaaagtct 252180
ttcaccagca cacaagagtt tgattgtaca aatatatctt ctgcattaac atctctgcct 252240
gttgcttaag atcagttgct tttatactca gaatggaaat acctgatctt ggctagtttt 252300
gttataagat attgatttca tttagatttc cctccacgag gtcagcaaac tatcatgttc 252360
ttatgtaaac ttaggccaag gccagagtta tcatagtccc taggttgcta cggcttatca 252420
tgtgcttggt aaaaggtgat cgcaggttct cagacgagtt tactttacat gagatggaat 252480
caggcagaga ggctgggatg atggagaaag ctcgaggtga agttttaaaa aaaaagttgt 252540
ggaaaggaaa gttccaaaga ggtggtttct gaggaagtca gagcgcccag ggccagagca 252600
gtcagtaatg ggtgaatgag gttgtttgga aagtcggtgt gacagacaca tggatgccat 252660
ctacttctag gttgctggtg ggtattaaat atgcacaata ttccatagct cactgaggat 252720
tttaaaatta taagcatagg attttatatt ttggggtgaa agaattatct ggcacattag 252780
gtattggagt ttaaaaaaaa agccaaattt cacagtctta ataacttttt ttaaaaaaaa 252840
ctaaaaggcg cttcatgtcc agtgtgtggc ccttctgaaa cttatggtca tctctcccac 252900
tgaaaccaag gtcttttcaa atgtggctaa atggggatga ggagacacgg gtaggacttt 252960
cttggtgtgt gtgcattctt taaagagcca agttgcttcg gggaaacagc caggaaaatg 253020
gtcaagatta tttttagagg ttattttatt ggggatttta agaactaata acatcttgag 253080
```

ttatttttaa ttcaggggga tgtggaaagg tttgcaattg tcaagtgttt tgttgtagct 253140
tagtatccat aagggaaact tagactatag acataactac aaagccagtg cagcttttgt 253200
tttctgtatg ttgttggggg atcaactttc acacatagca agcacatggc ctccctgatg 253260
tcaggatgcc tttgttagga tctgtatttg cccttaattt tgttgaaatc ttttttcctt 253320
cttcctcttg aaaagttcca aaatatagtt tattgtatct ttcatcacta aaaatttgtt 253380
cctttttcac tatgggcagt tcacacaagg caaaaactat tgaacagttg gttttagtgt 253440
gttgtataac tttgctgtat atcaaactaa ttttgacaag ttttcatcct aagcctcaaa 253500
tcatgtaatt aataatttgc ctgtttattt atgacctaat tgtgattctt ttattaataa 253560
aagctaatgg gaaaaggatc cctgattaag ctgatgacta gacctacaat taattttcct 253620
gcagtatatg aagtattgta ccagagtatt aaaagatatg taatatttta ttgataaatc 253680
tatcctttaa aaggaatacg ttttaggatg tcatcatttt gatgtgaatc atgtaaatgt 253740 tgataaatatg ctgtttatta tacatttagt gtttcaagag attcacttaa ttgccttttt 253800
gcccacgtat attatgtagt ctatttgcaa ctgttcttaa aaaaatgaca ttaaaagaat 253860
agtttatgta gagaaacatt agtggatgtt aattgtctcc ccacctatat ttatgggtgt 253920
tagcgcaact gctttgctag ttgcaaagct gtattatcag agtaaaagtg tatttgtaaa 253980
ctgtatggga actaaaaatt aggaataaaa ccattttctt atatgatggc atttgtcgtt 254040
tgcttcatca gaaatgtcca ggaaaaaaat gggattattg gtcactccac ctctcacact 254100
ggcaaaatac tgacatttag cagctcttat ctagaagtga cttggaacat agaataaagg 254160
catgagttcc tgaagaattc attgagtgtt tcctgtagaa atagctttag gagataggga 254220
gttctatctg ggagaacata tgagtaactc aagagtaaaa agtatagtct gtgtaaacta 254280
tagaagaaat gctgggcatg gtggcgcgcc cctgtaatct cagctacttg gaggctgaga 254340
cgggaggatt ccttgaaccc aggagcccag gagttttaga ccagtctggg taacatagtg 254400
agaccctttc tcacctactc tcactgcatg ccccccaaaa atatatatgt gcgcgcacgc 254460
gcgcgcacac acacatacac acacacacac acacacacac acacagagga aattgttaga 254520
aaacacacag aactgaatgt aaatagtatt aggtgggaat aagaagtaaa gggatggtaa 254580
ggaggcttgg aggaggagta aattatctgc tatgggacat cagctcttcc tttagagtag 254640
gtttaggtca cataccaaca gggccacttt gttctgacaa cagtgtgcac tgacatgggc 254700
agaaagaaac cattttatag atagcaaaac aggtggttat tctttattag aaatataagg 254760
aatgatttgg attacttatt tacactgtaa aatactatga ccccccctctc agtctcattt 254820 gaattgttta atgcatctaa tcaaatctag ctggtttagt ttgttagtcc tgtcacctgt 254880
ccattcagaa atacagagca tgggccaggc acagtgactc atgcctgtaa tcccagcact 254940
ttgggaagcc aagacgggcg gatcacttga ggccaggggt tcgataccag cctggccgac 255000
atggcgaaac cccgcctcta ttaaagatac taaaattagt tggccatggt ggcgcatgct 255060
tgtaatccca gctactcggg aggctgaggc atgagacttg cttgagccca ggaggtggag 255120
gttgcagtga gccaaaattg cgccactgca ctctagccct ctagcctagg cgacagagtg 255180
agactctctc tcaaaagaat aaataaataa aaataacaga gcaccttcaa aatactaggc 255240
actacacctg tgccctgggg aggaacgctg cccgaaacaa cctgataggg tgcctgtcta 255300
ccagggagct aggccttgca ccgtcagaag gcagttcctg aagctgccca gagccaagac 255360
aaaagacaga agtgagacga ctagttccaa acaagataag agccatgaag aggggctaag 255420
agtgtgtatc gcaccggagg attactacgg ggttttcaaa ccatggtact gtttggtgat 255480

-continued

```
tacccttggg tttcagaaga ggtgctgtac acaatattgc ttggagacac ctcattccac 255540
ataatccttc ttgaggtcct ggattgcatg ttagagggca gtgacaatat cttgtccttg 255600
gccatgccat gaaatgacct tctgtttgtg tagttcctac tcacaagaag agttcccaag 255660
aaaatgagta cattaaaggc agagccggaa tccctgcaat aaatcctgcg gacagagatg 255720
aggaattatt caacgtggtc accttgtgaa tgaaaaagct tctggtgtga gggtctactg 255780
ttggctcata tgacatgtat gctttcatcc acctcttctc ttcgcctcta cgagggggta 255840
gcaaaaaggg gactgtgatc tcaagtgaat ggtttgattt tgcaggtgct gttatttttc 255900
ccctaggaac tagctaagtt tccaaacact gaatttgcaa atgggatgag ccagaaatag 255960
agatttgcta ttttgtcagt ggtgacagtt accagtgagc tggtaatatt caagtcactg 256020
gaggtcagat catttaaatc ctcaaatacc atcatgatag aaaatatagc tactgaaata 256080
agggttacaa gaaagcaata ccatactgcc aagatctgtg agcagtttac ggacaaagga 256140
attgtatgtg atgcgcagac atgatgtcat ttctacctgt tacactgaac taaacagagt 256200
ttgtttggga tccaaatttt ccatttggca aagattaaat ccccaataac agttaggcat 256260
cgggaagcag atgaataaaa tagttcatgc atctgaggag ctatgcatgg agtcatagtc 256320
agggagacat atatattcaa atatttgtca tttgactaga atagacaatg ataagattat 256380
taacttaaat tgatggttgc atagaggagt gaattatagt gaggttagaa ttcagagaag 256440
gggtcacctg agcttactct gtcccccagg ctggaatgca gtggtgagat ctcagctcac 256500
tgcaacctct gcctcccagg ttcaagtgat tctcctgcct cagcctcctg agtagctgga 256560
attacaggca tgtaccacca catcaggcta atttttgtat ttttattaga gattgggttt 256620
caccatgttg gccaggctgg tctcgaactc ctgacctcag gtgatccacc cacctcagcc 256680
acccaaagtg ctgggattac aggcgcgaac cagtgagcca ctgcgcccag ctccctgtct 256740
cttttttttt ttttttttt tgacacaagg tctcactgtg ttgcccaggc tggagtgtag 256800
tggcacaatc ttggctctgc aacctctccc tcccaggttc aagcaatttt catgcctcag 256860
cctcccgagt agctgagatt gcaggcgcaa accaccacgt ctggctattt tttgtatatt 256920
ttgtagaggg gagggttttg ccatgctgga caggctggtc tcgaacttct gagctcaagt 256980
gatctgccca ccttggcctc ccaaagtgtt gggattatag acgtgagtca ctgcacccag 257040
cagcatttct ctttaaagtg aggctgagcg tctttccatg tggttttcat gtgattttct 257100
gggaattctt catgtctctt ggcatttttg cctattgaat tctggttctg tcttgctttg 257160
agtttaggaa taaagatatt ttattattat tattattatt tcagacaggg tctcactccg 257220
ttgcttaggc tggaatgcag tggtgtgatc ttggctcact gcaacctcta tttgccaggc 257280
tcaagtgatc ctcccacttc agcctcctga gtagctggga ctataggcat gcgcgaccaa 257340
acccagctaa tttttttaaa ttttttgtgt agatggtgtc ccactatatt ctccaggctg 257400
gttttgcact cctgggctca aacaaacctc ctgtcttggt tcatcaaagt gctgggatta 257460
caagtgtgag tcactgtgcc cagccaagat atttaattct ttacaacgga ctgccatgac 257520
tggagttatt gaatcagtag gatcaatttc aatcaaatgc ctttttatag gtgcatgtgg 257580
gatagctacc cctatgtgtg agttgcagtt ttggccttgc tgtgattata attctcagtg 257640
cggatgggga gaacagcctg ggaaatgcat tctcagcact cccaagatgg tgaaaccttg 257700
tctcagctgc catgtgagac cagtcttaat tatcctggtg agtgagttga gaattatttc 257760
agattttctt tcatattcaa aaccaccaag cagtatgcat gcatgcaccc attcaagcac 257820
```

-continued tttttaatga gtacaatgaa ccaggcattg ggctaggtgc tttggggaat acaaaataaa 257880
tacttgtctt aatccctgtc tgaacggact ttatggcaat ggcccattta gggagaggag 257940
acacacacag gctgaataca agatggaaaa caaaacagct atggagggag cctggatcaa 258000
gaccttaaga tgaaggattg aaggaaatga taattccttt aatttactga caattaggtg 258060
ccaaacactg tcagcgggtt tatataatga tatggtttgg ctctgtgtcc ccacccaaat 258120
ctcatcttga cttgtaatcc ccacacgctg agagaatgac ctggtgggag gtgattggat 258180
caagggggca gtttccttca tgctgttttc atgatagtga gtaagttctc ctgagatcag 258240
atggtttaaa agtgtggcac tggccaggcg cagtggctca cgcctgcaat cccagcactt 258300
tgggaggcca aggtggttgg atcacctgag gtcaggagtt cgagaccagc ctgaccaata 258360
tggcgaaacc ccgtctctac taaaaatatg aaaattagct gggcgtggtg gcaggcacct 258420
gtaatcccag ctacttggga ggctgaggca ggaggattgc ttgaaccagg gagatggagg 258480
ttgcagtgag ccaagattgc gccactgcac tccaacctgg gtgacagagc gagactctgt 258540
ctcaaaacaa aaacaaaaac aaaaacaaaa aacacagagg ttggccttga ctccttcctt 258600
cccgctccca ttccagaccc tgcttgttca gcccccagcc acttctgctc atggtccttc 258660
caaaatatat atccacggtt tgtcgcctct ccctagctct gctaccacca caatggggag 258720
cctctgttat ctctgaaaga caagaaggta gggcaccagt cttcctggaa cctggttaga 258780 ttttttctc ccccactgga gacatggtct tgctctgtca cccaggctgg agtgcagtgg 258840
ccccatcata actcactgca gcctcctacc cctggattca agggatcccc ccaacctcag 258900
cctctttaat agctgggact acaggcgcag gccaccatac cggctaagtt ttttaatttt 258960
ttaatttatt attattattt tttgagacag agtctcactc tgtcacccag gctgcagtgc 259020
agtggcatga tctccactca ctgcagcctc cgcccccccca ggtttaagca attttcatgc 259080
ctcagcctct tgaatagctg agattacagc tgtgcgccac catgaccggc taattttta 259140 atatttttag cagagacggg gttttacaat gttggccagg ctggtctcaa actcctggcc 259200
tcaagtgacc ttcctgcctt ggcctcctgc atcgctggga ttacaggtgt gagccactgc 259260
acccagctcc gatctgctaa gatcttatgt ggcctcccca tctccactca gaccccactt 259320
ctgccattct ccccacagag ccatctgtta aacatgcaca tgggattctg ctgccctcct 259380
gttccccagt ggcctcccat cacattcaga ataaaagcca aattctttac tggccttttg 259440
gagtgggcag aactttactg catcagactc tctggtatat tttaggattt tttgcttcct 259500
gggcctccac ccagtaaatg tcaatagtgt tcatagttac tgtgacaacc acacacgtcc 259560
cacacattac caaattcccc cggaggccct tagtgtttcc cctgatggag aagcattgcg 259620
tgattctgtg gcctcttcca tgcctcctac ctcaccatgc catcattcac ccaacaatat 259680
atatcaaaca cttttttttt ttgtgagata gagtctcact ctgtagccca ggctggagtg 259740
cagtggcagg atctcagctc actgcagcct gcctcctggg ttcaagtgat tctcatgcct 259800
cagcctcctg agtagctgag accagaggca cacgccacca cgcccggcta atttttgtat 259860
ttttagtaga gatgggcagg gctggtctcg aactcctgac ctcaagagat ccacccgcct 259920
cagcctcccc atgtgccggg attacaggca tgagccacca cgcacggcct attctgctct 259980
ttttatttgt tgatgggttg tctgtcttct ccatgagaat gccagctcca agaggacagg 260040
gagttggcct tgtttattgc agtatcccca gtgcctacaa cagtgcctgg cccagggtag 260100
gtatgaatgg gtgattgaac aaacgagtga atgacatcat tctagagaag tcagccacgt 260160
gaggatctgg agggagagca tttcaggaaa gaggatgtgt acgtgcaaat gtcctgctgc 260220

-continued aggaatcagc ttgggcacgt ttgaggacta gacagctaaa aggaagagca gatttgggga 260280
aaaggtgctg ggttcagtct tgaacatttt acagttgtat ctgaggtgcc atatatctgc 260340
caggatctgg gaagaaaacg aagttcactc acaagggttg aactgaagag aattttaaga 260400
agggactgtt tgtgtaagta agcagggttc agggttgcaa cgtgggaggg tgaaacacca 260460
gggacctaca tcaggaggga gctccttaca cctacattag cagggatgct ttccttctgg 260520
gggctctagg ggagaatctg ctctcttgcc ttttccagct tttcgaggct gcccacattc 260580
cttagcttgt gacgcctctg tccatcttca aagccggcga tggccggtca agcctttctc 260640
acattacatt tctcattttg gacattcctg cctcttctcc cacttattaa caccctgatg 260700
atgaaatccg atccaccaga taatccagaa taatcttccc acctcaagat ccttgaccta 260760
atactatctg caaagtccct tttgccatgt aaagtaacat attcacaggt tccagggatg 260820
aggatgagga catctttggg ggcccattct gcttatcaca gtacccttgg gtcttaagga 260880
tataaggatg gtaggccagg catggtggct catgcctgta atcccagcac tttgggaggc 260940
cgaggcgggc agatcacctt gaccaacatg gtgtaacccc acctctacta aaaatacaga 261000
aattagccag gcgtggtggc acgtgcctgt aatcctagct acttgggagg ctgaggcagg 261060
agaatagctt gaacccagga ggtggaggtt gtagtgagct gagatagcgc tactgcactc 261120
caacctggac gatagagcga gactacattt cacacacaca cacacacaca cacacacaca 261180
cacacacaca cgctactgca ctccaacctg gacgatagag cgagactaca tttcacacac 261240
acacacacac acacacacac acacacacac acacacacac aaaaggatac agggatggaa 261300
gaacaggaac agtattcctg gaatctggaa agacctggag ccatggagaa ggactcccct 261360
gctggagctg cagccccaga agggctgagt gaggaagggc caaatgcact gaactctctc 261420
tcctgcctcc ctttgatctc cagggctgcc tctcattgtt ccagcctatc tgcaggccag 261480
gtggccaagc tgtgcaggtg ctgcagcctg cagggcttag cgtccccggc ccagagcagg 261540
gcaaataatg gatctggggt ggagatgggg ggcaaatgga gagtaacact taaggtgtgg 261600
cctgtgcatc agcagcctca gcctggtctg taactgttgg aaatgcagag tctcggatcc 261660
cacccaagcc ccactggatc agaatctgca ttttatccac gagatctcta ggggattcat 261720
aggtgcattt gcagtttgag acaagctgca ctggaggact attgatttat tcttagagac 261780
gggaccttgc tctgtctccc agactggagt gcagcagtgt aatcatagct cactacagcc 261840
tcgaactcct ggctcaggct atccccctgc ctcagcctcc caagtagctg ggaccacagg 261900
tgcacatcac cacatccagc taattaaaaa aaaaaatttt tttttaaata gagacatgat 261960
ttcactatgt tgcccacatt ggtcttgaac tcatggactc aagcgatcct cccactttgg 262020
tctcccaaag tgctgggatt acagatatga gccaccatgc gccgctgcac tggaggattt 262080
ccacgtggag ataaaggctg ttggaaatta tgcccatgct tgggtcagct catctcttga 262140
gaatcatttg atatcacaag agaagccacg aagtctaggc tatggagtaa gaagaaatcc 262200
aaagactaga tttcaaagaa caagacaagc attatcacaa aatgtcttga aaatagcttc 262260
agatattctt agacattaca cctaccaaaa ctgaatttgt gaaatcctaa gcatatgtta 262320
catccatcta accataggaa gagaagagaa aaaaaaaatg taaaggaagc aaactctaaa 262380
attaaaatct gttcaggagg tgacggatgt ctgggtcttg acggatttct agacttgtaa 262440
aaagtagttg ttttttttcat cttcattcat ccatgtttga ttgttgcttt ctcaggacca 262500
ttattttttt tttctcatag gaaaattaat ttctttcttt ctaaagtgtt gattctcccg 262560

-continued

```
tgttgctttg tatgaaggct ttagaaaatg tctaacaatg gtttgagtga tagacggaaa 262620
aaactccagt gcctcagcta cacaaaagac tctctagcga ggtcctattg tgcattgatt 262680
tactgtgttg aataactttt ccacattcga aaatgcatta aagctcttat ttaggaccat 262740
ctaattcctg tctttagagt taacaatcaa ccatcaggtt tctgcttagg gtaagttaaa 262800
acaggcgttt tggttgagga cgataaatac ctctgcgttt taggctgcag gtgcagatgg 262860
agcattctgt tctaggcatg ttgatttagg aggaaaatcg gagttttgga actttacagg 262920
cttgggttac tttcctggtt ttgccattta ctagctgtgc gaccttgggc ttgtcagtaa 262980
aggccttcgg tctgcccatc ctctttagaa aaatggagct acttttccta ctttgttggg 263040
aagggttgtt gagaagttta atattaatgg atggcctggc acatagtggg tgctcagtaa 263100
acagctgtgt ttttcctatg ggctagggga atgtctttca ggcttttgac atagcctgtt 263160
gctggggtcg tattgtgtcc ggaattggtg ggttcttgtt ctcactgact tcaagaatga 263220
agctgcggac cctcgcgatg agtgttacag ttcttaaagg cggcgtgtcc ggagtttgtt 263280
ccttctgacg ttcggatgtg ttcagtttct tccttctggt gggttcgtgg tctcactggc 263340
tcaggagtga agctgcagac tttcacggtg aatgttacag ctcttaaggc cgcgcgtctg 263400
gagttgttcc ttcctcccgg tgggctggtg ggctcgtggt ctcgctggct tcagaagtga 263460
agctgcagac cttcgcggtg agtgtttcag ctcataaagg cagtgtggac ccaaagagtg 263520
agcagtagca agatttattg caaagagcaa aagaacaaag cttccacagt gtggaagagg 263580
accccagtgg gttgccactg ctggctcggg cagcctgctt ttattctctt atctggcccc 263640
acccacatcc tgctgattgg tagagcggag tggtctgttt tgccagggca ctgattggtg 263700
cgtttacaat ccctgagcta gacacaaagg ttctccaagt ccccccccaga ttagctagat 263760
acagagtgtg gacacaaagg ttctccaagt ccccaccaga gtagctagat acagagtgtc 263820
gattggtgca ttcacaaacc cagagctaga cacagggtgc tgattggtgt gtttacaaac 263880
cttgagctag atacagagtg ccagttggtg tatttataat ccctgagtta gacacaaagg 263940
ttctccacgt ccccaccaga ctcaggagcc cagctggctt cacccagtag atcctgcacc 264000
agggctgcag gtggagctgc ctgccagtcc catgcagtgc gactgcactc ctcagccctt 264060
gggtggtcga tgggactggg caccctggag cagagggcgg tgctcgtagg cgaggctctg 264120
gccgcacagg agcctatgga ggtgggggga ggctcaggca tggcgggctg caggtcccaa 264180
gccctgctcc acgggaaggc agctaaggcc ctgcgagaaa ttgagcacag cagctgctgg 264240
cccaggtgct aagcccctca ctgcccgggg ccggtggggc cggcctgccg ctccaagtgt 264300
ggggtccgct gagcccacgc ccaccaggaa ctcgcgctgg cccgcaagca ccgcgcacag 264360
ccccggttcc tgcccgcgcc tctccctcca cacctccccg caagctgagg gagccggctc 264420
cggccttggc cagcccagaa aggggctccc acagtgcagt ggcgggctga agggctcctc 264480
aagtgccgcc aaaatgggag cccaggcaga ggaggcgcct agagcgaggg agggctgtta 264540
agggctgcca gcatgctgtc acctctcagt atgaatttac cagttggtaa cgcatagcag 264600
ggagaatcag tgcacaatat tcacagattg cattagggtt tagatagctc ttccaagagg 264660
taattgttaa gcaaaaacct tttactttta ttgcagtcta ttattagtat tggaagtcct 264720
cagttagatt ttctccctgg tatggaatga aaacttaatt caaacacaca caggagaggc 264780
aaacatgtta ttatttgcta atggctttta atcttgggaa gagagataga ttgattatca 264840
cctctgcctt ggataattgg gggaagtgct tccattttgg agagggtgat ttttaaagag 264900
ttgagagtgg gggaaggctg agagtcaaga gctggttagg agtcgtgcct gtgtgatttt 264960
```

-continued ggtaacttaa gcttctagag cctcagtttc ctcactgaag aatgtggctg acaattgtac 265020
cgtactgccc atgccactgt gaggattaaa tgagctaata gacatcatgg gaacaattgt 265080
tggttttttt ttttttttt tttgagactg agattagctc tgtcgcctag gctggactgc 265140
agtggcacga tctcagctca ctgcaacctc tgcctcccgg gttcaagtga ttctcgtgcc 265200
tcagcctccc aagtagctgg gattacaggc acctgccacc acgtttggct aatttttgta 265260
tttttagtag agacagggtt tcaccatgtt gtccaggctg gtctcaaact cctgacctca 265320
ggtgatctgc ccttcttggc ctcccaaagt attgagatta taggcatgag ccaccacgca 265380
tggcctgttt ttgaggcagg gtctcgctct gttgcttagg ctggagtaca gtggtgggat 265440
cttagcttac tgcaatctcc gcctcctggg ctcaagccat cctcctgtct cagcctcctg 265500
agtagctgga actacaggca cacaccacca cgctcggcta atttttgaat tttttgtaga 265560
gatgagggtc ttgctatgtt gcccaggctt gttttgaact cctgagctca agcgatccac 265620
ctgccttggc ctcccagagt gctgggatta caggcgtcag ccaccgcact ggcgagaatg 265680
attgtttatt tgtagtatcc cacaacagaa gtaccacccc ctgcaaatgt tcctttaaag 265740
aaaaatggtt atggtgtcag ttgtgctatt ttccatacac tgaagtctga tgcatcagtg 265800
gaaaggagtg gatcacatca acacagataa atcatacgaa gggttgaggg agacaagcca 265860
atcatagaat catatgaaca gaacgagacc atttattttg catgttcagc aacatgcaaa 265920
agcaaataat acaatgtttg cagaagaaaa attacaactg ggcatggtgg ctcacgcctg 265980
taatcccagc actttgggtg gctgaggcag gtggatcact tgaaatcagg agatcgagac 266040
cagcctggcc aacatggtga aaccacatct ctactaaaaa tacaaaaatt agccaggcgt 266100
ggtagcgggc gcctgtagtc ccagctactc gggaggctga ggcacaagaa tcacttgaac 266160
ccaggaggtg gaggttgcag tgagcccaga tggtgccatt gtactccagc ctcagcaaca 266220
gagcaagact ccgtctcaaa caatcaaaca aacaaacaac tgtgtatgga tctcaaagtt 266280
tttttgcacc aaaataaact catactaact tgttacaaca cgtctgaaca ggatctagtt 266340
tgaggcacta agaaggataa gacatctgtt tgaaaagaac ccctgtcaga gcaacatgaa 266400
ttctcctaaa actgaagtaa gaacaaacat caagtttatg gtgaagctcg ggtggaagga 266460
tggtgaaatc actaatgcct tatgaaaagt ttgtggggaa aatgtggtag ataaatcagc 266520
agtttacaaa tggatatctc attttaagaa gggacaagac aatattgact tgccaggcat 266580
ggtggcacac gcccgacatt ccagctactg tggaggctga ggtgggagaa ttgcttgagc 266640
ccaggaggtg gaggctgcac tgagtcaaga ttgcaccact gcactccagc ctgggtgaca 266700
gagtgagact ccatctcaaa aaagaaaaaa aagacaatgt cgaaaatgag gtgcacagtg 266760
gcagatcatc cacatcaatt ttcgaggaga aaattatctt atttgtgccc taactgaaga 266820
ggactgatga ttaacagcag aaacaatagc cagcaccata gacatctcca ttggttctgc 266880
ttacaccatt ctgagtgaaa aattaaagtt gagcaatgcc actcatgagt gtaaaattat 266940
tacacccaga tcagctgcag acaaaagcag agttttcaat ggaaatttaa acaaatgaga 267000
tcaagatcct gaacatttat ttgaagaatt gtaacaggag atgaaacatt taccattatg 267060
atcctgaaaa ctaagcccaa gcgaagccat ggatactaag aggtagaagt agtccagtca 267120
aagcaaaagc agaccggtca agagcaaggt catggcaaca gttttcgggg atgctccagg 267180
cattttgctt gttgactttc tggagggcca aagaatgata acatctgctg attatgagag 267240
tgttttgaga gagctagcta aagctttaac cagaaaaaca cctgggaaac cttcaccaga 267300

-continued

```
aagtcctcct ccactatgac aacactactg ctcattcctc tcatcaaaca aggacgattt 267360
tgtaagagtt tttatgggaa attattaggc atccacttta cagttctgat tctgcacctt 267420
ctgacttctt tttgtttctt aatcttaaaa aaatcttcaa agggcccatt tttctactgt 267480
taataatgta aaaaagactg cattgacagg gttcaattcc caggaccctc agttcttcag 267540
ggttggacta aatggctggt atcatgactt acaaaagtgt catgatcttt gctgggcaca 267600
gtggttcatg cctataagtg agaggattgc ttgaacctag gagattgagg ctgcagtgag 267660
ccatgatcat ggcactgcac tccagcctgg gtgacagagc aacaccctgt gtcaaaaaaa 267720
aaaaaaaaaa aaaaagtcat gatcttgatg gagcttatgt tgagaaataa aatttatatt 267780
ttatattttt atcttttact tcaatatcta tgaacttttt gaagtcccct tgtatataca 267840
ggcactgtgc taaggtgcct gacatggatt ctcttattaa atccacaaaa caaccatact 267900
gggtaggtgc tatggttatc ttcattttac agatgtgtaa actgaggcct gatatcattt 267960
ggctctgtgt cccacccaaa tctcataatc taaaactgta atccccatgt gtcagaggag 268020
gggcctggca ggagctgatt ggatcatcgg ggtggatttc cccttgctg ttcttgtgat 268080
agtgagttct catgagatct tacggtttaa aagtgtggca gtcccccttc actgtctcgc 268140
ctgccgccat ttaagatgtg ccttgcttct ccttcacttt gtgccataat tgtaagtttc 268200
ctgaggcctc cccacccatg tgagtcaatt aaacttctat cacccactct aagctatgtc 268260
tttatagcag tgtgagaacg gactaaccca aggctgttag ctgccatctg ttaattgagc 268320
atttattaag tgctatgtac catcttactg aagtaagatg catgatctta cttcacttcc 268380
agaaacctta ggaactatac tgaaaacaca actttagacc agggttggca aacttttcct 268440
ataaaggtcc agatagtaaa tatttgatgc ttttgtgagc cgtacgatga tctctgtcga 268500
gactgttcaa ctctgttgct gtggtgcaaa agcagccaga gatgattcat aaatggatga 268560
gcatgactgt gttccaataa aactttattg aggaacattg atgtttaaat tttatttcat 268620
tttcacttga aaacgatcac aaaatatcat ttttccttcc ttttttgttt ttttttttga 268680
gacagagttt cactctgtca cccaggctgg agtgcagtgg gaggatcaca gcccactcaa 268740
agggatcctc ccaccctaac ttcctaagta gctgggacta caggcatgca ccaccatgcc 268800
cagctaattt ttcttttaat tttttccaac tatttaaaaa tgtaaaattg ttcctaattc 268860
acaagtcata tgaaaacaag cagtggggct ggaactggct tgtgggccgg gctgtggttt 268920
gccaagcctg gctttaggcc atcagttccc tgagggctgg aaacttgctg accctgctca 268980
gtgtggtatg cccagtttcc gactcaccac caggtggtca gaacaagttt gctgaatgaa 269040
tgagtaaatg tacgttgata tctcagaagg tgaaagtgat gtttctactt tgggcaacaa 269100
ctctgacata cctagcattt tttagggtgc aatattaata atcatgtcag attacaggtg 269160
tacactgggg ctgtctcagg caaaccagga tgcatggcta tgccaatgtt cttcaccagg 269220
aagatgattc tttgccataa tgacagtagg acaccaaccc ctgtgtgtgt gtgtgtgtgt 269280
gtgtgtttgc acacatgcct gagagtgctg aacaaaatta tgaatttttc tttttttgtt 269340
ttgttttgtt tttttaagtc aaggtcttgc aatgttgccc aggttggagt gcagtggcta 269400
tttatgagtg tgatcatagc atactgcagt ctctaattcg tagtctcaag caatgctctt 269460
gcttcagctt cctgaatagc tggaactata ggtgtgtgcc atcacgccca gcctcccaca 269520
agcctgcaga agagctgcaa aaataatata ctgattcgat gaacacccat gcccgtcacc 269580
ctaatgtggc catctttaac attgtgccac atgtgcgcta tccaccacct atcatcgtta 269640
gctatcaatc caactatctg ttctatctat ctatctatct atctatctat ctatctatct 269700
```

-continued atctatctat ctatctgatc tacctgtatt catctatctg tatctatcat ctatcttgta 269760
tctatatctc tgtatctatc tatctatcta tcctatctat ctctatctta ttatttttc 269820 ctgggtacga agtgcagaca tcacggcatt tcaccccttc catactgcaa tgtgcatctc 269880
ttaagaacac agacatcctt tttcataacc acaatatatt gttcatattt agaaaattta 269940
acattgatac aatactatca tatgagatac agtcagtatt tgaattttcc cagtaatgta 270000
ttttacagga cccaattaag gatcatgcat ggcatttatt agtcattttt attcagtctc 270060
ttggaatcca gaacagtccc ttccttcttt ttgtctttca tggcgtgggt acttgaagag 270120
catagatcag gtgtttcgta cagagtctct caatgtggat ttgtttgatt gcttcctggt 270180
gattgcattg gagttaaata tttctggtaa aaatatgata ttggtgatgt tgtgttctta 270240
gtgcattcca tcaccaggca cgtaatgtca tttgtcccat tatcaatgac gttaaccttg 270300
attacctggt taaggtgata ttgtcagatt tctcccctgt aaaggaaact tttccattca 270360
taattaacaa ctgccatttt gtaactcagg agaaatatca ttcaggtgaa gaaatcattg 270420
aagagtgtaa gcaggaaaag acaaaacagg tgtaagaggc tctgtctggc agacactgtt 270480
ggcccagctt ccaggttctt acaagcttaa gggtgactgc atgcaaccag tgaaatagct 270540
gatggctttt tgctccgtgg ctgtatgtat gcaaaacagc gctcttgccc agcaactgta 270600
gatttattga ttgtgttaac tctccatgat tcagtaattc gggctgactg ccggggtgca 270660
gcaaatcttt cttgagaagt tgcattagtt ttcacatcat gtagctgcca aagtagagga 270720
cgtggccagc ttcccctcct ctctaccgtc tttccaaggg cagcagctca gacacatgct 270780
gttccagacc actatatctc tcacctgatg atgataatag tcccccacaa catccactct 270840
gctcgcctcc tcaccctggt gcattctcct tgaagcagcc tcagtgaact ttgcaaaaac 270900
ttaaatcagg ctgggcatgg tggctcacgc ctgtaatccc aacactttgg gaggctgagg 270960
cgggtggatc acctgaggtg aggagttcga gaccagctgg ccaacgtggt gaaaccccgt 271020
ctctactaaa aatacaaaaa ttagctgggt gtggtggtga gcgcctgtag tcccgcctat 271080
ttgggaggct gaggcaggag aatggcttga acccggtagg tggaggttgc agtgagccaa 271140
gattgtgcca ctgcactcca gcttgggtga cagagtaaga ctgtgtctta aaaaaaaaaa 271200
acccaaaaaa caaacacccc ccaccctcaa atcagatgat taaccctctc cttgaaactt 271260
ctcccattgc ccttagaata aagatctaaa tccttactgt gacctaccct ggatggcctg 271320
gcccttgcct ttctctcaga tctcattttc ttcctctctt gcctgttgct gctttctgaa 271380
ctcagccaca atgcctttct ttctgtttta caaaaatgct tctacctcag ggcctttgca 271440
tatgcttaca attcttctgc cagagacact cctctttcat tctcccacta agataacagt 271500
ttgtgttgtg tgctcactag ggagggctcc agtttcaggt atgactggat cccaaggctc 271560
caataaagtt ggagggaatt tatctcttga ctcagtgttg gctttgtgga ggccatttct 271620
cttctcatgg tggcaagacg gctgccaata tctccaggct tacatcctac cttctctgta 271680
gctcctatga aaagagagcc ccttttttcct gatagttctt aaacggatta tgggattggc 271740
ttgaattgga tcaccacagg tcccatgtct actcctgagc caattcctat gggcaggagg 271800
atggaatgca ctcattggtc aggcctgggt cctgtgacca cccctaggaa gagggcgtgg 271860
attggccttt cctacacctc atggactaaa aatgggggga ggcgaattcc cctaaagaaa 271920
acaggggtgc tgttaccaga tgagggggag tgcatactgg ggggcagcaa aataaaacat 271980
gcccattatg ggatgtagta tggattcaag gaggcaaagc ttgaagcacc tttatctgga 272040

-continued

```
agatgctaac ttcttttttt ttaaacggag tctcgctgtg tcgcccaggc tggagtgcag 272100
tggcactatc gcggctcact gcaagctccg cctcccgggt tcgcgccatt ctcctgcctc 272160
agcctcccga gtagctggga ctacaggcgc ccaccaccat gcccagctaa tttttttgta 272220
tttttagtag agacggggtt tcaccttgtt agccagcatg gtctcgatct cctgacctcg 272280
tgatccaccg gccttggcct cccaaagtgc tgggattaca ggcgtgagcc accgtgctcg 272340
gccctattta tttatttatt gagacagagt ctcgctctgt cacccaggct ggagtgcagt 272400
agtgcaatct cagctcactg tagtctccgc ctcctgggtt caagcgattc ttctgcctca 272460
gcctcctgag cagctgggat tacaggccac catggccggg taatttttgt atttttatta 272520
gagactgggt ttcaccatgt tggccaggct tgtctgaaac tactggcctc aggtgatctg 272580
cccaactcat cctcccaaag tgttgggatt ataggtgtga gccaccgtgc ccggcccagg 272640
ctgtctttta aattgtgcct ggcttttatt tacccttact gttttctcaa caggtcaagg 272700
acagaactga cacccccctta caacaaatct ccacaccttg gccactttaa gtaattggta 272760
ttttatttta atttttaag agacagggtc tcactctgtc atcctggctg agggcagtgg 272820
aaagatcatg gctcactgca gcctcaaact cctgggctca attgatcttc ctgcatctgc 272880
ctcttgagta gtggggactg taggcatgca ccaccatgcg ctgccaacca aagatactaa 272940
cattgtaact acaggtgtgc accaccatgc tcagcttatt tttttgtttt tgtttttgtt 273000
tttgagacag agtctcattc tgtcactgag gctggagtgc agtgactcaa tctcggctca 273060
ctgcaacctc tgcctcccag gttcaaatga ttctcttgcc tgagccaccc gagtagctgg 273120
gatgacaggt gcctgccacc atgcctggct aagttttgta tttttagtag agattgggtt 273180
tctccatgtt ggccaggctg gtctcgaact cctgacctca ggtgatccac ctgccttggc 273240
ctcccaaagt gttaggatta caggcgtgag ccactgcgcc cggccagcta attttttatt 273300
gttttatttt ttgtagagac agggttttat catgttgccc gggctggtct tgaactccta 273360
gactcatgca atccatctgc cttggcctct caaagtgctg gaattacagg cgtcagccac 273420
catgcccagc catgtgtttt tatttaaaaa ttttttatat taggccgggt gtgatggttt 273480
gtgcctgtga tcccagcact tcacgaggtc aaggtgggcg gatcacctga ggtcaggagt 273540
tcaagaccag cctggccaac atggtgaaac ccaatctcta ctaaaaatac aaaaattagc 273600
tgggcatggt ggcacgtgcc tataatccca gctagtccgg aggctgaggc aggagaattg 273660
cttgaaccca agaggcagag gctgcactcc agcctgggca acacagtgag actctctctc 273720
ttgaaaaaag tatttatttt aggtcaggtg aagtgtccat gcctgtaatc ctagcacttt 273780
gggaggccaa ggtgggagga ttgcttaaag ccaggacttc aagtccagcc tgggaaacac 273840
agcaagacct tgtctctaca aacaattaaa aaaaattatc ctgtgttttt atttcctttt 273900
tctccaggaa tgcaaacttg aattaatttc acaaaccaaa ggagaacatt gcaggaattt 273960
ttatttattt atttattttt aattttttgt atttacatac attgtttcat ttatttttct 274020
aattaccagt cctcaaagta gatgttattc ccattttaca aggaaaagtt gaggcttaat 274080
gagtttaact ttcccaagga cacttaatta atgatagaag aatgaggaat cccaatatag 274140
gactgatggt aaacctatcc ttttggttat gttgctgttc tctctctctc tgtctctgtc 274200
tctctgtgtg tgtattgtcc atataaagaa cccagttgat tatgaaatgc aattagaagc 274260
tgttattttt gggactcttg ccatggctgg agtaggctta aatttaagag acacagctct 274320
tgccactgat tagtttctca cagcactctc atgcctggga agggcgtcat caaccagttg 274380
atcacgtcag ctggagtaac tagcagtcgc taatgaggac ctttccccaa gcatctatat 274440
```

-continued ctgagaattt cagagattca caaatgcaat ttagaaatgt cattatgtag ttacataaat 274500
gtttaatttt tccacccata tgtttacact ttgaatattt ttgaatattt gaatattttc 274560
tataagccat gtattgtttt attattatta ttattattat tattattatt attattatac 274620
tttaagtttt agggtacatg tgcacaatgt gcaggttagt tacatatgta tacatgtgcc 274680
atgctggtgc gctgcaccca ctaactcgtc accttgcatt aggtatatct cccaatgcta 274740
tccctccgcc ctccccccac cccacaacag tccattgcag gaatttttaa tggcaaaaag 274800
aaaaaaaaaa atcaagttcc ctgaggctaa ctacaacatg gattgcaata taccagcatt 274860
caccacccct gggagggttg ctaaagcttt cacttttatg gccgttttgt ttttgttttg 274920
ttttcttcat aaaggcagtt tggagaagat gaagatattt tagtctttgg caaatcattt 274980
tgtttaatgg ccactgactg cttctcaagt ttttataaaa ttttataaaa gccttcattt 275040
ttgggaggct tttcatgttg gatacctaag gagatgaacc catttaacag agatctagac 275100
tgaagtgtcc agtctttcct cctaggatag gctctgggag tcctgatgtg cagagaatct 275160
ccaggcagac tgagaatgac atctgtgtaa atagtgcctt tggtcaagct ttctctatct 275220
tctggacctc ggtttgcctc tgtaattgga gggggaaacc acagagaaat gcagtgtatg 275280
gtactaagga tgactgtaga tcatgcaagg atagaacttt aaataccctt gaatcagctg 275340
gttagaaagt tctccctttt ctcagttctc ttttggtctt tctgaaaact tcagctttgt 275400
gctaataggg ttcgttacca cagactgaat gtttgtgcac cccacacccc ccaaaattca 275460
tagctttcag ctttaaccct ccagtggcat agtattagga ggtgaggcct ttgggaggtg 275520
attaggttta atggggttat gagggtaggg ggccttatga tggaattagt gcccttataa 275580
gaccaccaga gcttcatttc ttgccactga ggagacagca agaaggctgc tgtctacaag 275640
ccaggaaggg agtcctcacc agaactcaat catgatcttg gacttcccag cctccaaaac 275700
tgtgagaaga aaacacctgt tgtttaagcc actcagtcta tggtagtttg ctagagcagt 275760
tgaagttgac tacgacaatg gctttcacgc cagatgtttg ctgatctctc tttataacaa 275820
agaaaatgta ataacatcac ttttaatttt gtatttatgt ttttccctta acttctaatt 275880
tttttgtttt gtttttggag atggaatctc actctgttgc ccaggctgca gtgcagtggc 275940
acgatctcgg ctcactgcaa cctctgcctc ctgagttcaa gcgattctcc tacctcaggc 276000
tcttgagtag ctgggactac aggtgcacgg caccacaccc ggctaatttt tgtatttttt 276060
agtagagatg gggtttcatc atattggcca ggctggtctt gaactcctga cctcaggtca 276120
tccaccgttc tcggcctccc aaagtgttgg gattacaggc gtgagccact gcacccagcc 276180
tccccttaac ttctatgtag ccagtgctaa gtggttttc aattaaaaca acaacaacca 276240
ctaccatcac ttatgctact aattccaggt acttttctaa aggtttttac atgtatagct 276300
catttaatcc tcttaagggg taagatactg tcattattac cgttttatag atgagaaaac 276360
caaatcagag aggtgaaagc acttgcctaa ggtcacacag ctagtaagta ccagagctgg 276420
ggtctggact caggaaatct gcttccagag cctgtgctgt aaaccattct actttgctaa 276480
tgcatgacat aatgtttcct tttaaaatgt atttgcacac acacacacag aggatggggg 276540
agaggccatt aaaaaattaa tagaaaataa agtatctgta atagggaaat gggaaaatgg 276600
tgactgtagt tctgaacaac tgaaacatgg gaaacactgg acactcttgg tatctagaat 276660
tctatttttt aaattaatta attgattaat ttgacacaga gtctcactct gttttccagg 276720
ctggagtgca atggtgcaat ctcggctcac tgcaacttct gcctcccaga ttcaagcgat 276780

-continued

```
tctcctgcct cagtctcctg agtagctggg attacaggcc accacacctg gctaattttt 276840
ttgtatttta tgtatttttt tttttttgta tgtggtggct aaaaaattag ccaccacacc 276900
tggctaattt ttttgtattt taagtagaga caggatttca ccatgttggc caggctagtc 276960
ttgaactcct gacctcaggt gatctgcccg cctcggcctc gtaaagtgct aggattacag 277020
gcgtgagcca ccgtgcctgg cctatttttt atttttttga gatggagtct ctctctgtca 277080
cccagactgg agtgcagtgg catgatcttg gctcactgca acctcagcct ctggggttca 277140
agtgattctc ctgcctcagc ctcctgtgta gctgggatta caggcatgcg ccaccacacc 277200
tggctaattt ttgtattttt agtagagacg gggttttgcc atgttggcca ggctggtctt 277260
gaactcctga cttcaagtgg tccacctgcc tcagcctccc aaagtgctgg gattacagac 277320
gtgagccact gtgcctgccc aaggtatcta gaattctata cattacaaac atgcctgcac 277380
tggacacagg aggaagccag atggaagcac ctgagtatat gctaaacaac agtactgggt 277440
agtttaaaaa aaactgctta tttggctggg tgtggtggtt cacacctgtg gtgggaggat 277500
cacttgagac cagaagtttg aggctgcagt gagctatgat cgtgccactg cactccagcc 277560
tgggtgacaa agcaagacct tgtctctaag atagaataaa atgagataaa atcgcttatc 277620
taaagggaga aatgtcttcc tttcatagcc acagagcccg gtgccttcct ttaaggggat 277680
ggggagagct ggacttcttg catctgacct tgctcgaggc tggggtctga tgtcctttag 277740
tcgtgatgcc cgcacctcat cattgggtgg gtggttaaaa tgtactgtct gtggagtgag 277800
tgtgggtgtg ggagctgacc tccagccagc gtaattaatg ggctttttgc atcggacagg 277860
cacctcccat tctacaggca gcagagacgg atggaggagt cttaatgctg catcagggac 277920
agctgtgggc agctcacctg gatttttttt tcttcctgtt tttcaagaga caggctcttg 277980
ctctgtcacc caggctggag tgcaggggtg taatcttggc tcactgtgcc ctgggactcc 278040
tgggttcaag tcatcctcct gcctcagcct cctgtgtagc tgggactaca ggcgtgcacc 278100
accacatctg gctcattttt tatttattta tttatttatt tatttatttt ttgagatgga 278160
gtctcactct gtcgtccagg ctgtggtgca gtggtgcgat ctcggctcac tgcaagctcc 278220
gcctcccggg ttcacgccat tctcctgcct cagcctccca agtagctggg actacaggtg 278280
cccgccacca cgcctggcta attttttgta tttttagtag agatggggtc tcaccatgtt 278340
caccaggatg gtctcgatct cctgacctcg agatccgcct gcctcggcct cccaaagtgc 278400
tgggattaca ggtgtgagtc actgcgcccg gccatctggc tcatttttaa aaacttgttt 278460
gtagagatgg ggggtggggg tatctcacta tgttgcccag ctggtctcga actcctggcc 278520
tcaagcaatc ctcctacctt ggcttcccaa agtgttgaga ttacaggtgt gagccactgt 278580
gtccatcctt cacctggact tctgtgtcat cctgtctccc tctgctttgt aaacagatcc 278640
aaattctagt ttttacctta atcctaccct aaccctaacc ccatgtcaac acctacccta 278700
actttaacct ttatcctaac ccttatctat atcctaatcc taatcttacc tgtcccctcg 278760
tcctaagctt tgccataaac ttaaccctta tccctaacct ttttcttaac tgtaaccctt 278820
atctgtccct aacacttaac cctaatcctt ccctaatcct ccatttctcc tctgtagcca 278880
cacatttatt tgtttactta ttcatttatt tttcacccat atttattgag catctgctct 278940
gtcagtgagg gttccaccag gagagagaag gcacaattta actacgtaat tgaggcgaat 279000
ttgataaaag gacggtttac catgaggtgg gtgaggtcaa aggaactgaa gagtatactg 279060
aggcactgag ctgggggcta gcctggtgag gagcagttac cacccgtggg gtgaagggag 279120
tgttggggga acccagtgac aggcagtgct ctagaggagg ggctgctggc aggcactgtt 279180
```

-continued

```
gtcagggagg tgtattgtcg cagtttttgc cataaaacag cccagatcgg gaagggggcg 279240
agaagggagt acctggacct cctcctcctc ttgccttcct ggcctctgtg agtactagtt 279300
gctggacctg ccccctatag gctggacctg cctggaacca gagtgcagaa gtccgtgggg 279360
gtcagctcct ggcccaggac ataggcaggg tggaggatgg ctccgagtgg ggagcggaca 279420
ggaatgaggg taaccagcat gtatactgtg tgtcaggcac tgttctgggc ccagagtaac 279480
agcaagtgaa caaggcacac aaaaattccc accctctagc tgggcatgga gtctcacacc 279540
tataatccca gcacttgggt ggccgaggcg ggtgaatcac ctgaggtcag gagttcgtga 279600
ccagcctggc caacatggcg aaaccccgtc tctactaaaa atacaaaaat tagccaggtg 279660
tggaggcagg tgcctgtaac ccagctactc gggaggctga ggctggaaaa tcacttgaac 279720
ccggcaggca gaggttgcag tgagctgaga ttatgccatt gcgttccagc ctgggtgaca 279780
gagcgagact cggtctcaaa aaacaaaaca aaacaaaaca aaaaacccac cctcatgaaa 279840
tttgccttgt agtgggagaa gagagcccaa gtagcaagtt aacaaatgac aatttcaaac 279900
agtgagaaat gctgtgaaaa taaagaagga taacagaccg agcagagtca gcatattttt 279960
tttctgtaaa gggttggatg ttagatattt tggttttatg agccctagga tctttgtcac 280020
aactgttcaa ctctgtcatt gtagcacaaa agcagccaca aatgatctgc aaatggatgg 280080
gcacggctgt gttcaaataa aactttattt acagactggt acagtgtaat ctcagcactt 280140
tgggaagcta aggcaggagg aattacttga gcccagtgat cttgagtttg agaccaactt 280200
gggccacata gcaagacccc atctctccaa gaaaaaaaaa aattagctga catggtggtg 280260
tgtgcctata atcctggcta cttgggaggc tgaggtggga ggattgcttg agcccaagag 280320
tccgaggctg cagtgagcta tgatggtgcc actgaactgc agcctgggca acagagcaag 280380
accctgtctc aaaaaacaaa aacaaaaaca aaaacaaaac aaaaaagcag gcagtgggct 280440
ggatttggct tgctgatctc caggctagag aatgacttgg tggtagaggt ggaggggctg 280500
cggtaggcag tggttagata gggtggtcaa ggaaggcctc tctgaggagg tgacgttgac 280560
ctgaggcctg aaagacaaga gggcttgtca tgaaccaggc cggcaaagac ctggatctga 280620
gtcttagaga gggaacagca ttcatgcagc agcagatatt caccaagcca ggtaaatatc 280680
tctctgtgct aggtattatt gtaggcccgg gggtgctcag cagcaaacaa agcagacaaa 280740
acgcctgtcc tggtagaagt gacagtccag acaaaggcca tgagggtgca gtggtgggtt 280800
ggggcatggt gcggcaagag ttgagcatct tccaggattt gaggatctta aaggatttaa 280860
tagaacctaa gagaccagaa gacatggggt gggagggagg aatgggcaag gatacaggac 280920
ttgtggagag cagtttgcag gaaaaagctt atgtttagag atgatctttt tcaccctgct 280980
ctgcagtgcg ggtgcatcca ggcgcaagaa atgccaagtg ctggaggcag aggctgggtg 281040
aggccaagcc accagcgctg gttggaattg gcaggacaac tcggggaggg tggccctggc 281100
tatctctggc atggctttca ggggaatgaa acacacttca tatccccact tttagggaac 281160
acaaatggca ttgtttatgt acctgtctcc catgggatgc tgtactggag tgcccaggct 281220
gtcttccatt catggaacca gagctgggag gcttggtcca gggatcccat tcaacaaccc 281280
tcaggtggcc tctggcccat agatccatag ctgcatcttt tttttttttt tttttttgag 281340
acagagtctt acactgtcgc cgaggctgga ctgtagtggc atgataatag ctcactgcag 281400
cctccattcc ccaggctcaa gcaattctcc cacctcagcc tctggagttg ctgggaccac 281460
acatacgcac caccatgcct ggctaatttt ttaaattttt ttgtagagat gcggtctcct 281520
```

-continued tatgttgccc aggctggtct caaacttctg ggctccagca atcctcctac ctcggcctcc 281580
caaggtgctg gaattacagg tgtgagccac cacatctgcc tagatgcatc ttatttgatc 281640
ccagacagga tttttttgt ttttgtttct tttaaattga ggtgaaattc acataacata 281700
aaatgaagag ttttagcgag taccattcaa ggcatttcgt acattgtggt gcaaccataa 281760
cccctattta gttccaaaac attttcgtca ccccaaaaga aaatcctgtt tatcatacag 281820
tgacttccca ttttctcctc ccagacggga ttttaaaaat atgcaaatta gttaacatga 281880
agaggaaaag gagattttt catttaaatt agatttcagc tttctttttc tccttccttc 281940
tttccctcct tccttccttc cttcattcct ttcttccctt cctctctcct tccttccttc 282000
cttccttcct tccttccttc cttccttcct tccttccttc cttccttcct tccttctctc 282060
cttccctcct tctgagacag ggtctcactt tgttgtatag gctgaagtgc aatggcatga 282120
tcatagctca cttcagcctc gacctctagg gctcaagcaa ttctcctgtc tcagcctccc 282180
aagtacctgg gactgcaggc agatgtcacc acacccagcc cagatttcag ctttctcttg 282240
aaaaacagga ctgcctggca ataacaggtc tgcattcttc cctggcaaca aatggcagcc 282300
accccctttc caggggggccc aagcattcct ttcgccagag tccttaccac ttcctgtgtc 282360
tgtgacatgg tggttgagtg ccacttgttg tcatgtatca gcacattcct gttgttacag 282420
tagagttagg agaaaagtga agtatttctt ttaaccagtg ccactttgaa aggggaagaa 282480
caaaaggtgg attgagaggg ctgtgtgatc aaagtcgatg agaaatgagc atttttcttt 282540
tttcttttt ttttttttt tgagatggag tcttgctctg tcgcccaggc tgaagtgcag 282600
tggcacaatc tcggctcact gcaacctctg ccttctggtt tcaagtgatt ctcctgcctc 282660
agcctcccga gtagctggga ttacaggcac ccgtcaccag gcccagctaa tttttgtatt 282720
ttttttagt agagacgggg tttcaccatg ttggccaggc tggtctcgaa ctcctgacct 282780
cgtgatccgc ccaccttggc ctcccaaagt gctgggacaa gacatgagca tttttctttg 282840
tagaaataat gctcttctta caggcttaat gtgcaaagtg tgtctgtgac aaaaaaaaaa 282900
aatacaatct cagaaattac tggagacaaa cctttttgat ttcactccct attatacctg 282960
gcttctgtaa agcagacctc actcactcta ttcactgtaa ctcattctca ctgaggctca 283020
gagagggcaa gtggcttgct caaggacaca cagcatcttt gtcaatgcag agctggggct 283080
ggagctcaga ctgcttgctt cctcatcgtg tgcttgtttt actttgtcat catctgtgaa 283140
actgtctgca attgccacct ctctctgggg acacacctga gtcctcacag tctctggaag 283200
aaagtgcagt gggattcttt aatctctccg gctgcatttc atctttccca agtgttaatg 283260
gaaaaaaaaa aaacaaaaaa aaaaacacct gggttatctc cctggcattt tgccatctca 283320
gagagatgtt tttaaaaatg atgatttctt tatctttccc cgaatacaaa ttttcattct 283380
agcaacctct gctaaaggca gcttggccag acctgaccca gccatctctc cttgctctgg 283440
ccccacagcc cagccttcct atttatcagg ggtgacatca tatatccagg ctcccaggct 283500
gtccaacctt ggattgacac atttttgaat tttttctttt ttattcccgc tatccaagta 283560
gttatgaact cctttggtga atgcactgat ttttgccatc tagtggttaa aaaaaaaaaa 283620
aaagaaaaaa gggagtcggg agacatgggc atcagacagt cctgggttct gctcctgact 283680
ctgccagttt ttgtgtatga gctctgggca agtttggtaa tgtcatcaaa acctcagttc 283740
caagacccct ttcaatggag cacttgctgc cccaactgct gggggtgctg acagcagatg 283800
gctctcagct gttaacccct ttagcaatcc cttcagctgc agagccacct cgttcaaggt 283860
tattccactt cctgggacag ttcacagccc aagatagatc aagatggggc ataaaggctt 283920

-continued gtccatctgg acccaactgg agacatcacc aatttagctc caggactctc ggtagggtag 283980
gctaggatgt ggtcggccct gcatcacagc tcaacttccc cctatgccca ttcctgcttc 284040
cttcctcaat cttccccagg gattgattcc aagggacctc cttaatatgt caactggatg 284100
ctaaacttga tctcaaagac agcttgctgg ggaatgtcac ttgggatagt gggtggtaac 284160
cacacctaca ccactgcctt gtttcgggga tcaatgaggc agtcgtggta gctggcacat 284220
agtaagtgtt cagatagtgt cattaattat tagcatattt attcactaag tgccaggcat 284280
tgttcagggc acatgagaca caagtgggca ttatcagctc cggttcacag ttgagaagcc 284340
aagacttgcc aaaggtcaca cggttcattc atggtccagc tgaatctcag cttgggggca 284400
atcagctcct aaagagactg ggcttttcag aggagcctac ctggctggca ccagtcccaa 284460
ccctggactg cttgtctgtg tggtctctgg cacatcagga ctctctctga gcgccaagtt 284520
ccacaactgt aaaatgggat gaaacagagc ccgactttga gaattgttgt ggggatttga 284580
tgagtgaatc cttgtaaata aagtgcttag tgtggtgcct gccatacagt atatgctcaa 284640
tgaatgacag ttatcactat caccatttat gataattact cattattatt attcggcata 284700
ctctctgagc cccaggagct tgtatgatag ctagagggct aaaccataca tagtaaattt 284760
tttttttcg agtctgggtc tcactctgtc accgctggag tgcagtggtg aggtcttggc 284820
ttactgcaac ttccgcctct tgggctcaag caatgctccc acctcagcct cccgagtagc 284880
tgggactata ggcatgcacc actaaaccca gctaattttt gcatttttttg tacagaaaga 284940
gttttgccac atttgccagg ctggtcttga actcctgggc tcaagagatc ttcccgcctt 285000
ggccttctga agtgctgtga ttacaggcat gcgccactgt gtctgttcca tacatagttt 285060
ttttttttt ttttttttt tttgagacag tctcactctg ttgcccacgc tggagtgcag 285120
tggtgtgatc tcgggtcact gcaacctctg cctcctgggt tcaagcaatt ctcatgccac 285180
agcctcccga gtacttagga ttataggcac gtgccaccat gcctggctaa gttttgtgtg 285240
tgtgtgtgta tatatatata tatatgtata taaatatatg tatatatgta tatataaata 285300
tatgtatata tacatataat tatatacata tacatataaa taaatatata tatatatatt 285360
tattttagta gagatggggt gtcaccatgt tggccaggct agtctcgaac tcctgacctg 285420
aagtgatcca ccagcctggg cctcccaaag tgctgggatt acaggcgtga actgccatgc 285480
ccaaccccgt taattccttg tgaattgcct gctcaccatg tgccaggcac tgtgctaggt 285540
gctgcaactt cggctgtgaa caagatggac acgatctcta ccttgttgaa gtttataacc 285600
tggtggggaa acagatgaaa aaataaataa agacacaaat aagtatataa ttgcatcttg 285660
tgaaggaaaa atggcagcat gggtggatgg tgggaaaggt ggttggaggc atccatttta 285720
ggaggtcagg cagggtctct ctgaagaggg gacacttaaa aagaaacctg aagcatgaga 285780
aggaagcagc caactaagga atggggagaa gagctttcct ggcagagaaa acagcacagg 285840
caacagtcct ggataggaag gagtcatgcc tattctagga gttaaaggta tgactgcagg 285900
aggtgaggga ggaggctagc cgcctgggaa aaggctgtgt cagaggcgtt ggaaccagag 285960
agactccatc ttgaataggg gctgggtaaa atgaggctga gacctgctgg gctgcattcc 286020
ctggaggtta ggcattctta gtgacaggat gagataggtg gttggcacaa gatgcaggtc 286080
acaaagacct tgttgataga acagttttcc ataaagaagt cagctaaaac ccaccaaaac 286140
caagaaggcg atgaaagtga cctcggattg tcctcgctgc tcattacacg ctaattagaa 286200
tacattagca tgcgaagaga cactcccacg agcgtcatga cagttcacaa atgccatggc 286260

-continued

```
aacgtcagga agttacccta tatggtctaa aaggggaagg aacccaccga tccaggaatt 286320
gcccaccctg ttcccagaaa actcatgaat aatacacctc ttgtttagca tgtaatcacg 286380
aaataactat aagtataccc agctgagcag tccatgctgc tgctctgccc atggaatagc 286440
cattctttat tccttcactt ccttttttt ttgagacaga gtctctctct gtcgcccagg 286500
ctggggtgca gtggcgccat ctcagctcac tgcaagctcc gcctcctggg ttcacgccat 286560
tctcctgcct cagcctcctg agtagctggg actaacgccc gccaccgtgc ccagcaagtt 286620
ttttgtattt ttagtagaga cggggtttca ctgtggtctt gatctcctga cctcgtgatc 286680
ctcccacctc ggcctcccaa agtgctggga ttacaggcgt gagccaccgc gcccggccta 286740
ttccttcact ttcttaataa acttactttc actttactct atggactcac cccgaattct 286800
ttcttgcgtg agatccaaga accctctctt ggggcctgga ttgggaccgc tttctgataa 286860
cagctggaga agtagaaaga agccccatca tgcgaggggt acaggggtgg cggctcttag 286920
gcctcagcat gagggctttg attgtacttt aggtagaacg ggaagccgct aaaagccttt 286980
aaacaggtaa aagtcacaat acaattttct taaaaaaaaa aaaaaaagaa aggaaaaaac 287040
tctggcaaat gaatgaggtt attattagca gtattaacat ccacactgaa aataacagac 287100
gctggtctct gttgtgcaaa acgtctgtca tttctctcat ttaccctgaa aactgaactt 287160
tttttccagg ttgtctcaca tctataagac cttctgctcg gaaggaatcc cattcttccc 287220
aatctttttg gaatatttgg agctgctgtt acaagtattc ttgatctaca gccacaacat 287280
ctgaaggatt taattactgt aatttaaggg gaatgactaa gatttttgca tattttcttt 287340
ctctttcttt ctttctttct tttttcttcc ttccttcctt tccttctttc tttccttcct 287400
tcccttccct tcccctcccc ctccctccct ccctcccccc tccctccctc ccttccttcc 287460
tttcttcctt ccttccttct ctctctctct ctctctctct ctctctctct ctttctttat 287520
gagacagagt ctctctctgt tgcccaggct ggagtgcaat ggcgcaatct cagttcactg 287580
caacctctgc ttcccggatt caagcaattc tcctgcctca gcctcctgag tagttgggac 287640
tacaggcacc caccaccatg cttggctaat ttttgcattt ttagtagaga tggagtttca 287700
ccatgttggc caggctggcc tcgaactcct gacctcaagt gatctgccca cctcagcctc 287760
ccaaagtgct ggattatagg catgagccac caagcccgac tgaaattttt gcatatttca 287820
agtgagaaat tgacgcagga gcaaacttac tgcacaaaga ccgacctctt ccgtgggccg 287880
ttcccagcct ccagtatcct ccacccactc tagtgtctca taatctctct tcctccctcc 287940
caatctctct tcctccctcc caatctctct tcctccctcc tgctgccccg cagagaatgg 288000
tcggctccca gctggagcaa gttcatccag ttgagaggat gatgtttgca taatttgaat 288060
aataattttg cataatagag gctctctttg aaatgatgta aatcagccct cagttctctc 288120
ttcagattat tattcattca ttcagtgaga tcacttttag ggatgagat agaaatattt 288180
acagaagaca gaggatcaag tgtggaggct ttgatgattt ctagtgaaaa aaatgttttt 288240
gtcttgtctg gtttgatgca tttgagggtg gagactggag ctgaatgtgc aacattttta 288300
tgcaacgcag tggatctttt ttttgagaca tggtctcact ctgttgctca gggtggagtg 288360
caatggtgcc atcttggctc actgcaacct caacctcctg ggcttaagag attctcctgg 288420
cttggcctcc caagtagctg ggactacagg tgcgtgccac catgcctggc tgatttttaa 288480
attcttttgt agagacaggg cctcccacag tgttgggatt atgagcatga gctcccacca 288540
tgcctggcct catgactcag tggatcttaa tgcgaaattt gccctgggtc agtgggggta 288600
ggggaaagag gggtagagga tggggataag aagtaggtct aagggtaggg aggaaggagt 288660
```

-continued gggaccaact cagtctctgg acacctcctc ctgagatata cctgaggatg ccttcccatc 288720
ctctctttct ccctctctgt atcctctatc tttaatggat acagacctag tatgtattta 288780
cccccgcttt aaaaaaaatt tttttttttg agacggagtt tcactcttgt tgcccaggct 288840
ggagagcaat ggcacgatct cggctcatcg caaactctgc ctcctgggtt caagcggttc 288900
tcctgcctca gcctcctgag tagctgggat tacaggcatg caccaccacg ctcggctaat 288960
tttgtatttt tagtacagac ggggtttcac catgttggtc aggctggtct cgaactcccg 289020
accttaggtg atcagcccac ttcagcctcc caaagtgctg ggattacagg cgtgagccac 289080
cacgtccagc ccctcctttt ctaatggaaa gaaaaatggg ctttggggct gagcagacct 289140
gttagtgttc tttggttgca agcaacggaa acctgttcac ttttggttaa gccaaaggtt 289200
taggaagtag attgtaggca gggggcatcc aattggccaa gcttgggttc catgcctgct 289260
tcttgccctg gggtggtgga ggtaccttgc agccgcaccc ccctcatttg tggcactcag 289320
agcaagagta caaaaggaag cctttacacc acttgtctac aagtgataaa gcaaccagat 289380
aaactattag atgaagtatg atctgtcatc ctaccttggc acatatacgt gaataaggac 289440
ctggaaggcc aggtttgaat tagaatcttg gagtcctcag agttatcgac cagcatgtgg 289500
tgacttggga ggggccagcc ttggtttatg gtccactctg cttctcttct aacccttggc 289560
tctgtcctac actctgagag gctggggtgt ggacccccag cccctgtgtt caagctctgt 289620
tttctaactc cccaaatggc tgtcccttgg ccacttctca ggtcttaaga tgcccacagt 289680
ggtggcatgg ttcactcttt ggaggacgac ctgggaaagg ggcccaggct ggccctgaag 289740
caggagccct gggtacctgg atgagctcta gaaggagggg catggactca gggtgggcgc 289800
atccctggga ccccacaaac gctttaccca catggccaga ggccaagcag gaccctttaa 289860
agagcagtcc ccagggcagg gtgggcctgg caccaaaatt gacagcctgc tcgtctgtag 289920
caaaaggggc agggcaattc ctcaaatcaa aaaggaaatg gaagctgcgt agagaggaga 289980
caaatatcaa ccccacctga ggtcttatct aggcttttct gcagctaggg gtcttttggt 290040
agcaagaaag aaaaacccag ccgggcacgg tggctcactc ctgtaatccc agcactttgg 290100
gaggctaagc cgggcagatc acctgaggtc aggagttcaa gaccagcctg gccaacatgg 290160
tgaaacccca tctctactaa aaatataaaa attagctggg catgttgatg ggcacctgca 290220
atctcagcta ctcgagaggc tgaggcaggg agaattgctt gaactgagga ggcggaggtt 290280
gcagtgagcc aagattgctc actgcactct agcctgggtg acagagcaag actccgtctc 290340
aaaaaaaaaa aaaagagaaa ctcactctga cactggcttg agcccaagga gtctctgtgg 290400
tggtggtggt ggtatccata ggggtggctc acggacccag gaaggtggaa gtatggccag 290460
tcctcttgag gaacaggagt caggactgag aagctgctga ggatcagggc gtctctcctc 290520
tctatctcta ctcttctatg catctaacag cagagtggct tcacgggctt tcctcaagga 290580
ctcgaaagag atacaacatg gggatctcaa acttagaacc tttgtcaggc aggtgatgtc 290640
aatgggaaca acagtggagg gaaactcaca gggccttctc agttcccttt tcttttcttt 290700
taagagacaa gatctcgctc tgttatccag tctggaatgc agtggcacga tcatagctca 290760
ctgcagcctt gacctcctgg gcttaagcga tcttcccacc tcagcctcct gagtagctgg 290820
aactacagat gtgcaccacc atgcccagct aatttttaag attttttgta gagacagggt 290880
cccaccatgt tgcccaggct ggtcttgaac tcctgggctc aaaagatcct cctgccttgg 290940
cctcccaaag tgaggggatt agaggcatga gccactgtgg ctgacccgtc tccctttctt 291000

-continued

```
gataggaaca tggcatatca gtcaggaaac agatgacaaa tcctcattag gatgccccga 291060
ggaggcaggg ttaacacagg gactgtttac taaggtatgg atcagctgtg ggaagccaca 291120
gggccagtac cccagggcta gttctgaaag agctgtcacc attcctatgc ccaaaaggat 291180
agggatggga gtggttctgg aatccagaag ccgtgggtgg ttggagaggg ctgcctggac 291240
agcagatgtg gccttccttg gagagttgca gtcagtcctc agcaacccca ctgggagcca 291300
gtcaaataaa taacctgaca gcacactctt catgccctgg atctcctgct ggcattgccc 291360
attggccaaa cccaactgaa atcctgagag cccattcatg cagtccttgg gcaggatggg 291420
gaagccagag aggggtgtgg aggggcaaag ggaagacagc tgccacgtgt gggtataaga 291480
gacatttccc tgctgaaagg cataccatag cttaaacctg agggacgatg ttcatggata 291540
ctgggtcttg ggaagcgaat gagatgttgt ggttcatggg accaagagga aagtacaaac 291600
ccccttttaa ccactcagct ctggccaatt attgccatgc aggagtgtgg gctcctagtg 291660
gcaggggctc tgaacttgga agagaagtag gcaatccaga atctgaaatt atgaaatttc 291720
aagattaaat catattggca actagttaaa acaaacaaaa atagttttaa aatgctgtat 291780
gagtccagta aatcccattc acaagccaga tttggcccga ggatgctcta aacagaaact 291840
catttggggc ttttgtctca attccaaatt ccccaggaag gagagatgct gtttgatgtt 291900
tttttttttg tttttgtttt tttttgagat ggagtcttgt tctgtcaccc aggctggagt 291960
gtagtggtgt gattttggct cactgcaatc tctgcctttt gggttcaagt gattctcctg 292020
cctcagcctc cctagtagct gcgactacag gtgcatgcca ccacgcctgg ctattttttt 292080
atttttagag acgaggtttt cctgtgttgg ccaggttggt tttgaactcc tgacctcaag 292140
tgatcagcct gcctcagcct cccaaagtgc tgggattaca ggcgtgagct actgagcctg 292200
gcctatttga cctattttgg tttggctgtc cctcccaggt gcaatcagtc gtggccagga 292260
ggggtcatgt ccctgctgct cactcagctc gggacaggat agtccctctg agagctgagc 292320
atgtgccctt ggaaagcagt caatgatctg tgggtctaat cgcaatcact tactcctctg 292380
tgatggggaa gtgtgtgctt gtcttccatg gctgctgtaa tgaatgacca caaactcggg 292440
cttaaaaacc acagattcat tatctgacag ttctgaaagt cagaactgca atgggctaaa 292500
ggcaataggc aaaaatcaag gtgtcaaaaa gctgcattgc tttttggagt cttttttttt 292560
tttttttttt ttttttgaga cagagtctcg ctctgttgcc taggctggag tacagtggtg 292620
tgatctcagt tcactgcaac ctctgcctcc caggttcaag ggattctcct gcctcagctg 292680
taatcccagg tagctgggat tacaggtgtg tgccaccatg cctggctaat tttgtatttt 292740
ttagtagaga cagggtttca ccatgttggt caggctggtc tcaaacctga cctcaggtga 292800
tccacccacc ttgtcctccc aaagtgctag gattacaggc acgagccact gcgcccggcc 292860
cactttttgg aggctttagg gggagaatct gtttccttgc cttcttcagc ttcttagagc 292920
agtggtcccc aacctttttg gcaccaggga ctggtttcat ggaagacagt ttttccgcgg 292980
gatggtgatg gtgtagggga tggtttcagg atgattcaag tatatcacat ttattgtgca 293040
ctttatttct attattatta cattgtaatg tataatgaaa taattataca actcaccata 293100
atgtagaatc agtgggagcc ctgagcttgt ttttctgcaa gtagatggtc ccatctggga 293160
gtgatgggag acagtgacag atcatcaggc atttgatttt cataaggagt gcacaagcta 293220
gatcccttgc atgagcagtt cacgataggg ttcgtgctcc tatgagaatc taatgccgca 293280
gctgatctga caggaggcgg agctcaggtg gtaatgtgag agatggggag tggctataaa 293340
tacagatgaa gctttgctca cttgcctgct gcttgcctcc tgctgtgtgg cctggttcct 293400
```

-continued aagaggccac agacagtacc aaccggtggc ctgggggttg gggacccctg tcttagagga 293460
tgcctgcatt ctttggctca tggccccttc aaccttcaaa gccagtaaca gctggtttag 293520
tctttctcat gttgcattcc tttgactctg cctccctcat atatatatat atatatatat 293580
gtgtgtgtgt gtgtgtgtgt gtgtgtgtgt gtgtgtgtgt gtattttgag acacagtctc 293640
actctgttgc ccaggctgga gtgcagtggc atgatcatgg ttcactgcag cctcgacctc 293700
ctgggctcaa gtgatcttcc catctcagcc tcccaagtgc tcttcaatct ttaaaggacc 293760
cttgtgatta cattgagtcc acccagataa tccaggataa tttctttatt ttaaggttag 293820
caaacttaat tctgtttaat ttttaaaaag ttcttttgtt tcactctgtc gcccaggctg 293880
gagtgcagtg gtacaatcat ggctcacggc agcctccatt tcctttgctc aagcgatgct 293940
cttgcctcag ccgcccaagt agctgggact acaggtgtgc aaaatcaagc ctggctaatt 294000
tttttgtttg tttgttgttg ttgttcttgt tgttgttttg tagagacggg gtttctctgt 294060
gttgcccagg ctggtctcaa actcctgggc tcaagtgatc ctcccacctt ggcctcccaa 294120
agtgctgaga ttacaggtat aagtcactgc atccagccaa caaacttaat tctatctgca 294180
accataatta ccctttgcac catgtaaagt aacatattca caggttccaa ggattaggat 294240
gtggatatct tgtgggggt gggggggtg ttattctgtc taccacaagg cagtttctga 294300
actttgctag tcatccataa tatatgggta accctgactt cttcatgggt tgttaacggg 294360
ttcagatgag agaacctatg caatacacct ggcgcagtcc gtggcacaca gcaggcattc 294420
ctgttagtcc ctttcccttc tcctccttgg gctattggct tcagtgtggc tgagcgtgtt 294480
tcttcagctg ttaaatgacg tagatatatc agtcccgcct acctcaaagt gctgttcctt 294540
tcttccttca ttcactttct cattcactca tgcaacaaat atgtattgag ggcctacgat 294600
gcgtgagacg cttgtgctag gtgccggagc agagccgcag ataagggaga catgaggttt 294660
attttcaggt gaggaaggaa atagtgagaa aacagataaa caatcctaat ttggtatagt 294720
aataagtaca agaagacaaa gtagggtaag agaacacaga agggtggaga tggtggaggg 294780
tgggcagtgg gatgctattt taaatagaga ggtcagaaag agcatgtcta ggctgggtgc 294840
ggtggctcac ccctataatc ccagcacttt gggaggctga ggtgggcgga tcacttgagt 294900
ccaggagttt gagaccagcc tggccaacaa ggtgaaaccc catctctact aaaaatacaa 294960
aaatttgccg ggtgtattgg cacatgcctg taatctcagc tactcgggag gttgaggcaa 295020
gataatcgct tgaacctggg aggcagaagt tgcagtgagc tacactccat cctgggtgac 295080
agagtgagac tctatctcaa aaaaaaaaaa aaaagaaaag aaagaaagaa agaaagagca 295140
tgtctgagtg acatgagaaa tgacagtgag tgtttgttga tcgcctgaat gacatgatgc 295200
tgatttccag cttgattgtg gcagaagtgg ataagctgat tgctggtaat cagtttaatt 295260
atgtaagatt cctttcacaa cattttaaga ttttctggct tctcttttct gtgttgcatt 295320
ttactagcat tgaaagaagt gacccaaagc atagattcat ttttcctttt ggaactggac 295380
agatatttct cagatttagc tgctattcct cctggaggcc tctcaaaggc agcaggaaga 295440
gagaccctga cagctctgtc cccagctctg tttgtgacct gctccacttg cttggcagct 295500
gggaacctca gcagcctcat taacgttgga aagcactttg ggtctcttgc tgaaagacgc 295560
taggaaaggc aggtcataat tattttgttt ttcctacatc ttcaaggccg tcagatgcag 295620
cttgaacctt ctccatcaag aacaagaggc tggccgggcg cagtggctca tgcctgtaat 295680
cccaggactt tgggaggccg aggcaggaga attgcttgaa tctgggagct ggaggttgca 295740

-continued

```
gtgagccaag atcgcgccac tgcactccag cctgggcaac agagctaggc tctgtctatt 295800
aaaaaaaaaa aagaacaaga ggctgcagtt agtgcaggga ggagaggaga tgggcaagga 295860
agagagaggc tgaggctgga aagtgggaag gaagacaggc agtgactgct cctggcctct 295920
ggctgaggat gggtcatagg caggccagtc ccctcccatg cctgtgatgc gtgtttgcat 295980
gttgctggtg acatcagcat cttagagtcc atctccaatc agacccattt ccctttccac 296040
actagaacat agctccatga cccctggtgg cctctgaaag tcgttgtggg gtggtttgca 296100
gagccactgg gagagggaca ttggctgagg cagacgataa aaatgataat agcagccagt 296160
cgagttagct gacgcctgta atcccagcaa tttgggaggc caaggtggga gaatcacttg 296220
aggtcaggag ttcaagacaa gcctggacaa aatggtgaaa ccccatctct actaaaaata 296280
caaaaattag ctgggtgtgg tggtgtgcgc ctatagtccc agctactggg gaggctgagg 296340
tgggaggatc acctgagccc aggaggtgga gattgcagtg agctatgatc gcgccactgc 296400
actccagctt aggcaacaga gcgagaccct gtcttaaaat aaataaataa ataactacta 296460
ctactgccac taatagcagc tttgattcac tgtgcaccag ctcacttgcc ttctcatcca 296520
tagccctgtt gggaatgatt atccccattt tacaggtgag gaaactgagg ctcaccaaag 296580
gtaggtgata tgcctatgag ctgggattcg aactcagttt tatttggagt cagtatagtc 296640
tattgattct acttttattt agttaattaa ttaattaatt aattttatta tactttaagt 296700
tctggggtac atgtgtagaa cgtgcagttt tgttacatag gtatacacaa gccatggtgg 296760
tttgctgcac acatcaatcc gtcatctaca ttaggttttt ctcctaatgg tatccctccc 296820
ctagacccca cccccgacag gccccagtgt atgatgttcc cctccctgtg tccgtgtgtt 296880
ctcattgttc agctcccact tatgagtgag aacatgcgat gtttggtttt ctgttcttgt 296940
gttagtttcc tgagaatgat gatttccagc ttcatccatg tctctgcaaa ggacatgaac 297000
tcatgctttt taatggccgc atagtattcc atggtgtcta cgtgtcactg attctacttt 297060
taaaatatac ttagtacctc ccttctcttc cccatgcctg ctggggagcc cgctgctccc 297120
acctggtcca tgcaccatca ccttttacct ggactattgc aatagcctct tcctgggtct 297180
ccctgattat gtcctcccca ctcccttcca ccttatagtc tgttctcaaa ccagcagcct 297240
gaggaatgct actcaaagtt ctcctgtgac tcccctacgg taaaagccaa aagtcttact 297300
ctggttataa gccccagatg ttctctctct gtcctgcaat tcatctcctt gctcactgta 297360
gttgagttat acaggccccc tgactcttcc ttaagcagac cagacacgct cttaccacag 297420
ggtctttgca ctggctgttg ttccccctgc ctggaatact cttcctcaaa tatccacata 297480
ggcttgtttc cttttaaagt ctctacccag gagccatctc attgaccctt ctctgacagc 297540
cctgttgaca cttgcaatta tttcctagta ccctaattgc tccttctttc cttctttttc 297600
tctctagcac ctctcattat ctaacatact ctttgactta cttattttgt gtgtggttca 297660
cgcttatcca tgagaacatc agctccatgg caaggcattt tgtctgtctt actctctgct 297720
gcattcccag caccaagaat agcgcctggc acctagtagg cgctcaataa atatttgttg 297780
aatgaatgac tctgaagcca tcattctgtc caccacacaa actgccacct tcctacaccg 297840
acttcttgtc tataagaatt ccacatcctt gccaacactt gctatggtca tgtttccatt 297900
ttctctaact tatggctgta aaatggtatc tgattgtggt tttaacatgc atttcttgag 297960
atgcctgggc actcaggtac tgacatgtct gagggacaga gagtgggtct ttgtctccct 298020
ctggctggaa gtccagagct ccaaaataga ccatctccca gcattttttg agaaaatggg 298080
aaatgagtct ttgttttggg ttataataag ataagcaact catgtacaac aaaagttagc 298140
```

```
atctgctctg cacacaaggt ttaatattta gagataattt aaaaccaagg aaaaggcaga 298200

gttattaata aacacttggg gggaggtgtg aagagagagt atgaaaatct ccatttgaaa 298260

aagctactgt agttagcatc caaaataaga ccttacttag cattcggttc tgctcatttg 298320

caaattaaga gatgtattgt tttaaaaata attaagtcta attttgcatg tttgggagat 298380

ggctctccac tggctttaaa aatctttatt tatcagtaat gttctgaata cagatttttt 298440

ttctttttcg agacagaatc ttgctctgtc gtccaggcta gagtgcagtg gcacaatctc 298500

agctcactgc aacctctgcc tcccaggctc aagcaatctt cccacctcag cctcccaagt 298560

agctgggact acaggcatgt gccaccacac ctggctaatt tttgtgtttt ttttttggta 298620

gagatggtgg ggttctgtca tgtttcccag gctggtcttg aactcctggg ctgaagcgat 298680

cctcctgcct tggcctccca aagtggtgtg attataggca tgaaccactg cgcctgactc 298740

tgaatacaga ttaatctcca tcgctaagct aagtgtttgc tgttctaggt agtcacaaat 298800

gttcactaag gcaagccaca gttgaagctg aagtcgctac aggagtgatg tctggggtcc 298860

ccaggaatta ctttggggtt ctatagatcc ccagaattcc tgtcatttac agcagggatc 298920

ttagcaacca ctgagcccag ttttcttcat ttttacaggt aaagacatag aagctcagag 298980

agatgaagag gcttttctga ggtcacacag tagggcagtg gaagaactca gattagaata 299040

caggcctttt ctagccttat aaatggtatt ttcagctggg tatggtggct cacacctgta 299100

ataccaacac tttaggaggc caagacggga ggattgcttg aaactaggag tttgagacca 299160

gcctgggaag caaagtgaga ccccacctct acaaaaataa aaataaaaat aaattagctg 299220

ggtgtggtgg catgcacctg tagtcccagc tactcaggtg gctgaggcag gaagatagct 299280

tgagctcagg agttcaaggc gacagtgagc tacgatggca ccactgcact ccagcctggg 299340

tgacagagca agaccttgtc tctaaagata taaaaacaga caaaaataaa taaataaatt 299400

gtattttcca tcaaacctgt gtatctcata tttcagttac gcttttaaca tatccctgta 299460

ccacccatac tattgtttag tgaactcttt tttcccctta aatcaattca cttttaaaaa 299520

tgtaaagaca tttatttaaa aggaaaaatg tcacaaatat aaatggaaaa tcctattgct 299580

tgccaaatag aaagtaaatg acaataaata tgaggcaaac aaaacaacgt tattaagctc 299640

tagtaaggca acttgcttga taaaacgtca actcttgtga aacaaaagtt agcatctgct 299700

ccgacaccag gtttaatacc gagggatatc tagggatgct taaagccctg ggccgagacc 299760

tgctccctct ttgttaaaag gagacattag caaaggcagg agaggtttca gaaccctgta 299820

gcaccaacct gagactttct cctcctcata agcagaagga ttggaaggga atggaaaagg 299880

gaatgaattt ctcccaaggt gattgcgtgc aatctcaaca accaccacaa gtcctcgctc 299940

tagatgaatc tggacagcga gaacttcttt tgaaaccatg ctccaaagag ttaaagagac 300000
```

<210> SEQ ID NO 34
<211> LENGTH: 16
<212> TYPE: DNA
<213> ORGANISM: Artificial Sequence
<220> FEATURE:
<223> OTHER INFORMATION: forward PCR primer - with GC clamps added at the 5' end for DHPLC analysis

<400> SEQUENCE: 34

```
cccgccgccc ccgccg                                                  16
```

<210> SEQ ID NO 35
<211> LENGTH: 15

```
<212> TYPE: DNA
<213> ORGANISM: Artificial Sequence
<220> FEATURE:
<223> OTHER INFORMATION: reverse PCR primer - with GC clamps added at
      the 5' end for DHPLC analysis

<400> SEQUENCE: 35

ccgcgccccc gcccg                                                    15


<210> SEQ ID NO 36
<211> LENGTH: 570
<212> TYPE: DNA
<213> ORGANISM: Homo sapiens

<400> SEQUENCE: 36

atgactgagt acaaactggt ggtggttgga gcaggtggtg ttgggaaaag cgcactgaca      60

atccagctaa tccagaacca ctttgtagat gaatatgatc ccaccataga ggattcttac     120

agaaaacaag tggttataga tggtgaaacc tgtttgttgg acatactgga tacagctgga     180

caagaagagt acagtgccat gagagaccaa tacatgagga caggcgaagg cttcctctgt     240

gtatttgcca tcaataatag caagtcattt gcggatatta acctctacag ggagcagatt     300

aagcgagtaa aagactcgga tgatgtacct atggtgctag tgggaaacaa gtgtgatttg     360

ccaacaagga cagttgatac aaaacaagcc cacgaactgg ccaagagtta cgggattcca     420

ttcattgaaa cctcagccaa gaccagacag ggtgttgaag atgcttttta cacactggta     480

agagaaatac gccagtaccg aatgaaaaaa ctcaacagca gtgatgatgg gactcagggt     540

tgtatgggat tgccatgtgt ggtgatgtaa                                      570


<210> SEQ ID NO 37
<211> LENGTH: 189
<212> TYPE: PRT
<213> ORGANISM: Homo sapiens

<400> SEQUENCE: 37

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175
```

-continued

```
Gly Thr Gln Gly Cys Met Gly Leu Pro Cys Val Val Met
            180                 185


<210> SEQ ID NO 38
<211> LENGTH: 567
<212> TYPE: DNA
<213> ORGANISM: Homo sapiens

<400> SEQUENCE: 38

atgactgaat ataaacttgt ggtagttgga gctggtggcg taggcaagag tgccttgacg      60

atacagctaa ttcagaatca ttttgtggac gaatatgatc caacaataga ggattcctac     120

aggaagcaag tagtaattga tggagaaacc tgtctcttgg atattctcga cacagcaggt     180

caagaggagt acagtgcaat gagggaccag tacatgagga ctggggaggg ctttctttgt     240

gtatttgcca taaataatac taaatcattt gaagatattc accattatag agaacaaatt     300

aaaagagtta aggactctga agatgtacct atggtcctag taggaaataa atgtgatttg     360

ccttctagaa cagtagacac aaaacaggct caggacttag caagaagtta tggaattcct     420

tttattgaaa catcagcaaa gacaagacag ggtgttgatg atgccttcta tacattagtt     480

cgagaaattc gaaaacataa agaaaagatg agcaaagatg gtaaaaagaa gaaaaagaag     540

tcaaagacaa agtgtgtaat tatgtaa                                         567


<210> SEQ ID NO 39
<211> LENGTH: 188
<212> TYPE: PRT
<213> ORGANISM: Homo sapiens

<400> SEQUENCE: 39

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

PTPN11 (SHP-2) MUTATIONS AND CANCER

This application claims priority from U.S. Provisional Application Ser. No. 60/424,170, filed Nov. 5, 2002, which is hereby incorporated by reference in its entirety.

FEDERALLY SPONSORED RESEARCH OR DEVELOPMENT

Research and development leading to certain aspects of the present invention were supported, in part, by a grant from NIH grant number HL71207. Accordingly, the U.S. government may have certain rights in the invention.

FIELD OF THE INVENTION

The present invention relates to methods of diagnosing and treating certain types of cancer and pre-cancerous conditions, including those deriving from hematopoietic cells such as myeloid cells and lymphoid cells. In particular, the invention pertains to diagnostic and therapeutic applications based on mutations in the protein tyrosine phosphatase gene PTPN11, also known as SHP-2, or its expression product, PTPN11, also known as SHP-2.

BACKGROUND OF THE INVENTION

Cellular responses to a variety of extracellular signals are typically mediated by intracellular signaling pathways, and dysregulation of such pathways, especially those involved in cell growth and differentiation, is considered to be the main cause of cancer. Ras proteins, including H-RAS, N-RAS, and K-RAS, play key roles in signal transduction, and mutations in RAS proto-oncogenes are estimated to be implicated in about 20% to 30% of all human tumors. The highest rate of RAS mutations are found in adenocarcinomas of the pancreas (90%), the colon (50%), and the lung (30%), as well as in follicular and undifferentiated carcinomas of the thyroid (50%). RAS mutations are also found in hematologic malignancies, including acute lymphoblastic leukemia (ALL), acute myeloid leukemia (AML), and juvenile myelomonocytic leukemia (JMML) (Reuter et al., Blood 2000;96: 1655-1669).

Reversible tyrosyl phosphorylation represents a major regulatory mechanism to orchestrate cellular responses to external stimuli, including cell proliferation, survival and differentiation. Tyrosyl phosphorylation levels are modulated by the antagonistic actions of protein tyrosine kinases and protein tyrosine phosphatases, and are frequently deregulated in cancer. PTPN11 is a cytoplasmic Src homology-2 (SH2) domain-containing protein tyrosine phosphatase that plays a key-role in intracellular signaling elicited by a number of growth factors, hormones and cytokines (Neel, et al., Trends Biochem Sci. 2003;28:284-293; Tartaglia et al., Nat Genet. 2001;29: 465-468). The accumulated data provide evidence that PTPN11 positively modulates the signal flow in most circumstances, even though it can also function as negative regulator depending upon its binding partner and interactions with downstream signaling networks. Specifically, PTPN11 positively controls RAS function, and is required for the activation of the mitogen-activated protein kinase (MAPK) cascade induced by several growth factors and cytokines (Maroun et al., Mol Cell Biol. 2000;20:8513-8525; Shi et al., Mol Cell Biol. 2000;20:1526-1536; Yu et al., Oncogene 2003; 22:5995-6004). In contrast to the structurally related SHP-1, which is expressed primarily in hematopoietic cells, PTPN11 ("SHP-2") is widely expressed in both embryonic and adult tissues, and is required in several developmental processes, including hematopoiesis (Tang et al., Cell 1995;80:473-483; Qu et al., Mol Cell Biol. 1997;17:5499-5507; Saxton et al., EMBO J. 1997;16:2352-2364; Qu et al., Mol Cell Biol. 1998; 18:6075-82; Saxton et al., Nat Genet. 2000;24:420-423; Chen et al., Nat Genet. 2000;24:296-9; Qu et al., Blood 2001; 97: 911-914; Chan et al., Blood 2003;102: 2074-80).

JMML, formerly termed chronic myeloid leukemia or chronic myelomonocytic leukemia, is a myeloproliferative/myelo-dysplastic disorder of childhood characterized by excessive proliferation of immature and mature myelomonocytic cells that originate from a pluripotent stem cell (Emanuel P D, et al., Mol Med Today 1996; 2:468-475; Arico M., et al., Blood 1997; 90:479-488). In childhood, JMML accounts for approximately 30% of cases of myelodysplastic (MDS) and myeloproliferative (MPS) syndromes and 2% of leukemia's (Hasle H, et al., Leukemia 1999;13:376-385). JMML typically presents in infancy and early childhood, and is often lethal (Niemeyer C M, et al., Blood 1997; 89:3534-43; Luna-Fineman S, et al., Blood 1999;15:93459-466). Chromosomal abnormalities are observed in approximately 35% of cases, with monosomy of chromosome 7 being the most prevalent aberration. The distinctive characteristic of JMML in vitro is the "spontaneous" proliferation of leukemic cells that are hypersensitive to granulocyte-macrophage colony stimulating factor (GM-CSF) (Emanuel P D, et al., Blood 1991;77: 925-929).

Approximately 15-30% of JMML cases are believed to result from oncogenic RAS mutations that specifically affect GTP hydrolysis, leading to the accumulation of RAS in the GTP-bound active conformation (Kalra R, et al., Blood 1994; 84:3435-9; Miyauchi J, et al., Blood 1994;83:2248-54; Side L E, et al., Blood 1998;92:267-72; Flotho C, et al., Leukemia 1999; 13:32-7). In addition, JMML has been reported in children with neurofibromatosis type 1 (NF1), an autosomal dominant disorder resulting from germ line loss-of-function mutations of the NF1 tumor suppressor gene (Niemeyer C M, et al., Blood 1997;89:3534-43). In children with NF1 and JMML, the proliferative advantage of the leukemic cells resulting from a second hit, the somatic loss or inactivation of the normal NF1 allele (Shannon K M, et al., N Engl J Med 1994;330:597-601; Side L, et al., N Engl J Med 1997;336: 1713-20). Since the NF1 gene product, neurofibromin, is a negative modulator of RAS function, this loss is associated with RAS hyperactivity (Bollag G, et al., Nat Genet 1996;12: 144-8) and appears to be restricted to GM-CSF signaling in hematopoietic cells in vivo (Birnbaum R A, et al., Mol Cell 2000;5:189-95). There is also strong evidence that hypersensitivity to GM-CSF, due to a selective inability to down-regulate the RAS-MAPK cascade, plays a central role in the clonal cell growth characteristics of JMML (Birnbaum R A, et al., Mol Cell 2000;5:189-95; Iverson P O, et al., Blood 2002;99;4147-53). Nevertheless, mutations in NRAS, KRAS2, or NF1 account only for about 40% of JMML cases (Kalra R, et al., Blood 1994;84:3435-9; Miyauchi J, et al., Blood 1994;83:2248-54; Side L E, et al., Blood 1998;92:267-72; Flotho C, et al., Leukemia 1999;13:32-7).

Acute leukemia is the most common malignancy among children and adolescents, and groups a number of biologically diverse clonal disorders of hematopoietic stem cells (Greaves M., Eur J Cancer. 1999;35:1941-1953). Among these malignancies, acute lymphoblastic leukemia (ALL) accounts for 75-85 percent of cases, with precursor B-cell ALL being the most prevalent condition. Although remarkable progress has been made in the treatment of childhood ALL (Pui et al., Rev Clin Exp Hematol. 2002;6: 161-180), the underlying molecular events resulting in malignant transformation still remain poorly understood. Gene rearrangements and other chromosomal abnormalities are common, with prevalence of individual rearrangements depending on age, cell lineage and differentiation stage (Greaves M., Eur J Cancer. 1999;35:1941-1953; Harrison C J, Foroni L., Rev Clin Exp Hematol. 2002;6:91-113). Mutations affecting tumor-suppressor genes and oncogenes have also been documented, at initial presentation or during relapse (Luibbert et al., Blood 1990;75:1163-1169; Felix et al., J Clin Invest. 1992;89:640-647; Drexler H G., Leukemia 1998; 12:845-59), and genetic susceptibility associated with deficiency or low activity of enzymes that detoxify carcinogens have been reported (Krajinovic et al., Blood 1999;93:1496-1501; Wiemels et al., Proc Natl Acad Sci USA. 2001;98:4004-4009). Nevertheless, in a relatively large percentage of cases, malignant transformation does not appear to be associated with any known molecular lesion.

The respective prevalences of JMML, ALL, and acute myeloid leukemia (AML) are increased in Noonan syndrome (NS), an autosomal dominant disorder characterized by short stature, facial dysmorphia, skeletal defects, congenital cardiac defects, and hematological anomalies (Noonan, Am. J. Dis. Child. 1968,116:373-380; Allanson, J. Med. Genet. 1987;24:9-13). NS is a relatively common syndrome with an estimated incidence of 1:1000 to 1:2500 live births. It was recently demonstrated that germ-line mutations in PTPN11, the gene encoding the ubiquitously expressed protein tyrosine phosphatase PTPN11 or SHP-2, is associated with about 50% of NS cases (Tartaglia et al., Nat Genet 2001; 29:465-68; Tartaglia et al., Am J Hum Genet 2002; 70:1555-63). PTPN11 is involved in the regulation of the MAPK kinase pathway parallel to or upstream of Ras (Cunnick J M, et al., Journ. Biol. Chem. 2002;277:9498-9504; O'Reilly et al., Cell Res 2000; 10:279-288). Methods of diagnosing and treating NS based on perturbation of PTPN11 activity or signaling, are described in co-pending application Ser. No. 10/262,552, filed Oct. 1, 2002, claiming priority from provisional application 60/326,532, filed Oct. 1, 2001, each of which is hereby incorporated by reference in its entirety.

While a number of therapeutic or surgical treatments are available for leukemia and other cancers, the elucidation of the molecular events ultimately responsible for the development and progression of the disease will allow for the design of drugs and treatments strategies that more specifically target the aberrant mechanism or component. The development of specific diagnostic, preventive, and therapeutic methods, however, continue to depend on the identification and characterization of specific disease targets. The present invention addresses these and other needs in the art.

SUMMARY OF THE INVENTION

The present invention provides methods of characterizing and treating certain types of cancers and pre-stages thereof. By identifying mutations in protein tyrosine phosphatase gene PTPN11 in subjects with cancer or a hematopoietic or myeloid disorder, tools for developing diagnostic and therapeutic applications are provided.

Thus, the invention provides a method for characterizing a hematologic disorder in a subject, which method comprises detecting a mutation in a PTPN11 gene in the subject, wherein the mutation results in an increased expression or activity of a PTPN11 protein encoded by the gene as compared to a control. The activity can be, for example, phosphatase activity. In one embodiment, the mutation is a missense mutation. In another embodiment, the mutation is in a coding region of the gene, and the mutation may result in a mutation in the PTPN11 protein. Preferably, the mutation in the PTPN11 protein is in an src-homology-2 (SH2) domain or protein tyrosine phosphatase (PTP) domain. The hematologic disorder can be, for example, acute lymphoblastic leukemia (ALL), acute myeloid leukemia (AML), juvenile myelomonocytic leukemia (JMML), or myelodysplastic syndrome (MDS). In a particular embodiment, the mutation in the PTPN11 protein corresponds to an amino acid substitution selected from the group consisting of Asn58Tyr, Gly60Val, Asp61Tyr, Asp61Val, Tyr62Asp, Glu69Lys, Phe71Lys, Phe71Leu, Ala72Thr, Ala72Val, Ala72Asp, Thr73Ile, Glu76Lys, Glu76Gln, Glu76Val, Glu76Gly, Glu76Ala, Pro491Ser, Pro491Leu, Ser502Pro, Gly503Arg, Gly503Ala, Thr507Lys, Gln510Lys, and combinations thereof, in the PTPN11 protein having the amino acid sequence of SEQ ID NO:2. The mutation in the PTPN11 gene can correspond to, for example, a nucleotide substitution selected from the group consisting of A172T, G179T, G181T, A182T, T184G, G205A, TTT(211-213)AAA, T213A, G214A, C215T, C215A, C218T, G226A, G226C, A227T, A227G, A227C, C1471T, C1472T, T1504C, G1507C, G1508C, C1520A, C1528A, and combinations thereof, in the PTPN11 coding sequence of SEQ. ID NO:1.

The invention also provides for a kit for diagnosing a hematologic disorder, comprising oligonucleotide that specifically hybridizes to or adjacent to a site of mutation in a PTPN11 gene that results in an increased activity of a PTPN11 protein encoded by the gene; and instructions for diagnosing a hematologic disorder based on the results of a hybridization test using the kit. The site of mutation may, for example, comprise a nucleotide selected from the group consisting of nucleotides 172, 179, 181, 182, 184, 205, 211, 212, 213, 214, 215, 218, 226, 227, 1471, 1472, 1504, 1507, 1508, 1520, 1528, and combinations thereof, of SEQ ID NO:1. In one embodiment, the mutation is not associated with Noonan's syndrome (NS). In another embodiment, the site of mutation is in a range of nucleotides corresponding to from 194,431 to 194,625 or from 233,137-233.288 of a PTPN11 genomic sequence comprising the sequence of SEQ ID NO:33. In an exemplary embodiment, the kit comprises at least one probe comprising the site of mutation. In another exemplary embodiment, the kit comprises a first oligonucleotide primer comprising at least 15 consecutive nucleotides of SEQ ID NO:33, and a second oligonucleotide primer comprising at least 15 consecutive nucleotides of a sequence complementary to SEQ ID NO:33. In a specific embodiment, the kit comprises a first primer comprising a nucleotide sequence selected from the group consisting of SEQ ID NOS: 3, 5, 7, 9, 11, 13, 15, 17, 19, 21, 23, 25, 27, 29 and 31, and a second primer selected from the group consisting of SEQ ID NOS: 4, 6, 8, 10, 12, 14, 16, 18, 20, 22, 24, 26, 28, 30, 32.

The invention also provides for a kit for diagnosing a hematologic disorder, comprising an antibody that specifically recognizes a mutation in a PTPN11 protein; and instructions for use in diagnosing a hematologic disorder based on the results of an antibody binding test using the kit. In a preferred embodiment, the mutation results in an increased PTPN11 activity as compared to a PTPN11 protein having the amino acid sequence of SEQ ID NO:2. The mutation can be, for example, in an SH2 domain or a PTP domain. In a particular embodiment, the mutation is not associated with Noonan's syndrome. Non-limiting examples of the hematologic disorder include ALL, AML, JMML, and MDS. The mutation may be, for example, an amino acid substitution corresponding to Asn58Tyr, Gly60Val, Asp61Tyr, Asp61Val, Tyr62Asp, Glu69Lys, Phe71Lys, Phe71Leu, Ala72Thr, Ala72Val, Ala72Asp, Thr73Ile, Glu76Lys, Glu76Gln, Glu76Val, Glu76Gly, Glu76Ala, Pro491Ser, Pro491Leu, Ser502Pro, Gly503Arg, Gly503Ala, Thr507Lys, Gln510Lys, or combinations thereof, in the PTPN11 protein having the amino acid sequence of SEQ ID NO:2.

The invention also provides for a method of characterizing a hematologic disorder in a subject, which method comprises assessing the level of expression or activity of a PTPN11 protein in the test subject and comparing it to a control. In one embodiment, the level of expression is assessed by determining the amount of mRNA that encodes the PTPN11 protein in a biological sample. In another embodiment, the level of expression of PTPN11 is assessed by determining the concentration of PTPN11 protein in a biological sample. For example, the level of activity can be assessed by determining the level of phosphatase activity of the PTPN11 protein. In this embodiment, the control can be the level of expression or activity in a control subject. Non-limiting examples of the hematologic disorder include ALL, AML, JMML, and MDS.

The invention also provides for a method for treating a hematologic disorder in a patient, which method comprises administering to the patient in need of such treatment an effective amount of an agent that modulates the expression or activity of a PTPN11 protein, in association with a pharmaceutically acceptable carrier. In one embodiment, the PTPN11 protein comprises the amino acid sequence of SEQ ID NO:2 having an amino acid substitution. Preferred but non-limiting examples of hematologic disorders include ALL, AML, JMML, and MDS. The agent can be, for example, a PTPN11 antisense nucleic acid. In a particular embodiment, the antisense nucleic acid hybridizes to a segment of SEQ ID NO:1 comprising at least one nucleotide substitution selected from the group consisting of A172T, G179T, G181T, A182T, T184G, G205A, TTT(211-213) AAA, T213A, G214A, C215T, C215A, C218T, G226A, G226C, A227T, A227G, A227C, C1471T, C1472T, T1504C, G1507C, G1508C, C1520A, and C1528A, and complementary segments thereof. In another particular embodiment, the agent inhibits PTPN11 activity by blocking a PTP domain. This may be accomplished by, e.g., use of an anti-PTPN11 inhibitory antibody. The antibody may, for example, specifically recognize a PTPN11 protein having the amino acid sequence of SEQ ID NO:2 and comprising mutation selected from the group consisting of Asn58Tyr, Gly60Val, Asp61Tyr, Asp61Val, Tyr62Asp, Glu69Lys, Phe71Lys, Phe71Leu, Ala72Thr, Ala72Val, Ala72Asp, Thr73Ile, Glu76Lys, Glu76Gln, Glu76Val, Glu76Gly, Glu76Ala, Pro491Ser, Pro491Leu, Ser502Pro, Gly503Arg, Gly503Ala, Thr507Lys, Gln510Lys, and combinations thereof.

The invention also provides for an isolated PTPN11 variant associated with a hematologic disorder and comprising a mutation resulting in an increased level of a PTPN11 activity, wherein the mutation corresponds to an amino acid substitution selected from the group consisting of Asn58Tyr, Gly60Val, Asp61Tyr, Asp61Val, Glu69Lys, Phe71Lys, Phe71Leu, Ala72Thr, Ala72Val, Ala72Asp, Glu76Lys, Glu76Gln, Glu76Val, Glu76Gly, Glu76Ala, Pro491Ser, Pro491Leu, Ser502Pro, Gly503Arg, Gly503Ala, Thr507Lys, Gln510Lys, and combinations thereof, in a PTPN11 protein having the amino acid sequence of SEQ ID NO:2. The invention further provides for an isolated cell comprising a vector, which vector comprises a nucleic acid encoding such an PTPN11 variant, the nucleic acid operatively associated with an expression control sequence. In one embodiment, the cell is a eukaryotic cell. The invention additionally provides for an isolated nucleic acid encoding such a PTPN11 variant.

The invention also provides for a method for characterizing a cancer or pre-cancerous condition in a subject, which comprises detecting a mutation in a protein tyrosine phosphatase 11 (PTPN11) gene in the subject, wherein the mutation results in an increased expression or activity of a PTPN11 protein encoded by the gene as compared to a control. In one embodiment, the subject does not have a mutation in a H-RAS, N-RAS, K-RAS, or NF1 protein. The cancer may be, e.g., lung cancer, colorectal cancer, pancreatic cancer, bladder cancer, kidney cancer, thyroid cancer, melanoma, or leukemia. In a particular embodiment, the mutation is in a coding region and results in a mutation in the PTPN11 protein. In this embodiment, non-limiting examples of the leukemia include ALL, AML, or JMML, and the mutation in the PTPN11 protein may corresponds to an amino acid substitution selected from, e.g., Asn58Tyr, Gly60Val, Asp61Tyr, Asp61Val, Tyr62Asp, Glu69Lys, Phe71Lys, Ala72Thr, Ala72Val, Ala72Asp, Thr73Ile, Glu76Lys, Glu76Gln, Glu76Val, Glu76Gly, Glu76Ala, Pro491Ser, Pro491Leu, Ser502Pro, Gly503Arg, Gly503Ala, Thr507Lys, Gln510Lys, and combinations thereof, in the PTPN11 protein having the amino acid sequence of SEQ ID NO:2. In another particular embodiment, the precancerous condition is an MDS, and the mutation in the PTPN11 protein may correspond to an amino acid substitution selected from, e.g., Gly60Val, Phe71Leu, Asp61Val, Glu69Lys, Phe71Leu, Glu76Ala, and combinations thereof, in the PTPN11 protein having the amino acid sequence of SEQ ID NO:2.

BRIEF DESCRIPTION OF THE DRAWINGS

FIGS. 6A and 6B show the main biological features of the acute lymphoblastic leukemia cohort included in the study described in Example 4. Percentage values are in italic. [1]Values refer to the prevalence of cases with PTPN11 mutations within each immunophenotype subgroup. [2]Percentage of cases with mutated PTPN11 in B-cell precursor ALL. [3]Among the 168 children with common ALL tested for the TEL-AML1 rearrangement, 41 were positive (24.4%), and 127 negative.

DETAILED DESCRIPTION OF THE INVENTION

Figure 1:
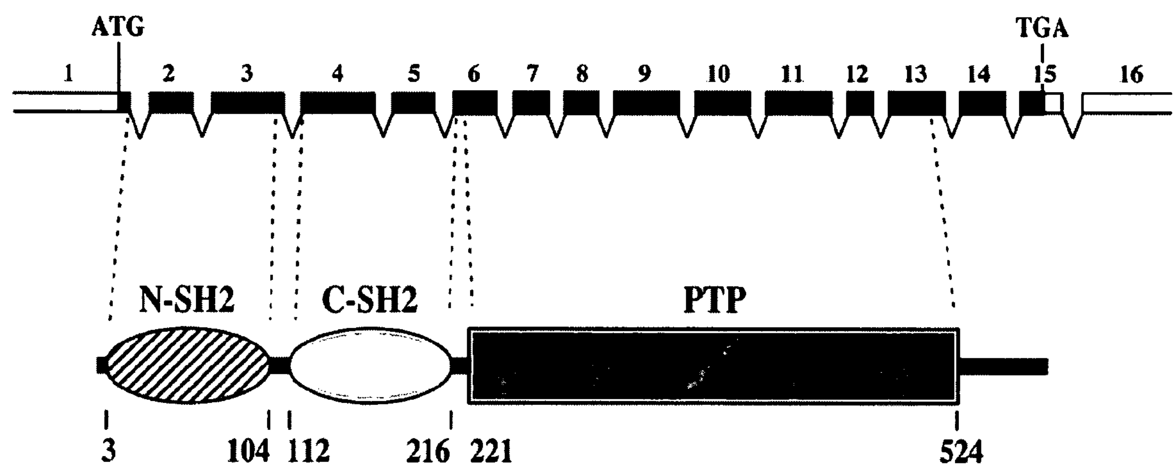
FIG. 1 is a schematic drawing showing PTPN11 gene organization and the PTPN11 domain structure. The numbered, filled boxes at the top indicate the coding exons; the positions of the ATG and TGA codons are shown. The functional domains of the PTPN11 protein, consisting of two tandemly arranged src-homology 2(SH2) domains at the N-terminus (N-SH2 and C-SH2) followed by a protein tyrosine phosphatase (PTP) domain, are shown below. The numbers below that cartoon indicate the amino acid boundaries of those domains.

The present invention is, in part, based on the identification of mutations in the protein tyrosine phosphatase gene, PTPN11, that are associated with certain types of cancer and pre-cancerous conditions, including hematologic cancer and disorders such as myeloid or lymphoid cancers and disorders. In particular, the invention contemplates characterization of cancers and pre-cancerous disorders characterized by up-regulated signaling through the RAS-MAP kinase pathway. Accordingly, the invention provides mutant PTPN11 coding nucleotide sequences associated with cancer and pre-stages thereof such as, but not limited to, ALL, JMML, MDS and AML. Preferably, the PTPN11 variants are characterized by an increased PTPN11 activity, i.e., gain-of-function in PTPN11 activity; or by higher PTPN11 expression levels, as compared to controls. Characterization of such cancers and pre-cancerous conditions, particular hematologic disorders, provides a basis for therapy, prognosis, or diagnosis, as detailed below.

The invention is also based, in part, on the discovery that acquired mutations in PTPN11 represent a recurrent event in B-cell precursor ALL, are prevalently observed in children with the CD19+/CD10−/cyIgM− immunotype, and are not associated with major gene rearrangements or lesions commonly observed in precursor B-lineage ALL. In addition, among children with acute myeloid leukemia (AML), PTPN11 mutations occur specifically in children with acute monocytic leukemia with high prevalence (25% of cases). These findings provide the first genetic evidence for a lineage- and differentiation stage-specific contribution of these lesions to clonal expansion, and show a major role of up-regulated RAS signaling in precursor B-cell ALL.

Antibodies that specifically bind to the variant PTPN11 polypeptides described herein can be used in the methods of the invention to detect a variant PTPN11 gene. Alternatively, oligonucleotides sequences described herein may be used, e.g., to detect a mutation in a PTPN11 gene, or to amplify a PTPN11 nucleic acid (for example, a specific locus on a PTPN11 gene) having or suspected of having a mutation indicative of a cancer or precancerous condition such as a hematologic disorder.

As part of the present invention, methods to diagnose and/or treat cancer and precancerous conditions, including those originating from hematopoietic cells can use the nucleic acids, polypeptides and antibodies described herein. For example, methods are described for evaluate individuals for, JMML, MDS, ALL and AML, and other pre-cancerous and cancerous conditions, and for detecting a variant PTPN11 nucleic acid or polypeptide, such as the variants described herein. The methods can also evaluate individuals for cancer or precancerous conditions by detecting a gain-of-function PTPN11 mutant. In addition, the invention offers therapeutic methods for treating cancers, precancerous conditions, and myeloid disorders by administering a compound that modulates (e.g., enhances or inhibits) the expression or activity of either a PTPN11 nucleic acid (e.g., a PTPN11 gene) or a PTPN11 gene product (e.g., a PTPN11 polypeptide).

Based on the present invention, tools for the characterization, diagnosis and treatment planning of cancer, in particular cancers and pre-cancerous conditions that may be associated with up-regulation of the RAS-MAP kinase pathway by genetic perturbation of pathway components such as N-RAS, K-RAS, H-RAS, NF1, and, as shown herein, PTPN11, can be used. Such cancers include, but are not limited to, hematologic malignancies, e.g., JMML, ALL, and AML, as well as melanoma, hepatocellular carcinoma, and lung, colorectal, pancreatic, bladder, kidney, and thyroid cancers. The method of the invention can comprise, for example, characterizing a biological sample, e.g., a tumor biopsy, for mutations in and/or levels of PTPN11, as well as of other known markers or RAS-pathway components. In a preferred embodiment, in such a biological sample, the detection of an abnormal PTPN11 expression or activity, or the identification of a PTPN11 mutant, is mutually exclusive of the detection of a RAS or NF1 mutation.

In one embodiment, the presence of higher levels of PTPN11 or PTPN11 gain-of-function mutants in such a sample as compared to a control is indicative of a cancer or pre-cancerous condition treatable with PTPN11 inhibitory agents or agents decreasing the signaling flux downstream from PTPN11. In another embodiment, the presence of a higher level of PTPN11 and/or PTPN11 gain-of-function mutants are contra-indicative of a treatment regimen applying agents up-regulating PTPN11 signaling flux.

The present invention also contemplates the use of the novel MAMS/NRAS and KRAS2/KRAS2 mutations described herein (see Example 4 and Table 7) for making diagnostic, prognostic, and/or therapeutic tools for hematopoietic disorders, including acute leukemia. The same type of diagnostic, therapeutic, and screening methods, and the same type of production and design of antibodies and probes, described for PTPN11 in the present disclosure can, with appropriate modifications known by the skilled artisan to, be similarly applied for the identified ARAS and KRAS2 mutations.

The Examples provided herein show various aspects of the invention, including the association of PTPN11 with hematologic disorders and cancer. Example 1 shows the prevalence of mutations in PTPN11 in DNAs from children with JMML (with or without Noonan syndrome or pulmonic stenosis), MDS, or AML. Example 2 describes the characterization of mutant PTPN11 proteins. Example 3 describes the expression and analysis of a mutant Ptpn11 in Xenopus. Examples 4 describes the prevalence of PTPN11, NRAS, and KRAS2 mutations in childrens and adolescents with ALL or de novo AML.

Definitions a) Cancer: Cancer is a generic term for diseases in which abnormal cells divide without control and avoid natural cell death. These cells further invade nearby tissues and spread through the blood stream and lymphatic system to other parts of the body. As used herein, the term "cancer" encompasses metastatic and primary cancers, including solid tumors and non-solid tumors such as hematologic malignancies. Examples of solid tumors include sarcomas, carcinomas, and other tumors such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, thyroid cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias (e.g., JMML, AML, and ALL; especially B-cell precursor ALL), lymphomas, and multiple myelomas.

Preferably, although not necessarily, a cancer patient selected for characterization according to the present invention is a patient suffering from a cancer type in which, generally, a certain portion of patients exhibit mutations in either a RAS protein or NF1. In one embodiment, the detection of a PTPN11 gain-of-function mutant in a biological sample taken from the patient is mutually exclusive of the detection of a mutant RAS protein or mutant NF1, or otherwise abnormal expression of a RAS protein or NF1.

b) Precancerous conditions, pre-stages of cancer: A precancerous condition or pre-stage of a type of cancer is a condition associated with a risk of the condition turning into the particular type of cancer. The condition may be, for example, a genetic predisposition for the cancer, cellular or morphological changes in a tissue, also known as a "lesion", indicative of a pre-cancerous condition, or a gene mutation or mutations associated increased risk for the particular type of cancer. An exemplary, although non-limiting, pre-cancerous condition is myelodysplastic disorders (MDS). MDS are conditions in which the bone marrow shows qualitative and quantitative changes suggestive of preleukemic process. MDS may, although not necessarily, terminate as AML.

c) Hematologic Disorders: The term "hematologic disorders" herein encompasses conditions of abnormal growth and/or differentiation of cell lineages derived from pluripotent hematopoietic stem cells, i.e., the type of stem cells giving rise to granulocytes, monocytes, platelets and erythrocytes (from "myeloid stem cells") or lymphocytes (from "lymphoid stem cells"). These disorders include both cancerous and pre-cancerous conditions, such as, but not limited to, JMML, ALL, MDS and AML, which are all characterized by defective differentiation or maturation of a hematopoietic, including a myeloid or lymphoid, stem cell. Patients with "JMML and Noonan syndrome" or "JMML and PS" refers to individuals who display symptoms of both JMML and Noonan syndrome or pulmonic stenosis, respectively. Patients with "isolated" JMML or Noonan syndrome regards individuals who harbor the characteristics of only the respective condition. A hematologic disorder may be associated with a mutation, particularly a gain-of-function mutation of PTPN11.

"Characterizing a cancer/hematologic/myeloid/lymphoid disorder" according to the invention involves determining whether there is a mutation in PTPN11 and/or PTPN11. Such a characterization has implications for mode of therapy, prognosis, and can aid in a specific diagnosis.

d) PTPN11: "PTPN11" or "SHP-2", used interchangeably herein, also known as Syp, SHPTP2, PTP2C, PTP1D and BPTP3, is a member of the family of non-membrane tyrosine phosphatases and is ubiquitously expressed in all tissues examined, with higher levels of expression in the heart and the brain (Ahmad et al, Proc Natl Acad Sci USA 1993;90: 2197-2201; Bastien et al, Biochem Biophys Res Commun 1993;196:124-133; Freeman et al, Proc Natl Acad Sci USA, 1992;89:11239-11243). The function of the SH2 domain is to specifically recognize the phosphorylated state of tyrosine residues, thereby allowing PTPN11 to localize to tyrosine-phosphorylated sites.

In the context of the present invention, the PTPN11 gene encompasses a gene of human origin, comprising a coding nucleotide sequence set forth in SEQ ID NO:1, or homologs, including allelic variants and orthologs. The PTPN11 protein encompasses a PTPN11 protein of human origin having the amino acid sequence set forth in SEQ ID NO:2, or homologs, including orthologs thereof. As used herein, the term "PTPN11" in italicized form refers to a nucleotide sequence (genomic, cDNA, etc.), whereas the non-italicized form refers to a peptide or protein sequence.

FIG. 1 shows the organization of the PTPN11 gene and the functional domains of the PTPN11 protein. The PTPN11 protein comprises two SH2 (src-homology 2) domains, one from amino acid 3 to amino acid 104, the other from amino acid 112 to amino acid 216, and one PTP (protein tyrosine phosphatase) domain, from amino acid 221 to amino acid 524.

"PTPN11 variants" are PTPN11 genomic DNA, cDNA, or mRNA nucleic acids comprising at least one mutation, preferably a nucleotide substitution. The nucleotide substitution may be in a coding or non-coding region. Preferred PTPN11 variants are those resulting in the expression of higher levels of PTPN11 as compared to a control, and those encoding PTPN11 variants characterized by increased PTPN11 activity (i.e., "gain-of-function variants").

"PTPN11 variants" are PTPN11 proteins or polypeptides comprising at least one mutation. The PTPN11 variants can be function-conservative variants, including gain-of-function-variants, i.e., variants capable of increased PTPN11 activity, such as higher tyrosine phosphatase activity. The increase in PTPN11 activity includes, for example, increased phosphatase activity, prolonged activity of PTPN11, and a higher proportion of PTPN11 remaining in an active state (see below). This may be assessed either by direct measurement of PTPN11 activity or by measuring the activity of components regulated by PTPN11 activity. Preferred mutations are amino acid substitutions, in particular those described in FIG. 2 and Table 1.

PTPN11 plays a role in modulating cellular proliferation, differentiation and migration. Following ligand-induced receptor activation, PTPN11 is recruited through its SH2 domains directly by the receptor or indirectly via docking proteins. The C-terminal tail of PTPN11 also has tyrosine residues that can become phosphorylated, providing SH2 binding sites for other proteins. Thus, PTPN11 may act as a phosphatase and as an adapter molecule with docking function, both functions being relevant in signal transduction. Depending on the specific signaling pathway, PTPN11 can act as either a positive or negative regulator of ERK, Jnk kinase, Jak/STAT, and NF-κB cascades (Saxton, et al, EMBO J.,1997; 16:2352-2364; Shi et al, J. Biol. Chem., 1998;273: 4904-4908; You et al, Mol. Cell. Biol., 1999;19:2416-2424; Maroun et al, Mol. Cell. Biol., 2000;20:8513-8525; You et al, J. Exp. Med., 2001;193:101-110). These various roles of PTPN11, as described herein, are also referred to as "functions" or "activities" of the protein.

An "increased activity" of PTPN11 in a test subject or a biological sample refers to a higher total PTPN11 activity in the test subject or biological sample in comparison with a control, e.g., a healthy subject or a standard sample. Preferably, although not necessarily, the activity is at least 10%, more preferably at least 50%, even more preferably at least 100%, and still more preferably at least 150% higher in the test subject or sample than in the control. The increased activity may results from increased basal PTPN11 activity, prolonged stimulation of a downstream component (e.g., ERK2) of an otherwise unperturbed PTPN11-associated pathway, and a higher PTPN11 expression level.

Basal level of PTPN11 activity is dependent on the conformation of the protein. Wild-type PTPN11 exists in an inactive (I) or an active (A) conformation, with the N-SH2 domain acting as a molecular switch. In the I state, N-SH2 assumes a conformation that blocks the PTP active site and disrupts its own, separate phosphopeptide-binding cleft. On binding of phosphopeptide, the N-SH2 domain assumes the A conformation that disrupts its PTP recognition surface. Without being bound to any specific theory, it is believed that mutations in PTPN11 provided in Table 1 herein could result in destabilization of the I state, favoring the A state.

A higher expression level of wild-type or variant PTPN11 may result from, for example, a mutation in a non-coding region of a PTPN11 gene or a mutation in a coding or non-coding gene involved in PTPN11 transcription or translation. The expression level of PTPN11 can be determined, for example, comparing PTPN11 mRNA or level of PTPN11 protein in a test subject as compared to a control.

e) Signal Transduction Pathways: PTPN11 participates in signaling cascades elicited by a number of growth factors, cytokines and hormones (Feng, Exp. Cell Res. 1999;253:47-54; Stein-Gerlach et al, Int. J. Biochem. Cell. Biol. 1998;30: 559-566; Tamir, et al, Curr. Opin. Immunol., 2000;12:307-315). Much of what is known of the PTPN11 pathway in humans derives from studies of its Drosophila homologue, "corkscrew" (csw), as well as from transgenic mice studies (Van Vactor et al., Curr Opin Genetics Development 1998;8: 112-126). For example, PTPN11 (SHP-2) has been implicated in regulating fibroblast growth factor receptor (FGFR) and platelet-derived growth factor receptor (PDGFR) signaling and Dos-like scaffolding proteins in several mammalian signaling pathways, including the insulin and IGF1R pathways.

A preferred "PTPN11 signaling pathway" is the RAS-MAP kinase or "RAS-to-MAPK" pathway (ERK1/2). Briefly, transmission of the stimulatory signals from Ras to nuclear targets involves regulation of the family of kinases known as MAPKs ("mitogen-activated protein kinases") or ERKs ("extracellular signal regulated kinases"). This pathway includes, but is not limited to, components such as PTPN11 and ERK2. Additional components of this pathway have been identified and described (see, e.g., Lee and McCubrey, Leukemia 2002; 16:486-507), its role with respect to RAS mutations in certain types of cancers have recently been reviewed (Macaluso et al., J Cell Physiol 2002; 192; 125-130). A portion of the pathway, termed the RAF/MEK/ERK signal transduction cascade (downstream from Ras) and its involvement in leukemia has also recently been reviewed (Lee et al., Leukemia 2002; 16:486-507).

The classical RAS-to-MAPK comprises signaling induced by both cytokine receptors and receptor tyrosine kinases. As outlined by Reuter et al. (Blood 2000;96:1655-1669; see, especially, FIG. 4 in Reuter et al.), in the case of cytokine receptors, after ligand binding, the α- and β-subunits of IL-3, IL-5, and GM-CSF receptors are thought to dimerize, thus activating the receptor-bound NRTKs and causing a cascade of tyrosine phosphorylations. The phosphotyrosine residues represent docking sites for various signaling molecules, including PTPN11 (SHP-2). ERKs are activated by RAS via RAF and MEK, and the MAPKs p38 and JNK are believed to become activated by mechanisms involving RAS or HPK-1 (hematopoietic progenitor kinase, a mammalian Ste20-related protein). Activated JAK2 phosphorylates nuclear factors which, in turn, translocate to the nucleus and activate the promoter region of various genes.

An "upregulation" or "increased activity" of a signaling pathway such as the PTPN11 or RAS-MAPK pathway herein means a detectable change in signaling flux or output of the pathway that could also result from a gain-of-function PTPN11 mutant. Preferred examples of output signals include, but are not limited to, an increased PTPN11 phosphatase activity or increased ERK2 kinase activity.

Molecular Biology Terms

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein ASambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

The terms "polypeptide" and "protein" may be used herein interchangeably to refer to the gene product (or corresponding synthetic product) of a PTPN11 gene. The term "protein" may also refer specifically to the polypeptide as expressed in cells.

A "gene" is used herein to refer to a portion of a DNA molecule that includes a polypeptide coding sequence operatively associated with expression control sequences. Thus, a gene includes both transcribed and untranscribed regions. The transcribed region may include introns, which are spliced out of the mRNA, and 5'- and 3'-untranslated (UTR) sequences along with protein coding sequences. In one embodiment, the gene can be a genomic or partial genomic sequence, in that it contains one or more introns. In another embodiment, the term gene may refer to a cDNA molecule (i.e., the coding sequence lacking introns). In yet another embodiment, the term gene may refer to expression control sequences, such as the promoter or the enhancer sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease SI), as well as protein binding domains (consensus sequences) responsible for the binding of RNA polymerase.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide.

Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "variant" also includes a polypeptide or enzyme which has at least 60% amino acid identity as determined by BLAST or FASTA algorithms, preferably at least 75%, most preferably at least 85%, and even more preferably at least 90%, 91%, 92%, 93%, 94%, 95%, 96%, 97%, 98%, or 99%, and which has the same or substantially similar properties or functions as the native or parent protein or enzyme to which it is compared. A particular variant is a "gain-of-function" variant, meaning a polypeptide variant in which the change of at least one given amino acid residue in a protein or enzyme improves a specific function of the polypeptide, including, but not limited to, protein activity. The change in amino acid residue can be replacement of an amino acid with one having similar properties (such as, for example, polarity, hydrogen bonding potential, acidic, basic, hydrophobic, aromatic, and the like), or different properties.

An amino acid residue in a given polypeptide is said to "correspond to" a residue in another polypeptide (typically referred to as a "reference polypeptide") when the residues align with each other in a routine sequence alignment. Such alignments can be readily determined or otherwise obtained, e.g., by using a sequence alignment scheme, such as, e.g., the Cluster method or MEGALIGN, or the ClustalW alignment program available at the European Bioinformatics Institute (EMBL-EBI) world-wide web site ebi.ac.uk/clustalw), using the default settings of the program or the settings recommended by the manufacturer of the program used. In the particular context where a specific amino acid is disclosed to be at a specific position in a reference polypeptide (e.g., Gly53), the amino acid at the "corresponding" position in the other polypeptide aligns with the position in the first polypeptide, and has similar properties as the amino acid at the aligned position (e.g., Val, Leu, or Ile), or is the same type of amino acid (e.g., Gly). The same approach can be used to identify nucleotide positions that "correspond" or are "corresponding" to each other in different nucleic acid or oligonucleotide sequences or in variants or fragments of the same sequences.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 1987;50:667). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or at least 95%) of the nucleotides match over the defined length of the DNA sequences, as determined by sequence comparison algorithms, such as BLAST, FASTA, DNA Strider, etc. An example of such a sequence is an allelic or species variant of the PTPN11 gene. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80%, 90%, 91%, 92%, 93%, 94%, 95%, 96%, 97%, 98%, or 99% of the amino acids are identical, or greater than about 90%, 91%, 92%, 93%, 94%, 95%, 96%, 97%, 98%, or 99% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

The terms "mutant" and "mutation" mean any detectable change in genetic material, e.g., DNA, or any process, mechanism, or result of such a change. When compared to a control material, such change may be referred to as an "abnormality". This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Amplification" of DNA as used herein encompasses the use of polymerase chain reaction (PCR) to increase the concentration of a particular DNA sequence within a mixture of DNA sequences. For a description of PCR see Saiki et al., Science 1988;239:487.

"Sequencing" of a nucleic acid incldudes chemical or enzymatic sequencing. "Chemical sequencing" of DNA denotes methods such as that of Maxam and Gilbert (Maxam-Gilbert sequencing, Maxam and Gilbert, Proc. Natl. Acad. Sci. USA 1977;74:560), in which DNA is randomly cleaved using individual base-specific reactions. "Enzymatic sequencing" of DNA denotes methods such as that of Sanger (Sanger et al., Proc. Natl. Acad. Sci. USA 1977;74:5463), in which a single-stranded DNA is copied and randomly terminated using DNA polymerase, including variations thereof, which are well-known in the art. Preferably, oligonucleotide sequencing is conducted using automatic, computerized equipment in a high-throughput setting, for example, microarray technology, as described herein. Such high-throughput equipment are commercially available, and techniques well known in the art.

The term "polymorphism" refers, generally, to the coexistence of more than one form of a gene (e.g., more than one allele) within a population of individuals. The different alleles may differ at one or more positions of their nucleic acid sequences, which are referred to herein as "polymorphic locuses". When used herein to describe polypeptides that are encoded by different alleles of a gene, the term "polymorphic locus" also refers to the positions in an amino acid sequence that differ among variant polypeptides encoded by different alleles. Polymorphisms include "single nucleotide polymorphisms" (SNPs), referring to a polymorphic site occupied by a single nucleotide, which is the site of variation between allelic sequences. Typically, the polymorphic site of an SNP is flanked by highly conserved sequences (e.g., sequences that vary in less than 1/100 and, more preferably, in less than 1/1000 individuals in a population). The polymorphic locus of an SNP may be a single base deletion, a single base insertion, or a single base substitution. Single base substitutions are particularly preferred.

As used herein, "sequence-specific oligonucleotides" refers to related sets of oligonucleotides that can be used to detect variations or mutations in the PTPN11 gene.

A "probe" refers to a nucleic acid or oligonucleotide that forms a hybrid structure with a sequence in a target region due to complementarity of at least one sequence in the probe with a sequence in the target protein.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of PTPN11, or to detect the presence of nucleic acids encoding PTPN11. In a further embodiment, an oligonucleotide of the invention can form a triple helix with a PTPN11 DNA molecule. In still another embodiment, a library of oligonucleotides arranged on a solid support, such as a silicon wafer or chip, can be used to detect various mutations of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Specific non-limiting examples of synthetic oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—N(CH)$_3$—O—$CH_2$, $CH_2$—O—N(CH)$_3$—$CH_2$, $CH_2$—$N(CH)_3$—$N(CH)_3$—$CH_2$ and O—$N(CH)_3$—$CH_2$—$CH_2$ backbones (where the phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from $_1$ to about $_{10}$; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; SOCH3; $SO_2$CH3; $ONO_2$;$NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

The present invention provides antisense nucleic acids (including ribozymes), which may be used to inhibit expression of PTPN11. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes, RNAi (i.e., RNA interference, see below) and RNase-H mediated arrest. Antisense nucleic acid molecules can be encoded by a recombinant gene for expression in a cell (e.g., U.S. Pat. No. 5,814, 500; U.S. Pat. No. 5,811,234), or alternatively they can be prepared synthetically (e.g., U.S. Pat. No. 5,780,607). Synthetic oligonucleotides are suitable for antisense use. The term "RNA interference" or "RNAi" refers to the ability of double stranded RNA (dsRNA) to suppress the expression of a specific gene of interest in a homology-dependent manner. It is currently believed that RNA interference acts post-transcriptionally by targeting mRNA molecules for degradation. RNA interference commonly involves the use of dsRNAs that are greater than 500 bp; however, it can also be mediated through small interfering RNAs (siRNAs) or small hairpin RNAs (shRNAs), which are typically greater than 18 nucleotides in length. For reviews, see Bosner and Labouesse, *Nature Cell Biol.* 2000; 2: E31-E36 and Sharp and Zamore, *Science* 2000; 287: 2431-2433.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.

The term "linkage" refers to the tendency of genes, alleles, loci or genetic markers to be inherited together as a result of their location on the same chromosome. Linkage may be measured, e.g., by the percent recombination between two genes, alleles, loci or genetic markers.

PTPN11

PTPN11 is a member of a small subfamily of cytoplasmic, SH2-domain-containing protein tyrosine phoshatases that control cellular proliferation and differentiation (Feng, Exp Cell Res 1999;253:47-54; Tartaglia et al., Nat genet 2001;29: 465-68; Tartaglia et al., Am J Hum Genet 2002;70: 1555-63). It is a key molecule in intracellular signaling and is necessary for activation of the RAS/MAPK cascade in response to a variety of growth factors, hormones and cytokines (Maroun et al., Mol Cell Biol 2000;20:8513-25; Shi Z-Q, et al., Mol Cell Biol 2000; 20:1526-1536; Cunnick et al., J Biol Chem 2002; 277:9498-504). PTPN11 is widely expressed and is required during embryogenesis for mesodermal patterning (Tang et al., Cell 1995;80:473-483), semilunar valvuogenesis (Chen et al., Nat Genet 2000;24:296-9) and skeletal and limb development (Qu et al., Mol Cell Biol 1998;18:6075-82; Saxon et al., Nat Genet 2000;24:420-3). Loss of murine Shp-2 severely suppresses development of erythroid/myeloid and lymphoid cell progenitors, (Qu et al., Mol Cell Biol 1998;18:6075-82; Qu et al., Mol Cell Biol 1997;17:5499-507; Qu et al., Blood 2001;97:911-4), suggesting that it participates in early events during hematopoetic stem/progenitor cell commitment and differentiation. PTPN11 also controls cell differentiation at later stages of hematopoiesis, and has a role in the function of differentiated erythroid, myeloid and lymphoid cells (Pazdrak et al., J Exp Med 1997;186:561-8; Edmead et al., FEBS Lett 1999;459:27-32; Ohtani et al., Immunity 2000;12: 95-105; Tamir et al., Curr Opin Immunol 2000;12:307-15; Bordin et al., Blood 2002; 100:276-82). These effects appear to be mediated through signal relay downstream of receptors for a number of hematopoietic growth factors and cytokines, including GM-CSF (Pazdrak et al., J Exp Med 1997;186:561-8; Welham et al., J Biol Chem 1994;269:23764-8; Tauchi et al., J Biol Chem 1995;270:5631-5; Tauchi et al., J Biol Chem 1994;269:25206-1138; Ward et al., Biochem Biophys Acta 1998;1448:70-6; Lecoq-Lafon et al., Blood 1999;93:2578-85; You et al., J exp Med 2001;193:101-10).

The PTPN11 gene organization and intron boundary sequence can be established using cDNA (GENBANK Accession Nos. NM_002834; nucleotide and amino acid sequences represented herein as SEQ ID NOS:1 and 2, respectively) and genomic sequences ( GENBANK Accession No. NT_009770, residues 3,000,001-3,300,000 of which represented herein as SEQ ID NO:33; Bacterial Artificial Chromosome (BAC) clone RP3-329E11).

The genomic sequence of PTPN11, is organized as follows (residues referring to SEQ ID NO:33): Exon 1, residues 123211-123604; Exon 2, residues 136831-136953; Exon 3, residues 194431-194625; Exon 4, residues 197308-197500; Exon 5, residues 198677-198793; Exon 6, residues 200063-200176; Exon 7, residues 217057-217153; Exon 8, residues 221764-221843; Exon 9, residues 221970-222128; Exon 10, residues 226187-226318; Exon 11, residues 230588-230742; Exon 12, residues 232556-232623; Exon 13, residues 233 137-233288; Exon 14, residues 246257-246369; Exon 15, 248808-248909; Exon 16, residues 249938-250510. The adenine nucleotide of the start codon "ATG" is located at residue No. 123591 of SEQ ID NO:33. A partial genomic sequence is also provided by GENBANK Accession No. AC004086.

Expression of PTPN11 Polypeptides

A nucleotide sequence coding for PTPN11, for an antigenic fragment, derivative or analog of PTPN11, of for a functionally active derivative of PTPN11 (including a chimeric protein) may be inserted into an appropriate expression vector, i.e., a vector which contains the necessary elements for the transcription and translation of the inserted protein-coding sequence. Thus, a nucleic acid encoding a PTPN11 polypeptide of the invention can be operationally associated with a promoter in an expression vector of the invention. Both cDNA and genomic sequences can be cloned and expressed under control of such regulatory sequences. Such vectors can be used to express functional or functionally inactivated PTPN11 polypeptides. In particular, the PTPNL1 nucleic acids which may be cloned and expressed according to these methods include, not only wild-type PTPN11 nucleic acids, but also mutant or variant PTPN11 nucleic acids. These include, for example, a PTPN11 nucleic acid having one or more of the mutations or polymorphisms set forth in Table 1. In addition, nucleic acids that encode a variant PTPN11 polypeptide, for example a variant PTPN11 polypeptide comprising one or more of the amino acid substitutions listed in Table 1 may be cloned and expressed according to the methods described here.

The necessary transcriptional and translational signals can be provided on a recombinant expression vector. Potential host-vector systems include but are not limited to mammalian cell systems transfected with expression plasmids or infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Expression of a PTPN11 protein may be controlled by any promoter/enhancer element known in the art, but these regulatory elements must be functional in the host selected for expression. Promoters which may be used to control PTPN11 gene expression include, but are not limited to, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. U.S.A. 1981, 78:1441-1445), the regulatory sequences of the metallothionein gene (Brinster et al., Nature 1982;296:3942); prokaryotic expression vectors such as the β-lactamase promoter (Villa-Komaroff et al., Proc. Natl. Acad. Sci. U.S.A. 1978;75:3727-3731), or the tac promoter (DeBoer et al., Proc. Natl. Acad. Sci. U.S.A. 1983;80:21-25); see also "Useful proteins from recombinant bacteria" in Scientific American 1980;242:74-94. Still other useful promoter elements which may be used include promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 1985;315:338-340; Kollias et al., Cell 1986;46:89-94), hematopoietic stem cell differentiation factor promoters, erythropoietin receptor promoter (Maouche et al., Blood 1991;15:2557), etc.

Soluble forms of the protein can be obtained by collecting culture fluid, or solubilizing-inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2 dimensional gel electrophoresis, chromatography (e.g., ion exchange, affinity, immunoaffinity, and sizing column chromatography), centrifugation, differential solubility, immunoprecipitation, or by any other standard technique for the purification of proteins.

A wide variety of host/expression vector combinations may be employed in expressing the DNA sequences of this invention. Useful expression vectors, for example, may consist of segments of chromosomal, non chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 1988;67:31-40), pCR2.1 and pcDNA 3.1+(Invitrogen, Carlsbad, Calif.), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Preferred vectors are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant PTPN11 protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures (see below), as well as in vitro expression, are DNA-based vectors and retroviral vectors. Methods for constructing and using viral vectors are known in the art (see, e.g., Miller and Rosman, BioTechniques 1992;7:980-990). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or can be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), baculovirus, and the like. RNA viral vectors include, for example, retroviruses, lentiviruses, and alphaviruses (e.g., Sindbis virus and Venezuelan Equine Encephalitis virus), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991;2:320-330), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 1992;90:626-630; see also La Salle et al., Science 1993;259:988-990); and a defective adeno-associated virus vector (Samulski et al., J. Virol. 1987;61:3096-3101; Samulski et al., J. Virol. 1989;63:3822-3828; Lebkowski et al., Mol. Cell. Biol. 1988;8:3988-3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), Transgene (Strasbourg, France; adenoviral, vaccinia, retroviral, and lentiviral vectors) and Invitrogen (Carlbad, Calif.).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner et al., Proc. Natl. Acad. Sci. U.S.A. 1987;84:7413-7417; Felgner and Ringold, Science 1989;337:387-388; Mackey et al., Proc. Natl. Acad. Sci. U.S.A. 1988;85:8027-8031; Ulmer et al., Science 1993;259:1745-1748). Useful lipid compounds and compositions for transfer of nucleic acids are described in International Patent Publications WO 95/18863 and WO 96/17823, and in U.S. Pat. No. 5,459,127. Lipids may be chemically coupled to other molecules for the purpose of targeting (see, Mackey et al., Proc. Natl. Acad. Sci. U.S.A. 1988;85:8027-8031). Targeted peptides, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce the vector in vivo as a naked DNA plasmid. Naked DNA vectors for gene therapy can be introduced into the desired host cells by methods known in the art; e.g., electroporation, microinjection, cell fusion, DEAE dextran, calcium phosphate precipitation, use of a gene gun, or use of a DNA vector transporter (see, e.g., Wu et al., J. Biol. Chem. 1992;267:963-967; Wu and Wu, J. Biol. Chem. 1988;263:14621-14624; Hartmut et al., Canadian Patent Application No. 2,012,311, filed Mar. 15, 1990; Williams et al., Proc. Natl. Acad. Sci. U.S.A. 1991;88:2726-2730). Receptor-mediated DNA delivery approaches can also be used (Curiel et al., Hum. Gene Ther. 1992;3:147-154; Wu and Wu, J. Biol. Chem. 1987;262:4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci. 1998;321:893; WO 99/01157; WO99/01158; WO 99/01175).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nat. Med. 1995;1:887-889). In that regard, it is advantageous to employ a viral vector that is engineered to express a minimal number of antigens.

Diagnostic Methods

According to the present invention, mutated forms of PTPN11 can be detected to diagnose cancer and precancerous conditions, including those originating from myeloid cells. As used herein, "diagnostic methods" include both diagnostic and prognostic methods, i.e., methods of providing a prognosis of potential therapeutic outcome or severity of the cancer or pre-cancerous condition.

Accordingly, diagnostic methods may comprise, for example, detecting a mutation in a PTPN11 gene, wherein the mutation results in increased PTPN11 activity. The mutation may especially affect a coding region of the gene, such as a region of the PTPN11 gene that encodes a SH2 (src-homology 2) domain of the PTPN11 protein, or a region of the PTPN11 gene that encodes a PTP (phosphotyrosine phosphatase) domain of the PTPN11 protein. The mutation may be a missense mutation, preferably a missense mutation resulting in nucleic acid substitution, or a deletion, or a combination of both. Preferably, especially in the case of myeloid disorders, the mutation results in an amino acid substitution set forth in Table 1. Most preferably, the nucleotide substitutions are selected from the ones described in Table 1.

The diagnostic methods of the invention also encompass detecting a mutation in PTPN11 protein, in particular a mutation that results in increased activity or function of the PTPN11 protein. The mutation is preferably an amino acid substitution. More preferably, the mutation is in the SH2 (src-homology 2) domain of the PTPN11 protein, including the N-SH2 and C-SH2 domains, the domain between the N-SH2 and C-SH2 domain, or the PTP (phosphotyrosine phosphatase) domain of the PTPN11 protein. Preferred, although non-limiting, amino acid substitutions are set forth in Table 1. In a particular embodiment, no mutation in a RAS protein or NF1 is detected.

In a further embodiment, the diagnosis or characterization of a cancer or precancerous condition such as a myeloid disorder in a subject comprises assessing the level of expression or activity of PTPN11 protein in the test subject and comparing it to the level of expression or activity in a control subject, wherein an increased expression and/or activity of the PTPN11 protein in the test subject compared to the control subject is indicative of a cancer or precancerous condition. In a preferred embodiment, the subject is also tested for RAS or NF1 expression or activity.

The level of expression of PTPN11 may be assessed by determining the amount of mRNA that encodes the PTPN11 protein in a biological sample, or by determining the concentration of PTPN11 protein in a biological sample. The level of PTPN11 protein or activity may be assessed by determining the level of phosphatase activity in a sample or subject, as described herein.

The invention also provides kits for performing these diagnostic methods. A particular subject of the invention is a kit for diagnosing different types of cancers or precancerous conditions, especially those deriving from myeloid cells, comprising an oligonucleotide that specifically hybridizes to a site harboring a mutation of the PTPN11 gene, or an adjacent site, wherein the mutation results in increased basal activity of the PTPN11 protein. The site of mutation may particularly comprise a nucleotide selected from the group consisting of nucleotides 172, 179, 181, 182, 184, 205, 211, 212, 213, 214, 215, 218, 226, 227, 1471, 1472, 1504, 1507, 1508, 1520, and 1528 of SEQ ID NO:1, or any nucleotide recited in Table 1, as described below. A further subject of the invention is a kit for diagnosing a cancer or pre-cancerous condition, including a cancerous or pre-cancerous myeloid disorder, comprising an antibody that specifically recognizes a mutated form of PTPN11 protein that results in increased basal activity of the protein.

As used herein, the term "diagnosis" refers to the identification of the disease at any stage of its development, and also includes the determination of a predisposition of a subject to develop the disease. Importantly, the invention permits, in part, testing for precancerous conditions, including pre-leukemic conditions, occurring in a subject. The diagnostic method of the invention is also envisioned in, but not restricted to, screening individuals for the potential of different types of cancers such as ALL, JMML, AML, as well as lung, colon, and bladder cancer, melanoma, and leukemia.

"Prognosis" refers to predicting the course or severity of the disease or condition. For example, if the disease or condition is associated with a PTPN11 gain-of-function mutation, there is a better prognosis if therapy to inhibit PTPN11 activity is instituted. Also, the identification of a somatic PTPN11 mutation can indicate a more severe form of a disease than a germ-line mutation.

The term "biological sample" refers to any cell source from which DNA may be obtained. Non-limiting examples of cell sources available in clinical practice include without limitation blood cells, buccal cells, cervicovaginal cells, epithelial cells from urine, fetal cells, or any cells present in tissue obtained by biopsy. Cells may also be obtained from body fluids, including without limitation blood, plasma, serum, lymph, milk, cerebrospinal fluid, saliva, sweat, urine, feces, and tissue exudates (e.g., pus) at a site of infection or inflammation. For prenatal testing, genetic material can be obtained from fetal cells, e.g., from amniotic fluid (through amniocentesis), chronic villi, blood, or any tissue of a pregnant woman. DNA is extracted using any of the numerous methods that are standard in the art. It will be understood that the particular method used to extract DNA will depend on the nature of the source. Generally, the minimum amount of DNA to be extracted for use in the present invention is about 25 pg (corresponding to about 5 cell equivalents of a genome size of $4\times10^9$ base pairs). Various methods for detecting mutated forms of PTPN11 are described herein.

The present invention especially contemplates detecting abnormalities, i.e., mutations in the PTPN11 gene that result in an increased basal activity of the PTPN11 protein, render the protein in a constitutively active conformation, provides prolonged increased PTPN11 activity, or increases the level of expressed PTPN11 protein.

Figure 9:
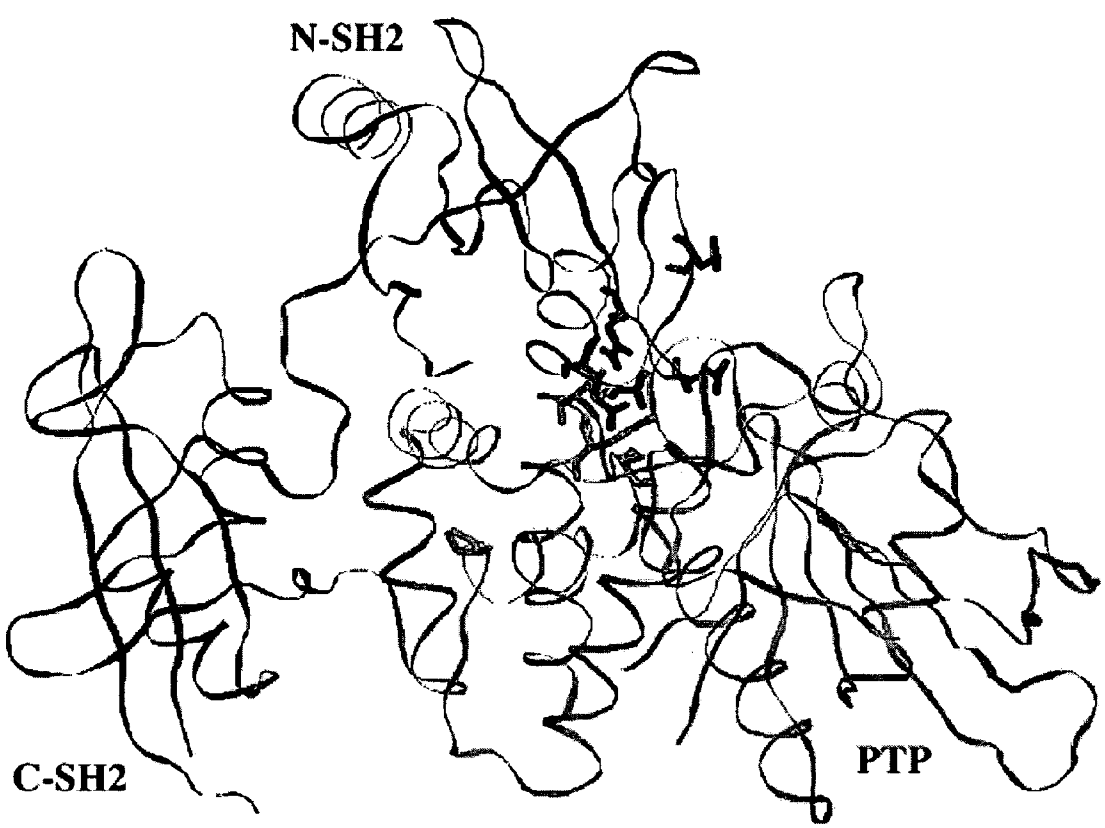
FIG. 9 shows location of residues mutated in childhood acute leukemia (A) and SHP-2 domain organization (B). CaL trace of N-SH2, C-SH2 and PTP domains, and N-SH2/C-SH2 and C-SH2/PTP linkers of the catalytically inactive conformation of SHP-2 (Hoff et al., 1998). Mutated residues are indicated with their side chains as sticks: N-SH2 residues (G58, D61, E69, A72 and E76); PTP (P491, S502; T507 and N510) residues. The numbers below the domain structure indicate the amino acid boundaries of those domains. Dots above the domain structure refer to number of cases with mutations documented as described herein. See Example 6.

Mutations may include an insertion in the gene, a truncation of or deletion in the gene, a nonsense mutation, a frameshift mutation, a splice-site mutation, and a missense mutation. Such mutations can occur in the coding region of the PTPN11 gene, more particularly in any of the functional domains, as well as in the untranslated regions, more particularly in the promoter or enhancer regions. Preferred mutations are missense mutations resulting in amino acid substitutions. Specific mutations observed in different types of myeloid disorders are listed in Table 1. Any one of these mutations may, according to the present invention, occur in any hematologic disorder, including myeloid or lymphoid cancer and pre-cancerous conditions, particularly any of JMML, AML, ALL, and MDS. See, also, Table 4, 5, 6, and 7, and FIGS. 2 and 9.

TABLE 1

Mutations in PTPN11 Gene in Myeloid Disorders. The nucleotide and amino acid substitutions refer to SEQ ID NOS: 1 or 2, respectively.

| Nucleotide Substitution | Exon | Predicted Amino Acid Substitution | Functional Domain | Observed Condition |
|---|---|---|---|---|
| A172T | 3 | Asn58Tyr | N-SH2 | ALL |
| G179T | 3 | Gly60Val | N-SH2 | MDS |
| G181T | 3 | Asp61Tyr | N-SH2 | ALL, JMML |
| A182T | 3 | Asp61Val | N-SH2 | ALL, JMML, MDS |
| T184G[a] | 3 | Tyr62Asp | N-SH2 | JMML |
| G205A | 3 | Glu69Lys | N-SH2 | ALL, JMML, MDS |
| TTT(211-213)AAA | 3 | Phe71Lys | N-SH2 | AML |
| T213A | 3 | Phe71Leu | N-SH2 | MDS |
| G214A | 3 | Ala72Thr | N-SH2 | ALL, JMML, AML |
| C215T | 3 | Ala72Val | N-SH2 | ALL, JMML |
| C215A | 3 | Ala72Asp | N-SH2 | ALL |
| C218T[b] | 3 | Thr73Ile | N-SH2 | JMML |
| G226A | 3 | Glu76Lys | N-SH2 | ALL, JMML, AML |
| G226C | 3 | Glu76Gln | N-SH2 | ALL |
| A227T | 3 | Glu76Val | N-SH2 | JMML |
| A227G | 3 | Glu76Gly | N-SH2 | ALL, JMML |
| A227C | 3 | Glu76Ala | N-SH2 | JMML, MDS |
| C1471T | 13 | Pro491Ser | PTP | ALL |
| C1472T | 13 | Pro491Leu | PTP | ALL |
| T1504C | 13 | Ser502Pro | PTP | ALL |
| G1507C[a] | 13 | Gly503Arg | PTP | JMML |
| G1508C | 13 | Gly503Ala | PTP | JMML |
| C1520A | 13 | Thr507Lys | PTP | AML |
| C1528A | 13 | Gln510Lys | PTP | ALL |

[a]Mutation found in JMML patients with NS
[b]Mutation found in JMML patients with NS or PS

Nucleic Acid Based Assays

According to the invention, mutated forms of PTPN11 nucleic acids, i.e. in the PTPN11 DNA or in its transcripts, as well as a deregulated expression, e.g. over-expression of PTPN11, can be detected by a variety of suitable methods.

Standard methods for analyzing the nucleic acid contained in a biological sample and for diagnosing or characterizing a genetic perturbation can be employed, and many strategies for genotypic analysis are known to those of skilled in the art.

In a preferred embodiment, the determination of mutations in the PTPN11 gene encompasses the use of nucleic acid sequences such as specific oligonucleotides, to detect mutations in. PTPN11 genomic DNA or mRNA in a biological sample. Such oligonucleotides may be specifically hybridize to a site of mutation, or to a region adjacent to this site of mutation present in a PTPN11 nucleic acid. One may also employ primers that permit amplification of all or part of PTPN11. Alternatively, or in combination with such techniques, oligonucleotide sequencing described herein or known to the skilled artisan can be applied to detect the PTPN11 mutations.

One skilled in the art may use hybridization probes in solution and in embodiments employing solid-phase procedures. In embodiments involving solid-phase procedures, the test nucleic acid is adsorbed or otherwise affixed to a selected matrix or surface. The fixed, single-stranded nucleic acid is then subjected to specific hybridization with selected probes.

In another embodiment, one skilled in the art may use oligonucleotide primers in an amplification technique, such as PCR or reverse-PCR ("reverse polymerase chain reaction"), to specifically amplify the target DNA or mRNA, respectively, that is potentially present in the biological sample.

Useful oligonucleotides include primers that permit amplification of PTPN11 exons, such as:

```
Exon 1:
Forward primer:  5'-GCTGACGGGAAGCAGGAAGTGG-3'      (SEQ ID NO:3)

Reverse primer:  5'-CTGGCACCCGTGGTTCCCTC-3'        (SEQ ID NO:4)

Exon 2:
Forward primer:  5'-ACTGAATCCCAGGTCTCTACCAAG-3'    (SEQ ID NO:5)

Reverse primer:  5'-CAGCAAGCTATCCAAGCATGGT-3'      (SEQ ID NO:6)

Exon 3:
Forward primer:  5'-CGACGTGGAAGATGAGATCTGA-3'      (SEQ ID NO:7)

Reverse primer:  5'-CAGTCACAAGCCTTTGGAGTCAG-3'     (SEQ ID NO:8)

Exon 4:
Forward primer:  5'-GATTGATCAATCCCTTGGAGGAATG-3'   (SEQ ID NO:9)

Reverse primer:  5'-GTCACCAGACCCAACGTGGTG-3'       (SEQ ID NO:10)

Exon 5:
Forward primer:  5'-CTGCAGTGAACATGAGAGTGCTTG-3'    (SEQ ID NO:11)

Reverse primer:  5'-GTTGAAGCTGCAATGGGTACATG-3      (SEQ ID NO:12)

Exon 6:
Forward primer:  5'-TGCATTAACACCGTTTTCTGT-3'       (SEQ ID NO:13)

Reverse primer:  5'-GTCAGTTTCAAGTCTCTCAGGTC-3'     (SEQ ID NO:14)

Exon 7:
Forward primer:  5'-GAACATTTCCTAGGATGAATTCC-3'     (SEQ ID NO:15)

Reverse primer:  5'-GGTACAGAGGTGCTAGGAATCA-3'      (SEQ ID NO:16)

Exon 8:
Forward primer:  5'-GACATCAGGCAGTGTTCACGTTAC-3'    (SEQ ID NO:17)

Reverse primer:  5'-CCTTAAAGTTACTTTCAGGACATG-3'    (SEQ ID NO:18)

Exon 9:
Forward primer:  5'-GTAAGCTTTGCTTTTCACAGTG-3'      (SEQ ID NO:19)

Reverse primer:  5'-CTAAACATGGCCAATCTGACATGTC-3'   (SEQ ID NO:20)

Exon 10:
Forward primer:  5'-GCAAGACTTGAACATTTGTTTGTTGC-3'  (SEQ ID NO:21)

Reverse primer:  5'-GACCCTGAATTCCTACACACCATC-3'    (SEQ ID NO:22)

Exon 11:
Forward primer:  5'-CAAAAGGAGACGAGTTCTGGGAAC-3'    (SEQ ID NO:23)

Reverse primer:  5'-GCAGTTGCTCTATGCCTCAAACAG-3'    (SEQ ID NO:24)

Exon 12:
Forward primer:  5'-GCTCCAAAGAGTAGACATTGTTTC-3'    (SEQ ID NO:25)

Reverse primer:  5'-GACTGTTTTCGTGAGCACTTTC-3'      (SEQ ID NO:26)

Exon 13:
Forward primer:  5'-CAACACTGTAGCCATTGCAACA-3'      (SEQ ID NO:27)

Reverse primer:  5'-CGTATCCAAGAGGCCTAGCAAG-3'      (SEQ ID NO:28)
```

-continued

```
Exon 14:
Forward primer:  5'-ACCATTGTCCCTCACATGTGC-3'      (SEQ ID NO:29)

Reverse primer:  5'-CAGTGAAAGGCATGTGCTACAAAC-3'   (SEQ ID NO:30)

Exon 15:
Forward primer:  5'-CAGGTCCTAGGCACAGGAACTG-3'     (SEQ ID NO:31)

Reverse primer:  5'-ACATTCCCAAATTGCTTGCCT-3'      (SEQ ID NO:32)
```

The present invention is more particularly directed to a method of in vitro diagnosis or characterization of different types of cancer or pre-cancerous conditions, including those deriving from myeloid cells, comprising the steps of:

contacting a biological sample containing DNA with specific oligonucleotides permitting the amplification of all or part of the PTPN11 gene, the DNA contained in the sample having being rendered accessible, where appropriate, to hybridization, and under conditions permitting a hybridization of the primers with the DNA contained in the biological sample;

amplifying the DNA;

detecting the amplification products;

comparing the amplified products as obtained to the amplified products obtained with a normal control biological sample, and thereby detecting a possible abnormality in the PTPN11 gene.

The method of the invention can also be applied to the detection of an abnormality in the transcript of the PTPN11 gene, e.g. by amplifying the mRNAs contained in a biological sample, for example by RT-PCR.

Thus another subject of the present invention is a method of in vitro diagnosis of cancers, precancerous conditions, and different types of myeloid disorders, as previously defined comprising the steps of:

a) producing cDNA from mRNA contained in a biological sample;

b) contacting the cDNA with specific oligonucleotides permitting the amplification of all or part of the transcript of the PTPN11 gene, under conditions permitting a hybridization of the primers with the cDNA;

c) amplifying the cDNA;

d) detecting the amplification products;

comparing the amplified products as obtained to the amplified products obtained with a normal control biological sample, and thereby detecting a possible abnormality in the transcript of the PTPN11 gene.

For RNA analysis, the biological sample may be any cell source, as described above, such as a biopsy tissue, from which RNA is isolated using standard methods well known to those of ordinary skill in the art such as guanidium thiocyanate-phenol-chloroform extraction (Chomocyznski et al., Anal. Biochem. 1987; 162:156). The isolated RNA is then subjected to coupled reverse transcription and amplification by polymerase chain reaction (RT-PCR), using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, cDNA obtained from the RNA can be cloned and sequenced to identify a mutation.

The PTPN11 nucleic acids of the invention can also be used as probes, e.g., in therapeutic and diagnostic assays. For instance, the present invention provides a probe comprising a substantially purified oligonucleotide, which oligonucleotide comprises a region having a nucleotide sequence that is capable of hybridizing specifically to a region of a PTPN11 gene which differs from that of the wild-type gene (SEQ ID NO: 33), e.g., a mutant or polymorphic region. Such probes can then be used to specifically detect which mutation of the PTPN11 gene is present in a sample taken from a subject. The mutant or polymorphic region can be located in the promoter, exon, or intron sequences of the PTPN11 gene.

For example, preferred probes of the invention include one or more of the nucleotide substitutions listed in Table 1, as well as the wild-type flanking regions (see, e.g., SEQ ID NOS:1 or 33). For each such probe, the complement of that probe is also included in the Table as a preferred probe of the invention. Particularly preferred probes of the invention have a number of nucleotides sufficient to allow specific hybridization to the target nucleotide sequence. Thus, probes of suitable lengths based on SEQ ID NO:1 or 33 and complementary to the mutant sequences provided herein can be constructed and tested by the skilled artisan for appropriate level of specificity depending on the application intended. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of the PTPN11 gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient, although probes of about 15 nucleotides, even more preferably 20 nucleotides, are preferred.

In a preferred embodiment, the probe or primer further comprises a label attached thereto, which preferably is capable of being detected. The label can, for example, be selected from radioisotopes, fluorescent compounds, enzymes, and enzyme co-factors.

In another preferred embodiment of the invention, the isolated nucleic acid, which is used, e.g., as a probe or a primer, is modified, such as to become more stable. Exemplary nucleic acid molecules which are modified include phosphoramidate, phosphothioate and methylphosphonate analogs of DNA (see also U.S. Pat. Nos. 5,176,996; 5,264,564; and 5,256,775).

In yet another embodiment, one may use HPLC or denaturing HPLC (DHPLC) techniques to analyze the PTPN11 nucleic acids. DHPLC was developed when observing that, when HPLC analyses are carried out at a partially denaturing temperature, i.e., a temperature sufficient to denature a heteroduplex at the site of base pair mismatch, homoduplexes can be separated from heteroduplexes having the same base pair length (Hayward-Lester et al., Genome Research 1995; 5:494; Underhill et al., Proc. Natl. Acad. Sci. USA 1996;93: 193; Doris et al., DHPLC Workshop 1997, Stanford University). Thus, the use of DHPLC was applied to mutation detection (Underhill et al., Genome Research 1997;7:996; Liu et al., Nucleic Acid Res. 1998;26:1396). DHPLC can separate heteroduplexes that differ by as little as one base pair. "Matched Ion Polynucleotide Chromatography" (MIPC), or Denaturing "Matched Ion Polynucleotide Chromatography" (DMIPC) as described in U.S. Pat. No. 6,287,822 or 6,024, 878, are separation methods that can also be useful in connection with the present invention.

Alternatively, one can use the DGGE method (Denaturing Gradient Gel Electrophoresis), or the SSCP method (Single Strand Conformation Polymorphism) for detecting an abnormality in the PTPNIJ gene. DGGE is a method for resolving two DNA fragments of identical length on the basis of sequence differences as small as a single base pair change, using electrophoresis through a gel containing varying concentrations of denaturant (Guldberg et al., Nuc. Acids Res. 1994;22:880). SSCP is a method for detecting sequence differences between two DNAs, comprising hybridization of the two species with subsequent mismatch detection by gel electrophoresis (Ravnik-Glavac et al., Hum. Mol. Genet. 1994;3: 801). "HOT cleavage", a method for detecting sequence differences between two DNAs, comprising hybridization of the two species with subsequent mismatch detection by chemical cleavage (Cotton et al., Proc. Natl. Acad. Sci. USA 1988;85: 4397), can also be used. Such methods are preferably followed by direct sequencing. Advantageously, the RT-PCR method may be used for detecting abnormalities in the PTPN11 transcript, as it allows to visualize the consequences of a splicing mutation such as exon skipping or aberrant splicing due to the activation of a cryptic site. Preferably this method is followed by direct sequencing as well.

More recently developed techniques using microarrays, preferably microarray techniques allowing for high-throughput screening, can also be advantageously implemented for detecting an abnormality in the PTPN11 gene or for assaying expression of the PTPN11 gene. Microarrays may be designed so that the same set of identical oligonucleotides is attached to at least two selected discrete regions of the array, so that one can easily compare a normal sample, contacted with one of the selected regions of the array, against a test sample, contacted with another of the selected regions. These arrays avoid the mixture of normal sample and test sample, using microfluidic conduits. Useful microarray techniques include those developed by Nanogen, Inc (San Diego, Calif.) and those developed by Affymetrix. However, all types of microarrays, also called "gene chips" or "DNA chips", may be adapted for the identification of mutations. Such microarrays are well known in the art (see for example the following: U.S. Pat. Nos. 6,045,996; 6,040,138; 6,027,880;6,020,135; 5,968,740; 5,959,098; 5,945,334; 5,885,837; 5,874,219; 5,861,242; 5,843,655; 5,837,832; 5,677,195 and 5,593,839).

The solid support on which oligonucleotides are attached may be made from glass, silicon, plastic (e.g., polypropylene, nylon), polyacrylamide, nitrocellulose, or other materials. One method for attaching the nucleic acids to a surface is by printing on glass plates, as is described generally by Schena et al., Science 1995;270:467-470. This method is especially useful for preparing microarrays of cDNA. See also DeRisi et al., Nature Genetics 1996;14:457-460; Shalon et al., Genome Res. 1996;6:639-645; and Schena et al., Proc. Natl. Acad. Sci. USA 1995;93:10539-11286. Another method of making microarrays is by use of an inkjet printing process to bind genes or oligonucleotides directly on a solid phase, as described, e.g., in U.S. Pat. No. 5,965,352.

Other methods for making microarrays, e.g., by masking (Maskos and Southern, Nuc. Acids Res. 1992;20:1679-1684), may also be used. In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art, very small arrays will be preferred because hybridization volumes will be smaller. For these assays nucleic acid hybridization and wash conditions are chosen so that the attached oligonucleotides "specifically bind" or "specifically hybridize" to at least a portion of the PTPN11 gene present in the tested sample, i.e., the probe hybridizes, duplexes or binds to the PTPN11 locus with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., Science 1996;274:610-614).

A variety of methods are available for detection and analysis of the hybridization events. Depending on the reporter group (fluorophore, enzyme, radioisotope, etc.) used to label the DNA probe, detection and analysis are carried out fluorimetrically, calorimetrically or by autoradiography. By observing and measuring emitted radiation, such as fluorescent radiation or a particle emission, information may be obtained about the hybridization events. When fluorescently labeled probes are used, the fluorescence emissions at each site of transcript array can, preferably be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. Genome Res. 1996;6:639-695).

Protein Based Assays

As an alternative to analyzing PTPN11 nucleic acids, aberrant PTPN11 levels or function on the basis of mutations in the protein or dysregulated expression, e.g. overproduction, of the protein, can be evaluated. In addition, PTPN11 phosphatase activity can be evaluated to determine increased PTPN11 activity.

In preferred embodiments, PTPN11 is detected by immunoassay. For example, Western blotting permits detection of a specific variant, or the presence or absence of PTPN11. In particular, an immunoassay can detect a specific (wild-type or mutant) amino acid sequence in a PTPN11 protein. Other immunoassay formats can also be used in place of Western blotting, as described below for the production of antibodies. These include ELISA assays.

In ELISA assays, an antibody against PTPN11, or an epitopic fragment of PTPN11 is immobilized onto a selected surface, for example, a surface capable of binding proteins such as the wells of a polystyrene microtiter plate. After washing to remove incompletely adsorbed polypeptides, a nonspecific protein such as a solution of bovine serum albumin (BSA) may be bound to the selected surface. This allows for blocking of nonspecific adsorption sites on the immobilizing surface and thus reduces the background caused by nonspecific bindings of antisera onto the surface. The immobilizing surface is then contacted with a sample, to be tested in a manner conductive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures between about 25° to 37° C. Following incubation, the sample-contacted surface is washed to remove non-immunocomplexed material. The washing procedure may include washing with a solution, such as PBS/Tween or borate buffer. Following formation of specific immunocomplexes between the test sample and the bound antibody, and subsequent washing, the occurrence, and an even amount of immunocomplex formation may be determined by subjecting the immunocomplex to a second antibody against PTPN11 that recognizes a different epitope on the protein. To provide detecting means, the second antibody may have an associated activity such as an enzymatic activity that will generate, for example, a color development upon incubating with an appropriate chromogenic substrate. Quantification may then be achieved by measuring the degree of color generation using, for example, a visible spectra spectrophotometer.

Typically the detection antibody is conjugated to an enzyme such as peroxidase and the protein is detected by the addition of a soluble chromophore peroxidase substrate such as tetramethylbenzidine followed by 1 M sulfuric acid. The test protein concentration is determined by comparison with standard curves.

These protocols are detailed in Current Protocols in Molecular Biology, V. 2 Ch. 11 and Antibodies, a Laboratory Manual, Ed Harlow, David Lane, Cold Spring Harbor Laboratory (1988) pp 579-593.

Alternatively, a biochemical assay can be used to detect expression, or accumulation of PTPN11, e.g., by detecting the presence or absence of a band in samples analyzed by polyacrylamide gel electrophoresis; by the presence or absence of a chromatographic peak in samples analyzed by any of the various methods of high performance liquid chromatography, including reverse phase, ion exchange, and gel permeation; by the presence or absence of PTPN11 in analytical capillary electrophoresis chromatography, or any other quantitative or qualitative biochemical technique known in the art.

The immunoassays discussed above involve using antibodies directed against the PTPN11 protein or fragments thereof. The production of such antibodies is described below.

Anti-PTPN11 Antibodies

Such antibodies include but are not limited to polyclonal, monoclonal, chimeric, single chain, Fab fragments, and Fab expression library.

Various procedures known in the art may be used for the production of polyclonal antibodies to PTPN11 polypeptides or derivative or analog thereof. For the production of antibody, various host animals can be immunized by injection with the antigenic polypeptide, including but not limited to rabbits, mice, rats, sheep, goats, etc.

For preparation of monoclonal antibodies directed toward the PTPN11 polypeptides, any technique that provides for the production of antibody molecules by continuous cell lines in culture may be used. These include but are not limited to the hybridoma technique originally developed by Kohler and Milstein (Nature 1975;256:495-497), as well as the trioma technique, the human B-cell hybridoma technique (Kozbor et al., Immunology Today 1983;4:72; Cote et al., Proc. Natl. Acad. Sci. U.S.A. 1983;80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec., 1989).

According to the invention, techniques described for the production of single chain antibodies (U.S. Pat. Nos. 5,476,786 and 5,132,405 to Huston; U.S. Pat. No. 4,946,778) can be adapted to produce the PTPN11 polypeptide-specific single chain antibodies. Indeed, these genes can be delivered for expression in vivo. An additional embodiment of the invention utilizes the techniques described for the construction of Fab expression libraries (Huse et al., Science 1989;246:1275-1281) to allow rapid and easy identification of monoclonal Fab fragments with the desired specificity for a PTPN11 polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

PTPN11 Activity Assays

As described herein, increased activity or level of PTPN11 can be used for the detection or characterization of a cancer or precancerous condition, especially those of originating from myeloid cells.

In one embodiment one may assess the activity of the PTPN11 protein in a test subject or biological sample taken from the subject and compare it with a control. An increased activity of the PTPN11 protein in the test subject or biological sample compared with the control is indicative of a cancer, precancerous condition, or a myeloid disorder in the test subject.

Since PTPN11 is a phosphatase, the basal activity of PTPN11 in a test subject may be easily determined by assessing the phosphorylation level of peptides or proteins contacted with the test PTPN11 protein. For example, phosphorylation of PTPN11 docking partners such as Gab1, Gab2, Grb2, or gp130, as well as peptides such as src, may be assessed. The levels of phosphorylation of proteins can be assessed by various methods, including immunoassays or radiolabeling. Kits for assessing phosphorylation activity are commercially available, e.g., from Upstate Biotechnology, Inc. (Lake Placid, N.Y.) under the name "PTP Assay Kit 1", and from Calbiochem (San Diego, Calif.) under the name "Fluorometric Protein Tyrosine Phosphatase Assay Kit."

One example of a PTPase activity assay is as follows: To activate PTPase activity, a synthesized phosphotyrosine peptide (Genemed Synthesis), PY627PY659, is used over a concentration range of 0-20 μM. PTPase reactions are carried out in 25 μl mixtures at 30° C. for 5 min in 50 mM Hepes (pH 7.2), 0.2% BSA, 1 mM EDTA, and 1 mM DTT, and the reactions stopped by addition of 20 pl Malachite Green/Tween-20 solution. After 30 min at RT, absorbance at 620 nm is determined with a microplate reader. A standard curve of free phosphate concentrations is prepared using $KH_2PO_4$, treated identically to the PTPase conditions. All conditions are repeated in triplicate.

In one embodiment, the level of phosphorylation of a peptide or protein is assessed by utilizing a binding partner, which should preferably be highly specific for the phosphoepitope on the target protein. It is preferred that the binding partner is an antibody. The antibody is preferably generated against a unique epitope of the substrate. In an alternative embodiment, the binding partner should be specific for the phosphorylated form of the target protein. The detection procedure used to assess the phosphorylation state of the protein may for instance employ an antibody or a peptide that recognizes and binds to phosphorylated serines, threonines or tyrosines. The detection antibody is preferably a polyclonal antibody, to maximize the signal, but may also be specific monoclonal antibodies which have been optimized for signal generation.

An exemplary PTPase assay based on immunoprecipitation is as follows:

Step 1: Immunoprecipation of Phosphatase

To maximize Phosphatase activity, all reactions should be carried out on ice, and pulse spinning should be carried out in a centrifuge equilibrated at 4° C.

1. Add 4μl-5μl of an anti-Phosphatase antibody to a microcentrifuge tube.
2. Add 100μl (50μl packed beads) of Protein A or G agarose bead slurry, (which has been washed free of phosphate) and suspended in a cell lysis buffer optimized for phosphatases.
3. Add 100 μl of ice-cold phosphatase cell lysis buffer (optionally containing protease inhibitors, but must be free of phosphatase inhibitors).
4. Incubate for 30 minutes to 1 hour at 4° C. on a rotator to thoroughly mix the components during the incubation.
5. Pellet the agarose beads at 14,000 rpm for 15 seconds.
6. Remove the supernanant. Wash the protein A or G agarose beads in cell lysis buffer to remove weakly bound antibodies. This wash removes any form of antibody that does not bind to the protein A or G agarose, but which may bind to a tissue extract or cell lysate.
7. Resuspend the washed beads pellet in 100μl of phosphatase cell lysis buffer.
8. Add whole cell/tissue extracts (about 500μg-1 mg) containing active phosphatase to the beads.
9. Incubate for 2 hours on a rotator at 4° C. to immunoprecipitate active phosphatase.
10. Wash the protein A or G agarose/enzyme immunocomplex two to three times with 500μl of phosphatase cell lysis buffer.
11. Wash the protein A or G agarose/enzyme immunocomplex twice with 100μl of 1×phosphatase assay dilution buffer found to be suitable (e.g., HEPES, glycerol and EDTA buffer can be used as a start, and modified as necessary).
12. Pellet the immunocomplex at 14,000 rpm for 15 minutes and remove the supernatant fraction from the immunocomplex. Place on ice and proceed to Step II.

Step 11: Malachite Green Phosphatase Assay of the Enzyme Immunocomplex

1. Add 50μl of a 1× phosphatase buffer containing phosphothreonine peptide (KRμTIRR) to the immunocomplex.
2. Incubate overnight at 37° C. or, if preferred, for 30 minutes in a 30° C. shaking incubator. After the incubation, pulse spin to pellet the protein A or G—Agarose/enzyme immunocomplex. Note: the assay mixture must be thoroughly mixed throughout the reaction time to ensure that the peptide substrate and the enzyme immunocomplex achieve maximum interaction.
3. Add a suitable amount (e.g., 1, 2, 5, or 10 μl) of the supernatant into a 96 well plate and add Malachite Green solution (Van Veldhoven et al., Anal Biochem 1987; 161:45-48) to assess for the liberation of phosphate measured in picomoles from the standard curve.

To assess for specific phosphatase activity, the phosphate levels detected with protein A or G-agarose beads incubated with cell lysates in the absence of antibody can be used as a control. Any buffer components should be checked for free phosphate, and the assay optimized as to not inhibit phosphatase activity. In addition, because the assay measures free phosphate, phosphate buffers are not compatible with this system. Thus, reaction components that contain phosphate (i.e., glycerol phosphate) may interfere with the analysis, depending on their concentration, purity and stability in strong acid. Also, high concentrations of reductants may bleach the dye color over time resulting in lower sensitivity. A final concentration of 0.02% p-mercaptoethanol has no effect on sensitivity; 0.05% p-mercaptoethanol has only a slight effect, and 0.1% p-mercaptoethanol results in an approximate 20% reduction in sensitivity. Many detergents at or below 0.1% can be used, but higher concentrations may generate high backgrounds. If high concentrations of detergent are required in the reaction, the background can be determined by including the corresponding concentration of the detergent in the Phosphate Standard curve.

Alternatively, immunoassays may be replaced by the detection of radiolabeled phosphate according to a standard technique. This involves incubating cells with the test substances and radiolabeled phosphate, lysing the cells, separating cellular protein components of the lysate using as SDS-polyacrylamide gel (SDS-PAGE) technique, in either one or two dimensions, and detecting the presence of phosphorylated proteins by exposing X-ray film.

The phosphorylation of a protein may also be conveniently detected by migration on gel subject to electrophoresis, followed by Western blotting. Phosphorylation is detected by a shift of the molecular weight of the protein occurs, a phosphorylated protein being heavier than the corresponding non-phosphorylated form.

Treatment Planning

The results of the assays used to diagnose or characterize a biological sample taken from a person suffering from or being at risk for a cancer or pre-cancerous condition can be employed for treatment planning. Such tests can be employed in patients, including children and adolescents that suffer from or are at risk for a myeloid disorder such as JMML, AML, or ALL.

The tests can also advantageously be applied in Noonan syndrome patients. For example, about 50% of Noonan Syndrome patients have PTPN11 mutations, and certain PTPN11 mutations in NS are associated with JMML or AML. Thus, detection of a JMML mutation in a patient with NS can prompt clinicians to monitor for the development of JMML. The same methodology can be applied to children with apparently isolated pulmonic stenosis. Screening of those individuals can show that a percentage has PTPN11 mutations and, among those, some are at risk for JMML.

In addition, some cases of JMML are somatic and others are germline (NS-JMML, PS-JMML). Since, in general, germline JMML can behave more mildly with spontaneous remissions, the application of bone marrow transplantation as a therapy could be postponed or, possibly, avoided. Thus, detection of a PTPN11 mutation in the JMML cells should prompt similar mutation analysis from non-leukemic cells (e.g., buccal cells or skin fibroblasts) to establish whether or not the mutation was somatic.

In the case of a patient suspected of suffering from a cancer or pre-cancerous condition, especially a cancer or condition associated with myeloid or lymphoid cells, the detection of a PTPN11 gain-of-function mutation is indicative of an increased likelihood of the cancer or precancerous condition, especially when the cancer is JMML or ALL. Such testing may prompt a physician to initiate early treatment of the disease, advantageously a treatment specifically directed to reducing PTPN11 activity or RAS-MAPK signaling downstream from PTPN11. Examples of anti-PTPN11 and anti-RAS-MAPK treatment options are described below.

Furthermore, in a patient known to suffer from a cancer such as JMML, ALL, or AML, PTPN11 testing can be used to further characterize the cancer. For example, since, according to a preferred embodiment, a PTPN11 gain-of-function mutation is mutually exclusive with any gain-of function RAS or NF1 mutation, PTPN11 testing can aid a physician in selecting a treatment suitable for the individual patient. In one embodiment, the detection of PTPN11 over-expression or a PTPN11 gain-of-function mutation may prompt the selection of a treatment specifically directed against PTPN11 activity, including PTPN11 inhibitory antibodies and anti-sense therapy, or a treatment inhibiting PTPN11 signaling. In yet another embodiment, the detection of a PTPN11 mutation is contraindicative of the selection of a treatment stimulating PTPN11 or RAS-MAPK signaling.

Diagnostic Kits

The present invention further provides kits for the determination of the sequence within the PTPN11 gene in an individual. The kits comprise a means for determining the sequence at the variant positions, and may optionally include data for analysis of mutations. The means for sequence determination may comprise suitable nucleic acid-based and immunological reagents. Preferably, the kits also comprise suitable buffers, control reagents where appropriate, and directions for determining the sequence at a variant position.

Nucleic Acid Based Diagnostic Kits

The invention provides nucleic acid-based methods for detecting genetic variations of PTPN11 in a biological sample. The sequence at particular positions in the PTPN11 gene is determined using any suitable means known in the art, including without limitation one or more of hybridization with specific probes for PCR amplification (e.g., primer pairs selected from SEQ ID NOS:3-32), restriction fragmentation, direct sequencing, SSCP, and other techniques known in the art.

The present invention also provides kits suitable for nucleic acid-based diagnostic applications. In one embodiment, diagnostic kits include the following components:

a) Probe DNA: The probe DNA may be pre-labeled; alternatively, the probe DNA may be unlabeled and the ingredients for labeling may be included in the kit in separate containers; and b) Hybridization reagents: The kit may also contain other suitably packaged reagents and materials needed for the particular hybridization protocol, including solid-phase matrices, if applicable, and standards.

In another embodiment, diagnostic kits include:

sequence determination primers: Sequencing primers may be pre-labeled or may contain an affinity purification or attachment moiety; and sequence determination reagents: The kit may also contain other suitably packaged reagents and materials needed for the particular sequencing protocol.

In one preferred embodiment, the kit comprises a panel of sequencing primers, whose sequences correspond to sequences adjacent to variant positions.

Antibody Based Diagnostic Kits

The invention also provides antibody-based methods for detecting mutant (or wild type) PTPN 1 proteins in a biological sample. The methods comprise the steps of: (i) contacting a sample with one or more antibody preparations, wherein each of the antibody preparations is specific for mutant (or wild type) PTPN11 under conditions in which a stable antigen-antibody complex can form between the antibody and PTPN11 in the sample; and (ii) detecting any antigen-antibody complex formed in step (i) using any suitable means known in the art, wherein the detection of a complex indicates the presence of mutant (or wild type) PTPN11.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

The present invention also provides kits suitable for antibody-based diagnostic applications. Diagnostic kits typically include one or more of the following components:

(i) PTPN11-specific antibodies: The antibodies may be pre-labeled; alternatively, the antibody may be unlabeled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Therapeutics

The present invention further provides a method for the treatment of cancer and precancerous conditions, preferably those deriving from myeloid cells, which method comprises modulating PTPN11 activity or signaling in a subject or patient. The method comprises administering to a patient in need of such treatment an effective amount of an agent that modulates PTPN11 expression, activity, or signaling, with a pharmaceutically acceptable carrier. For example, the therapeutic agent may be a PTPN11 antisense nucleic acid, or an anti-PTPN11 intracellular inhibitory antibody. Agents that block either the N-SH2, C-SH2, or PTP domains of the PTPN11 proteins are of particular interest. Preferably, although not necessarily, the agent blocks the PTP domain so that PTPase activity is inhibited.

A "subject" or "patient" is a human or an animal with, or likely to develop, a cancer or precancerous condition, including those deriving from myeloid cells, more particularly a mammal, preferably a rodent or a primate, as described above in connection with diagnostic applications.

The term "treatment" means to therapeutically intervene in the development of a disease in a subject showing a symptom of this disease. The term "treatment" also encompasses prevention, which means to prophylactically interfere with a pathological mechanism that results in the disease.

The term "modulating PTPN11 activity" in a subject means modifying it so that it is rendered as close as possible to the normal PTPN11 activity of a control subject. It especially encompasses inhibiting, or blocking the activity of the PTPN11 protein in patients with a cancer, precancerous condition, or a myeloid disorder. Preferred modulators block any of the functional domains of the PTPN11 of the protein, especially the constitutively active PTP domain. "Modulating PTPN11 activity" also encompasses restoring SH2 domain activity.

The modulation activity may be achieved by various methods, as described hereafter.

In one embodiment, the modulatory agent may be a substance that is known or has been identified to modulate, especially inhibit, whether fully or partially, PTPN11 activity. Such compounds can include any compound(s) described in, for example, the International Patent Publication WO99/46267 and in Ann Rev Pharmocol Toxicol 2002;42:209-234; Exp Mol Med 2002;31:211-223; Biochem 2002;41:10700-10709; and J Immunol 2001;167:3391-3397, as well as other compounds shown to inhibit PTPN11 activity as described herein. For example, this modulatory agent may be a candidate drug as identified by a screening method. It may also be an inhibitory antibody directed against PTPN11. In a further embodiment, it may be an antisense nucleic acid. All these embodiments are described in greater detail below.

The term "therapeutically effective amount" is used herein to mean an amount or dose sufficient to modulate, e.g., decrease the level of PTPN11 activity e.g., by about 10 percent, preferably by about 50 percent, and more preferably by about 90 percent. Preferably, a therapeutically effective amount can ameliorate or present a clinically significant deficit in the activity, function and response of the subject. Alternatively, a therapeutically effective amount is sufficient to cause an improvement in a clinically significant condition in the host.

The substance that modulates or inhibits PTPN11 activity is advantageously formulated in a pharmaceutical composition, with a pharmaceutically acceptable carrier. This substance may be then called active ingredient or therapeutic agent against myelois disorders.

The concentration or amount of the active ingredient depends on the desired dosage and administration regimen, as discussed below. Suitable dose ranges may include from about 0.01 mg/kg to about 100 mg/kg of body weight per day.

The pharmaceutical compositions may also include other biologically active compounds.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

According to the invention, the pharmaceutical composition of the invention can be introduced parenterally, transmucosally, e.g., orally (per os), nasally, or rectally, or transdermally. Parental routes include intravenous, intra-arteriole, intra-muscular, intradermal, subcutaneous, intraperitoneal, intraventricular, and intracranial administration. Targeting heart, e.g. by direct administration to heart muscle or cavities, may be advantageous.

The pharmaceutical compositions may be added to a retained physiological fluid such as blood or synovial fluid.

In another embodiment, the active ingredient can be delivered in a vesicle, in particular a liposome (see Langer, Science 1990;249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound can be delivered in a controlled release system. For example, a pplypeptide may be administered using intravenous infusion with a continuous pump, in a polymer matrix such as poly-lactic/glutamic acid (PLGA), a pellet containing a mixture of cholesterol and the active ingredient (SilasticR™; Dow Corning, Midland, Mich.; see U.S. Pat. No. 5,554,601) implanted subcutaneously, an implantable osmotic pump, a transdermal patch, liposomes, or other modes of administration.

Inhibitory Antibodies

The modulatory substance may also be an antibody that is directed against PTPN11. Antibodies that block the activity of PTPN11 may be produced and selected according to any standard method well-known by one skilled in the art, such as those described above in the context of diagnostic applications.

Intracellular antibodies (sometime referred to as "intrabodies") have been used to regulate the activity of intracellular proteins in a number of systems (see, Marasco, Gene Ther. 1997;4:11; Chen et al., Hum. Gene Ther. 1994;5:595), e.g., viral infections (Marasco et al., Hum. Gene Ther. 1998;9: 1627) and other infectious diseases (Rondon et al., Annu. Rev. Microbiol. 1997;51:257), and oncogenes, such as p21 (Cardinale et al., FEBS Lett. 1998;439:197-202; Cochet et al., Cancer Res. 1998;58:1170-6), myb (Kasono et al., Biochem Biophys Res Commun. 1998;251:124-30), erbB-2 (Graus-Porta et al., Mol Cell Biol. 1995;15:1182-91), etc. This technology can be adapted to inhibit PTPN11 activity by expression of an anti-PTPN11 intracellular antibody.

Antisense Therapy

In another embodiment, vectors comprising a sequence encoding an antisense nucleic acid according to the invention may be administered by any known methods, such as the methods for gene therapy available in the art. Exemplary methods are described below. For general reviews of the methods of gene therapy, see, Goldspiel et al., Clinical Pharmacy 1993;12:488-505; Wu and Wu, Biotherapy 1991;3:87-95; Tolstoshev, Ann. Rev. Pharmacol. Toxicol. 1993;32:573-596; Mulligan, Science 1993;260:926-932; and Morgan and Anderson, Ann. Rev. Biochem. 1993;62:191-217; May, TIBTECH 1993;11:155-215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al.; (eds.), 1994, Current Protocols in Human Genetics, John Wiley & Sons, NY. Further, RNAi or siRNA technology, using double stranded RNA (dsRNA) to suppress the expression of a PTPN11 gene or other gene of interest in a homology-dependent manner, can be applied (see, e.g., Bosner and Labouesse, *Nature Cell Biol.* 2000; 2: E31-E36 and Sharp and Zamore, *Science* 2000; 287: 2431-2433).

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA 1989;86:8932-8935; Zijlstra et al., Nature 1989;342:435-438).

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

In a specific embodiment, the vector is directly administered in vivo, where it enters the cells of the organism and mediates expression of the construct. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-p-1-4-N-acetylglucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, J. Biol. Chem. 1987;62: 4429-4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., Mol. Therapy 2000;2:339-47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188).

Preferred examples of specific anti-PTPN11 antisense sequences are any of the sequences described in U.S. Pat. No. 6,200,807, owned by Isis Pharmaceuticals. Antisense compounds that are 8 to 30 nucleotide bases in length and are targeted to a region selected from the 5' untranslated region, the start codon, the region from nucleotides 298 through 1883 of the coding region, the stop codon, or the 3' untranslated region of human PTPN11, are of particular interest.

Reducing RAS-MAPK Signaling

As an alternative to targeting the mutant or overexpressed PTPN11 protein itself, or the mutant NRAS and KRAS2 proteins described in Example 4, therapies directed against the effects caused by the increased PTPN11 activity or RAS-MAPK signaling can be employed. Preferably, although not necessarily, the treatment strategies of the invention comprise targeting one or more components of the RAS-MAPK pathway, including agents modulating RAS, RAF, MEK, and ERK activity. Such agents are known in the art, and include inhibitors of farnesyltransferases, which inhibit Ras post-translational modification, and compounds such as PD098059, inhibiting the activation of MEK-1 and/or MEK-2. These and other agents have been described, for example, by Reuter et al. (Blood 2000;96:1655-1669) Shinohara et al. (Urol Res 2002;30:273-281), and Walchli et al., J Biol Chem 2003, Oct 24 (epub ahead of print).

Screening Methods

A "test substance" is a chemically defined compound or mixture of compounds (as in the case of a natural extract or tissue culture supernatant), whose ability to modulate PTPN11 activity may be defined by various assays. A "test substance" is also referred to as a "candidate drug" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996; 14:60).

A modulatory effect may be determined by an in vitro method using a recombinant PTPN11-reporter gene promoter activity system.

Reporter genes for use in the invention encode detectable proteins, include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen according to the invention involves detecting expression of the reporter gene by the host cell when contacted with a test substance. If there is no change in expression of the reporter gene, the test substance is not an effective modulator. If reporter gene expression is modified, in particular reduced or eliminated, the test substance has modulated, e.g., inhibited, PTPN11-mediated gene expression, and is thus a candidate for development of a therapeutic agent for patients or potential patients with cancer or pre-cancerous conditions, including myeloid disorders. The reporter gene assay system described here may be used in a high-throughput primary screen for antagonists, or it may be used as a secondary functional screen for candidate compounds identified by a different primary screen, e.g., a binding assay screen that identifies compounds that modulate PTPN11 transcription activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable.

Intact cells or whole animals expressing a gene encoding PTPN11 can be used in screening methods to identify candidate drugs.

In one series of embodiments, a permanent cell line is established. Alternatively, cells are transiently programmed to express a PTPN11 gene by introduction of appropriate DNA or mRNA.

Identification of candidate substances can be achieved using any suitable assay, including without limitation (i) assays that measure selective binding of test compounds to PTPN11 (ii) assays that measure the ability of a test substance to modify (i.e., inhibit) a measurable activity or function of PTPN11 and (iii) assays that measure the ability of a substance to modify (i.e., inhibit) the transcriptional activity of sequences derived from the promoter (i.e., regulatory) regions of the PTPN11 gene.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability.

EXAMPLES

Examples of practicing the invention are provided, and are understood to be exemplary only, and do not limit the scope of the invention or the appended claims. A person of ordinary skill in the art will appreciate that the invention can be practiced in many forms according to the claims and disclosures here.

Example 1

Detection of Mutations in the PTPN11 Gene

This Example describes the an investigation of the prevalence of PTPN11 mutations in children with JMML with and without Noonan syndrome (n=5 and n=62, respectively), myelodysplastic syndrome (MDS) (n=50) and de novo acute myeloid leukemia (AML) (n=24). Genomic DNAs isolated from bone marrow and peripheral blood mononuclear cells were screened for PTPN11 mutations. Briefly, PTPN11 mutations were detected in all five subjects with Noonan syndrome and JMML. Somatic PTPN11 defects were detected in 34% of children with JMML without Noonan syndrome and in smaller percentages of subjects with MDS and AML. All mutations were mis-sense changes increasing PTPN11's phosphatase activity. The distribution of PTPN11 mutations differed between the isolated Noonan syndrome, Noonan syndrome with JMML and isolated JMML phenotypes. PTPN11, RAS, and NF11 mutations were mutually exclusive in JMML. This Example thus documents that mutant PTPN11 occupies an important role in human oncogenesis, and the genotype-phenotype correlation for the Noonan syndrome and JMML phenotypes suggests that the highest PTPN11 activity levels are requisite for pathological myeloproliferation.

Subject Recruitment

Children with JMML (n=69), MDS (n=50), and de novo AML (n=24) were studied. JMML was associated with Noonan syndrome or neurofibromatosis type 1 in five and eight children, respectively. Two subjects with JMML had pulmonic stenosis and growth retardation, but did not meet criteria for Noonan syndrome. The 62 patients with isolated JMML (41 boys and 21 girls) had been diagnosed consecutively between 1991 and 2001. In this cohort, median age at diagnosis was 2.1 years (0.1-13.2 years). The karyotype was normal in 42 cases, while nine had monosomy 7 and eleven harboured other abnormalities.

In the MDS cohort, median age of 29 males and 21 females was 10.6 years (1.0-20.1 years). FAB subtypes at the time of sample collection included refractory anemia (RA) in 23 cases, refractory anemia with excess of blasts (RAEB) in 20, refractory anemia with excess blasts in transformation (RAEBT) in five, and myelodysplasia-related AML (MDR-AML) in two. Eleven MDS cases were secondary (chemotherapy or radiation therapy, n=7; aplastic anemia, n=3; an unspecified defect with congenital bone marrow failure, n=1). The karyotype was normal in 25 of the 46 cases for which it was available, while monosomy 7 or other aberrations were noted in eleven and ten cases, respectively.

Eight of the 24 cases of de novo AML were studied at first relapse. Median age was 8.3 (0.7-15.4 years). Morphological subtypes for the entire AML cohort included eight cases with FAB M5, five with FAB M7 (including three with Down's syndrome), five with FAB M4 (including one with abnormal eosinophils), three with FAB M2 and one case each with FAB M1, FAB M3 and undefined subtype. Chromosomal aberrations characteristic for de novo AML, i e., t(8;21), t(15;17), inv(16), as well as other complex abnormalities were noted.

All cases were subjected to the reference morphology review of the European Working Group of MDS in childhood (EWOG-MDS). Informed consent was obtained for all subjects participating in this study.

Molecular Analysis

DNA sample acquisition. Granulocytes and mononuclear cells were separated from heparinized peripheral blood or aspirated bone marrow samples using a Ficoll gradient (Flotho et al., Leukemia 1999; 13:32-7). Genomic DNA was isolated from lysates of these cells in a standard fashion. Genomic DNA also was extracted form buccal mucosal cells or paraffin-embedded fixed tissue using standard protocols.

PTPN11 mutation analysis. The PTPN11 coding region (exons 1-15) was screened for mutations using denaturing high performance liquid chromatography (DHPLC) (Tartaglia et al., Am J Hum Genet 2002;70: 1555-63).

Mutational Analysis. The entire PTPN11 coding region (exons 1-15) was screened for mutations. For exons 2-15, PCRs were performed in a 25-el reaction volume containing 20-80 ng genomic DNA, 1 U AMPLITAQ Gold (Roche), 20 pmol each primer, 1.5 mM $MgCl_2$, 7 μM each dNTP, and 1XPCR Buffer 11 (Roche), through use of a GENEAMP PCR System 9700 (Applied Biosystems). Exon 1 amplifications were performed using the GC-rich PCR System (Roche), according to the manufacturer's specifications. Cycling parameters were as follows: 94 C for 8 min (first denaturing step); 33 cycles of 94° C. for 45 s, 54-60° C. (see table 1) for 30 s, and 72° C. for 45 s; and 72° C. for 10 min (last extension step).

Primer pairs were designed to amplify exons, exon/intron boundaries, and short intron flanking stretches. Primer sequences, annealing temperatures, and sizes of PCR products are listed in Table 2. Mutational analysis of the amplimers was performed by means of denaturing high-performance liquid chromatography (DHPLC), through use of the Wave DNA Fragment Analysis System (Transgenomics) at column temperatures recommended by the WAVEMAKER version 4.1.31 software (Transgenomics). DHPLC buffers and run conditions were as follows: buffer A (0.1 M triethylammonium acetate (TEAA), 0.025% acetonitrile (ACN)), buffer B (0.1 M TEAA, 25% ACN); a flow rate of 0.9 ml/mm; and a gradient duration of 3 mm, with active clean (75% ACN). Buffer B gradients and temperatures are reported in table 3. Positive controls—that is, PCR products expected to result in variant elution profiles-were used in all DHPLC runs.

TABLE 2

Primer Pairs and Annealing Temperatures Used to Amplify the PTPN11 Coding Sequence and Sizes of PCR Products

| Exon | Primer Sequence Forward (SEQ ID NO) | Primer Sequence Reverse (SEQ ID NO) | Annealing Temp (° C.) | Product Length (bp) |
|---|---|---|---|---|
| 1 | 3 | 4 | 60 | 589 |
| 2 | 5 | 6 | 60 | 405 |
| 3 | 7 | 8 | 60 | 384 |
| 4 | 9 | 10 | 58 | 447 |
| 5 | 11 | 12 | 60 | 329 |
| 6 | 13 | 14 | 54 | 282 |
| 7 | 15 | 16 | 56 | 271 |
| 8 | 17 | 18 | 57 | 350 |
| 9 | 19 | 20 | 56 | 357 |
| 10 | 21 | 22 | 60 | 284 |
| 11 | 23 | 24 | 60 | 453 |
| 12 | 25 | 26 | 56 | 250 |
| 13 | 27 | 28 | 60 | 356 |
| 14[a] | 29 | 30 | 60 | 259 |
| 15 | 31 | 32 | 60 | 321 |

[a]GC clamps were added at the 5' end for DHPLC analysis: forward primer, 5'-CCCGCCGCCCCCGCCG-3' (SEQ ID NO: 34); reverse primer, 5'-CCGCGCCCCCGCCCG-3' (SEQ ID NO: 35) (product length = 290 bp).

TABLE 3

Percent Buffer B and Temperatures Used in DHPLC Analysis for PTPN11 Mutation Detection

| EXON | % BUFFER B[a] Loading | Initial | Final | TEMPERATURE(S) (° C.) |
|---|---|---|---|---|
| 1 | 56 | 61 | 67 | 67 |
| 2 | 55 | 60 | 66 | 56, 57 |
| 3 | 54 | 59 | 65 | 57, 58 |
| 4 | 53 | 58 | 64 | 56, 57 |
| 5 | 51 | 56 | 62 | 56, 58 |
| 6 | 50 | 55 | 61 | 56, 57 |
| 7 | 50 | 55 | 61 | 56, 57 |
| 8 | 51 | 56 | 62 | 57, 58 |
| 9 | 52 | 57 | 63 | 56, 57 |
| 10 | 50 | 55 | 61 | 57, 58 |
| 11 | 54 | 59 | 65 | 59 |
| | 49 | 54 | 60 | 64 |
| 12 | 48 | 53 | 59 | 58, 59 |
| 13 | 51 | 56 | 62 | 59 |
| | 50 | 55 | 61 | 60 |
| 14 | 52 | 57 | 63 | 57 |
| | 49 | 54 | 60 | 60 |
| 15 | 51 | 56 | 62 | 56, 57 |

[a]% buffer A = 100 − % buffer B

Heterozygous templates with previously identified mutations or single-nucleotide polymorphisms (SNPs) were used as positive controls for exons 3, 4, 7, 8, and 13. For each of the remaining exons, a synthetic template containing a single nucleotide change was conducted using the overlap extension method in a two-step PCR procedure. Wild-type and mutated PCR products were denatured together at 94° C. for 5 min and were slowly cooled at room temperature, to allow heteroduplex formation. Bidirectional direct sequencing of purified PCR products (Qiagen) was performed using the ABI BIGDYE Terminator Sequencing Kit (Perkin Elmer) and an ABI 3700 Capillary Array Sequencer (Perkin Elmer). Sequences were analyzed by the Sequencing Analysis v.3.6.1 and AutoAssembler v.1.4.0 software packages (Perkin Elmer).

Amplimers having abnormal denaturing profiles were purified (Qiagen) and sequenced bi-directionally using the ABI BIGDYE terminator Sequencing Kit (Perkin Elmer) and AIM 3700 Capillary Array Sequencer (Perkin Elmer). Sequencing results were analyzed using the Sequencing Analysis v.3.6.1 and AutoAssembler v.1.4.0 software packages (Perkin Elmer).

RAS mutation analysis. Exons 1 and 2 of the K-RAS2 and N-RAS genes were amplified from genomic DNA. Amplimers were sequenced bi-directionally using forward and reverse primers corresponding to sequences that were included at the 5' ends of the PCR primers.

TABLE 4

PTPN11 Mutations In Juvenile Myelomonocytic Leukemia, Myelodysplastic Syndromes And De Novo Acute Myeloid Leukemia.

| Disorder | N. of cases | Nucleotide substitution | Amino acid substitution |
|---|---|---|---|
| NS/JMML | 5 | | |
| | 1 | T→G at position 184 | Tyr62Asp |
| | 4 | C→T at position 218 | Thr73Ile |
| PS/JMML | 2 | | |
| | 1 | C→T at position 218 | Thr73Ile |
| | 1 | G→C at position 1507 | Gly503Arg |
| JMML | 62 | | |
| | 5 | G→T at position 181 | Asp61Tyr |
| | 1 | A→T at position 182 | Asp61Val |
| | 3 | G→A at position 205 | Glu69Lys |
| | 2 | G→A at position 214 | Ala72Thr |
| | 1 | C→T at position 215 | Ala72Val |
| | 5 | G→A at position 226 | Glu76Lys |
| | 1 | A→T at position 227 | Glu76Val |
| | 1 | A→G at position 227 | Glu76Gly |
| | 1 | A→C at position 227 | Glu76Ala |
| | 1 | G→C at position 1508 | Gly503Ala |
| MDS | 50 | | |
| | 1[a] | G→T at position 179 | Gly60Val |
| | 1[b] | A→T at position 182 | Asp61Val |
| | 1[c] | G→A at position 205 | Glu69Lys |
| | 1[d] | T→A at position 213 | Phe71Leu |
| | 1[e] | A→C at position 227 | Glu76Ala |
| AML | 26 | | |
| | 1[f] | TTT→AAA at position 211-213 | Phe71Lys |

[a]primary RAEB, −7, del(12)(p 12);
[b]primary RAEB, evolved in MDR-AML, −7;
[c]secondary RAEB to NHL therapy, t(5; 18)(q22; p11), evolved in MDR-AML;
[d]secondary RAEB to aplastic anemia, −7;
[e]primary RAEB, −7, del(6)(q21), evolved in RAEB-t;
[f]AML M5 with aplastic pre-phase, t(4; 11)(q1 1; q22), del(9)(p22).
NS indicates Noonan syndrome;
PS, pulmonic stenosis.

PTPN11 Mutations in Noonan Syndrome with JMML

The prevalence of mutations in PTPN 1 was investigated in leukemic cell DNAs from five children with Noonan syndrome and JMML. In each case, a heterozygous PTPN11 mutation was observed (Table 4). All mutations were missense changes in exon 3, predicted to alter the N terminal src homology 2 (N SH2) domain. Four children shared a C→T transition at position 218, predicting the Thr73Ile substitution. Two subjects with pulmonic stenosis and JMML also had missense PTPN11 defects. One exhibited the 218C→T transition, while the other carried a novel defect in exon 13 affecting the protein tyrosine phosphatase (PTP) domain (Table 4). Analysis of germ line DNAs for four cases indicated that the mutations were germline events. Screening of parental DNAs for two sporadic cases confirmed that mutations had occurred de novo.

PTPN11 Mutations in Isolated JMML

The prevalence of somatic mutations in the entire PTPN11 coding sequence in a cohort of 39 JMML subjects without Noonan syndrome or pulmonic stenosis was investigated. Missense mutations were identified in 15, with seven different molecular defects in exon 3 and one in exon 13 (Table 4). A second, similar JMML cohort (n=23) was screened for mutations in the exons frequently mutated in JMML and Noonan syndrome (exons 3, 7, 8 and 13). Six missense mutations, all in exon 3, were observed. Taken together, PTPN11 mutations were observed in 34% of JMML cases (95% C.I.: 22 47%). The G→4T transversion at position 181 and the G→A transition at position 226, predicting the Asp61Tyr and Glu76Lys substitutions within the N-SH2 domain, were the most common of the ten mutations, each accounting for 25% of the total. Codon 76 was a mutational hot spot for JMML, with four different amino acid substitutions predicted among eight individuals. Sequence comparison of SHP 2 with its orthologs and closely related protein tyrosine phosphatases showed complete conservation of all affected residues. Glu76 has been suggested to share a similar function as Asp61 and Ala72 in stabilizing the I state (Hof et al, Cell, 1998, 92, 441-450). Non hematologic DNAs were available for nine subjects with a PTPN11 mutation in their leukemic cells, and none harbored that defect.

No PTPN11 mutation was identified in eight cases of neurofibromatosis type 1 and JMML. Molecular screening for mutations in exons 2 and 3 of the N-RAS and K-RAS2 genes identified defects in twelve cases of isolated JMML, none of whom had a PTPN11 mutation. Comparison of phenotypes did not reveal clear differences between the ML groups with and without PTPN11 mutations. PTPN11 mutations were observed in JMML with normal karyotype as well as with monosomy 7.

PTPN11 Mutations in MDS and De Novo AML

The prevalence of somatic PTPN11 mutations among children with MDS (n=50) and AML (n=24) was investigated. Screening of exons 3, 8 and 13 revealed missense mutations in exon 3 for five of 27 patients with MDS with excess of blasts (19%; 95% C.I.: 6 38%). Three of these cases were primary MbS associated with monosomy 7, and two were secondary (Table 4). No mutation was observed among 23 children with refractory anemia (RA).

A novel TTT→AAA trinucleotide substitution at position 211-213 (Phe71Lys) was identified in one of 24 patients with de novo AML (Table 4). This leukemia was classified as FAB M5.

Discussion

All PTPN11 mutations identified in the present study were missense defects that affected specific portions of the N-SH2 and PTP functional domains, and are predicted to result in a gain of function. Normally, PTPN11 switches between inactive and active conformations depending upon the binding of phosphotyrosyl-containing ligands. In the inactive conformation, the N-SH2 domain extensively interacts with the PTP domain, blocking the phosphatase active site. When a distinct N-SH2 sub-domain not involved in the interaction with PTP binds to a phosphotyrosyl moiety, it induces a conformational change that leads to the disruption of the N-SH2/PTP interaction and activation of the phosphatase. All mutations identified in children with JMML, MDS or AML affected residues located at the N-SH2 and PTP interacting surfaces and involved in their binding. By destabilizing the inactive conformation, these mutations increase PTPN11's phosphatase activity. It is noted that no nonsense, frameshift or splicing mutation was observed among the 33 mutations identified in the present study, and no mutation affected residues essential for phosphatase activity, thus further supporting gain-of-function mutations in PTPN11. In addition, two prevously engineered PTPN11 mutants, Asp61Ala and Glu76Ala exhibit increased phosphatase activity and, when expressed in *Xenopus laevis* ectodermal explants, induced ventrolateral mesoderm, documenting basal activation of the FGF cascade (O'Reilly et al., Mol Cell Biol 2000;20:299-311).

It was also found that acquired somatic mutations in PTPN11 represent an important mutational event in pediatric myeloid malignancies, accounting for 34% of JMML and smaller proportions of advanced MDS and de novo AML, showing that mutant PTPN11 occupies an important role in human oncogenesis. Examples of mutations and their relative prevalence in these myeloid disorders are listed in Table 5. Note that the relative prevalence may change as more patients are added to the study.

TABLE 5

Mutations in PTPN11 Gene (combined data for juvenile myelomonocytic leukemia, myelodysplastic syndromes and acute myeloid leukemia patients, n = 39). Nucleotide and amino acid substitutions are numbered as set forth in SEQ ID NO: 1 and 2, respectively. See also FIG. 2 and Table 4.

| Nucleotide Substitution | Exon | Predicted Amino Acid Substitution | Functional Domain | Relative Prevalence |
|---|---|---|---|---|
| G179T | 3 | Gly60Val | N-SH2 | 5% |
| G181T | 3 | Asp61Tyr | N-SH2 | 14% |
| A182T | 3 | Asp61Val | N-SH2 | 8% |
| T184G[a] | 3 | Tyr62Asp | N-SH2 | 3% |
| G205A | 3 | Glu69Lys | N-SH2 | 10% |
| TTT(211-213)AAA | 3 | Phe71Lys | N-SH2 | 3% |
| T213A | 3 | Phe71Leu | N-SH2 | 3% |
| G214A | 3 | Ala72Thr | N-SH2 | 5% |
| C215T | 3 | Ala72Val | N-SH2 | 3% |
| C218T[b] | 3 | Thr73Ile | N-SH2 | 13% |
| G226A | 3 | Glu76Lys | N-SH2 | 14% |
| A227T | 3 | Glu76Val | N-SH2 | 3% |
| A227G | 3 | Glu76Gly | N-SH2 | 5% |
| A227C | 3 | Glu76Ala | N-SH2 | 5% |
| G1507C[c] | 13 | Gly503Arg | PTP | 3% |
| G1508C | 13 | Gly503Ala | PTP | 3% |

[a]Mutation found in JMML patients with NS
[b]Mutation found in JMML patients with NS or PS
[c]Mutation found in JMML patients with PS The present study extends the spectrum of molecular events underlying JMML that result in RAS/MAPK activation to a class of gain-of-function mutations in PTPN11. Mutations in the PTPN11, RAS, and NF1 genes were mutually exclusive in JMML and their combined prevalence accounts for approximately three-quarters of this disease. This suggests the existence of one or more additional JMML genes, which are likely to be other members of the RAS/MAPK pathway.

PTPN11 mutations in MDS and AML were also identified. In MDS, defects were found only in advanced MDS, particularly with monosomy 7, suggesting specificity in the role of mutated PTPN11 proteins in the initiation of the myeloid pre-leukemic condition. In contrast, only one of 24 cases of de novo AML had a PTPN11 mutation. AML is associated with non-random chromosomal abnormalities, each with characteristic clinical and biologic features (Alcalay M, et al., Oncogene 2001; 20:5680-94). Screening of large, well-characterized cohorts will be necessary to define the role of PTPN11 in leukemogenesis of these generally chemosensitive disorders.

Figure 2:
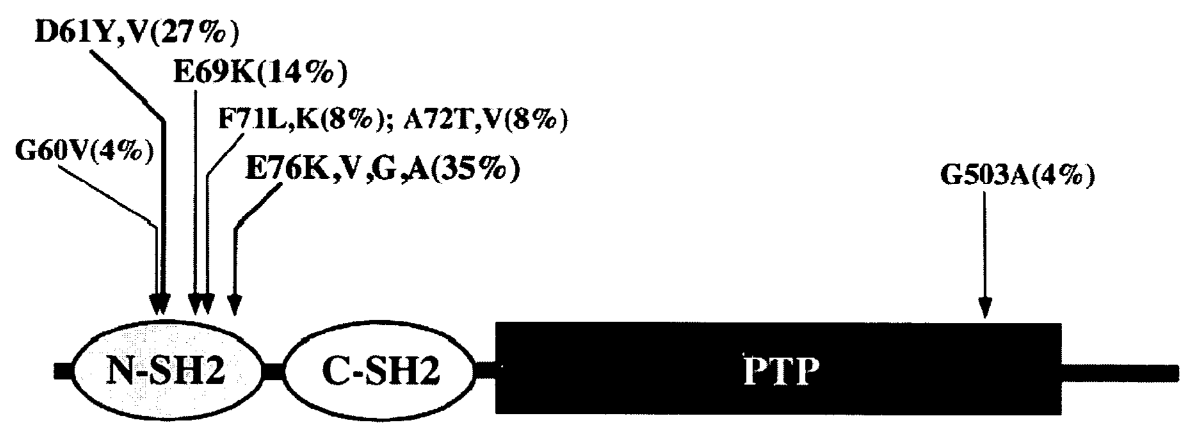
FIG. 2 is a schematic representation of SHP-2 showing the distribution of mutations and their relative prevalence in JMML, MDS and AML. The functional domains of the SHP2 protein, consisting of two tandemly arranged src-homology 2(SH2) domains at the N-terminus (N-SH2 and C-SH2) followed by a protein tyrosine phosphatase (PTP) domain, are shown below.

Missense PTPNIJ mutations occurred as acquired, somatic defects in isolated JMML and as inherited, germline changes in Noonan syndrome with JMML, establishing a common molecular basis for this form of leukemia. The molecular defects in both circumstances were similar, altering residues at the interface between the N-SH2 and PTP domains and affecting the molecular switching mechanism of PTPN11. The distribution of mutations, however, differed, suggesting a genotype-phenotype relationship underlying isolated Noonan syndrome, Noonan syndrome with JMML and isolated JMML. Among isolated Noonan syndrome cases with PTPN11 mutations, defects in exons 4, 7 and 8 accounted for one-half of the cases with the Asn308Asp substitution constituting about one-third of all lesions (FIG. 2). In contrast, no mutation affecting exons 4, 7 or 8 was identified in isolated JMML. Rather 96% of the mutations clustered in exon 3, with lesions altering Glu76 accounting for 33% of defects (FIG. 2). A Glu76 mutation was found in only one subject with Noonan syndrome (1% of mutations) and the change was more conservative (Glu76Asp). The distribution of PTPN11 mutations in Noonan syndrome with JMML also revealed specificity since four of five cases harbored a Thr73Ile allele, a mutation observed in only 2% of PTPN11 defects in isolated Noonan syndrome. This finding demonstrates that the subgroup of patients with Noonan syndrome at risk for JMML can be identified by the presence of specific mutant alleles of PTPN11.

JMML is a rare complication of Noonan syndrome and, when it does occur, the clinical course tends to be relatively benign compared to isolated JMML (Bader-Meunier, et al., J Pediatr 1997; 130:885-9; Fukuda M, et al., J Pediatr Hematol Oncol 1997; 19:177-8; Choong K, et al., J Pediatr Hematol Oncol 1999; 523-7). This occurs despite the fact that the PTPN11 defects associated with Noonan syndrome with or without JMML as well as isolated JMML cause a PTPN11 gain-of-function. Aside from the mechanism of the mutagenesis (germ line versus somatic), a potential, although non-limiting, model, would be that distinct gain-of-function thresholds for PTPN11 activity are required to induce cell-, tissue- or developmental-specific phenotypes, each depending on the transduction network context involved in the phenotype. In a such a model, mutations responsible for smaller increments in PTPN11 activity would perturb biological processes regulated by transduction pathways delicately modulated by PTPN11, but would not affect processes with signaling networks that are less strictly controlled by PTPN11. These latter networks become compromised only when the gain-of-function of PTPN11 exceeds some minimum threshold.

Thus, PTPN11 mutants associated with isolated Noonan syndrome could have relatively milder gain-of-function effects, which are sufficient to perturb heart, craniofacial and skeletal development controlled by signaling networks from various ligands (e.g., EGF, FGF, IGF, and GH), but inadequate to disturb GM-CSF-mediated myeloid proliferation. The PTPN11 mutations observed in isolated JMML, such as the assorted non-conservative Glu76 substitutions, produce mutant PTPN11 proteins with the highest gains of functions. Since these molecular lesions have been observed only as somatic defects, it is likely that will be associated with embryonic lethality. The PTPN11 mutations observed in Noonan syndrome with JMML produce PTPN11 with intermediate activity, which would explain the milder course of the leukemia. When the phosphatase activities of the Glu76Ala and Asp61Ala mutant proteins were tested in vitro, the patterns were strikingly dissimilar despite the fact that these two missense substitutions in the N-SH2 domain appear superfically similar (O'Reilly et al., supra). The Glu76Ala mutant was constitutively active while the Asp61Ala protein showed hypersensitivity to stimulation with phosphotyrosine peptide compared to wild type PTPN11. The specificity of PTPN11 mutations seen in the isolated JMML and Noonan syndrome disorders, provide a rationale for the phenotypic diversity associated with this gene.

Example 2

Characterization of Mutant PTPN11 Proteins

A. Analysis Of Basal And Signal-Dependent Phosphatase Activity Of Mutated PTPN11 In Vitro The full length PTPN11 cDNA was cloned into pRc/CMV vector (Invitrogen) and the cDNA was shuttled into pcDNA6/V5-his A vector (Invitrogen). Mutations were introduced into the PTPN11-V5 fusion construct using site-directed mutagenesis (QUICKCHANGE Site-Directed Mutagenesis Kit, Stratagene): N308D (the most common Noonan syndrome mutant) and E76K (a JMML mutant). After sequence confirmation, the wild type and mutant PTPN11-lV5 constructs were transfected into COS-7 cells using LipofectaminePlus (Invitrogen) according to the manufacturer's protocol. After growing the transfected cells in complete growth medium (DMEM supplemented with 10% fetal bovine serum (FBS)) for 24 h, they were starved for 20 h in DMEM with 0.1% FBS and then exposed to epidermal growth factor (EGF). Cells were lysed, and the fusion protein was purified by immunoprecipitation using anti-V5 (Invitrogen).

PTPase assays were determined by measuring the phosphate released from phosphopeptides using the Malachite Green assay (Harder et al, Biochem J, 1994;298:395-401). SrcPY 80 nM (Calbiochem), a phosphopeptide derived from the c-Src carboxyl-terminal region, was used as substrate.

After 30 min at RT, absorbance at 620 nm was determined with a microplate reader. A standard curve of free phosphate concentrations is prepared using $KH_2PO_4$, treated identically to the PTPase conditions.

Figure 3:
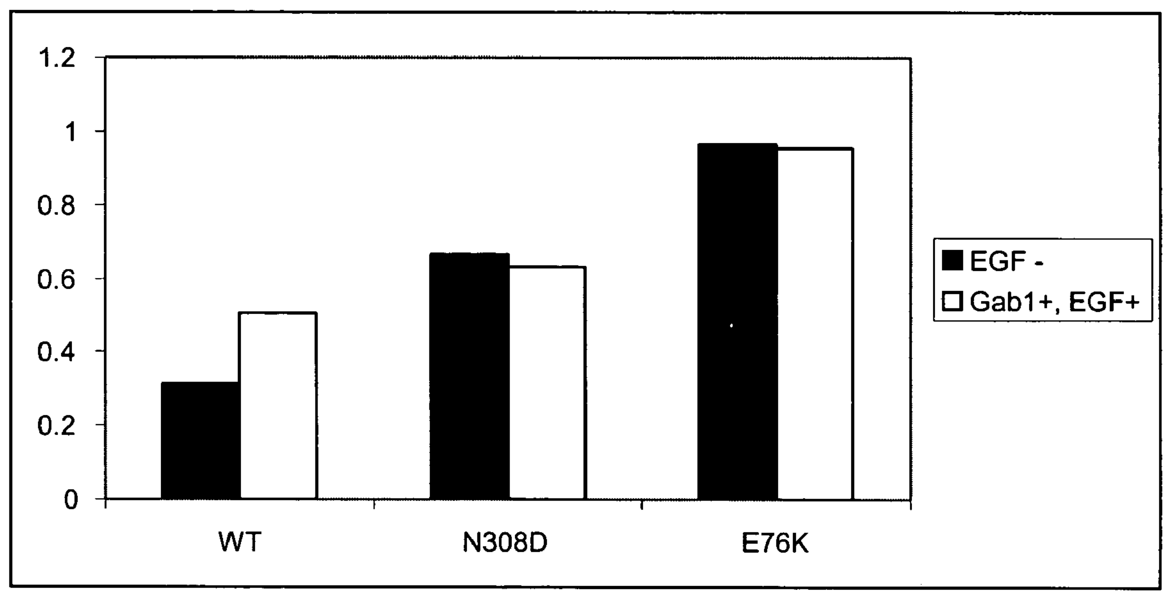
FIG. 3 shows the increased phosphatase activity observed in mutant PTPN11 proteins. Wild type and mutant PTPN11-V5 proteins were immunoprecipitated using anti-V5 and the phosphatase activity measured with the malachite green assay. The absorbance at 620 nm is indicated on the y axis. A phosphate standard curve was performed, documenting linearity in this range of absorbance. The black bars indicate the phosphatase activities of wild type and mutant PTPN11 proteins isolated from starved, unstimulated COS-7 cells. The white bars indicate the phosphatase activities of wild type and mutant PTPN11 proteins isolated from COS-7 cell that were stimulated for 5 min with EGF. See Example 3.

As shown in FIG. 3, the N308D and E76K mutant PTPN11 proteins have significantly increased phosphatase activity, even without stimulation of the COS-7 cells with EGF, compared to wild type. In addition, the JMML mutant (E76K) has greater activity than the Noonan syndrome (N308D) mutant under both culture conditions.

B. Analysis Of The Docking Function Of Mutated PTPN11

To evaluate the docking function of PTPN11, COS-7 cells were transfected with wild type and mutant PTPN11-V5 constructs as well as a FLAG-Gab1 construct. After starvation for 20 h, the cells were stimulated with EGF 0.25 ng/ml for 5 min and then lysed. Anti-FLAG monoclonal antibody (Sigma) was used for immunoprecipitation. Precipitated proteins were resolved by SDS-PAGE and transferred to nitrocellulose filters. Standard immunoblotting was carried out using anti-Gab1 (Upstate Biotechnology), anti-phosphotyrosine (Transduction Laboratories) and anti-PTPN11 (Santa Cruz) antibodies. Gab1 immunoblotting determined equivalence of Gab1 levels. Anti-phosphotyrosine immunoblotting documents that EGF stimulation results in Gab1 phosphorylation.

Figure 4:
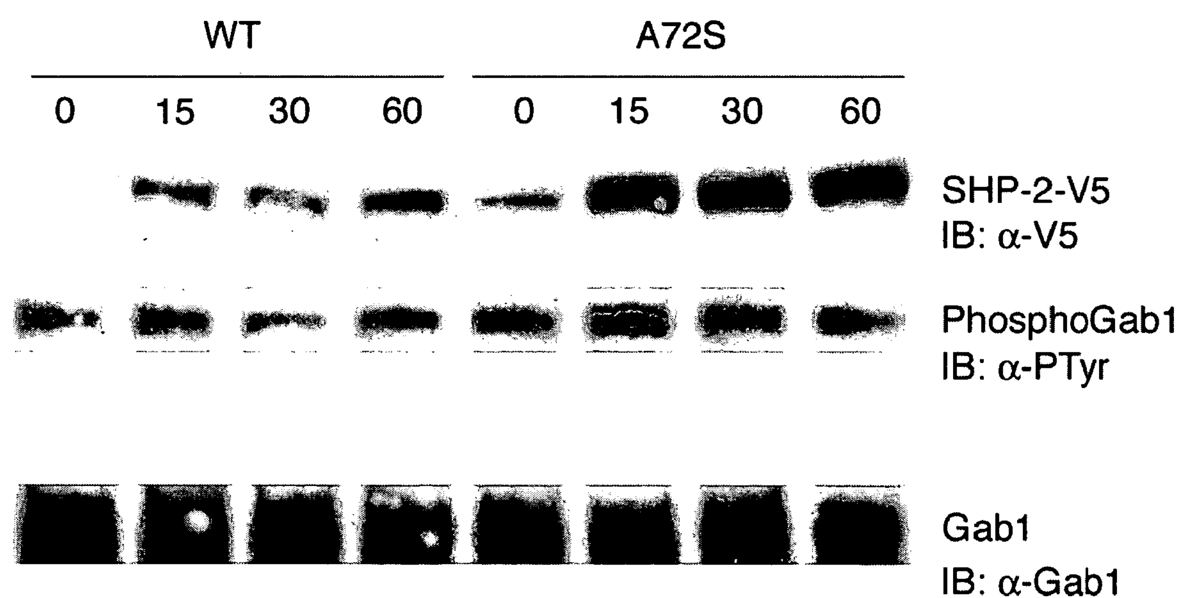
FIG. 4 describes the results of immunoblotting experiments comparing docking activity of PTPN11 and a PTPN11 variant V5-construct to Gab1 (docking partner) under basal and activated conditions (i.e., with or without EGF-stimulation), showing increased docking function of the PTPN11 variant. Comparison of the quantities of PTPN11 detected revealed that there was almost none docked to Gab1 prior to EGF stimulation and modest amounts thereafter. By contrast, the A72S PTPN11 mutant co-isolated with Gab1 without EGF stimulation and was present in much larger amounts compared to wild type PTPN11 after EGF stimulation. See Example 3.

As shown in FIG. 4, anti-PTPN11 immunoblotting revealed that there was an increase in docking between Gab1 and mutant PTPN11 under basal and activated conditions compared to the wild type PTPN11. Briefly, COS-7 cells were transfected with constructs for FLAG-Gab1 and PTPN11-V5 (also referred to as SHP-2-V5). Gab1 was immunoprecipitated with anti-FLAG antibodies from cell lysates at 0, 15, 30, and 60 min after EGF stimulation. Proteins were separated with SDS-PAGE and immunoblotted. As shown in the bottom panel of FIG. 4, the level of Gab1 was nearly equal for all conditions. Comparison of the quantities of PTPN11 detected revealed that there was almost none docked to Gab1 prior to EGF stimulation and modest amounts thereafter. By contrast, the A72S PTPN11 mutant co-isolated with Gab1 without EGF stimulation and was present in much larger amounts compared to wild type PTPN11 after EGF stimulation.

Example 3

Expression of Mutant PTPN11 Proteins in Xenopus

A mutant Xenopus Ptpn11 (XPtpn11) construct, comparable to the JMML mutant E76K, was created by site-directed mutagenesis using wild type XPtpn11 cDNA, followed by shuttling of the sequence into the Xenopus expression plasmid, pCS2. Wild-type and mutant cRNAs were transcribed in vitro in the presence of cap analog using the mMessage mMachine kit (Ambion). Similarly, constructs were available for a dominant-negative form of the FGF receptor (XFD) and a dominant-negative form of Ras.

Xenopus embryos were obtained at the 2-cell stage and injected at the animal pole with cRNAs (1 ng except Ras for which 2 ng was used). Injected embryos were cultured in 0.5×MMR with 3.5% Ficoll. Animal caps were excised from midblastulae (stage 8) and cultured in 0.5×MMR, with or without bFGF (Boehringer Mannheim), until stage 11.

To determine the status of mesoderm development, total RNA was extracted from the injected animal caps and RT-PCR analysis performed for HoxB9 and cardiac actin, mesodermal markers. EF1-$\alpha$ levels were assessed as an internal control for RNA recovery and RT-PCR efficiency.

Figure 5:
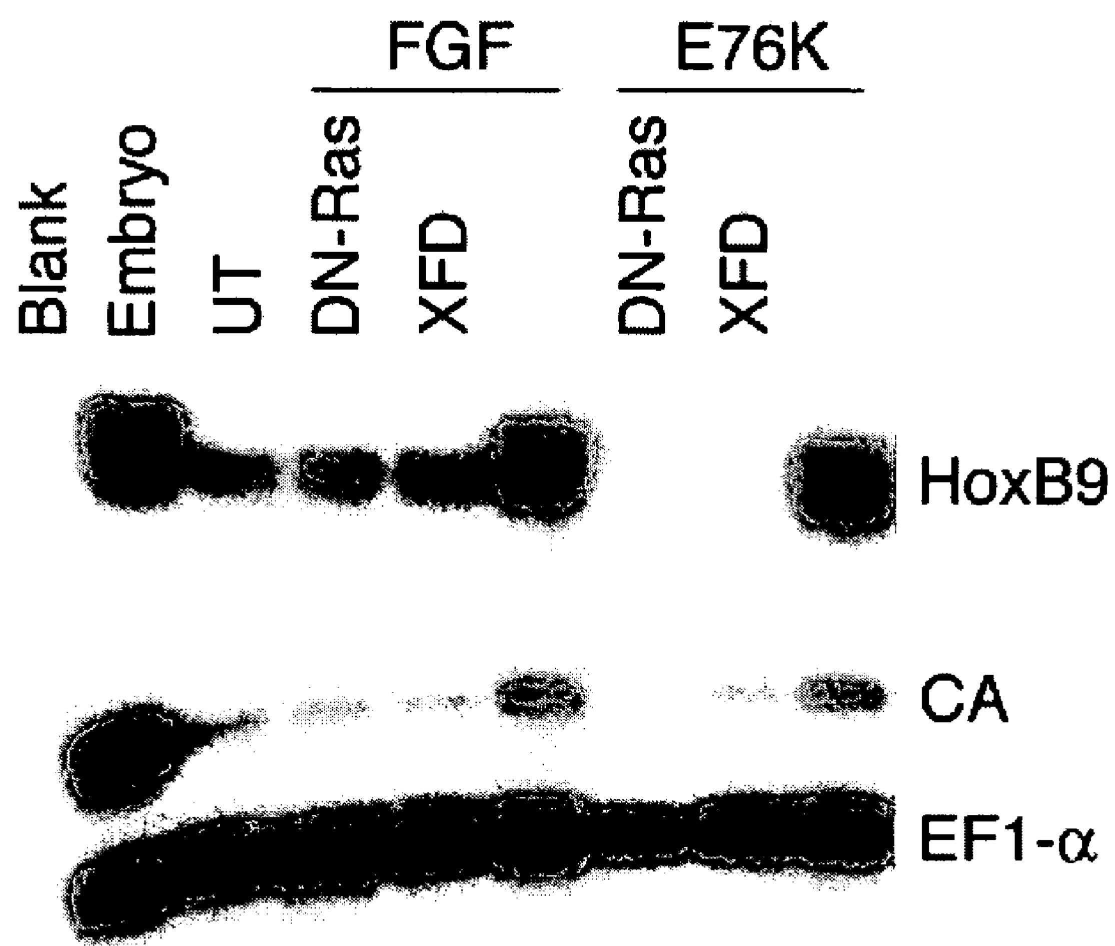
FIG. 5 shows the effects of JMML mutant PTPN11 on mesoderm induction in Xenopus animal caps. Embryos were injected with water and then treated with FGF or with E76K XPtpn11. Embryos and untreated (UT) animal caps were used as positive and negative controls, respectively. EFI-α was co-injected as a control. RT-PCR analysis of the genes HoxB9 and cardiac actin (CA) were performed.

Expression of E76K XPtpn11 resulted in the induction of dorsal mesoderm, similar to the effect of FGF treatment (FIG. 5). This induction was blocked when dominant-negative Ras was co-expressed, documenting that this developmental effect is mediated through the Ras-Map kinase pathway and that the gain-of-function Ptpn11 acts at or above Ras in that pathway. Co-expression of XFD also blocked the inductive effects E76K XPtpn11. Another E76 mutant, E76A, as well as a D61A mutant, has previously been shown to also display increased basal phosphatase activity (E76A>>D61A>WT) and retained normal phosphopeptide binding properties (O'Reilly et al, Mol. Cell. Biol. 2000, 20, 299-311).

Thus, as shown in the present Example, when expressed in Xenopus ectodermal explants, both the FGF and the XPtpn11 mutants induced changes mimicking some aspects of development that are fibroblast growth factor-inducible, documenting basal stimulation of some signaling cascades in vivo. These results show that docking of XPtpn11 to the FGF RTK is essential for signal transduction.

Example 4

Somatic PTPN11 Mutations In Childhood Acute Leukemia

As demonstrated above, somatic PTPN11 mutations are the most frequent lesion in juvenile myelomonocytic leukemia (JMML), and occur in a smaller percentage of children with other myeloid malignancies. This Example reports that PTPN11 defects represent a recurrent event in precursor B-lineage ALL, but do not appear to contribute to T-lineage ALL pathogenesis. In the former, PTPN11 lesions are prevalently observed in children with $CD19^+/CD10^-/cyIgM^-$ immunophenotype, and are associated neither with the TEL-AML1 gene rearrangement, nor with oncogenic RAS mutations. It is also shown that, among children with acute myeloid leukemia (AML), mutations specifically occur in cases with acute monocytic leukemia, with high prevalence. Leukemia-associated PTPN11 mutations are missense, and are predicted to result in SHP-2 gain-of-function. These findings provide evidence for a wider role of PTPN11 lesions in leukemogenesis, support a lineage- and differentiation stage-specific contribution of these lesions to clonal expansion, but also suggest a relevant contribution of deregulated RAS signaling to precursor B-lineage ALL pathogenesis.

Patients

Children and adolescents with ALL (n=355) and de novo AML (n=69) were included in the study. ALL patients aged between 1 and 18 years, had been consecutively enrolled in the ongoing AIEOP-BFM ALL 2000 study protocol. All cases were subjected to the reference morphological and immunological review of the AIEOP. Diagnosis was established according to standard morphologic, cytochemical and immunological criteria (Bene M C, Castoldi G, Knapp W, et al. Proposals for the immunological classification of acute leukemias. 1995; 1783-1786). According to surface antigen expression, B-cell precursor ALL was classified as pro-B ALL ($CD19^+$, $CD10^-$, $CD20^-$ and $cyIgM^-$), common ALL ($CD19^+$, $CD10^+$, $cyIgM^-$), pre-B ($CD19^+$, $CD10^{+/-}$, $cyIgM^+$) or pre-B/B ($CD19^+$, $CD10^{+/-}$, $cyIgM^+$, $smIgM^+$ and IgM $\kappa/\lambda^-$). One case exhibited a bi-lineage leukemic condition with a mixed population expressing $CD10^+/CD33^-$ (65% of cells) or $CD10^-/CD33^+$ (35% of cells). The main clinical and biological features are summarized in FIGS. 6A and 6B. No statistically significant differences in clinical and laboratory features were observed between patients included or not in the study.

Frozen material from 69 de novo AML cases out of 135 (52.7%) diagnosed in a single institution since 1981, were available for the study. Diagnosis was established by standard morphologic, cytochemical and immunological criteria. According to the French-American-British (FAB) classification, patients were classified as MO (n=1, 1.4%), M1 (n=15, 21.7%), M2 (18, 26.2%), M3 (11, 15.9%), M4 (8, 11.6%), M5 (12, 17.5%), M6 (1, 1.4%), and M7 (2, 2.9%); in 1 case the FAB subtype was unknown. Karyotype information was available for 60 patients (87%). Chromosomal aberrations characteristic for de novo AML, i.e. t(8;21), t(15;17), inv(16), as well as other complex abnormalities were documented. Median age was 6.3 years (range 0.2 to 17.6), 45 were male (65.2%) and 24 female (34.8%). Median white blood cells (WBC) count was $26{,}000\times10^3/\mu l$ (range 800-296,000).

Molecular Analyses

DNA sample acquisition. Bone marrow aspirates were obtained at diagnosis, prior to therapy, as well as during the follow up. Mononuclear cells were separated from aspirated bone marrow samples using a Ficoll gradient, and genomic DNA was isolated from lysates of these cells using a standard protocol.

Mutation analysis. The entire PTPN11 coding region (exons 1-15 and flanking intronic stretches) was screened for mutations. PCR reactions to amplify exons 2 to 15 were carried out as previously described (Tartaglia et al., Am J Hum Genet. 2002;70:1555-1563); exon 1 was amplified in 25 μl reaction volume containing 50 ng genomic DNA, 1 U AMPLITAQ Gold (Applied Biosystem), 20 pmoles of each primer (MWG-Biotech AG), 1.5 mM $MgCl_2$, 10% DMSO, 75 μM each dNTP and 1X PCR Buffer II (Applied Biosystem), using primer pairs PTPN11-lsF, 5'-CGG AGC CTG AGC AAG GAG CG-3'; PTPN11-lsR, 5'-CGA GGG GAC GAG GAG GGA ACC-3', and the following cycling parameters: 94° C., 8 min (first denaturing step); 94° C., 45 sec; 60° C., 30 sec; 72° C., 45 sec; 33 cycles; 72° C., 15 min (last extension step). Mutational analysis was also performed on exons 1 and 2 of the NRAS and KRAS2 genes (primer sequences and PCR conditions are available upon request). Unpurified PCR products were analyzed by denaturing high performance liquid chromatography (DHPLC), using the Wave DNA Fragment Analysis System (Transgenomics) at column temperatures recommended by the WAVEMAKER version 4.1.31 software (Transgenomics). Heterozygous templates with previously identified mutations or synthetic templates containing heterozygous exonic single nucleotide changes were used as positive controls for all exons. Amplimers having abnormal denaturing profiles were purified (Microcon PCR, Millipore) and sequenced bi-directionally using the ABI BIGDYE terminator Sequencing Kit v.3.1 (Applied Biosystem) and an ABI PRISM 310 Genetic Analyzer (Applied Biosystem). Sequencing results were analyzed using the Sequencing Analysis v.3.6.1 (Applied Biosystem) and AutoAssembler v.2.1 software packages (Perkin Elmer).

Reverse transcriptase-polymerase chain reaction (RT-PCR) assay. RNA was purified from bone marrow mononuclear cells by standard phenol-chlorophorm extraction method. RT-PCR was performed as previously described (van Dongen et al., Leukemia 1999;13:1901-1928). All samples were analyzed by single-step PCR for the presence of the MLL-AF4, BCR-ABL and TEL-AML1 fusion transcripts; in addition, PTPN11 mutated cases were also analyzed for the presence of the E2A-PBX1 fusion gene product. Amplification of the housekeeping ABL gene transcript was performed in all samples to guarantee for good quality cDNA synthesis. After amplification, 10 μl of PCR products were run on a 2.5% agarose gel stained with ethidium bromide and visualized under a UV lamp.

Cytogenetic, FISH, and DNA index analyses. Cytogenetic analysis was performed on leukemic bone marrow mononuclear cells methanol:acetic acid fixed chromosome preparations by standard QFQ-banding. Rearrangement of the MLL gene was investigated by FISH analysis from methanol: acetic acid fixed interphase nuclei, by using the "Dual colour, break apart MLL probe" (Vysis, Downers Grove, Ill., USA), covering the MLL locus on chromosome 11q23. DNA index was calculated according to the guidelines provided by the Committee on Nomenclature of the Society for Analytical Cytology (Hiddemann et al., Cancer Genet Cytogenet. 1984; 13: 181-183).

PTPN11 Mutations in Childhood ALL

Figure 7:
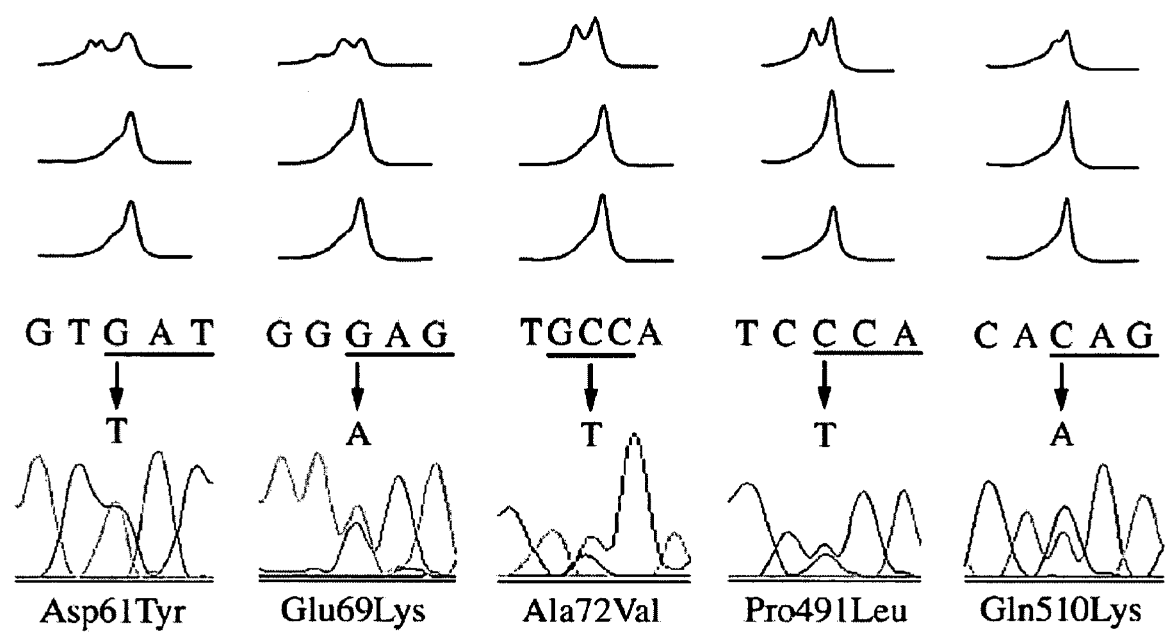
FIG. 7 shows representative DHPLC profiles showing occurrence of missense mutations in five children with B-cell precursor ALL: in all cases, mutations were observed at diagnosis (top), but were undetectable during remission, after 33 (middle) and 78 days of follow up (bottom). Corresponding nucleotide changes and electropherograms are also shown.

The prevalence of PTPN11 mutations in bone marrow mononuclear cells from a cohort of 355 children and adolescents with ALL was investigated using DHPLC. PTPN11 defects were identified in 23 children with B-cell precursor ALL (Table 6), while no mutation was observed in the T-lineage ALL cohort. All mutations were missense changes; eighteen affecting exon 3 and five residing in exon 13. Among them, the G181T (Asp61Tyr), A182T (Asp61Val), G205A (Glu69Lys), G214A (Ala72Thr), C215T (Ala72Val), G226A (Glu76Lys), and A227G (Glu76Gly) changes were previously found in children with JMML. Several lesions were found recurrently, and mutations affecting residues Asp61, Glu69, Ala72, Glu76, and Pro491 accounted for 87% of all defects. As previously observed in JMML, codon 76 represented a mutational hot spot (35% of total mutations), with three different amino acid substitutions predicted among eight individuals. Mutation analysis of mononuclear cell DNAs from bone marrow biopsies obtained during disease remission demonstrated absence of the mutated allele in all cases (FIG. 7), providing evidence that all mutations were somatic events associated with the leukemic condition. Consistently, none of these defects has been observed among more than 200 control individuals. PTPN11 defects were not randomly distributed in the B-lineage ALL cohort, as the vast majority of lesions occurred in association with the common ($CD19^+/CD10^-/cyIgM^-$) immunophenotype, where they accounted for 11% of cases. Three mutations occurred in children with pre-B ALL (3% of cases). One of the common ALL cases with mutated PTPNllshowed CD10 antigen expression only in a subset of cells, and expression of the CD33 myeloid antigen in a different subset of cells, indicating a mixed population. All PTP11 defects affected amino acid residues located in the N-SH2 and PTP functional domains (FIGS. 9A and 9B). According to the SHP-2's crystal structure (Hof et al., Cell 1998;92:441-450), the vast majority of affected residues, i.e. Asn58, Asp61, Glu69, Ala72, Glu76 and Ser502, are clustered in the specific regions of those domains that are involved in the N-SH2/PTP intramolecular interaction. This interaction normally stabilizes SHP-2 in its catalytically inactive conformation.

TABLE 6

Somatic PTPN11 mutations in pediatric acute leukemia. Nucleotide and amino acid substitutions are numbered as set forth in SEQ ID NO: 1 and 2, respectively.

| Malignancy and subtype | No. of cases | Nucleotide substitution | Amino acid substitution |
|---|---|---|---|
| ALL | | | |
| Common | 1 | A172T | Asn58Tyr |
| | 1 | G181T | Asp61Tyr |
| | 1 | A182T | Asp61Val |
| | 2 | G205A | Glu69Lys |
| | 1 | G214A | Ala72Thr |
| | 3 | C215T | Ala72Val |
| | 3 | G226A | Glu76Lys |
| | 2 | G226C | Glu76Gln |
| | 1 | A227G | Glu76Gly |
| | 1 | C1471T | Pro491Ser |
| | 1 | C1472T | Pro491Leu |
| | 1 | T1504C | Ser502Pro |
| | 1 | C1528A | Gln510Lys |
| Pre-B | 1 | C215A | Ala72Asp |
| | 1 | G226A | Glu76Lys |
| | 1 | C1472T | Pro491Leu |
| Bi-lineage | 1[a] | A227G | Glu76Gly |
| AML | | | |
| FAB-M5 | 2[b] | C215T | Ala72Val |
| | 1[b] | G226A | Glu76Lys |
| | 1 | C1520A | Thr507Lys |

[a]Mixed leukemic cell population expressing $CD10^+/CD33^-$ (66% of cells) and $CD10^-/CD33^+$ (33% of cells).
[b]Acute monocytic leukemia, poorly differentiated (FAB-M5a AML).

As gene rearrangements and other chromosomal abnormalities account for a relatively large portion of childhood ALL cases, major chromosomal translocations and hyperdiploidy were systematically investigated in all patients carrying a mutated PTPN11 gene. Significantly, none of cases exhibited the TEL-AML1 fusion gene. That karyotypically cryptic gene rearrangement represents the most recurrent lesion in children with B-lineage ALL, and was observed in 24% of common ALL cases in our series. This mutually exclusive distribution was statistically significant ($P \approx 0.01$, $\chi^2$ test). Similarly, we did not observe the E2A-PBX1, BCR-ABL, and MLL-AF4 gene arrangements among the 23 children carrying a mutated PTPN11 gene. Thirteen out of the 21 analyzed patients showed hyperdiploidy (DNA index>1).

Comparison of biological features within the ALL cohort did not reveal any statistically significant differences between patients with and without PTPN11 mutations. Similarly, no significant association with age of diagnosis was observed.

Deregulated RAS Signaling in Common ALL Cases

Without being bound to any specific theory, PTPN11 (SHP-2) may positively control cell proliferation and survival of hematopoietic cells by acting as positive modulator of RAS function (Pazdrak et al., J Exp Med. 1997;186:561-568; Chauhan et al., J Biol Chem. 2000;275:27845-50; Yu et al., Oncogene 2003;22:5995-6004). Because of the relatively high incidence of PTPN11 lesions among children with common ALL, we investigated the cumulative prevalence of up-regulated RAS signaling in this cohort by performing mutational screening of exons 1 and 2 of the NAIS and KRAS2 genes. Mutations affecting codons 12 and 13 of NRAS were observed in eight and six children respectively, accounting for 9% of cases (Table 6). These results are consistent with available data from previous studies (Luibbert et al., Blood. 1990; 75:1163-1169; Yokota et al., Int J Hematol. 1998;67:379-387; Nakao et al., Leukemia 2000;14:312-315). A slightly higher prevalence of mutations affecting exon 1 of KRAS2 was also observed (13% of cases) (Table 7). Even though mutated KRAS2 had been documented in childhood common ALL, the prevalence of mutations we observed is considerably higher than that previously documented (Browett et al., Oncogene 1989;4:1029-1036; Lübbert et al., Blood. 1990;75: 1163-1169). Occurrence of the TEL-AML1 gene rearrangement was investigated among cases with mutations in the RAS genes, and lesions were found to be largely mutually exclusive, as the chimeric gene occurred only in two children with mutated KRAS2. Significantly, among the 23 cases with mutated PTPN11 gene, only one showed concomitant lesions in the NAS or KRAS2 genes.

TABLE 7

Somatic NRAS and KRAS2 mutations in pediatric acute leukemia. NRAS nucleotide and amino acid substitutions or insertions are numbered as set forth in SEQ ID NOS: 36 and 37, respectively. KRAS2 nucleotide and amino acid substitutions are numbered as set forth in SEQ ID NOS: 38 and 39, respectively (Note: alternative splicing leads to variants encoding two isoforms that differ in the KRAS2 C-terminal region. Transcript Variant: This variant (b) is composed of five exons and lacks exon 4a which the longer transcript variant (a) includes. This predominant variant (b) has a cds that terminates in exon 4b, encoding a unique C terminus.

| Malignancy and affected gene | No. of cases | Nucleotide substitution | Amino acid substitution |
|---|---|---|---|
| Common ALL | | | |
| NRAS | 2 | G34A | Gly12Ser |
| | 1 | G35C | Gly12Ala |

TABLE 7-continued

Somatic NRAS and KRAS2 mutations in pediatric acute leukemia. NRAS nucleotide and amino acid substitutions or insertions are numbered as set forth in SEQ ID NOS: 36 and 37, respectively. KRAS2 nucleotide and amino acid substitutions are numbered as set forth in SEQ ID NOS: 38 and 39, respectively (Note: alternative splicing leads to variants encoding two isoforms that differ in the KRAS2 C-terminal region. Transcript Variant: This variant (b) is composed of five exons and lacks exon 4a which the longer transcript variant (a) includes. This predominant variant (b) has a cds that terminates in exon 4b, encoding a unique C terminus.

| Malignancy and affected gene | No. of cases | Nucleotide substitution | Amino acid substitution |
|---|---|---|---|
| | 5 | G35A | Gly12Asp |
| | 6 | G38A | Gly13Asp |
| KRAS2 | 1 | ins. GTA, 28-30 | ins. Val, 10 |
| | 1 | G34C | Gly12Arg |
| | 1 | G34A | Gly12Ser |
| | 1[a] | G34T | Gly12Cys |
| | 8 | G35A | Gly12Asp |
| | 1 | G35T | Gly12Val |
| | 1 | G35C | Gly12Ala |
| | 5 | G38A | Gly13Asp |
| | 1 | G57C | Leu19Phe |
| | 1 | C64A | Gln22Lys |
| AML | | | |
| NRAS | 1 | G34A | Gly12Ser |
| | 1 | G35A | Gly12Asp |
| | 1 | G35T | Gly12Val |
| | 1 | G37C | Gly13Arg |
| | 1 | G38A | Gly13Asp |

[a]This case showed the C(1528)A change in PTPN11 (Gln510Lys).

On the whole, these data documented that PTPN11, NRAS and KRAS2 lesions and the TEL-AML1 rearrangement are largely mutually exclusive among common ALL cases. These findings suggest that leukemia-associated PTPN11 (SHP-2) mutants might contribute to leukemogenesis through a RAS-mediated mechanism, and that molecular lesions promoting up-regulation of RAS function might represent a relatively frequent event contributing to B-lineage ALL (33% of common ALL cases, in our series)

PTPN11 Mutations in Childhood AML

Figure 8:
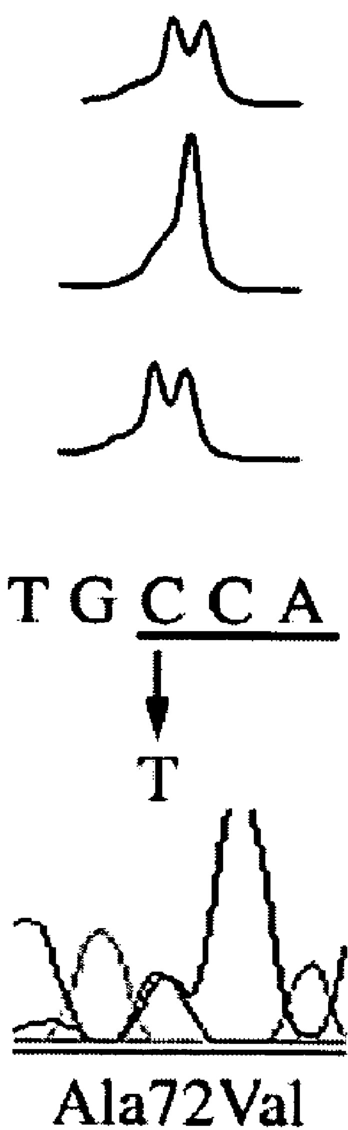
FIG. 8 shows DHPLC profiles, and corresponding nucleotide change and electropherogram, showing the C215T substitution in one case of ALL with FAB-M5a identified at diagnosis (top) and relapse (bottom), but not during remission (middle).

Sixty-nine children with de novo AML were included in the study in order to investigate prevalence, spectrum and distribution of PTPN11 lesions in this heterogenesous group of myeloid malignancies more thoroughly. Somatic PTPN11 lesions were identified in four children (5% of cases), confirming the relatively low prevalence of this class of molecular lesions. All mutations were missense (Table 6), and affected residues located in the interacting surfaces of the N-SH2 and PTP domains. Two amino acid substitutions (Ala72Val and Glu76Lys) had been identified previously in JMML, MDS and ALL. A novel change (C1520A), resulting in the substitution of residue Thr507 by lysine was identified in one case. Bone marrow specimens at remission were available in three cases, and showed absence of the mutated allele. A subsequent relapse occurred in one child, and the presence of the mutated allele was also documented (FIG. 8). Cytogenetic data were available for two of the four cases. One patient exhibited the complex karyotype 46, XX, invdup(1)(q31), t(2; 17)(q14;q24), t(2; 19)(p22;q13); mosaicism for t(2; 10) (q36;q22) was observed in the second case. FISH analysis carried out on three of the four cases showed rearrangement of the MLL gene in a large percentage of leukemic cells of these patients. Significantly, all cases carrying a mutated PTPN11 gene exhibited acute monocytic leukemia (FAB-M5 subtype). These results indicate that PTPN11 is frequently mutated in children within this leukemia condition (25% of cases). The distribution of NRAS and KRAS2 gene mutations in the AML cohort was also investigated. Genomic DNA was available for forty-nine cases, and mutational screening identified NAIS lesions in five (10%), including two with FAB-M1 (Gly12Ser and Gly13Asp), two with FAB-M2 (Gly12Asp and Gly13Arg), and one with FAB-M4 (Gly12Val) (Table 7). These findings suggest that the impact of SHP-2 gain-of-function on clonal expansion of the myeloid leukemic clone is lineage- and differentiation stage-specific, and possibly acts preferentially on monocyte precursors, although it is unclear whether these cells possess a proliferative or survival advantage.

Discussion

Here, it is documented that somatic missense mutations in PTPN11 represent a novel recurrent molecular event with role in precursor B-lineage ALL pathogenesis. A novel scenario emerging from the present study also regards the relevant role of deregulated RAS signaling in precursor B-lineage ALL, previously considered as minor pathogenetic event. The data herein suggest that, as observed in myeloid malignancies, upregulated RAS, due to mutations in the RAS genes or in genes coding for proteins controlling RAS function, may represent a major node that drives the aberrant growth of malignant B-cell precursors. Finally, the relevance of PTPN11 lesions in pediatric AML was established by documenting a relatively high prevalence of these defects among children with acute monocytic leukemia.

Several lines of evidence thus show that PTPN11 mutations represent events with a role in leukemogenesis. First, molecular analysis of bone marrow specimens documented that mutations were observed at disease presentation, but were undetectable at remission, supporting the presence of the mutated gene in the leukemic clone. Consistently, none of these mutations was observed in more than 200 control individuals. Second, the spectrum and distribution of mutations indicated that these lesions are not random, but are predicted to promote SHP-2 gain-of-function. Third, among children with ALL, PTPN11 defects were associated neither with major gene rearrangements (TEL-AML1, E2A-PBX1, BCR-ABL and AF4-MLL), nor with other gene lesions (NRAS and KRAS2). Fourth, PTPN11 mutations appeared to be associated preferentially with specific leukemia conditions, suggesting a specific role in disease pathogenesis. Finally, the same mutation was documented at initial diagnosis and relapse in the only case with a PTPN11 lesion in our series.

PTPN11 (SHP-2) contains two tandemly arranged amino-terminal SH2 domains (N-SH2 and C-SH2), a single catalytic (PTP) domain, and a carboxy-terminal tail (FIGS. 9A and 9B). Crystallographic data indicate that PTPN11 is basally inactive, with an auto-inhibited conformation, because of the intramolecular interaction between the N-SH2 and PTP domains (Hof et al., Cell. 1998;92:441-450). Catalytic activation requires disruption of such interaction, which is promoted by the conformational change of the N-SH2 domain subsequent to its binding to phosphotyrosyl-containing motifs of signaling partners. Similarly to that observed for the vast majority of the Noonan syndrome-causative mutations (Tartaglia et al., Nat Genet. 2001;29:465-468; Tartaglia et al., Am J Hum Genet. 2002;70:1555-1563), the data documented that leukemia-associated PTPN11 lesions specifically affect residues located at or close to the N-SH2/PTP interacting surfaces. Significantly, both the spectrum and location of mutations support a model in which PTPN11 lesions up-regulate SHP-2 physiological activation by impairing the switch between the active and inactive conformation, favoring a shift in the equilibrium toward the active conformation. Consistent with this view, neither mutations affecting residues that are essential for phosphatase activity, nor nonsense, frameshift, or splicing defects have been observed among the numerous mutations (N>200) identified thus far. Accordingly, first in vitro functional studies on two JMML-associated PTPN11 mutants, i.e. D61G and E76K, the latter recurrent in acute leukemia, and three mutants identified in Noonan syndrome (S72A, 1282V and N308D), documented increased basal PTPase activity, supporting the idea that these substitutions weaken the autoinhibitory interaction between the N-SH2 and PTP domains controlling PTPN11 activation.

The present findings provide the first genetic evidence of a mutated protein tyrosine phosphatase acting as oncoprotein in both lymphoid and myeloid malignancies. The existing data do not permit any firm conclusions regarding whether somatic PTPN11 mutations represent primary permissive events, or second hits acquired during disease progression that are important for emergence of fully developed leukemia. The finding, however, that they are restricted prevalently to specific leukemic conditions, i.e. common ALL and acute monocytic leukemia (the latter consistent with PTPN11 involvement in JMML), strongly suggests that PTPN11's gain-of-function contributes to expansion of the leukemic clone depending upon the cellular context, i.e. stage of differentiation and lineage of precursor cell.

It was documented that the vast majority of cases with precursor B-lineage ALL do not harbor mutations in both PTPN11 and RAS genes. As PTPN11 is a positive modulator of RAS function, without being bound to any specific theory, this finding suggests that mutated PTPN11 and RAS proteins might elicit their effects through a common pathway, and that missense mutations in PTPN11 might represent a novel class of lesions that lead to hyperactive RAS. PTPN11, ARRAS, KRAS2, and NF1 mutations are also largely mutually exclusive in JMML (Kalra et al., Blood 1994;84:3435-3439; Tartaglia et al., Nat Genet. 2001;29:465-468). This is supported by functional analyses documenting ligand-dependent prolonged activation of ERK2 in cells expressing mutated PTPN11 proteins (see, above, and Tartaglia et al., Nat Genet. 2001;29:465-468). RAS activation is an essential component of proliferative and anti-apoptotic responses to a number of hematopoietic growth factors and cytokines (de Groot et al., Cell Signal. 1998;10:619-628; Miyajima et al., Int J Hematol. 1999;69:137-146; Chang et al., Leukemia 2003; 17:1263-1293), and up-regulation of RAS signaling has a pivotal role in promoting proliferation and/or survival of malignant myeloid cells, as documented by RAS point mutations and a number of genetic lesions that deregulate RAS function, including those altering growth factor receptors (KIT, FLT-3, PDGFRβ, FGFR1), tyrosine kinases (BCR-ABL), and positive modulators of RAS GTPase activity (neurofibromin) (Kelly L M, Gilliland D G., Annu Rev Genomics Hum Genet. 2002;3:179-198). Here, it is shown that the combined prevalence of PTPN11, JWMS and KRAS2 mutations accounts for approximately one-third of pediatric cases with common ALL. As there are some limitations to the accuracy of this estimate, the true prevalence of NRAS and KRAS2 oncogenic lesions in our series could be slightly higher. Consequently, these data support a relevant role of deregulated RAS signaling also in precursor B-lineage ALL, and suggest that additional genes coding for transducers involved in this signal transduction pathway might represent novel candidate genes in B lineage ALL pathogenesis.

The data thus show that missense PTPN11 mutations occur as somatic defects in ALL, AML, JMML and MDS, and as germ-line lesions in Noonan syndrome (see co-pending application Ser. No. 10/262,522, supra). The molecular defects are similar, i.e. missense gain-of-function mutations; however, identity of affected residues or type of substitution differ. Among Noonan syndrome cases, defects in exons 4, 7 and 8 accounted for one-half of cases, with the most prevalent substitution A922G (Asn308Asp) observed in approximately one-third of cases with mutations. In contrast, no mutation affecting these exons has been identified in ALL, AML, JMML and MDS, thus far. Rather 85% of the mutations cluster in exon 3, with lesions altering Glu76 (replaced by Lys, Val, Gly, Ala or Gln) accounting for one-third of defects. Significantly, mutations affecting this residue are exceptionally rare among individuals with Noonan syndrome (2% of mutations), and are more conservative (Glu→Asp). As all leukemia-associated PTPN11 mutations have been observed exclusively as somatic lesions, they might represent embryonic-lethal events. Such dramatic genotype/phenotype relationship, defines a novel class of missense mutations in the PTPN11 gene with an oncogenic role in hematologic malignancies.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for characterizing a hematologic disorder in a human subject comprising detecting in a sample from the subject the presence of a mutation in the subject's protein tyrosine phosphatase 11 (PTPN11) gene encoding any of the following amino acid substitutions in PTPN11: Glu76Gly, Glu76Val, Glu76Ala, Glu76Gln and Glu76Lys, wherein Glu76Gly is indicative of juvenile myelomonocytic leukemia (JMML) or acute lymphoblastic leukemia (ALL), Glu76Val is indicative of JMML, Glu76Ala is indicative of JMML or myelodysplastic syndrome (MDS), Glu76Gln is indicative of ALL, and Glu76Lys is indicative of JMML, ALL, or acute myeloid leukemia (AML).

2. The method of claim 1, wherein said detecting comprises a method selected from the group consisting of antibody binding, oligonucleotide sequencing, Denaturing Gradient Gel Electrophoresis, Single Strand Conformation Polymorphism, HOT cleavage, reverse-transcription POR, microarray analysis, immunoassay, POR, and restriction fragmentation.

* * * * *

UNITED STATES PATENT AND TRADEMARK OFFICE

CERTIFICATE OF CORRECTION

PATENT NO. : 7,550,262 B2
APPLICATION NO. : 10/703210
DATED : June 23, 2009
INVENTOR(S) : Bruce D. Gelb et al.

It is certified that error appears in the above-identified patent and that said Letters Patent is hereby corrected as shown below:

Title Page, item [73] In the Assignee, after "Mount Sinai School of Medicine of New York University, New York, NY (US)":

Please insert -- UNIVERSITAETSKLINIKUM FREIBURG, Frieburg (DE) --

Signed and Sealed this

Twenty-sixth Day of January, 2010

David J. Kappos
*Director of the United States Patent and Trademark Office*